(12) United States Patent
Abbott et al.

(10) Patent No.: US 8,579,936 B2
(45) Date of Patent: Nov. 12, 2013

(54) CENTERING OF DELIVERY DEVICES WITH RESPECT TO A SEPTAL DEFECT

(75) Inventors: Ryan Abbott, San Jose, CA (US); W. Martin Belef, San Jose, CA (US); Dean Carson, Mountain View, CA (US); Taylor A. Heanue, Oakland, CA (US); Ronald J. Jabba, Redwood City, CA (US); Anthony J. Pantages, San Jose, CA (US)

(73) Assignee: ProMed, Inc., Santa Clara, CA (US)

( * ) Notice: Subject to any disclaimer, the term of this patent is extended or adjusted under 35 U.S.C. 154(b) by 420 days.

(21) Appl. No.: 12/819,911

(22) Filed: Jun. 21, 2010

(65) Prior Publication Data

US 2011/0093007 A1 Apr. 21, 2011

Related U.S. Application Data

(63) Continuation-in-part of application No. 12/176,175, filed on Jul. 18, 2008, now abandoned, which is a continuation-in-part of application No. 11/744,784, filed on May 4, 2007, now abandoned, which is a continuation-in-part of application No. 11/427,572, filed on Jun. 29, 2006, now abandoned, which is a continuation-in-part of application No. 11/175,814, filed on Jul. 5, 2005, now abandoned, said application No. 12/819,911 is a continuation-in-part of application No. 11/295,338, filed on Dec. 5, 2005, now abandoned.

(51) Int. Cl.
*A61B 17/08* (2006.01)
*A61B 17/10* (2006.01)

(52) U.S. Cl.
USPC .......................................... 606/213; 606/142

(58) Field of Classification Search
USPC .......................... 606/142, 143, 205–208, 213
See application file for complete search history.

(56) References Cited

U.S. PATENT DOCUMENTS

| 2,670,673 A | 3/1954 | Gordon et al. |
| 3,874,388 A | 4/1975 | King et al. |

(Continued)

FOREIGN PATENT DOCUMENTS

| DE | 42 22 291 C1 | 7/1992 |
| EP | 0 432 320 A1 | 6/1991 |

(Continued)

OTHER PUBLICATIONS

Baim, D., Percutaneous Approach, Including Transseptal and Apical Puncture, Grossman's Cardiac Catheterization, Angiography, and Intervention, 6$^{th}$ Ed., 2000.

(Continued)

*Primary Examiner* — Gary Jackson
*Assistant Examiner* — Lindsey Bachman
(74) *Attorney, Agent, or Firm* — Mark Stirrat; One LLP

(57) ABSTRACT

A system for treating a septal defect having an implantable treatment apparatus and devices for delivering the implantable treatment apparatus, devices for controlling delivery of the treatment apparatus and methods for treating a septal defect are provided. The implantable treatment apparatus is preferably implantable through a septal wall or portion thereof. The treatment system can include a flexible elongate body member, a delivery device configured to deliver the implantable apparatus, and a proximal control device for controlling delivery of the implantable apparatus, among others.

26 Claims, 126 Drawing Sheets

(56) References Cited

U.S. PATENT DOCUMENTS

| | | |
|---|---|---|
| 3,875,648 A | 4/1975 | Bone |
| 4,006,747 A | 2/1977 | Kronenthal et al. |
| 4,007,743 A | 2/1977 | Blake |
| 4,316,469 A | 2/1982 | Kapitanov |
| 4,576,162 A | 3/1986 | McCorkle |
| 4,601,718 A | 7/1986 | Possis et al. |
| 4,665,906 A | 5/1987 | Jervis |
| 4,669,473 A | 6/1987 | Richards et al. |
| 4,696,300 A | 9/1987 | Anderson |
| 4,702,250 A | 10/1987 | Ovil et al. |
| 4,705,040 A | 11/1987 | Mueller et al. |
| 4,721,115 A | 1/1988 | Owens |
| 4,741,336 A | 5/1988 | Failla et al. |
| 4,779,616 A | 10/1988 | Johnson |
| 4,800,890 A | 1/1989 | Cramer |
| 4,802,478 A | 2/1989 | Powell |
| 4,836,204 A | 6/1989 | Landymore et al. |
| 4,850,960 A | 7/1989 | Grayzel |
| 4,861,336 A | 8/1989 | Helzel |
| 4,878,893 A | 11/1989 | Chin |
| 4,892,098 A | 1/1990 | Sauer |
| 4,902,508 A | 2/1990 | Badylak et al. |
| 4,917,089 A | 4/1990 | Sideris |
| 4,929,246 A | 5/1990 | Sinofsky |
| 4,946,467 A | 8/1990 | Ohi et al. |
| 4,985,014 A | 1/1991 | Orejola |
| 4,994,069 A | 2/1991 | Ritchart et al. |
| 5,021,059 A | 6/1991 | Kensey et al. |
| 5,037,433 A | 8/1991 | Wilk et al. |
| 5,041,129 A | 8/1991 | Hayhurst et al. |
| 5,049,153 A | 9/1991 | Nakao et al. |
| 5,067,957 A | 11/1991 | Jervis |
| 5,073,166 A | 12/1991 | Parks et al. |
| 5,108,420 A | 4/1992 | Marks |
| 5,112,310 A | 5/1992 | Grobe |
| 5,171,218 A | 12/1992 | Fonger et al. |
| 5,171,259 A | 12/1992 | Inoue |
| 5,190,050 A | 3/1993 | Nitzsche |
| 5,190,528 A | 3/1993 | Fonger et al. |
| 5,190,546 A | 3/1993 | Jervis |
| 5,192,301 A | 3/1993 | Kamiya et al. |
| 5,219,358 A | 6/1993 | Bendel et al. |
| 5,222,974 A | 6/1993 | Kensey et al. |
| 5,236,440 A | 8/1993 | Hlavacek |
| 5,242,427 A | 9/1993 | Bilweis |
| 5,250,054 A | 10/1993 | Li |
| 5,250,055 A | 10/1993 | Moore et al. |
| 5,257,637 A | 11/1993 | El Gazayerli |
| 5,281,234 A | 1/1994 | Wilk et al. |
| 5,282,827 A | 2/1994 | Kensey et al. |
| 5,284,488 A | 2/1994 | Sideris |
| 5,290,272 A | 3/1994 | Burstein et al. |
| 5,290,278 A | 3/1994 | Anderson |
| 5,300,065 A | 4/1994 | Anderson |
| 5,304,184 A | 4/1994 | Hathaway et al. |
| 5,304,185 A | 4/1994 | Taylor |
| 5,312,341 A | 5/1994 | Turi |
| 5,312,435 A | 5/1994 | Nash et al. |
| 5,318,525 A | 6/1994 | West et al. |
| 5,330,488 A | 7/1994 | Goldrath |
| 5,330,496 A | 7/1994 | Alferness |
| 5,334,191 A | 8/1994 | Poppas et al. |
| 5,334,217 A | 8/1994 | Das |
| 5,357,979 A | 10/1994 | Imran |
| 5,364,410 A | 11/1994 | Failla et al. |
| 5,370,679 A | 12/1994 | Atlee, III |
| 5,383,852 A | 1/1995 | Stevens-Wright |
| 5,387,227 A | 2/1995 | Grice |
| 5,394,880 A | 3/1995 | Atlee, III |
| 5,403,329 A | 4/1995 | Hinchcliffe |
| 5,403,338 A | 4/1995 | Milo |
| 5,409,469 A | 4/1995 | Schaerf |
| 5,409,481 A | 4/1995 | Poppas et al. |
| 5,413,584 A | 5/1995 | Schulze |
| 5,417,699 A | 5/1995 | Klein et al. |
| 5,417,713 A | 5/1995 | Cohen |
| 5,421,338 A | 6/1995 | Crowley et al. |
| 5,425,744 A | 6/1995 | Fagan et al. |
| 5,431,696 A | 7/1995 | Atlee, III |
| 5,433,727 A | 7/1995 | Sideris |
| 5,441,504 A | 8/1995 | Pohndorf et al. |
| 5,443,478 A | 8/1995 | Purdy |
| 5,451,235 A | 9/1995 | Lock et al. |
| 5,461,235 A | 10/1995 | Cottrell et al. |
| 5,462,560 A | 10/1995 | Stevens |
| 5,462,561 A | 10/1995 | Vode |
| 5,474,573 A | 12/1995 | Hatcher |
| 5,478,353 A | 12/1995 | Yoon |
| 5,486,183 A | 1/1996 | Middleman et al. |
| 5,486,193 A | 1/1996 | Bourne et al. |
| 5,503,634 A | 4/1996 | Christy |
| 5,507,744 A | 4/1996 | Tay et al. |
| 5,507,811 A | 4/1996 | Koike et al. |
| 5,522,873 A | 6/1996 | Jackman et al. |
| 5,527,388 A | 6/1996 | Berke et al. |
| 5,545,138 A | 8/1996 | Fugoso et al. |
| 5,548,872 A | 8/1996 | Oetiker |
| 5,554,162 A | 9/1996 | DeLange |
| 5,570,671 A | 11/1996 | Hickey |
| 5,573,540 A | 11/1996 | Yoon |
| 5,573,542 A | 11/1996 | Stevens |
| 5,575,772 A | 11/1996 | Lennox |
| 5,577,299 A | 11/1996 | Thompson et al. |
| 5,578,045 A | 11/1996 | Das |
| 5,582,616 A | 12/1996 | Bolduc et al. |
| 5,584,803 A | 12/1996 | Stevens et al. |
| 5,601,571 A | 2/1997 | Moss |
| 5,605,696 A | 2/1997 | Eury et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,645,557 A | 7/1997 | Yoon |
| 5,649,950 A | 7/1997 | Bourne et al. |
| 5,658,280 A | 8/1997 | Issa |
| 5,662,621 A | 9/1997 | Lafontaine |
| 5,662,643 A | 9/1997 | Kung et al. |
| 5,682,906 A | 11/1997 | Sterman et al. |
| 5,702,368 A | 12/1997 | Stevens et al. |
| 5,702,421 A | 12/1997 | Schneidt |
| 5,709,224 A | 1/1998 | Behl et al. |
| 5,709,707 A | 1/1998 | Lock et al. |
| 5,713,867 A | 2/1998 | Morris |
| 5,713,911 A | 2/1998 | Racenet et al. |
| 5,714,297 A | 2/1998 | Chamberlain et al. |
| 5,716,367 A | 2/1998 | Koike et al. |
| 5,720,754 A | 2/1998 | Middleman et al. |
| 5,722,981 A | 3/1998 | Stevens |
| 5,725,512 A | 3/1998 | Swartz et al. |
| 5,725,552 A | 3/1998 | Kotula et al. |
| 5,725,554 A | 3/1998 | Simon et al. |
| 5,728,151 A | 3/1998 | Garrison et al. |
| 5,733,294 A | 3/1998 | Forber et al. |
| 5,738,652 A | 4/1998 | Boyd et al. |
| 5,741,429 A | 4/1998 | Donadio, III et al. |
| 5,755,778 A | 5/1998 | Kleshinski |
| 5,759,170 A | 6/1998 | Peters |
| 5,769,812 A | 6/1998 | Stevens et al. |
| 5,772,672 A | 6/1998 | Toy et al. |
| 5,776,162 A | 7/1998 | Kleshinski |
| 5,782,860 A | 7/1998 | Epstein et al. |
| 5,792,094 A | 8/1998 | Stevens et al. |
| 5,797,960 A | 8/1998 | Stevens et al. |
| 5,807,339 A | 9/1998 | Bostrom et al. |
| 5,810,882 A | 9/1998 | Bolduc et al. |
| 5,810,884 A | 9/1998 | Kim |
| 5,814,016 A | 9/1998 | Valley et al. |
| 5,814,068 A | 9/1998 | Koike et al. |
| 5,814,097 A | 9/1998 | Sterman et al. |
| 5,823,956 A | 10/1998 | Roth et al. |
| 5,827,216 A | 10/1998 | Igo et al. |
| 5,829,447 A | 11/1998 | Stevens et al. |
| 5,836,311 A | 11/1998 | Borst et al. |
| 5,853,422 A | 12/1998 | Huebsch et al. |

(56) References Cited

U.S. PATENT DOCUMENTS

| | | |
|---|---|---|
| 5,855,614 A | 1/1999 | Stevens et al. |
| 5,861,003 A | 1/1999 | Latson et al. |
| 5,865,791 A | 2/1999 | Whayne et al. |
| 5,868,702 A | 2/1999 | Stevens et al. |
| 5,868,733 A | 2/1999 | Ockuly et al. |
| 5,868,753 A | 2/1999 | Schatz |
| 5,879,366 A | 3/1999 | Shaw et al. |
| 5,879,499 A | 3/1999 | Corvi |
| 5,885,238 A | 3/1999 | Stevens et al. |
| 5,893,856 A | 4/1999 | Jacob et al. |
| 5,895,404 A | 4/1999 | Ruiz |
| 5,902,319 A | 5/1999 | Daley |
| 5,904,703 A | 5/1999 | Gilson |
| 5,908,428 A | 6/1999 | Scirica et al. |
| 5,910,150 A | 6/1999 | Saadat |
| 5,911,717 A | 6/1999 | Jacobsen et al. |
| 5,913,810 A | 6/1999 | Andre |
| 5,913,842 A | 6/1999 | Boyd et al. |
| 5,919,200 A | 7/1999 | Stambaugh et al. |
| 5,924,424 A | 7/1999 | Stevens et al. |
| 5,927,284 A | 7/1999 | Borst et al. |
| 5,928,181 A | 7/1999 | Coleman et al. |
| 5,928,250 A | 7/1999 | Koike et al. |
| 5,931,848 A | 8/1999 | Saadat |
| 5,941,899 A | 8/1999 | Granger et al. |
| 5,944,738 A | 8/1999 | Amplatz et al. |
| 5,947,997 A | 9/1999 | Pavcnik et al. |
| 5,955,110 A | 9/1999 | Patel et al. |
| 5,967,977 A | 10/1999 | Mullis et al. |
| 5,972,013 A | 10/1999 | Schmidt |
| 5,976,174 A | 11/1999 | Ruiz |
| 5,980,503 A | 11/1999 | Chin |
| 5,989,268 A | 11/1999 | Pugsley, Jr. et al. |
| 5,993,475 A | 11/1999 | Lin et al. |
| 6,007,563 A | 12/1999 | Nash et al. |
| 6,010,517 A | 1/2000 | Baccaro |
| 6,013,052 A | 1/2000 | Durman et al. |
| 6,015,378 A | 1/2000 | Borst et al. |
| 6,015,417 A | 1/2000 | Reynolds, Jr. |
| 6,024,756 A | 2/2000 | Huebsch et al. |
| 6,027,476 A | 2/2000 | Sterman et al. |
| 6,030,007 A | 2/2000 | Bassily et al. |
| 6,036,699 A | 3/2000 | Andreas et al. |
| 6,036,720 A | 3/2000 | Abrams et al. |
| 6,056,760 A | 5/2000 | Koike et al. |
| 6,071,271 A | 6/2000 | Baker et al. |
| 6,071,292 A | 6/2000 | Makower et al. |
| 6,077,281 A | 6/2000 | Das |
| 6,077,291 A | 6/2000 | Das |
| 6,079,414 A | 6/2000 | Roth |
| 6,080,182 A | 6/2000 | Shaw et al. |
| 6,090,084 A | 7/2000 | Hassett et al. |
| 6,090,096 A | 7/2000 | St. Goar et al. |
| 6,093,199 A | 7/2000 | Brown et al. |
| 6,095,997 A | 8/2000 | French et al. |
| 6,110,145 A | 8/2000 | Macoviak |
| 6,113,609 A | 9/2000 | Adams |
| 6,113,610 A | 9/2000 | Poncet |
| 6,113,611 A | 9/2000 | Allen et al. |
| 6,117,145 A | 9/2000 | Wood et al. |
| 6,117,159 A | 9/2000 | Huebsch et al. |
| 6,126,658 A | 10/2000 | Baker |
| 6,127,410 A | 10/2000 | Duhaylongsod |
| 6,132,438 A | 10/2000 | Fleischman et al. |
| 6,135,981 A | 10/2000 | Dyke |
| 6,142,975 A | 11/2000 | Jalisi et al. |
| 6,149,664 A | 11/2000 | Kurz |
| 6,152,141 A | 11/2000 | Stevens et al. |
| 6,152,144 A | 11/2000 | Lesh et al. |
| 6,162,195 A | 12/2000 | Igo et al. |
| 6,162,202 A | 12/2000 | Sicurelli et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,171,338 B1 | 1/2001 | Talja et al. |
| 6,174,322 B1 | 1/2001 | Schneidt |
| 6,179,809 B1 | 1/2001 | Khairkhahan et al. |
| 6,187,039 B1 | 2/2001 | Hiles et al. |
| 6,200,313 B1 | 3/2001 | Abe et al. |
| 6,206,895 B1 | 3/2001 | Levinson |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,245,080 B1 | 6/2001 | Levinson |
| 6,254,550 B1 | 7/2001 | McNamara et al. |
| 6,270,490 B1 | 8/2001 | Hahnen |
| 6,270,515 B1 | 8/2001 | Linden et al. |
| 6,275,730 B1 | 8/2001 | KenKnight et al. |
| 6,277,138 B1 | 8/2001 | Levinson et al. |
| 6,277,139 B1 | 8/2001 | Levinson et al. |
| 6,280,432 B1 | 8/2001 | Turovskiy et al. |
| 6,280,460 B1 | 8/2001 | Bolduc et al. |
| 6,287,317 B1 | 9/2001 | Makower et al. |
| 6,290,674 B1 | 9/2001 | Roue et al. |
| 6,293,920 B1 | 9/2001 | Sweezer et al. |
| 6,302,903 B1 | 10/2001 | Mulier et al. |
| 6,305,378 B1 | 10/2001 | Lesh |
| 6,306,150 B1 | 10/2001 | Levinson |
| 6,306,424 B1 | 10/2001 | Vyakarnam et al. |
| 6,308,090 B1 | 10/2001 | Tu et al. |
| 6,309,415 B1 | 10/2001 | Pulnev et al. |
| 6,312,446 B1 | 11/2001 | Huebsch et al. |
| 6,319,263 B1 | 11/2001 | Levinson |
| 6,322,548 B1 | 11/2001 | Payne et al. |
| 6,328,727 B1 | 12/2001 | Frazier et al. |
| 6,336,898 B1 | 1/2002 | Borst et al. |
| 6,342,064 B1 | 1/2002 | Koike et al. |
| 6,346,074 B1 | 2/2002 | Roth |
| 6,346,099 B1 | 2/2002 | Altman |
| 6,346,112 B2 | 2/2002 | Adams |
| 6,350,229 B1 | 2/2002 | Borst et al. |
| 6,352,531 B1 | 3/2002 | O'Conner et al. |
| 6,352,552 B1 | 3/2002 | Levinson et al. |
| 6,355,052 B1 | 3/2002 | Neuss et al. |
| 6,364,826 B1 | 4/2002 | Borst et al. |
| 6,371,906 B1 | 4/2002 | Borst et al. |
| 6,375,671 B1 | 4/2002 | Kobayashi et al. |
| 6,379,368 B1 | 4/2002 | Corcoran et al. |
| 6,387,104 B1 | 5/2002 | Pugsley, Jr. et al. |
| 6,394,948 B1 | 5/2002 | Borst et al. |
| 6,398,796 B2 | 6/2002 | Levinson |
| 6,401,720 B1 | 6/2002 | Stevens et al. |
| 6,402,772 B1 | 6/2002 | Amplatz et al. |
| 6,416,493 B1 | 7/2002 | Del Giglio |
| 6,419,669 B1 | 7/2002 | Frazier et al. |
| 6,432,059 B2 | 8/2002 | Hickey |
| 6,436,088 B2 | 8/2002 | Frazier et al. |
| 6,440,152 B1 | 8/2002 | Gainor et al. |
| 6,458,100 B2 | 10/2002 | Roue et al. |
| 6,464,640 B1 | 10/2002 | Guracar et al. |
| 6,464,645 B1 | 10/2002 | Park et al. |
| 6,482,224 B1 | 11/2002 | Michler et al. |
| 6,482,228 B1 | 11/2002 | Norred |
| 6,485,504 B1 | 11/2002 | Johnson et al. |
| 6,488,706 B1 | 12/2002 | Solymar |
| 6,497,698 B1 | 12/2002 | Fonger et al. |
| 6,506,205 B2 | 1/2003 | Goldberg et al. |
| 6,532,388 B1 | 3/2003 | Hill et al. |
| 6,537,300 B2 | 3/2003 | Girton |
| 6,551,272 B2 | 4/2003 | Gobel |
| 6,551,303 B1 | 4/2003 | Van Tassel et al. |
| 6,551,344 B2 | 4/2003 | Thill |
| 6,560,489 B2 | 5/2003 | Hauck |
| 6,562,051 B1 | 5/2003 | Bolduc et al. |
| 6,562,052 B2 | 5/2003 | Nobles et al. |
| 6,572,593 B2 | 6/2003 | Daum |
| 6,579,259 B2 | 6/2003 | Stevens et al. |
| 6,585,716 B2 | 7/2003 | Altman |
| 6,592,552 B1 | 7/2003 | Schmidt |
| 6,592,557 B2 | 7/2003 | Barbut |
| 6,596,013 B2 | 7/2003 | Yang et al. |
| 6,606,513 B2 | 8/2003 | Lardo et al. |
| 6,613,062 B1 | 9/2003 | Leckrone et al. |

(56) References Cited

U.S. PATENT DOCUMENTS

| | | |
|---|---|---|
| 6,623,508 B2 | 9/2003 | Shaw et al. |
| 6,623,518 B2 | 9/2003 | Thompson et al. |
| 6,626,841 B1 | 9/2003 | Atlee, III |
| 6,626,890 B2 | 9/2003 | Nguyen et al. |
| 6,626,899 B2 | 9/2003 | Houser et al. |
| 6,626,930 B1 | 9/2003 | Allen et al. |
| 6,629,534 B1 | 10/2003 | Zheng et al. |
| 6,632,223 B1 | 10/2003 | Keane |
| 6,645,225 B1 | 11/2003 | Atkinson |
| 6,650,923 B1 | 11/2003 | Lesh et al. |
| 6,651,672 B2 | 11/2003 | Roth |
| 6,656,206 B2 | 12/2003 | Corcoran et al. |
| 6,659,981 B2 | 12/2003 | Stewart et al. |
| 6,662,045 B2 | 12/2003 | St. Goar et al. |
| 6,663,639 B1 | 12/2003 | Laufer et al. |
| 6,666,861 B1 | 12/2003 | Grabek |
| 6,679,268 B2 | 1/2004 | Stevens et al. |
| 6,685,728 B2 | 2/2004 | Sinnott et al. |
| 6,689,062 B1 | 2/2004 | Mesallum |
| 6,692,471 B2 | 2/2004 | Boudreaux |
| 6,692,512 B2 | 2/2004 | Jang |
| 6,695,838 B2 | 2/2004 | Wellman et al. |
| 6,699,231 B1 | 3/2004 | Sterman et al. |
| 6,702,835 B2 | 3/2004 | Ginn |
| 6,706,033 B1 | 3/2004 | Martinez et al. |
| 6,706,047 B2 | 3/2004 | Trout et al. |
| 6,712,804 B2 | 3/2004 | Roue et al. |
| 6,712,836 B1 | 3/2004 | Berg et al. |
| 6,726,662 B2 | 4/2004 | Altman |
| 6,730,061 B1 | 5/2004 | Cuschieri et al. |
| 6,735,471 B2 | 5/2004 | Hill et al. |
| 6,736,828 B1 | 5/2004 | Adams et al. |
| 6,746,404 B2 | 6/2004 | Schwartz |
| 6,746,456 B2 | 6/2004 | Xiao |
| 6,749,617 B1 | 6/2004 | Palasis et al. |
| 6,773,441 B1 | 8/2004 | Laufer et al. |
| 6,776,784 B2 | 8/2004 | Ginn |
| 6,776,797 B1 | 8/2004 | Blom et al. |
| 6,783,499 B2 | 8/2004 | Schwartz |
| 6,790,218 B2 | 9/2004 | Jayaraman |
| 6,802,840 B2 | 10/2004 | Chin et al. |
| 6,821,265 B1 | 11/2004 | Bertolero et al. |
| 6,840,246 B2 | 1/2005 | Downing |
| 6,854,467 B2 | 2/2005 | Boekstegers |
| 6,855,116 B2 | 2/2005 | Atlee, III |
| 6,866,650 B2 | 3/2005 | Stevens et al. |
| 6,878,118 B2 | 4/2005 | Atlee, III |
| 6,882,883 B2 | 4/2005 | Condie et al. |
| 6,889,694 B2 | 5/2005 | Hooven |
| 6,899,704 B2 | 5/2005 | Sterman et al. |
| 6,902,545 B2 | 6/2005 | Bertolero et al. |
| 6,913,600 B2 | 7/2005 | Valley et al. |
| 6,913,607 B2 | 7/2005 | Ainsworth et al. |
| 6,915,149 B2 | 7/2005 | Ben-Haim |
| 6,918,890 B2 | 7/2005 | Schmidt |
| 6,918,908 B2 | 7/2005 | Bonner et al. |
| 6,929,011 B2 | 8/2005 | Knudson et al. |
| 6,932,792 B1 | 8/2005 | St. Goar et al. |
| 6,932,811 B2 | 8/2005 | Hooven et al. |
| 6,934,583 B2 | 8/2005 | Weinberg et al. |
| 6,939,348 B2 | 9/2005 | Malecki et al. |
| 6,939,361 B1 | 9/2005 | Kleshinski |
| 6,952,613 B2 | 10/2005 | Swoyer et al. |
| 6,953,466 B2 | 10/2005 | Palasis et al. |
| 6,955,175 B2 | 10/2005 | Steven et al. |
| 6,960,220 B2 | 11/2005 | Marino et al. |
| 6,971,998 B2 | 12/2005 | Rosenman et al. |
| 6,976,990 B2 | 12/2005 | Mowry |
| 6,991,635 B2 | 1/2006 | Takamoto et al. |
| 6,994,094 B2 | 2/2006 | Schwartz |
| 6,994,713 B2 | 2/2006 | Berg et al. |
| 7,001,415 B2 | 2/2006 | Hooven |
| 7,004,952 B2 | 2/2006 | Nobles et al. |
| 7,018,390 B2 | 3/2006 | Turovskiy et al. |
| 7,020,518 B2 | 3/2006 | Zheng et al. |
| 7,039,467 B2 | 5/2006 | Hauck |
| 7,044,135 B2 | 5/2006 | Lesh |
| 7,048,733 B2 | 5/2006 | Hartley et al. |
| 7,056,331 B2 | 6/2006 | Kaplan et al. |
| 7,083,628 B2 | 8/2006 | Bachman |
| 7,087,072 B2 | 8/2006 | Marino et al. |
| 7,090,683 B2 | 8/2006 | Brock et al. |
| 7,090,686 B2 | 8/2006 | Nobles et al. |
| 7,094,244 B2 | 8/2006 | Schreck |
| 7,097,653 B2 | 8/2006 | Freudenthal et al. |
| 7,101,395 B2 | 9/2006 | Tremulis et al. |
| 7,108,660 B2 | 9/2006 | Stephens et al. |
| 7,112,219 B2 | 9/2006 | Vidlund et al. |
| 7,113,831 B2 | 9/2006 | Hooven |
| 7,115,135 B2 | 10/2006 | Corcoran et al. |
| 7,186,251 B2 | 3/2007 | Malecki et al. |
| 7,288,105 B2 | 10/2007 | Oman et al. |
| 7,320,692 B1 | 1/2008 | Bender et al. |
| 7,507,252 B2 | 3/2009 | Lashinski et al. |
| 2001/0014800 A1 | 8/2001 | Frazier et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0032462 A1 | 3/2002 | Houser et al. |
| 2002/0035361 A1 | 3/2002 | Houser et al. |
| 2002/0035374 A1 | 3/2002 | Borillo et al. |
| 2002/0039048 A1 | 4/2002 | Matsuge |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0099437 A1 | 7/2002 | Anson et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0138095 A1 | 9/2002 | Mazzocchi et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0025421 A1 | 2/2003 | Ebihara et al. |
| 2003/0028213 A1 | 2/2003 | Thill et al. |
| 2003/0033006 A1 | 2/2003 | Phillips et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0059640 A1 | 3/2003 | Marton et al. |
| 2003/0100920 A1 | 5/2003 | Akin et al. |
| 2003/0139819 A1 | 7/2003 | Beer et al. |
| 2003/0144694 A1 | 7/2003 | Chanduszko et al. |
| 2003/0167071 A1 | 9/2003 | Martin et al. |
| 2003/0191495 A1 | 10/2003 | Ryan et al. |
| 2003/0195530 A1 | 10/2003 | Thill |
| 2003/0195555 A1 | 10/2003 | Khairkhanhan et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0044361 A1 | 3/2004 | Frazier et al. |
| 2004/0073242 A1 | 4/2004 | Chanduszko |
| 2004/0092973 A1 | 5/2004 | Chanduszko et al. |
| 2004/0098042 A1 | 5/2004 | Devellian et al. |
| 2004/0098121 A1 | 5/2004 | Opolski |
| 2004/0133230 A1 | 7/2004 | Carpenter et al. |
| 2004/0133236 A1 | 7/2004 | Chanduszko |
| 2004/0138682 A1 | 7/2004 | Onuki et al. |
| 2004/0162568 A1 | 8/2004 | Saadat et al. |
| 2004/0176799 A1 | 9/2004 | Chanduszko et al. |

(56) References Cited

U.S. PATENT DOCUMENTS

| | | |
|---|---|---|
| 2004/0193185 A1 | 9/2004 | McBrayer |
| 2004/0210301 A1 | 10/2004 | Obermiller |
| 2004/0220596 A1 | 11/2004 | Frazier et al. |
| 2004/0225183 A1 | 11/2004 | Michlitsch et al. |
| 2004/0230185 A1 | 11/2004 | Malecki et al. |
| 2004/0243122 A1 | 12/2004 | Auth et al. |
| 2004/0267191 A1 | 12/2004 | Gifford, III et al. |
| 2004/0267306 A1 | 12/2004 | Blaeser et al. |
| 2005/0034735 A1 | 2/2005 | Deem et al. |
| 2005/0043759 A1 | 2/2005 | Chanduszko |
| 2005/0055050 A1 | 3/2005 | Alfaro |
| 2005/0059984 A1 | 3/2005 | Chanduszko et al. |
| 2005/0070923 A1 | 3/2005 | McIntosh |
| 2005/0075653 A1 | 4/2005 | Saadat et al. |
| 2005/0080406 A1 | 4/2005 | Malecki et al. |
| 2005/0119671 A1* | 6/2005 | Reydel et al. ............. 606/144 |
| 2005/0119675 A1 | 6/2005 | Adams et al. |
| 2005/0125032 A1 | 6/2005 | Whisenant et al. |
| 2005/0131460 A1 | 6/2005 | Gifford, III et al. |
| 2005/0149066 A1 | 7/2005 | Stafford |
| 2005/0149115 A1 | 7/2005 | Roue et al. |
| 2005/0187568 A1 | 8/2005 | Klenk et al. |
| 2005/0187588 A1 | 8/2005 | Stahmann et al. |
| 2005/0187620 A1 | 8/2005 | Pai et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0228434 A1 | 10/2005 | Amplatz et al. |
| 2005/0234509 A1 | 10/2005 | Widomski et al. |
| 2005/0250988 A1 | 11/2005 | Ewers et al. |
| 2005/0251154 A1 | 11/2005 | Chanduszko et al. |
| 2005/0251165 A1 | 11/2005 | Vaughan et al. |
| 2005/0251201 A1 | 11/2005 | Roue et al. |
| 2005/0256532 A1 | 11/2005 | Nayak et al. |
| 2005/0267493 A1 | 12/2005 | Schreck et al. |
| 2005/0267495 A1 | 12/2005 | Ginn et al. |
| 2005/0267523 A1 | 12/2005 | Devellian et al. |
| 2005/0267524 A1 | 12/2005 | Chanduszko |
| 2005/0267525 A1 | 12/2005 | Chanduszko |
| 2005/0267526 A1 | 12/2005 | Wahr et al. |
| 2005/0267529 A1 | 12/2005 | Crockett et al. |
| 2005/0271631 A1 | 12/2005 | Lee et al. |
| 2005/0273119 A1 | 12/2005 | Widomski et al. |
| 2005/0273124 A1 | 12/2005 | Chanduszko |
| 2005/0273135 A1 | 12/2005 | Chanduszko et al. |
| 2005/0277982 A1 | 12/2005 | Marino et al. |
| 2005/0288706 A1 | 12/2005 | Widomski et al. |
| 2005/0288786 A1 | 12/2005 | Chanduszko |
| 2006/0009800 A1 | 1/2006 | Christianson et al. |
| 2006/0015002 A1 | 1/2006 | Moaddeb et al. |
| 2006/0036282 A1 | 2/2006 | Wahr et al. |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0095052 A1 | 5/2006 | Chambers |
| 2006/0122633 A1 | 6/2006 | To et al. |
| 2006/0200197 A1 | 9/2006 | Brenzel et al. |
| 2006/0217764 A1 | 9/2006 | Abbott et al. |
| 2006/0241687 A1 | 10/2006 | Glaser et al. |
| 2006/0271089 A1 | 11/2006 | Alejandro et al. |
| 2007/0005018 A1 | 1/2007 | Tekbuchava |
| 2007/0010806 A1 | 1/2007 | Malecki et al. |
| 2007/0049970 A1 | 3/2007 | Belef et al. |
| 2007/0073337 A1 | 3/2007 | Abbott et al. |
| 2007/0123851 A1 | 5/2007 | Alejandro et al. |
| 2007/0185530 A1 | 8/2007 | Chin-Chen et al. |
| 2008/0015633 A1 | 1/2008 | Abbott et al. |

FOREIGN PATENT DOCUMENTS

| | | |
|---|---|---|
| EP | 0 553 259 B2 | 3/1995 |
| EP | 1 013 227 A2 | 6/2000 |
| EP | 1 222 897 A2 | 7/2002 |
| EP | 1 046 375 B1 | 11/2004 |
| JP | 04-226643 | 8/1992 |
| WO | WO 92/05828 A1 | 4/1992 |
| WO | WO 92/06733 A1 | 4/1992 |
| WO | WO 96/25179 A1 | 8/1996 |
| WO | WO 96/31157 A1 | 10/1996 |
| WO | WO 97/42878 A1 | 11/1997 |
| WO | WO 98/02100 A1 | 1/1998 |
| WO | WO 98/07375 A1 | 2/1998 |
| WO | WO 99/02100 A1 | 1/1999 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 00/07506 A2 | 2/2000 |
| WO | WO 00/27292 A1 | 5/2000 |
| WO | WO 00/35352 A2 | 6/2000 |
| WO | WO 00/44428 A2 | 8/2000 |
| WO | WO 01/21247 A1 | 3/2001 |
| WO | WO 01/49185 A1 | 7/2001 |
| WO | WO 01/78596 A1 | 10/2001 |
| WO | WO 02/024106 A2 | 3/2002 |
| WO | WO 02/062236 A1 | 8/2002 |
| WO | WO 03/059152 A2 | 7/2003 |
| WO | WO 03/063732 A2 | 8/2003 |
| WO | WO 03/077733 A2 | 9/2003 |
| WO | WO 03/094742 A1 | 11/2003 |
| WO | WO 03/103476 A2 | 12/2003 |
| WO | WO 2004/026146 A1 | 4/2004 |
| WO | WO 2004/043266 A2 | 5/2004 |
| WO | WO 2004/052213 A1 | 6/2004 |
| WO | 2004069054 A1 | 8/2004 |
| WO | WO 2004/069054 A2 | 8/2004 |
| WO | WO 2004/069055 A2 | 8/2004 |
| WO | WO 2004/086951 A2 | 10/2004 |
| WO | WO 2004/087235 A2 | 10/2004 |
| WO | WO 2005/006990 A2 | 1/2005 |
| WO | WO 2005/027752 A1 | 3/2005 |
| WO | WO 2005/034738 A2 | 4/2005 |
| WO | WO 2005/039419 A1 | 5/2005 |
| WO | WO 2005/074517 A2 | 8/2005 |
| WO | WO 2005/074814 A2 | 8/2005 |
| WO | WO 2005/082255 A1 | 9/2005 |
| WO | WO 2005/092203 A1 | 10/2005 |
| WO | WO 2005/110240 A1 | 11/2005 |
| WO | WO 2005/112779 A1 | 12/2005 |
| WO | WO 2006/036837 A2 | 4/2006 |
| WO | WO 2007/024615 A1 | 3/2007 |
| WO | WO 2008/024489 A2 | 2/2008 |
| WO | WO 2008/153872 A2 | 12/2008 |

OTHER PUBLICATIONS

Daoud, E., et al. Intracardiac Echocardiography to Guide Transseptal Left Heart Catheterization for Radiofrequency Catheter Ablation, Journal of Cardiovascular Electrophysiology, vol. 10, No. 3, Mar. 1999.

De Ponti, R., et al., Trans-septal catheterization for radiofrequency catheter ablation of cardiac arrhythmias, European Heart Journal, vol. 19, 1998.

Epstein, L., et al., Nonfluoroscopic Transseptal Catheterization: Safety and Efficacy of Intracardiac Echocardiographic Guidance, Journal of Cardiovascular Electrophysciology, vol. 9, No. 6, Jun. 1998.

Hara, H., et al., Patent Foramen Ovale: Current Pathology, Pathophysiology, and Clinical Status, Journal of the American College of Cardiology, vol. 46, No. 9, Nov. 2005:1768-1776.

Hurrell, D., et al., Echocardiography in the Invasive Laboratory: Utility of Two-Dimensional Echocardiography in Performing Transseptal Catherization, Mayo Clinic Proc., 1998:73:126-131.

Lesh, M., et al., Comparison of the Retrograde and Transseptal Methods for Ablation of Left Free Wall Accessory Pathways, Journal of American College of Cardiology, vol. 22, No. 2, Aug. 1993:542-549.

(56) References Cited

OTHER PUBLICATIONS

Lundqvist, C., et al., Transseptal Left Heart Catheterization: A Review of 278 Studies, Clin. Cardiol. 9, Jan. 1986.

Mitchel, J., et al., Intracardiac Ultrasound Imaging During Transseptal Catheterization, Chest, vol. 108, No. 1, Jul. 1995.

Montenero, A., et al., Catheter Ablation of Left Accessory Atrioventricular Connections: The Transseptal Approach, Journal of Interventional Cardiology, vol. 8, No. 6 (Suppl), 1995.

Peckham, G., et al., Combined Percutaneous Retrograde Aortic and Transseptal Left Heart Catheterization, Brit. Heart Journal, vol. 26, 1964.

Reig, J., et al., Morphologic characteristics of the fossa ovalis as an anatomic basis for transseptal catheterization, Surg. Radio!. Anat. vol. 19, No. 5, 1997.

Roelke, M., et al., The Technique and Safety of Transseptal Left Heart Catheterization: The Massachusetts General Hospital Experience With 1,279 Procedures, Catheterization and Cardiovascular Diagnosis, vol. 32, No. 4, Aug. 1994.

Ruiz, C., et al., The Puncture Technique: A New Method for Transcatheter Closure of Patent Foramen Ovale, Catherization and Cardiovascular Interventions 53:369-372 (2001).

St. Jude Medical, BRK™ Transseptal Needle (Instructions for Use), Nov. 2006.

Szili-Torok, T., Transseptal left heart catherisation guided by intracardiac echocardiography, Heart, vol. 86, e. 11, 2001.

Tucker, K., Transesophageal Echocardiographic Guidance of Transseptal Left Heart Catheterization During Radiofrequency Ablation of Left-Sided Accessory Pathways in Humans, PACE, vol. 19, Mar. 1996.

* cited by examiner

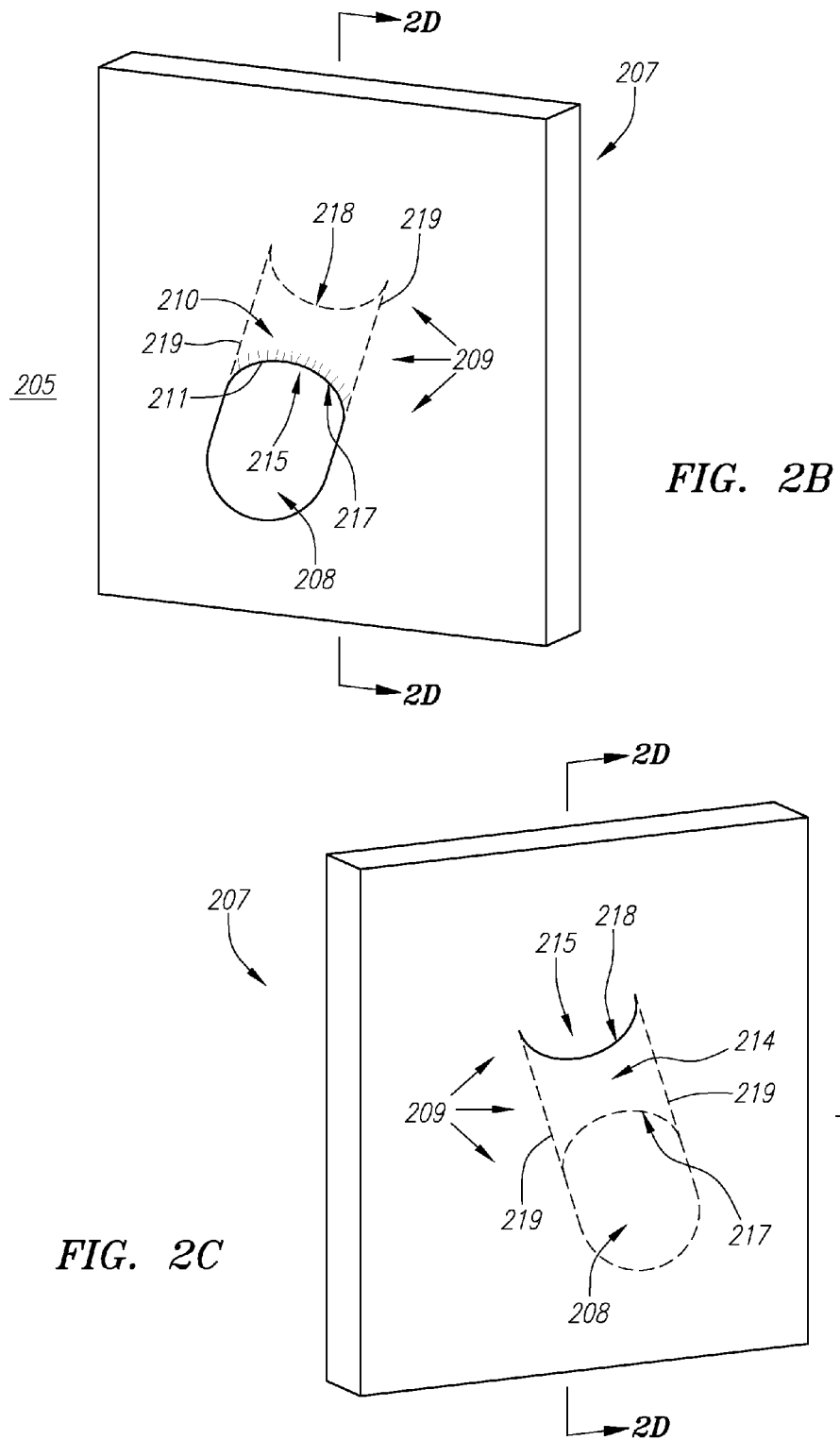

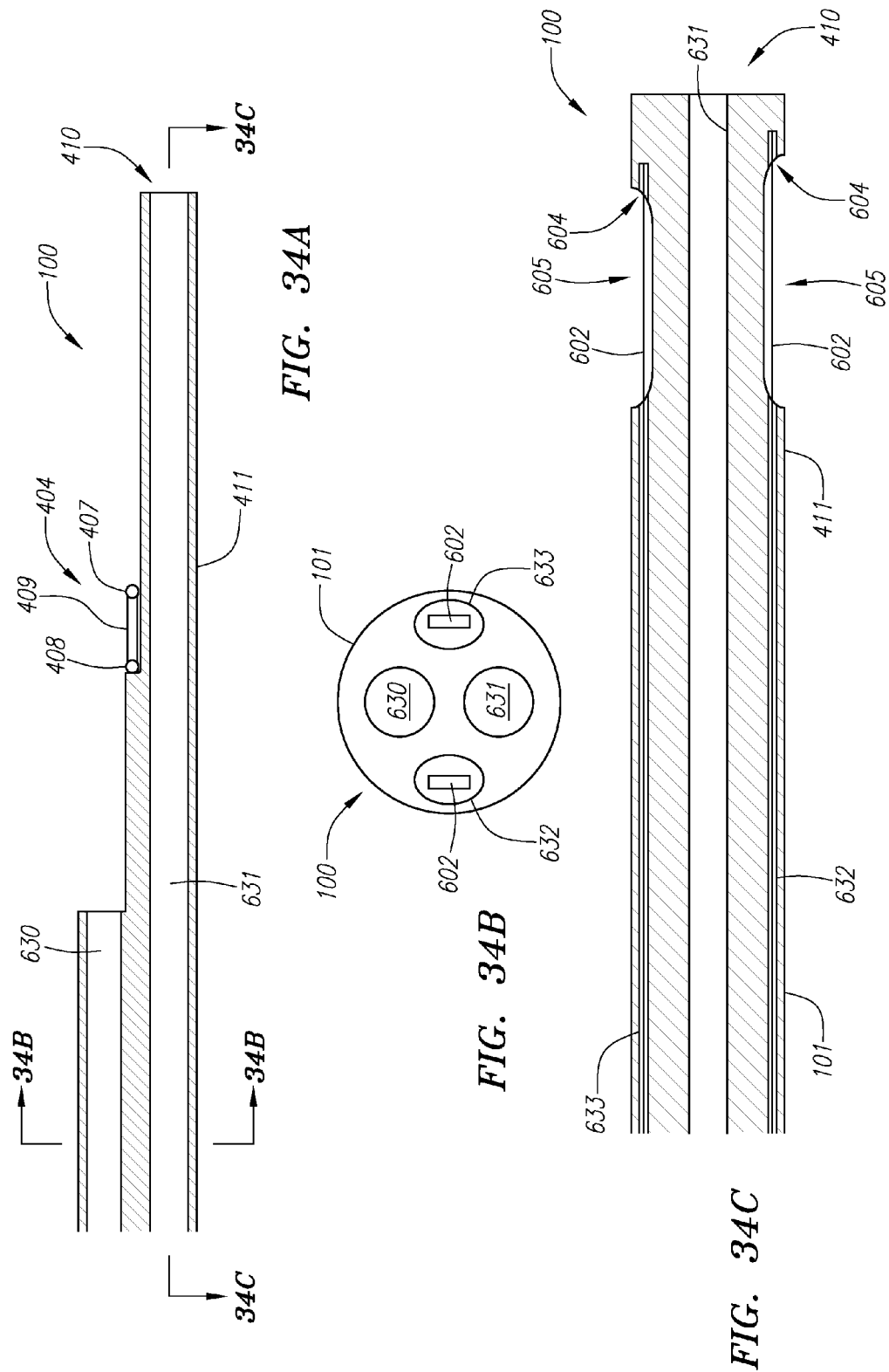

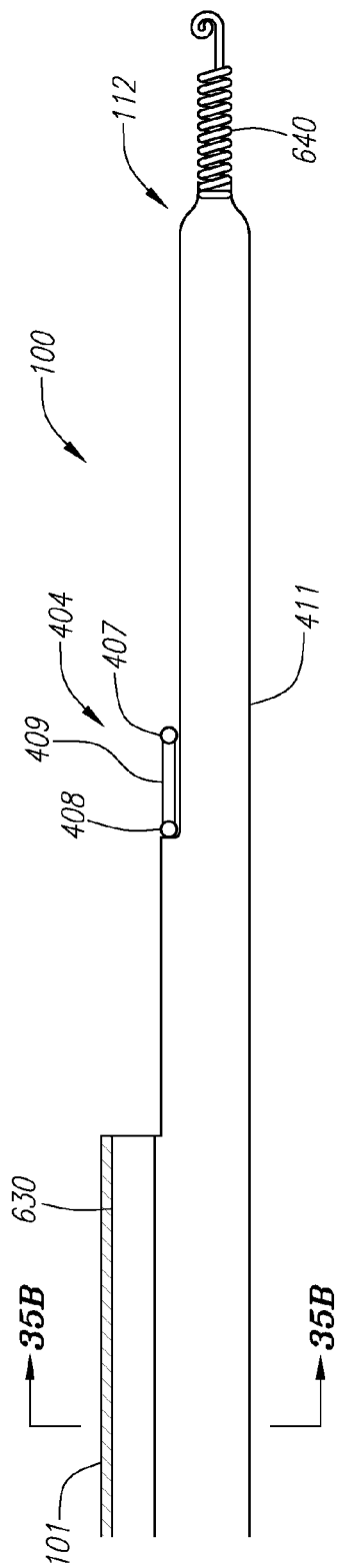
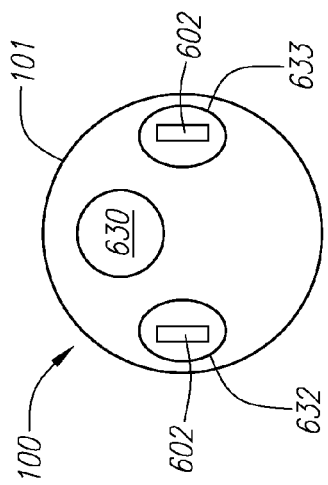
FIG. 35A
FIG. 35B

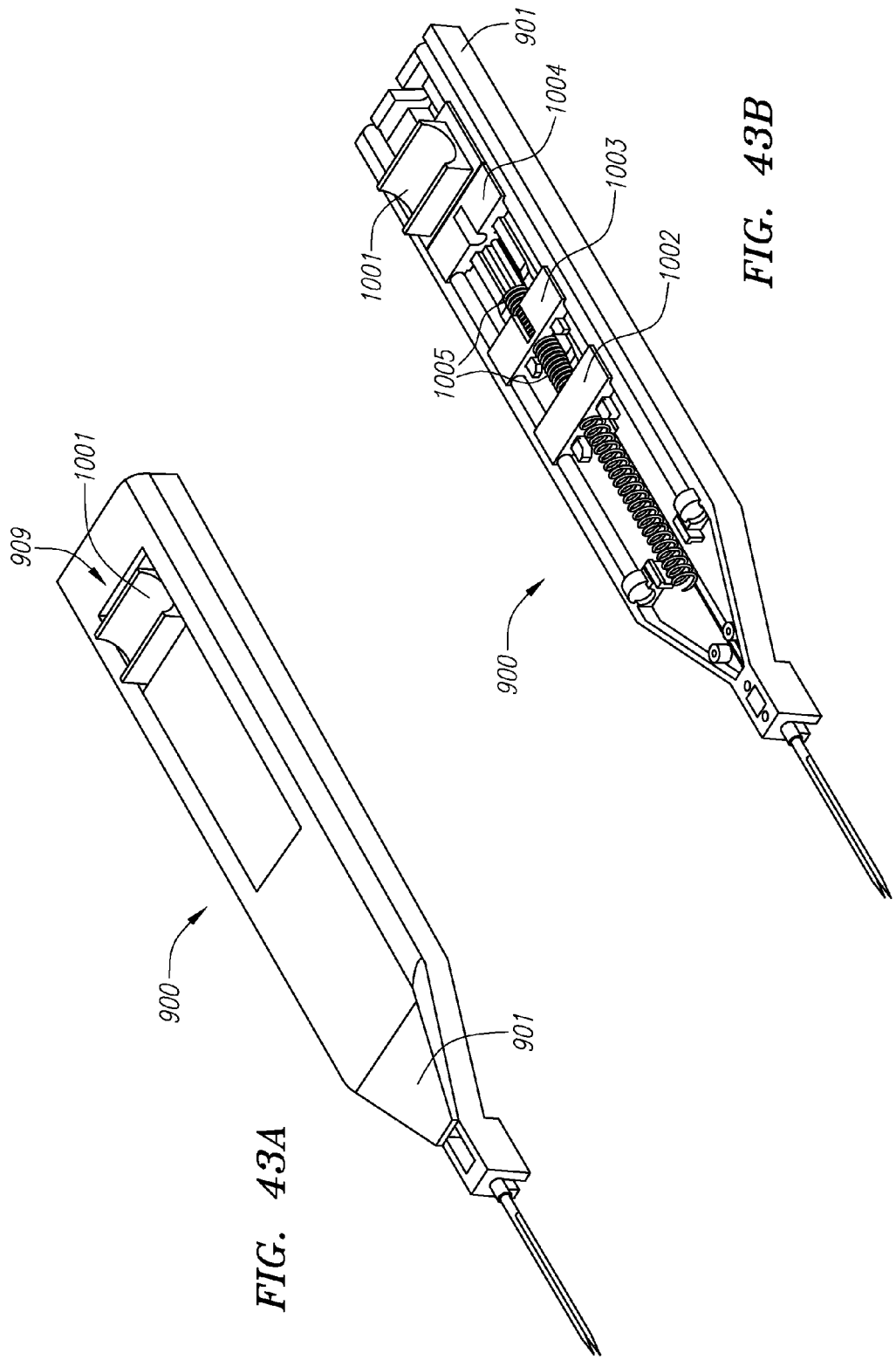

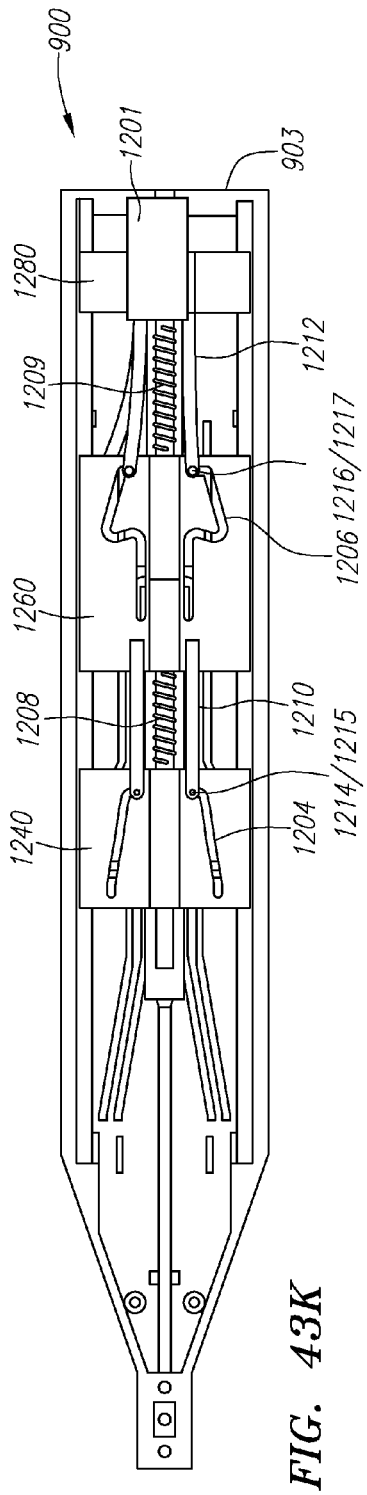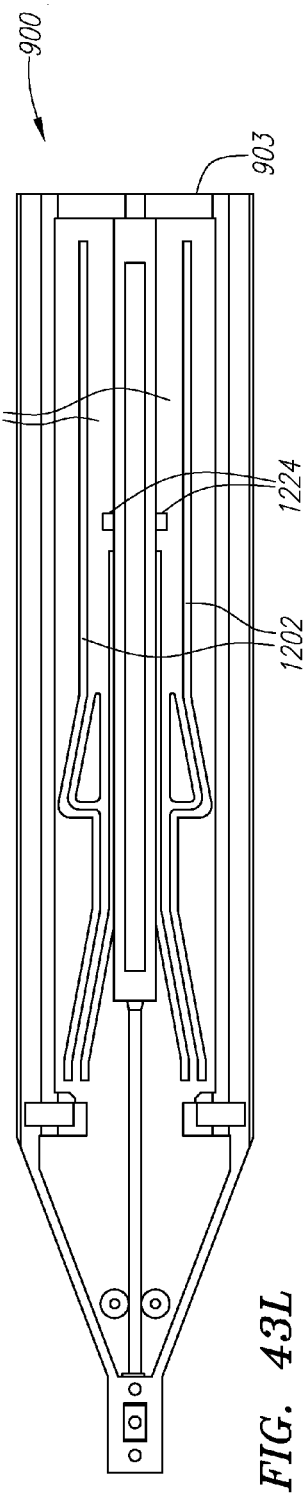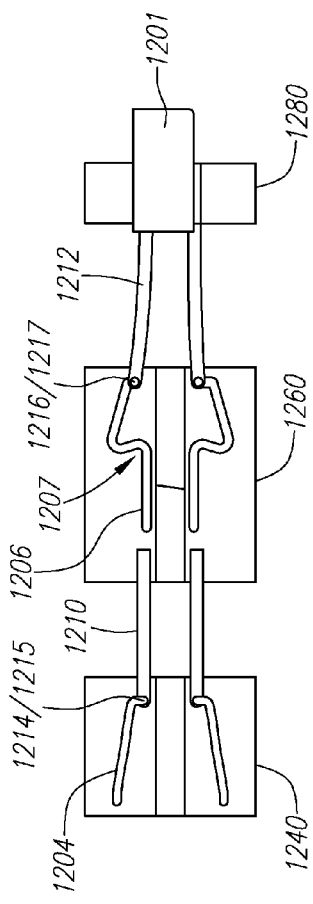
FIG. 43K
FIG. 43L
FIG. 43M

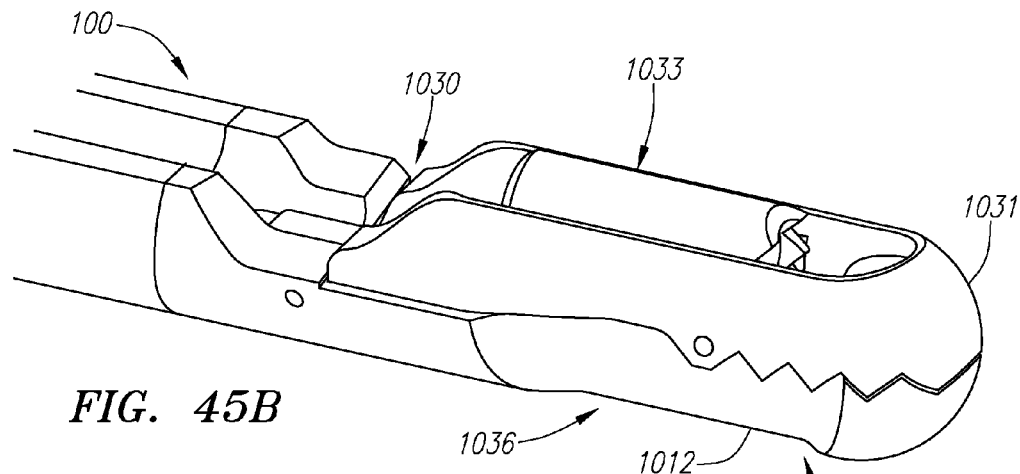
FIG. 45B
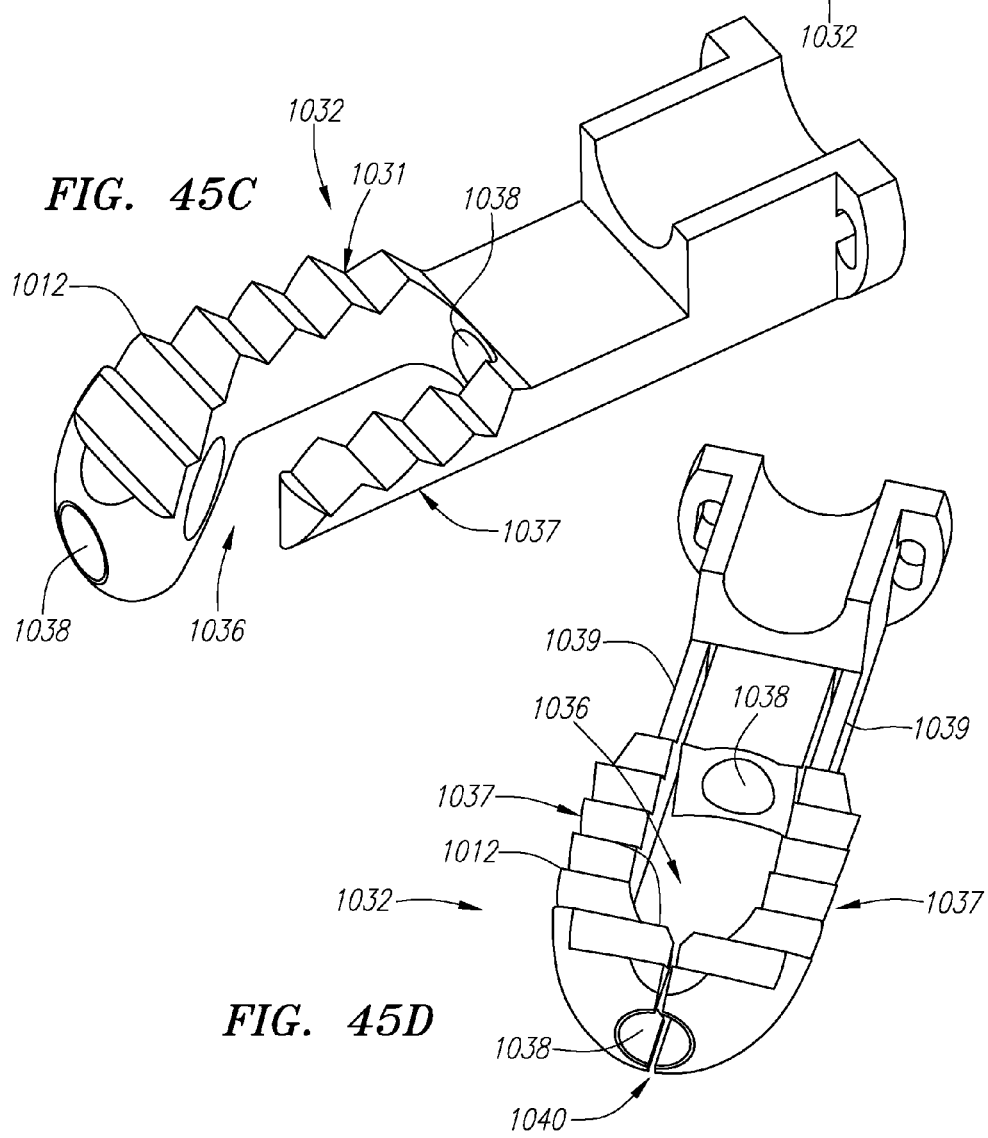
FIG. 45C
FIG. 45D

CENTERING OF DELIVERY DEVICES WITH RESPECT TO A SEPTAL DEFECT

CROSS-REFERENCE TO RELATED APPLICATIONS

This application is a continuation-in-part of U.S. patent application Ser. No. 12/176,175, filed Jul. 18, 2008 now abandoned, which is a continuation-in-part of U.S. patent application Ser. No. 11/744,784, filed May 4, 2007 now abandoned, which is a continuation-in-part of U.S. patent application Ser. No. 11/427,572, filed Jun. 29, 2006 now abandoned, which is a continuation-in-part of U.S. patent application Ser. No. 11/175,814, filed Jul. 5, 2005 now abandoned, each of which are fully incorporated herein by reference. This application is also a continuation-in-part of U.S. patent application Ser. No. 11/295,338, filed Dec. 5, 2005 now abandoned, which is fully incorporated herein by reference.

FIELD OF THE INVENTION

The present invention relates generally to systems and methods for treating internal tissue defects, such as septal defects.

BACKGROUND OF THE INVENTION

By nature of their location, the treatment of internal tissue defects is inherently difficult. Access to a defect through invasive surgery introduces a high level of risk that can result in serious complications for the subject. Access to the defect remotely with a catheter or equivalent device is less risky, but treatment of the defect itself is made more difficult given the limited physical abilities of the catheter. The difficulty in accessing and treating tissue defects is compounded when the defect is found in or near a vital organ. For instance, a patent foramen ovale ("PFO") is a serious septal defect that can occur between the left and right atria of the heart and a patent ductus arteriosus ("PDA") is an abnormal shunt between the aorta and pulmonary artery.

During development of a fetus in utero, oxygen is transferred from maternal blood to fetal blood through complex interactions between the developing fetal vasculature and the mother's placenta. During this process, blood is not oxygenated within the fetal lungs. In fact, most of the fetus' circulation is shunted away from the lungs through specialized vessels and foramens that are open during fetal life, but typically will close shortly after birth. Occasionally, however, these foramen fail to close and create hemodynamic problems, which, in extreme cases, can prove fatal. During fetal life, an opening called the foramen ovale allows blood to bypass the lungs and pass directly from the right atrium to the left atrium. Thus, blood that is oxygenated via gas exchange with the placenta may travel through the vena cava into the right atrium, through the foramen ovale into the left atrium, and from there into the left ventricle for delivery to the fetal systemic circulation. After birth, with pulmonary circulation established, the increased left atrial blood flow and pressure causes the functional closure of the foramen ovale and, as the heart continues to develop, this closure allows the foramen ovale to grow completely sealed.

In some cases, however, the foramen ovale fails to close entirely. This condition, known as a PFO, can allow blood to continue to shunt between the left and right atria of the heart throughout the adult life of the individual. A PFO can pose serious health risks for the individual, including strokes and migraines. The presence of PFO's have been implicated as a possible contributing factor in the pathogenesis of migraines. Two current hypothesis that link PFO's with migraine include the transit of vasoactive substances or thrombus/emboli from the venous circulation directly into the left atrium without passing through the lungs where they would normally be deactivated or filtered respectively. Other diseases that have been associated with PFO's (and which could benefit from PFO closure) include but are not limited to depression and affective disorders, personality and anxiety disorders, pain, stroke, TIA, dementia, epilepsy, and sleep disorders.

Still other septal defects can occur between the various chambers of the heart, such as atrial-septal defects (ASD's), ventricular-septal defects (VSD's), and the like. To treat these defects as well as PFO's, open heart surgery can be performed to ligate or patch the defect closed. Alternatively, catheter-based procedures have been developed that require introducing umbrella or disc-like devices into the heart. These devices include opposing expandable structures connected by a hub or waist. Generally, in an attempt to close the defect, the device is inserted through the natural opening of the defect and the expandable structures are deployed on either side of the septum to secure the tissue surrounding the defect between the umbrella or disc-like structure.

These devices suffer from numerous shortcomings. For instance, these devices typically involve frame structures that often support membranes, either of which may fail during the life of the subject, thereby introducing the risk that the defect may reopen or that portions of the device could be released within the subject's heart. These devices can fail to form a perfect seal of the septal defect, allowing blood to continue to shunt through the defect. Also, the size and expansive nature of these devices makes safe withdrawal from the subject difficult in instances where withdrawal becomes necessary. The presence of these devices within the heart typically requires the subject to use anti-coagulant drugs for prolonged periods of time, thereby introducing additional health risks to the subject. Furthermore, these devices can come into contact with other portions of the heart tissue and cause undesirable side effects such as an arrhythmia, local tissue damage, and perforation.

Accordingly, improved devices, systems and methods for treating and closing internal tissue defects within the heart are needed.

SUMMARY

Improved devices and systems for treating internal tissue defects, such as septal defects and the like, are provided herein by the way of exemplary embodiments. These embodiments are examples only and are not intended to limit the inventive subject matter described herein. Generally, these embodiments include devices for controlling a medical system remotely, devices for improved centering of a delivery device with respect to a septal wall, and improved operation while within a patient.

Other systems, methods, features and advantages of the subject matter described herein will be or will become apparent to one with skill in the art upon examination of the following figures and detailed description. It is intended that all such additional systems, methods, features and advantages be included within this description, be within the scope of the inventive subject matter described herein, and be protected by the accompanying claims.

BRIEF DESCRIPTION OF THE FIGURES

The details of the subject matter described herein, both as to its structure and operation, may be gleaned in part by study of the accompanying figures, in which like reference numerals refer to like parts. The components in the figures are not necessarily to scale, emphasis instead being placed upon illustrating the principles of the subject matter described herein. Moreover, all illustrations are intended to convey concepts, where relative sizes, shapes and other detailed attributes may be illustrated schematically rather than literally or precisely.

FIGS. 2B-2C are enlarged views of an example atrial septal wall.

FIG. 34A is a longitudinal cross-sectional view of an exemplary embodiment of a treatment system.

FIG. 34B is a radial cross-sectional view of another exemplary embodiment of a treatment system taken along line 34B-34B of FIG. 34A.

FIG. 34C is a longitudinal cross-sectional view of another exemplary embodiment of a treatment system taken along line 34C-34C of FIG. 34A.

FIG. 35A is a longitudinal cross-sectional view of an exemplary embodiment of a treatment system.

FIG. 35B is a radial cross-sectional view of another exemplary embodiment of a treatment system taken along line 35B-35B of FIG. 35A.

FIG. 43A is a perspective view depicting another exemplary embodiment of a proximal control device.

FIG. 43B is an internal perspective view depicting the exemplary embodiment of a proximal control device depicted in FIG. 43A.

FIGS. 43H-1 and 43H-2 are schematic views depicting the layout of exemplary embodiments of a portion of a proximal controller.

FIG. 43H-3 is a perspective view depicting another exemplary embodiment of a treatment system.

FIGS. 43K-M are internal views of the exemplary embodiment of the proximal controller depicted in FIG. 43J.

FIGS. 45A-B are a perspective view depicting additional exemplary embodiments of a treatment system.

FIG. 45C-D are perspective views depicting additional exemplary embodiments of a lower jaw-like portion of the treatment system.

DETAILED DESCRIPTION

Described herein are improved devices and methods for treating septal defects. For ease of discussion, the devices and methods will be described with reference to treatment of a PFO. However, it should be understood that the devices and methods can be used in treatment of any type of septal defect including ASD's, VSD's and the like, as well as PDA's or other structural cardiac or vascular defects.

Figure 1:
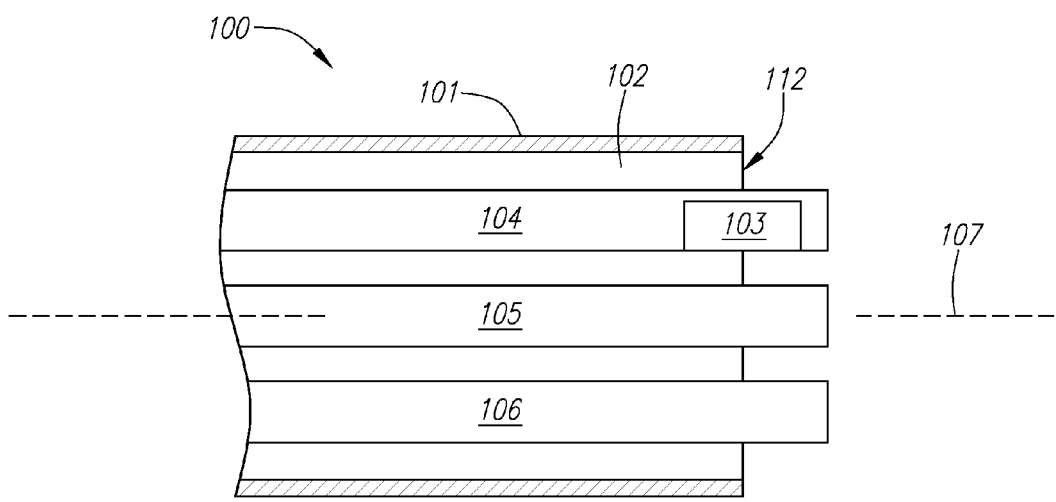
FIG. 1 is a block diagram depicting an exemplary embodiment of a treatment system.

FIG. 1 is a block diagram depicting a distal portion of an exemplary embodiment of a septal defect treatment system 100 configured to treat, and, preferably close, a PFO. In this embodiment, treatment system 100 includes an elongate body member 101 configured for insertion into the vasculature of a patient (human or animal) having a septal defect. Body member 101 has a longitudinal axis 107, distal end 112 and can include one or more lumens 102, each of which can be configured for achieving multiple functions. Preferably, treatment system 100 includes an implantable device 103 (referred to herein as an "implant") configured to at least partially close a septal defect. Treatment system 100 can include a flexible elongate delivery device 104 configured to house and deliver implant 103. To minimize the width of body member 101, implant 103 can be deformable from the configuration desired after implantation to a configuration having a smaller cross-section for storage and housing within delivery device 104 prior to implantation.

Treatment system 100 can also optionally include a stabilization device 105 for stabilization of body member 101 during delivery of implant 103 and a centering device 106 for facilitating the centering or the otherwise desired positioning of implant 103 for delivery. Although shown here as four separate components, any combination of body member 101, delivery device 104, stabilization device 105 and centering device 106 can be integrated together to reduce the number of components to three, two or one total components in treatment system 100.

The use of a similar treatment systems 100, capable of having body members 101, implants 103, delivery devices 104, stabilization devices 105 and positioning devices 106, are described in detail in co-pending U.S. patent application Ser. No. 11/218,794, filed Sep. 1, 2005 and entitled "Suture-based Systems and Methods for Treating Septal Defects," U.S. patent application Ser. No. 11/295,338, filed Dec. 5, 2005 and entitled "Clip-based Systems and Methods for Treating Septal Defects," and U.S. provisional patent application Ser. No. 60/986,229, filed Nov. 7, 2007 and entitled "Systems, Devices And Methods For Achieving Transverse Orientation In The Treatment Of Septal Defects," each of which are fully incorporated by reference herein. It should be noted that any of the types of implantable closure devices, systems for delivering the closure devices and methods for using the same that are described in these incorporated applications can be used with the systems and methods described herein.

Figure 2A:
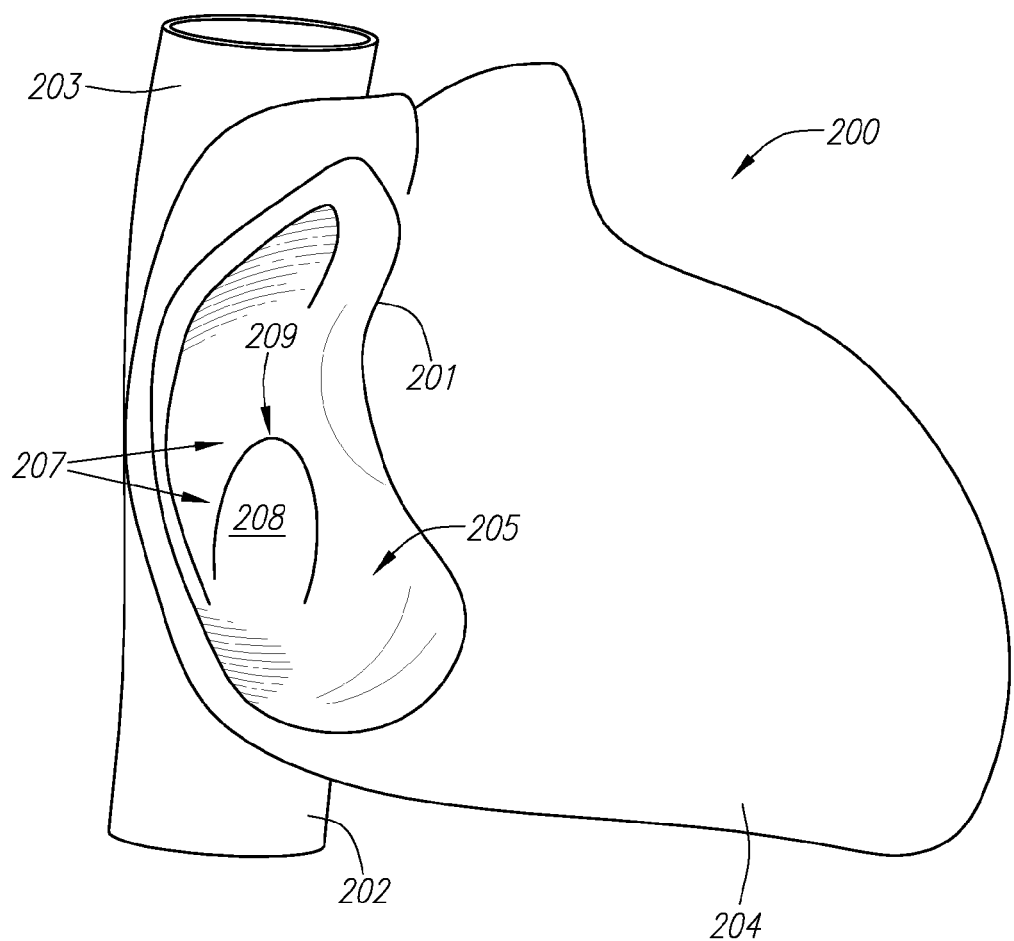
FIG. 2A is an exterior/interior view of the right atrium depicting an example human heart.

To better understand the many alternative embodiments of treatment system 100, the anatomical structure of an example human heart having a PFO will be described in brief. FIG. 2A is an exterior/interior view depicting an example human heart 200 with a portion of the inferior vena cava 202 and the superior vena cava 203 connected thereto. Outer tissue surface 204 of heart 200 is shown along with the interior of right atrium 205 via cutaway portion 201. Depicted within right atrium 205 is septal wall 207, which is placed between right atrium 205 and the left atrium located on the opposite side (not shown). Also depicted is fossa ovalis 208, which is a region of septal wall 207 where the tissue is relatively thinner than the surrounding tissue. PFO region 209 is located near the upper portion beyond the fossa ovalis 208.

FIG. 2B is an enlarged view of septal wall 207 depicting PFO region 209 in more detail as viewed from right atrium 205. PFO region 209 includes septum secundum 210, which is a first flap-like portion of septal wall 207. The edge of this flap above fossa ovalis 208 is referred to as the limbus 211. FIG. 2C is also an enlarged perspective view of septal wall 207, instead depicting septal wall 207 as viewed from left atrium 212. Here, PFO region 209 is seen to include septum primum 214, which is a second flap-like portion of septal wall 207. Septum primum 214 and septum secundum 210 partially overlap each other and define a tunnel-like opening 215 between sidewalls 219 (indicated as dashed lines in FIGS. 2B-C) that can allow blood to shunt between right atrium 205 and left atrium 212 and is commonly referred to as a PFO.

Figure 2D:
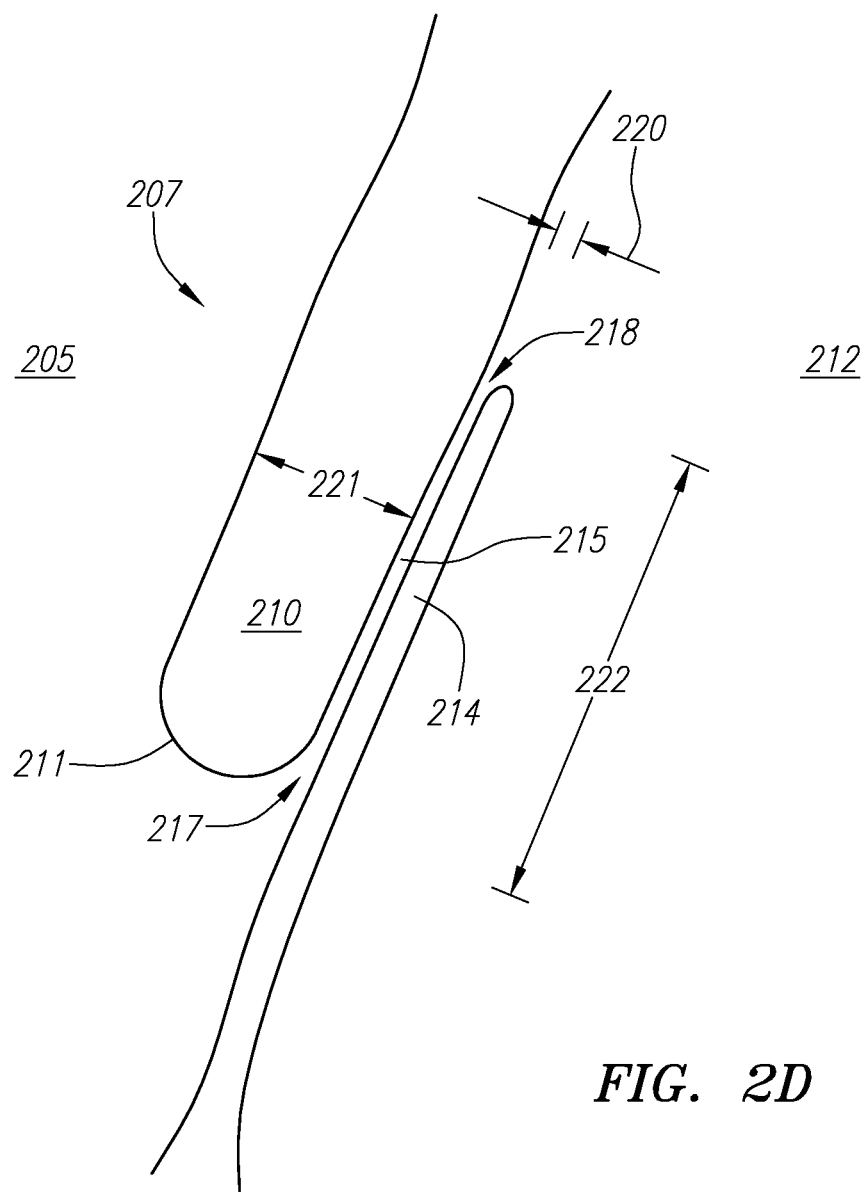
FIG. 2D is a cross-sectional view taken along line 2D-2D of FIGS. 2B-2C depicting another example septal wall.

FIG. 2D is a cross-sectional view depicting an example PFO region 209 taken along line 2D-2D of FIGS. 2B-C. Here, it can be seen that septum secundum 210 is thicker than septum primum 214. Typically, the blood pressure within left atrium 212 is higher than that within right atrium 205 and tunnel 215 remains sealed. However, under some circumstances a valsalva condition can occur where the blood pressure within right atrium 205 becomes higher than the blood pressure within left atrium 212 and blood shunts from right atrium 205 to left atrium 212. Because most typical shunts occur in this manner and for purposes of facilitating the discussion herein, region 217 in FIG. 2D will be referred to as PFO entrance 217, and region 218 will be referred to as PFO exit 218.

Many different variations of PFO's can occur. For instance, thickness 220 of septum primum 214, thickness 221 of septum secundum 210, overlap distance 222 and the flexibility and distensibility of both septum primum 214 and septum secundum 210 can all vary. In FIGS. 2B-C, PFO entrance 217 and PFO exit 218 are depicted as being relatively the same size with the width of tunnel 215, or the distance between sidewalls 219, remaining relatively constant. However, in some cases PFO entrance 217 can be larger than PFO exit 218, resulting in an tunnel 215 that converges as blood passes through. Conversely, PFO entrance 217 can be smaller than PFO exit 218, resulting in an opening that diverges as blood passes through. Furthermore, multiple PFO exits 218 can be present, with one or more individual tunnels 215 therebetween. Also, in FIGS. 2B-D, both septum primum 214 and septum secundum 210 are depicted as relatively planar tissue flaps, but in some cases one or both of septum primum 214 and septum secundum 210 can have folded, non-planar, highly irregular shapes.

As will be described in more detail below, treatment of a PFO preferably includes inserting treatment system 100 into the vasculature of a patient and advancing body member 101 through the vasculature to inferior vena cava 202, from which access to right atrium 205 can be obtained. Once properly positioned within right atrium 205, delivery device 104 can be used to deliver implant 103 to PFO region 209, preferably by inserting implant 103 through septum secundum 210 and primum 214 such that implant 103 lies transverse to tunnel 215 and can at least partially close tunnel 215.

Figure 3:
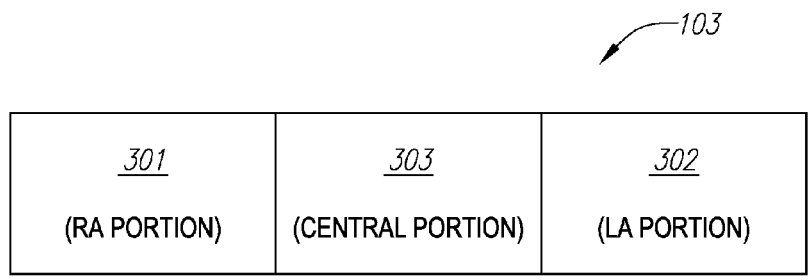
FIG. 3 is a block diagram depicting an exemplary embodiment of an implantable treatment device.

FIG. 3 is a block diagram depicting one exemplary embodiment of implant 103. Implant 103 can be configured in an almost limitless number of different ways, as this block diagram shows. Here, implant 103 includes a first end portion 301, a second end portion 302 and a central portion 303 preferably coupled therebetween. First and second end portions 301-302 are each preferably configured to engage opposing surfaces of septal wall 207. First end portion 301 can be configured to engage the surface of septal wall 207 on the right atrium (RA) side, while second end portion can be configured to engage the surface of septal wall 207 on the left atrium (LA) side. Although end portions 301-302 can be placed anywhere within heart 200 as desired, in order to facilitate the description of implant 103 herein, first end portion 301 will be referred to as RA portion 301 and second end portion will be referred to as LA portion 302.

Central portion 303 is preferably configured to fit within a manmade or surgically created opening in either septum primum 214, septum secundum 210 or both. Central portion 303 is also preferably configured to apply a force adequate to bring end portions 301-302 towards one another when implanted, to be implantable into septal walls 207 of varying thickness and to fit within elongate body member 101, the diameter of which is preferably minimized for ease of insertion within the patient's vasculature.

Implant 103 can be configured in any manner desired to fit the needs of the application. Implant 103 can have any size and shape and can include additional portions not shown in FIG. 3 to achieve a different set of functions. Implant 103 can also be fabricated in any desired manner and from any materials suitable for implantation within the patient including, but not limited to, elastic materials, superelastic materials, shape-memory materials, composite materials, polymeric materials, coatings, drug containing materials, blends with radio-opaque materials and biodegradable materials.

Figure 4A:
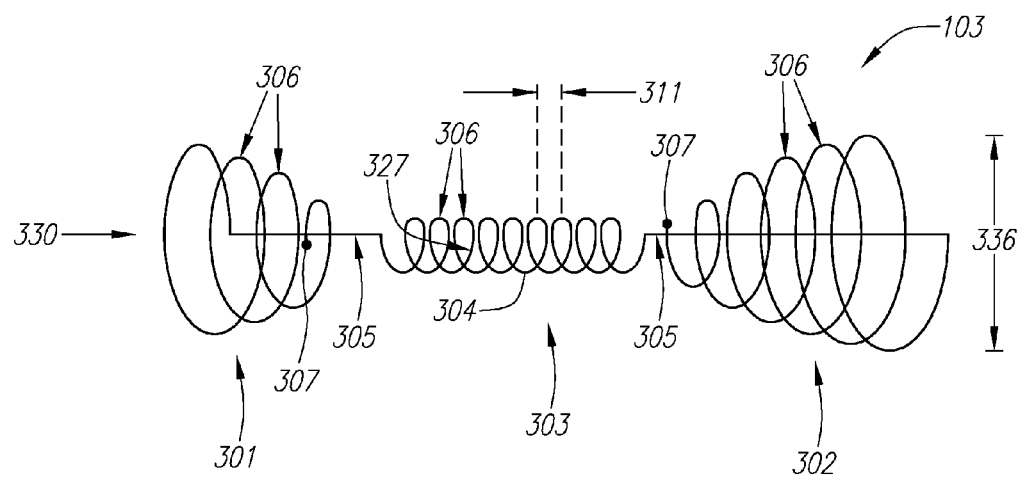
FIG. 4A is a perspective view depicting another exemplary embodiment of an implantable treatment device.
Figure 4B:
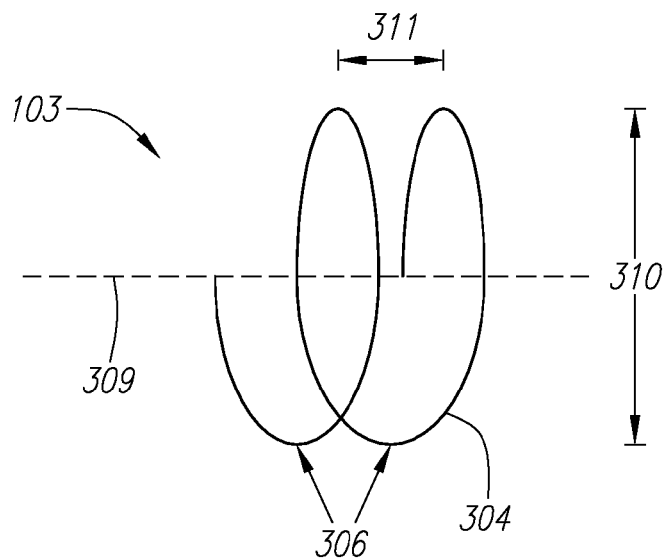
FIG. 4B is a perspective view depicting an exemplary embodiment of several coiled segments of an implantable treatment device.

FIG. 4A is a perspective view depicting another exemplary embodiment of implant 103 shown in an "at rest" configuration. In this embodiment, implant 103 is configured in a coil-shaped manner with a wire-like body 304 composed of an elastic material. Wire-like body 304 can have any wire-like cross-sectional shape including, but not limited to circular, elliptical, oval, rounded, arcuate, polygonal and any combination thereof. Each portion 301-303 can be composed of one or more coiled segments 306, with a coiled segment 306 being defined herein as a segment that is curved or otherwise shaped in any manner about one or more axes. Thus, rounded, straight, irregular and polygonal segments are all considered to be coiled. A coiled segment 306 can be curved or otherwise shaped less than 360 degrees about the one or more axes. FIG. 4B is a perspective view depicting an exemplary embodiment of several coiled segments 306, which could be used in any of portions 301-303. In this embodiment, each coiled segment 306 is coiled with a constant rate of curvature about the same axis 309. Coiled segments 306 have approximately the same width 310 and are stacked and separated by a distance 311, which will be referred to herein as stacking distance 311.

Referring back to FIG. 4A, implant 103 has an overall width 336. Central portion 303 includes a plurality of coiled segments 306 having substantially the same width 310. Each end portion 301-302 includes a plurality of coiled segments having varied widths or diameters 310. In this case, the width 310 of the outermost coiled segment 306 is the greatest and the widths 310 of each successive coiled segment 306 decreases as one approaches the innermost coiled segment 306. Each end portion 301-302 is coupled with central portion 303 via optional generally straight sections 305. Generally straight sections 305 can prevent blood from shunting between the right and left atria through open interior region 327 of coiled central portion 303, by allowing the adjacent tissue to encroach upon and surround straight section 305. Plugs of bioabsorbable or hydrophilic material may also be provided to minimize such shunting. Generally straight sections 305 can also prevent tissue from getting caught, or hung up, between central portion 303 and RA/LA portions 301/302. Each generally straight sections 305 is not required to be straight and, in fact, can have any non-coiled shape. Central portion 303 can be placed approximately equidistant from end portions 301-302, as depicted here, or central portion 303 can be placed closer to one of end portions 301-302 than the other. Generally straight sections 305 are optional and can be included on only one side of central portion 303 or omitted altogether, in which case the coiled segments 306 of central portion 303 extend directly up to a coiled segment 306 of each end portion 301-302.

The end tips 307 of body 304 are preferably atraumatic so as to minimize injury to cardiac tissue. In this embodiment, end tips 307 are rounded and have a larger diameter than body 304. End tips 307 can also be configured as floppy tips that are curled or coiled and can be flexible or non-flexible. Also, it should be noted that any part of implant 103 can be modified for imaging purposes. For instance, in this embodiment end tips 307 are radio-opaque to increase visibility of implant 103 during imaging. Also, end tips 307 can be configured to facilitate delivery. For instance, in one embodiment end tips 307 can be shaped to minimize the risk of becoming caught on any portion of the delivery device 104. In another embodiment, end tips 307 are configured to interface with the delivery device 104 to allow manipulation of implant 103 before, during or after delivery.

Figure 4C:
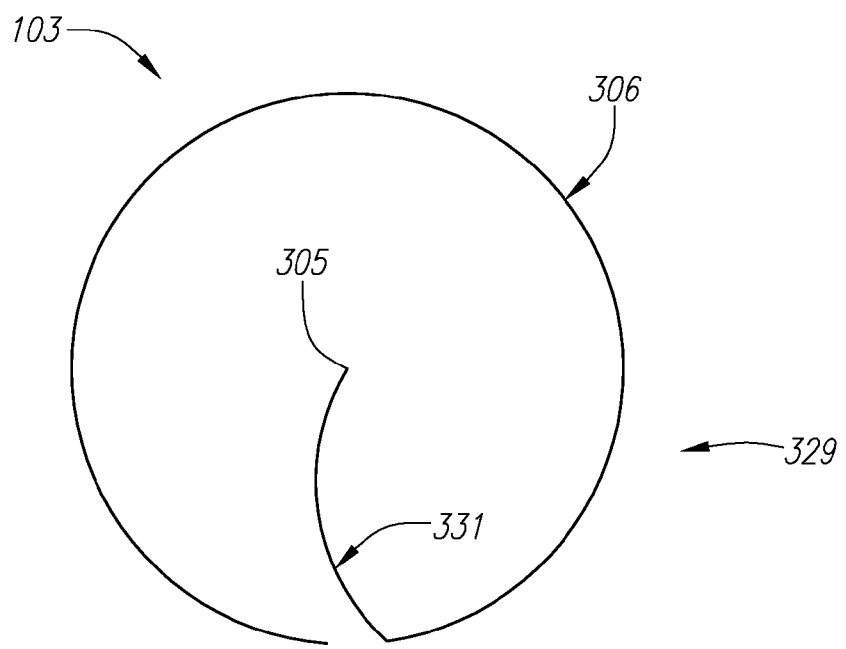
FIG. 4C depicts a side view of the embodiment of the implantable treatment device taken along direction 330 of FIG. 4A.
Figure 4D:
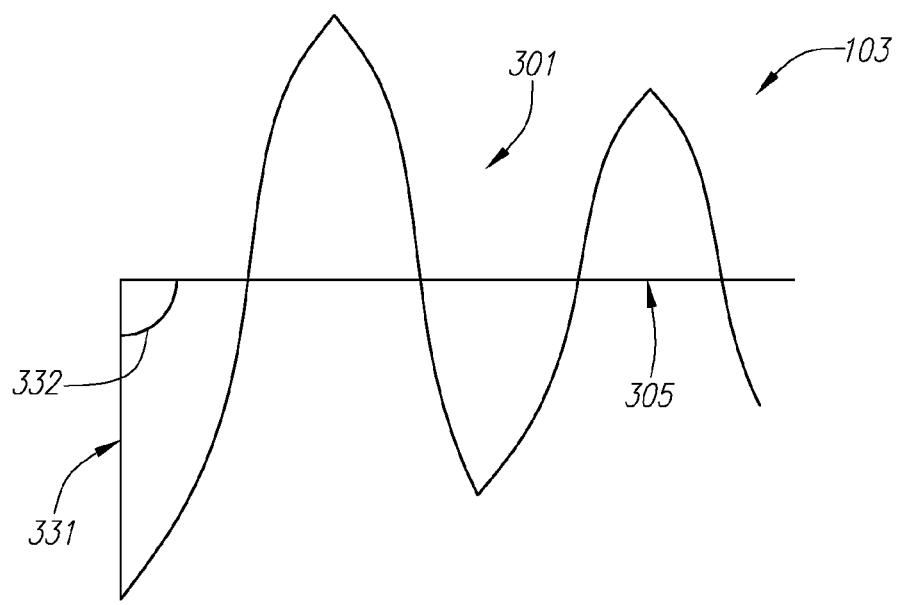
FIG. 4D is a schematic view depicting another exemplary embodiment of the implantable treatment device as viewed from direction 329 of FIG. 4C.

FIG. 4C depicts a side view of the embodiment of implant 303 taken along direction 330 of FIG. 4A. For ease of illustration, FIG. 4C depicts only the outermost coiled segment 306 of RA portion 301, transition section 331 and the generally straight section 305 located between RA portion 301 and central portion 303. Transition section 331 is an optional section of implant 103 that can be straight, curved or any other shape. FIG. 4D depicts RA portion 301, transition section 331 and the generally straight section 305 located between RA portion 301 and central portion 303 as viewed from direction 329 of FIG. 4C. Here, it can be seen that transition section 331 connects to generally straight section 305 at 90 degree angle 332. Angle 332 can be varied as desired, but values of angle 332 approaching 0 degrees or 180 degrees are less preferable due to the increased risk of RA portion 301 (or LA portion 302) being drawn into manmade opening 315, which is described in more detail below.

Figure 4E:
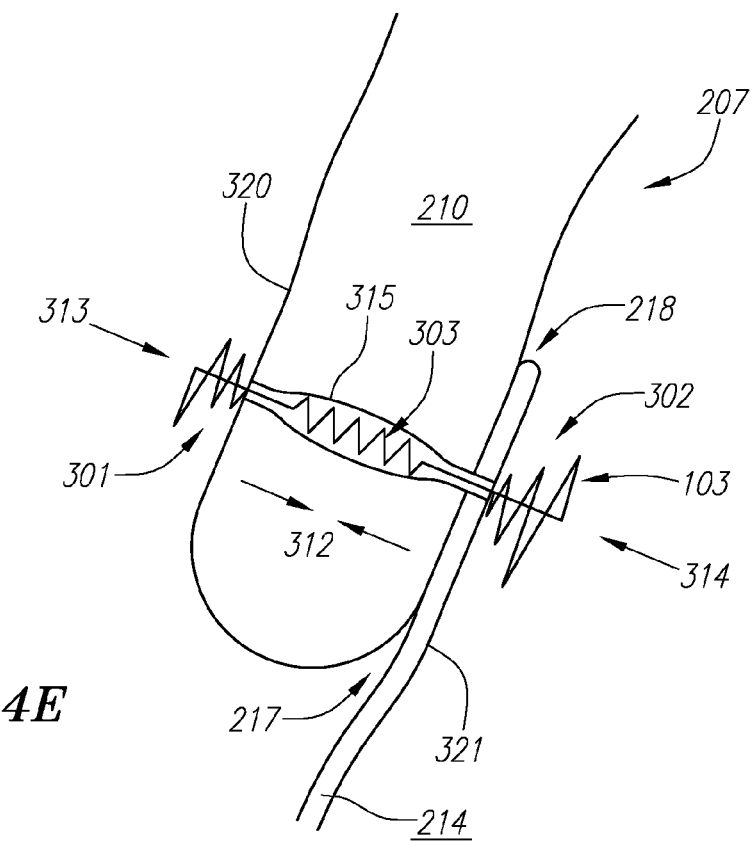
FIG. 4E is cross-sectional view depicting the exemplary embodiment of the implantable treatment device depicted in FIG. 4A implanted within an example heart.

FIG. 4E is cross-sectional view depicting the exemplary embodiment of implant 103 depicted in FIG. 4A implanted within heart 200 using one exemplary method of implantation. Here, an opening 315 has been surgically created in septum primum 214 and septum secundum 210 and implant 103 has been positioned such that central portion 303 resides within the opening 315. RA portion 301 and LA portion 302 are positioned on opposite sides of septal wall 207 to engage surface 320 of septum secundum 210 and surface 321 of septum primum 214, respectively. Central portion 303 preferably exerts a contractile force 312 to bring portions 301-302 towards one another, which in turn preferably draws septum primum 214 and septum secundum 210 together to at least partially close PFO tunnel 215. Typically, portions 301 and 302 will lie flat against the septa, but are illustrated as compressed conical coils for purposes of clarity. As mentioned above, the widths 310 of coiled segments 306 of RA and LA portions 301-302 get progressively larger from the innermost to the outermost segment 306. If the rate of change of width 310 is large enough to allow coiled segments 306 to pass through each other, then portions 301 and 302 can exert additional closure forces 313 and 314, respectively, which oppose each other and assist central portion 303 in closing PFO tunnel 215.

LA portion 302 and RA portion 301 can each be sized in any manner desired. Preferably, LA portion 302 is configured to have relatively larger coiled segment widths 310, include relatively more coiled segments 306 and exert a closure force over a relatively larger area 314 than RA portion 301. This can be for one of at least two reasons. As will be described in more detail below, preferably, LA portion 302 is deployed in PFO region 209 first and, once in contact with septal wall 207, LA portion 302 is used to help deploy, or pull, portions 303 and 301 from delivery device 104. Also, septum primum 214 is typically thinner than septum secundum 210 and more likely to tear or deform to the extent that LA portion 302 can be pulled though septum primum 214.

Preferably, implant 103 is configured to adjust to septal walls 207 having varying degrees of thickness. Accordingly, central portion 303 preferably has a compressibility sufficient to apply a closure force 312 to thinner septal walls 207 while at the same time having an expandability sufficient to accommodate thicker septal walls 207 without excessive permanent deformation. In one exemplary embodiment, which is for purposes of illustration only and should not be used to limit the scope of the inventive subject matter in any way, central portion 303 is expandable from 3 to 8 millimeters (mm) without excessive permanent deformation.

Figure 4F:
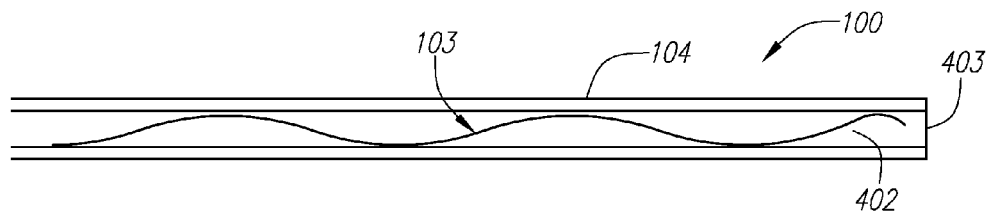
FIGS. 4F-G are cross-sectional views of additional exemplary embodiments of the treatment system with a delivery device.

As mentioned above, implant 103 can be deformable between a configuration suited for housing within delivery device 104 and the implanted configuration depicted in FIG. 4E. FIG. 4F is a cross-sectional view of an exemplary embodiment of treatment system 100 depicting delivery device 104 having an inner lumen 402 with implant 103 housed therein. Implant 103 is preferably housed within lumen 402 until body member 101 is advanced within the patient into the desired position within heart 200 for implantation, at which time implant 103 is delivered to PFO region 209 through open distal end 403. Here, implant 103 is deformed from the at rest, i.e., unbiased, configuration depicted in FIG. 4A into a generally straight configuration where coiled portions 301-303 are mostly unwound into a relatively straight state. This housed configuration significantly reduces the overall anchor width 336 of implant 103 and allows the size of delivery device 104 and, in turn, body member 101 to be minimized.

Figure 4G:
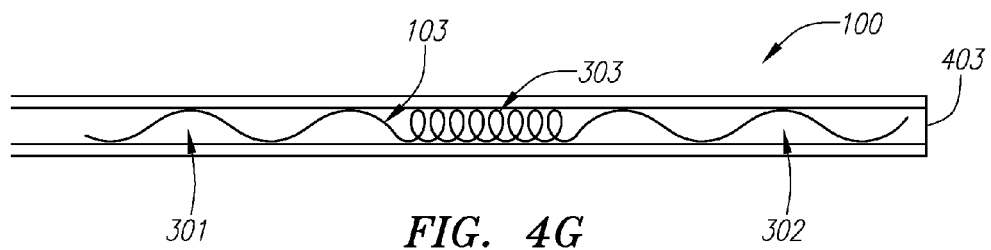

FIG. 4G is a cross-sectional view of another exemplary embodiment of treatment system 100 depicting delivery device 104 with implant 103 in the housed configuration. Here, central portion 303 of implant 103 remains coiled in a state similar to the resting state of FIG. 4A, while RA/LA portions 301/302 are partially unwound into a relatively straight state from the coiled rest state. Preferably, coiled segments 306 of central portion 303 generally have smaller widths 310 than most of the coiled segments 306 of RA/LA portions 301/302. Coiled segments 306 having a smaller width, i.e., more tightly wound coils, can be permanently deformed more easily when unwound and, therefore, by maintaining central portion 303 in the coiled state, the risk of permanent deformation to central portion 303 is reduced. Implant 103 can be deformed in any manner when housed within delivery device 104. For coil-like embodiments of implant 103, this can include deforming any or all of coiled segments 306, to any degree, in any portion 301-303.

To facilitate the deformation of implant 103 between the housed configuration and the implanted configuration depicted in FIG. 4E, implant 103 is preferably composed of an elastic material. Preferably, body 304 is composed of a titanium-nickel alloy such as NITINOL, although any elastic material can be used, including polymers, rubber-like materials, stainless steel, other metal alloys and the like. As one of skill in the art will recognize, the amount of closure force 312-314, the degree of allowable deformation and the like will depend, in part, on the type of material used to form body 304.

Figure 5A:
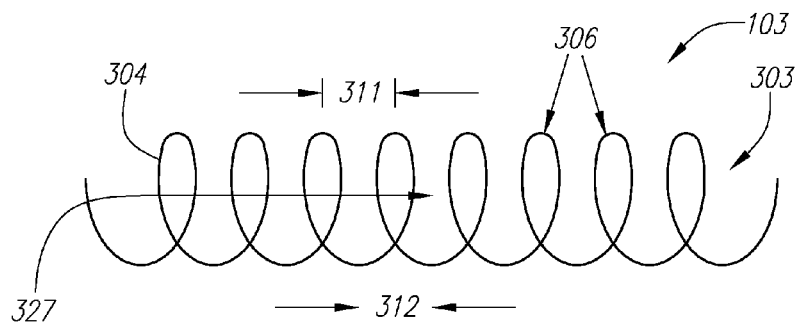
FIGS. 5A-E are perspective views depicting additional exemplary embodiments of the central portion the implantable treatment device.
Figure 5B:
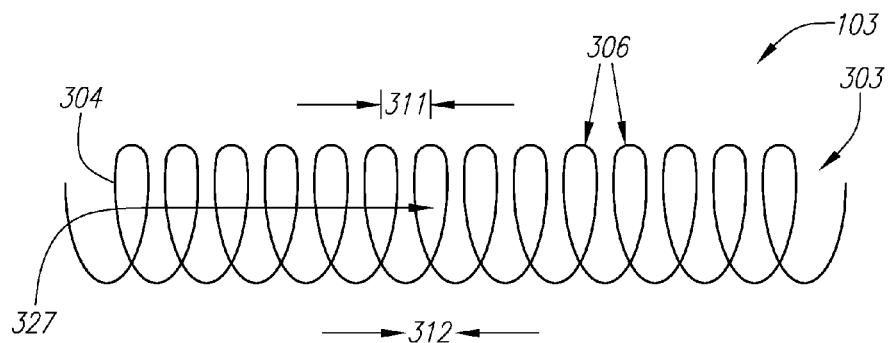

FIGS. 5A-E are perspective views depicting additional exemplary embodiments of central portion 303 of implant 103. Each of these embodiments can be used with any RA portion 301 and LA portion 302. In FIG. 5A, central portion 303 includes a plurality of coiled segments 306 where the stacking distance 311 between each segment 306 is relatively greater than the embodiment of central portion 303 depicted in FIG. 5B. Generally, a smaller stacking distance 311 will provide a greater closure force 312, if all other implant parameters remain the same. Any stacking distance 311 can be used in central portion 303 as desired, including configurations where there is no gap between each coiled segment 306, i.e., each coiled segment 306 lies flush with any adjacent coiled segment 306. Use of a larger stacking distance 311 that provides for gaps between adjacent coiled segments 306 allows the adjacent septal tissue to grow into the open interior region 327 of the coiled central portion 303, which can provide positional stability to the device and reduce any risk of blood shunting through open region 327.

Figure 5C:
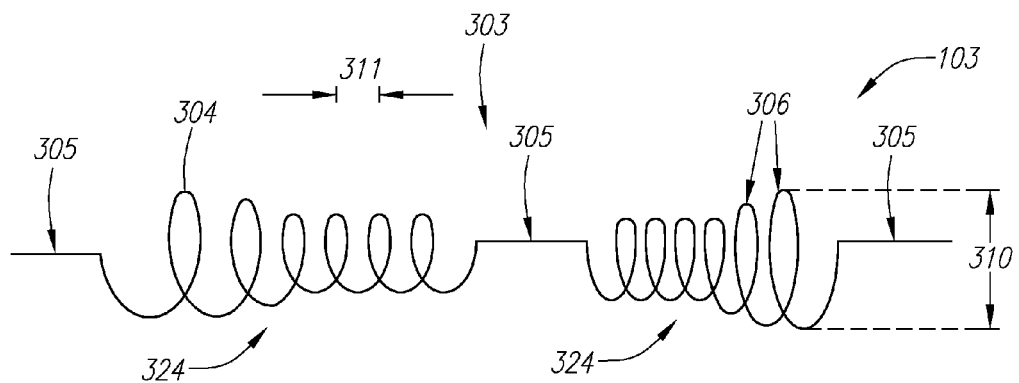

In FIG. 5C, central portion 303 includes a combination of coiled sections 324 and generally straight sections 305. It should be noted that central portion 303 can include any number of one or more coiled sections 324 in any combination with any number of one or more generally straight sections 305. As can be seen here, each coiled section 324 can be configured differently from any other coiled section 324, i.e., each coiled portion can include a different number of coiled segments 306, with different stacking distances 311 and different widths 310, etc.

Figure 5D:
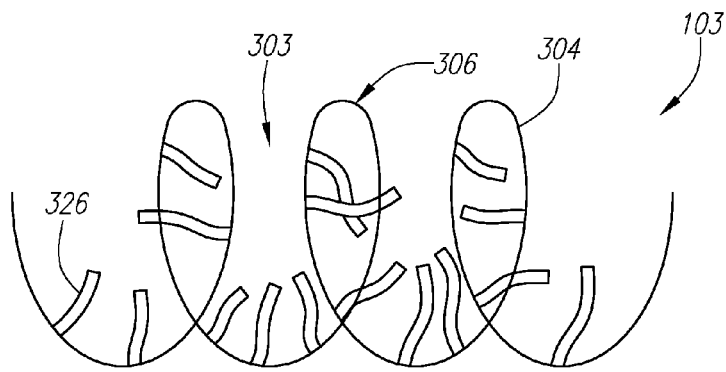

FIG. 5D depicts another exemplary embodiment where blocking material 326 has been coupled with coil body 304. Blocking material 326 preferably reduces any risk of blood shunting through the interior of coiled segments 306, either by blocking blood flow directly or by facilitating the formation of blood clots within open interior region 327. In one exemplary embodiment, blocking material 326 can include multiple DACRON fibers adhesively or mechanically coupled to the outer surface of body 304. In another exemplary embodiment, a polymer or metal plug is placed in open interior region 327 to prevent blood flow. As one of skill in the art will readily recognize, any type of plug, device, material or coating can be used and attached to body 304 in any manner, the numerous combinations of which will not be listed here.

Figure 5E:
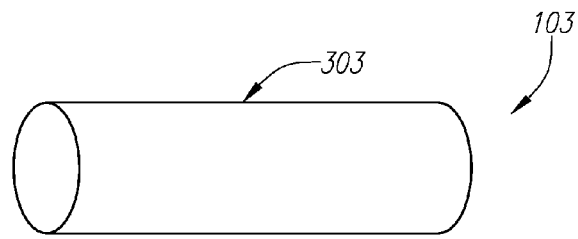

Central portion 303 is not required to include a coiled section 324 and can, in fact, be only a generally straight section 305. Furthermore, central portion 304 is not required to be formed from a wire-like body 304 and can be configured in any manner desired as depicted in the block diagram of FIG. 3. For instance, central portion 303 can be formed from an elastomeric or rubber-like stretchable member, as depicted in FIG. 5E.

Referring in more detail to RA portion 301 and LA portion 302, FIGS. 6A-I are perspective views depicting multiple embodiments exemplary of either RA portion 301 or LA portion 302. Any of the RA/LA portions 301/302 depicted here can be used with any embodiment of central portion 303 described with respect to FIGS. 5A-E. For instance, an exemplary embodiment of implant 103 can have RA portion 301 configured in a manner similar to that described with respect to FIG. 6A, central portion 303 configured in a manner similar to that described with respect to FIG. 5A, and LA portion 302 configured in a manner similar to that described with respect to FIG. 6B.

Figure 6A:
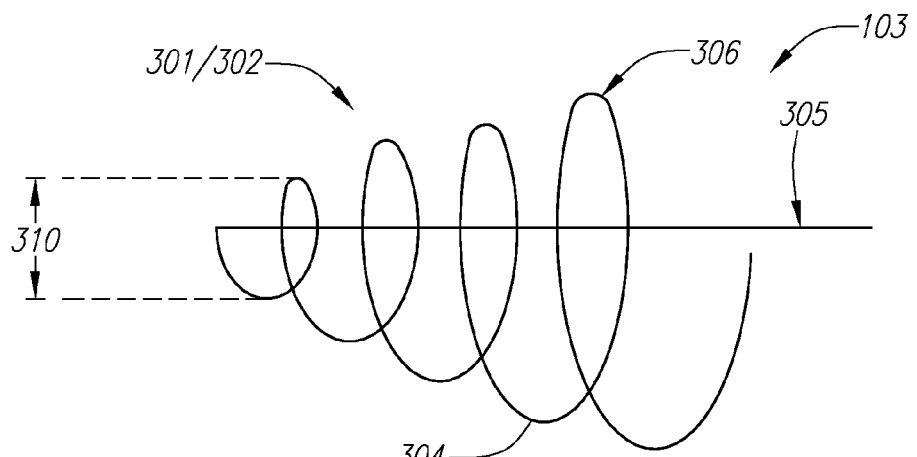
FIGS. 6A-I are perspective views depicting additional exemplary embodiments of either the first and/or the second end portions of the implantable treatment device.

In FIG. 4A, RA/LA portions 301/302 include multiple stacked coiled segments 306 having gradually decreasing widths 310 from the outermost to the innermost segment 306 (outermost being used to reference the segments 306 on the far left and right of FIG. 4A). In FIG. 6A, RA/LA portions 301/302 include multiple coiled segments 306 having gradually increasing widths 310 from the outermost to the innermost segment 306. The embodiment of portions 301-302 described with respect to FIG. 4A can be less susceptible to entering opening 315, due to the presence of a relatively larger coiled segment 306 coupled with transition region 305.

Figure 6B:
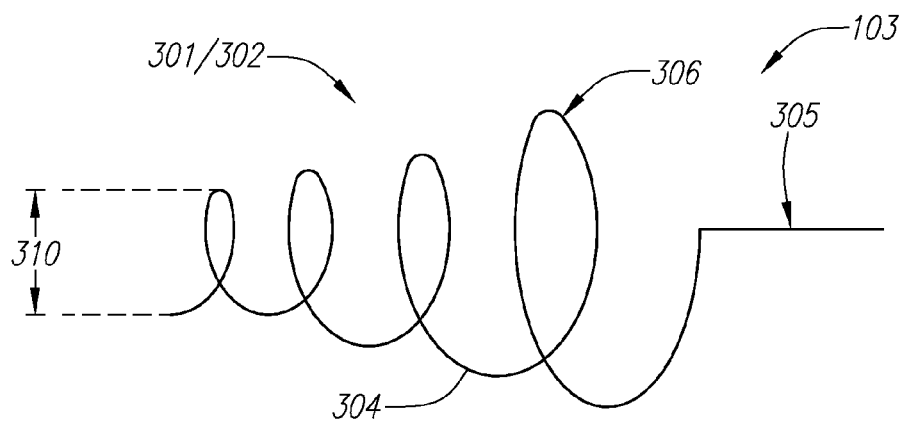
Figure 6C:
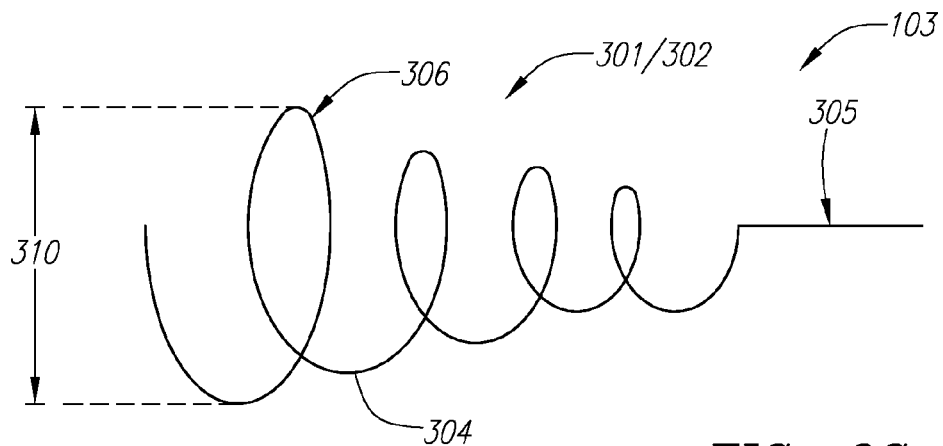

In both FIGS. 4A and 6A, coiled segments 306 of RA/LA portions 301/302 are stacked in an inwards manner, i.e., the outermost segment 306 is coupled with central portion 303 or generally straight section 305, if present (as shown here) and RA/LA portion 301/302 overlaps central portion 303. In FIGS. 6B-C, RA/LA portions 301/302 include multiple coiled segments 306 stacked in an outwards manner, i.e., the innermost segment 306 is coupled with central portion 303 or generally straight section 305, if present (as shown here). Generally, stacking segments 306 in an inwards manner will provide greater closure forces than stacking in an outwards manner. In FIG. 6B, RA/LA portions 301/302 include multiple coiled segments 306 having gradually increasing widths 310 from the outermost to the innermost segment 306, while in FIG. 6C, RA/LA portions 301/302 include multiple coiled segments 306 having gradually decreasing widths 310 from the outermost to the innermost segment 306.

Figure 6D:
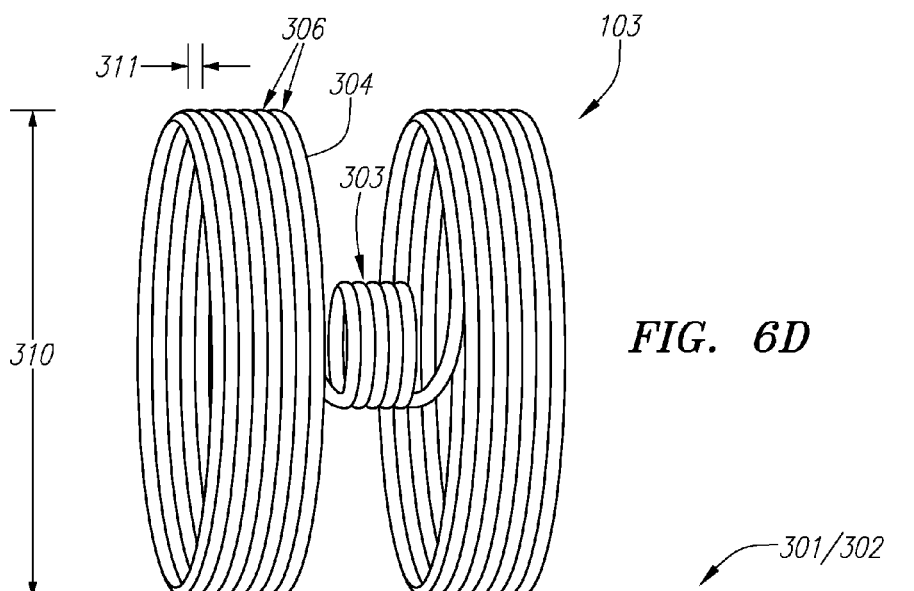

In FIG. 6D, RA/LA portions 301/302 are tightly stacked with a constant width 310 such that no gap exists between adjacent coiled segments 306. This embodiment of RA/LA portions 301/302 exhibits a high resistance to the potential for being pulled into opening 315.

Figure 6E:
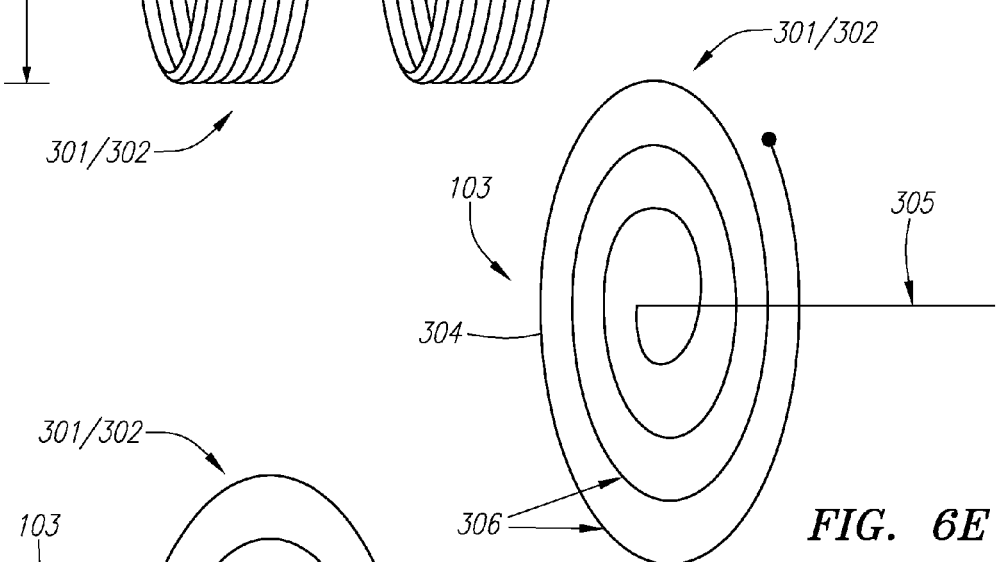
Figure 6F:
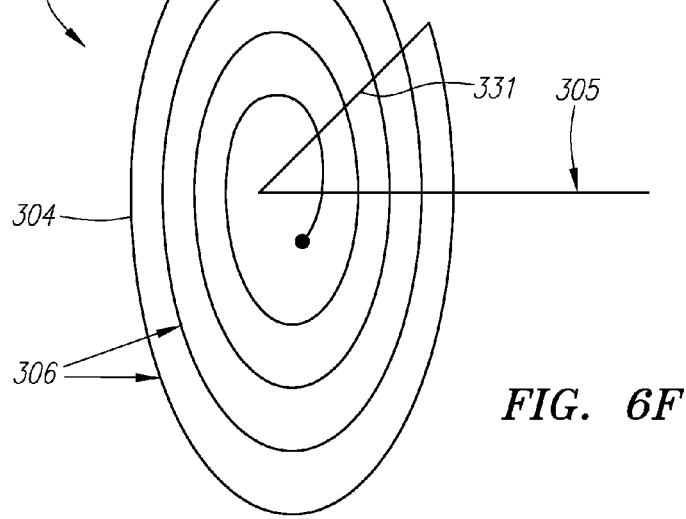

RA/LA portions 301/302 are not required to be implemented in a stacked configuration. For instance, in FIGS. 6E-F, RA/LA portions 301/302 each include multiple coiled segments 306 having varying widths 310 arranged in a generally co-planar fashion, i.e., for all segments 306 the stacking distance 311 is close to or equal to zero. In FIG. 6E, the smallest coiled segment 306 is coupled with generally straight section 305, while in FIG. 6F, the largest coiled segment 306 is coupled with generally straight section 305. To lessen the risk of RA/LA portions 301/302 being pulled into opening 315 in the embodiment depicted in FIG. 6F, transition section 331 is preferably positioned on the outside of coiled segments 306 such that, when implanted, coiled segments 306 are located between transition section 331 and septal wall 207.

Figure 6G:
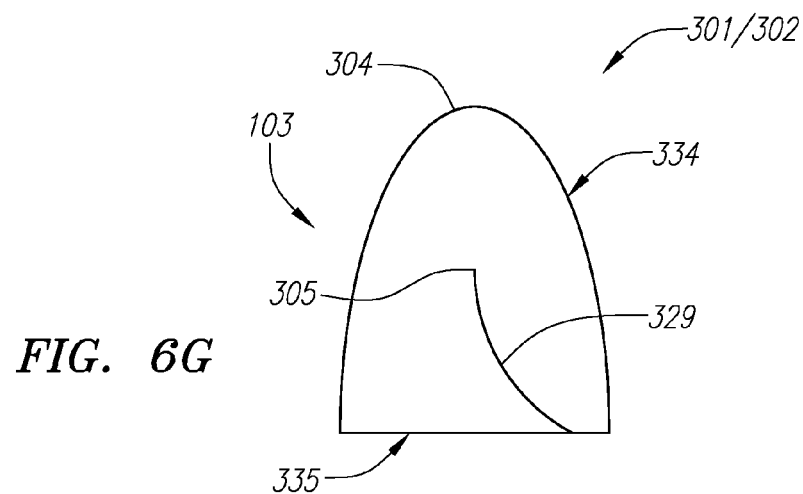
Figure 6H:
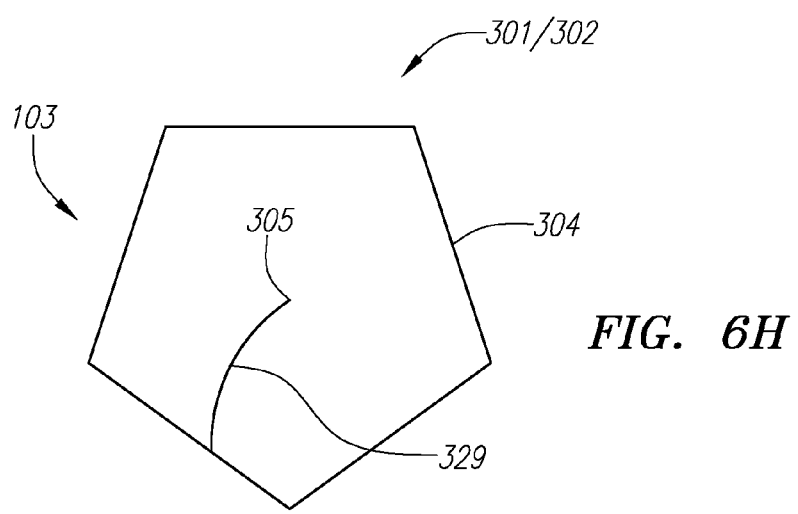
Figure 6I:
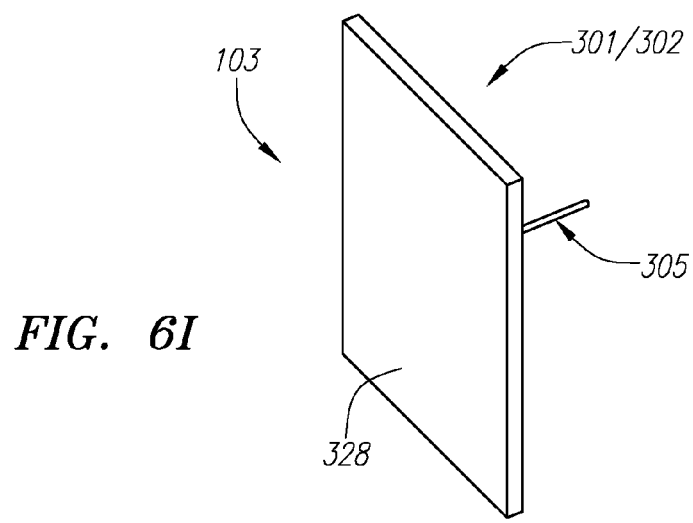

In the embodiments discussed above, the radius of curvature of the coiled segments 306, present in either RA/LA portions 301/302 or central portion 303, is generally constant or varies at a constant rate, resulting in a circular, spiral or helical appearance when viewed from the side (e.g., direction 330 of FIG. 4A). It should be understood that the radius of curvature can vary at any rate, abruptly or gradual, allowing coiled segments 306 to take any shape or form desired, whether in RA/LA portions 301/302 or central portion 303. For instance, FIGS. 6G-H are schematic views depicting additional exemplary embodiments of RA/LA portions 301/302 as viewed from the side. FIG. 6G depicts RA/LA portion 301/302 having an elliptical D shape. Here, RA/LA portion 301/302 has an elliptical portion 334 and a generally straight portion 335, which can be placed adjacent to fossa ovalis 208 to lessen the extent to which RA/LA portion 301/302 overlaps fossa ovalis 208 and minimize the risk of piercing or rupturing fossa ovalis 208. FIG. 6G depicts another exemplary embodiment of RA/LA portion 301/302 having a generally pentagonal shape.

RA/LA portions 301/302 are not required to include coiled segments 306 and are not required to be formed from a wire-like body 304. As mentioned above, RA/LA portions 301/302 can be configured in any manner desired as depicted in the block diagram of FIG. 3. For instance, RA/LA portions 301/302 can be formed from an elastomeric or rubber-like membrane 328 in an umbrella-like fashion, or a sheet-like fashion as depicted in the exemplary embodiment of FIG. 6I.

Figure 7A:
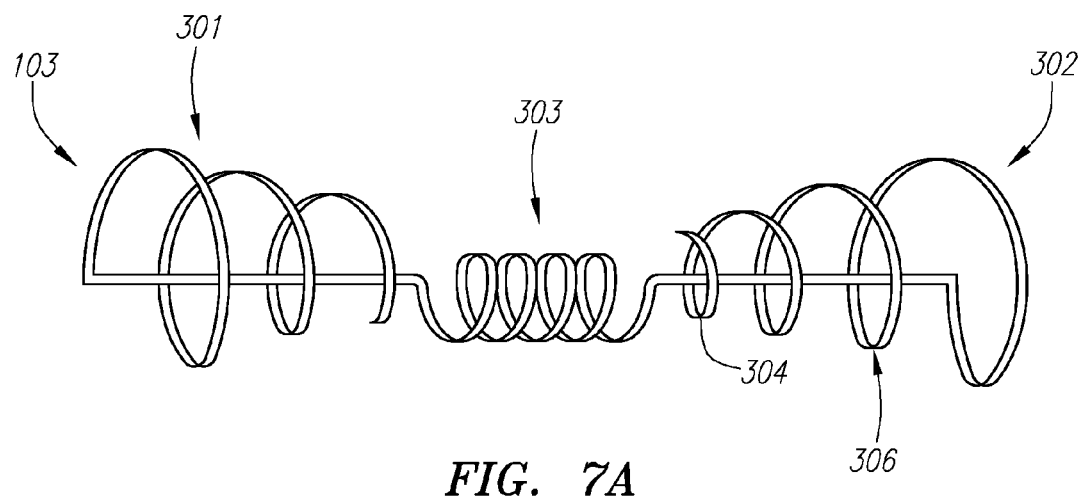
FIGS. 7A-C, 8 and 9A-C are perspective views depicting additional exemplary embodiments of the implantable treatment device.
Figure 7B:
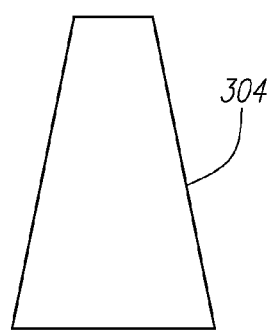
Figure 7C:
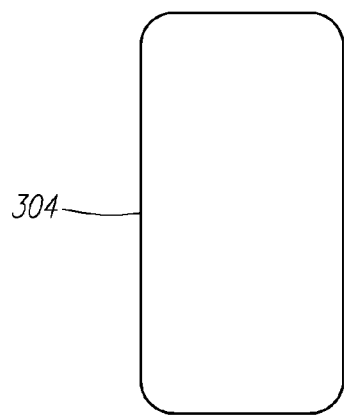

FIG. 7A-C are perspective views depicting additional exemplary embodiments of implant 103 having a ribbon-like body 304. Ribbon-like bodies 304 can have a generally polygonal cross-section and can be differentiated from the wire-like bodies 304 depicted in FIGS. 4A-5E, which can have generally circular, rounded etc. cross-sections as described above. FIG. 7A is an embodiment of implant 103 having a ribbon-like body 304 configured similar to that of the embodiment depicted in FIG. 4A. Generally, any of the embodiments described with respect to wire-like bodies 304 can also be implemented with ribbon-like bodies 304. Ribbon-like bodies 304 can have any ribbon-like cross-sectional shape desired. FIGS. 7B-C are cross-sectional views depicting ribbon-like body 304 having generally polygonal shapes. FIG. 7B is a cross-sectional view depicting ribbon-like body 304 having a generally tapered trapezoidal shape. FIG. 7C is a cross-sectional view depicting ribbon-like body 304 having a generally rectangular shape with rounded corners.

Figure 8:
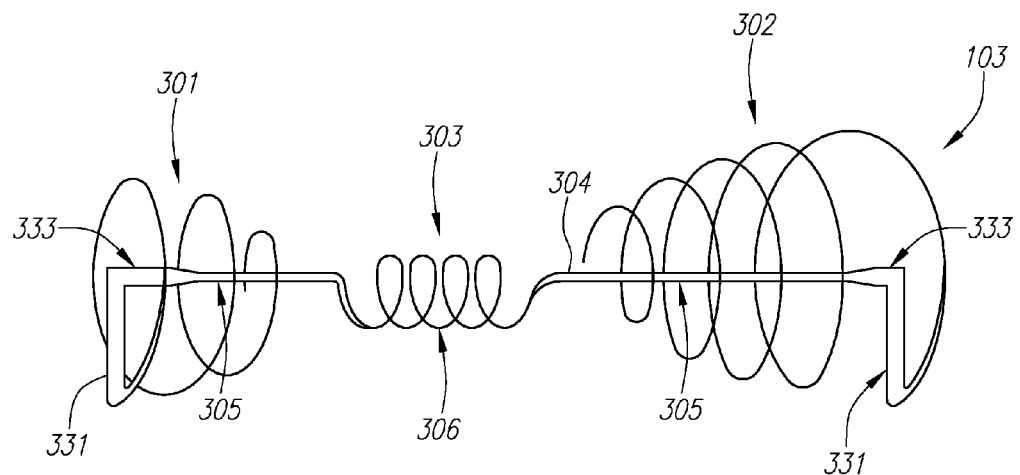

In addition to other parameters, the thickness of implant body 304 can vary as desired. For instance, FIG. 8 is a perspective view depicting another exemplary embodiment of implant 103 having a wire-like body 304 with varying thicknesses. Here, it can be seen that generally straight section 305 is relatively thicker than the coiled segments 306 of central portion 303, while interface 333 between generally straight sections 305 and transition sections 329 is relatively thicker still. Relatively thicker regions of body 304, whether formed from a wire, ribbon or other structure, generally have greater strength and less flexibility than relatively thinner regions of body 304. Thus, relatively thicker regions can be used to add strength while relatively thinner regions can be used where added flexibility is desired.

Like the thickness, the surface of body 304 can also be varied as desired. The surface can be modified directly or through etching, grinding, additional coatings or add-ons, which are applied to the underlying body 304. The surface can be modified for any purpose including, but not limited to, increasing surface friction with tissue, increasing the ability to engage tissue, allowing tissue in-growth, promoting healing, promoting scarring, promoting thrombogenicity, preventing blood passage or shunting around or through implant 103, minimizing thrombus formation, promoting anti-coagulation (e.g., with drugs such as heparin and the like), modifying imaging characteristics (e.g., radio-opacity and the like) and decreasing body surface friction (e.g., with a hydrophilic coating and the like).

Figure 9A:
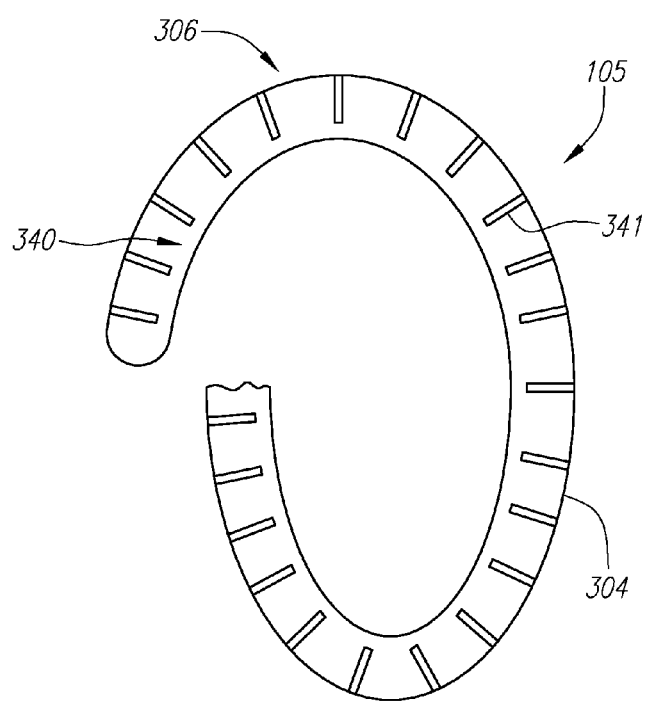
Figure 9B:
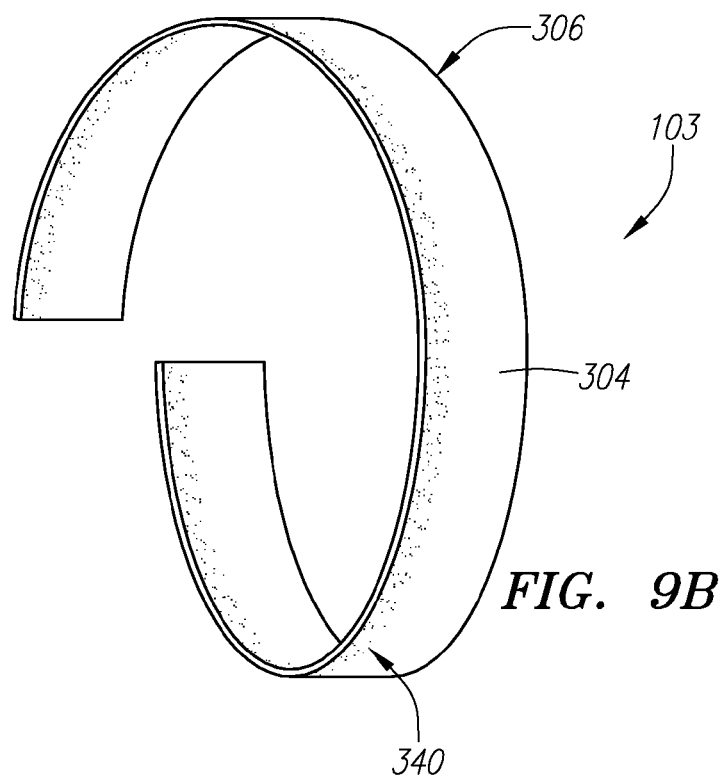
Figure 9C:
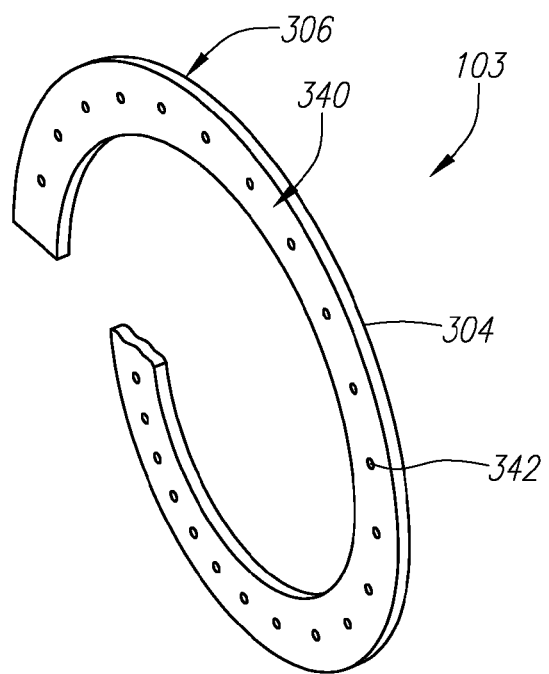

FIGS. 9A-C are perspective views depicting just several additional exemplary embodiments of implant 103 having a modified surface region 340. The surface of implant 103 can be modified in any location and in any manner desired, including, but not limited to, etching, grinding, coating, drilling, and cutting. For instance, FIGS. 9A-C depict the innermost coiled segment 306 of exemplary embodiments of RA/LA portion 301/302. In FIG. 9A, wire-like body 304 has been etched or otherwise treated such that modified surface region 340 is a textured surface including multiple recesses 341 for increasing surface friction and allowing coiled segment 306 to more easily grasp septal wall 207. It should be noted that any surface texture pattern can be used. In FIG. 9B, a coating has been applied to ribbon-like body 304 to create an abrasive surface region 340, also to increase surface friction. In FIG. 9C, apertures 342 in ribbon-like body 304 are present to facilitate tissue in-growth on and around modified surface region 340. Also, in this embodiment the orientation of ribbon-like body 340 has been rotated 90 degrees so that the widest surface is adjacent to the septal tissue.

As stated above, implant 103 can be configured in any manner desired in accordance with the needs of the application. The following is a non-exhaustive list of just some exemplary factors one of skill in the art may consider in designing, configuring, manufacturing and/or otherwise implementing implant 103.

LA portion 302 can be configured to use compressive force 312 from center portion 303 to hold septum primum 214 against septum secundum 210 and at least partially close or seal PFO tunnel 215. LA portion 302 can also be configured to maintain a stable position as central portion 303 and RA portion 301 are deployed without being pulled through septum primum 210. LA portion 302 can be configured to lie flush against septum primum 214 when deployed and not to distort the native geometry of tunnel 215 to create residual shunts. LA portion 302 can be sized to provide adequate coverage over PFO tunnel 215. (In one exemplary embodiment, which is included as an example only and should not be used to limit the inventive subject matter, LA portion 302 has a maximum width 310 of 1.2 centimeters to accommodate most large PFO tunnels 215.) LA portion 302, in combination with central portion 303 and RA portion 301, can be configured to exert enough closure force 314 to seal PFO tunnel 215 and prevent shunting during normal and valsalva atrial blood pressures. LA portion 302 can also be configured: to be deployable with minimal and consistent push force (e.g., push force on pusher member 406, which will be described in more detail below); so that the shape before and after deployment is predictable; to be devoid of characteristics that cause chronic or excessive tissue irritation, inflammation, etc.; and/or for visibility during imaging procedures.

Central portion 303 can be configured to maintain LA portion 302 and RA portion 301 in a state of contact with septal wall 207 with enough closure force 312 to at least partially close and seal PFO tunnel 215. Central portion 303 can also be configured: with an adequate spring constant (k) to prevent tunnel 215 from opening during normal and valsalva atrial blood pressures; not to distort the native geometry of tunnel 215 and create residual shunts; to be deployable with minimal and consistent push force (e.g., push force on pusher member 406, which will be described in more detail below); for visibility during imaging procedures; to expand or stretch to accommodate variable septal wall thicknesses without excessive permanent deformation; with adequate strength to withstand any motion it may experience in vivo; to allow LA portion 302 or RA portion 301 to tilt, for instance, if the area of delivery is wedge shaped; so that central portion 303 does not pinch or sever any tissue that could embolize, for instance, with a spring constant low enough to prevent severing tissue; to exert adequate closure force 312 to close any residual shunts that exist; and/or with maximized width 310 and minimized strains to optimize fatigue performance.

RA portion 301 can be configured to hold septum secundum 210 against septum primum 214 and at least partially close or seal PFO tunnel 215. RA portion 301 can also be configured: to lie flush against septum secundum 210 when deployed and not to distort the native geometry of tunnel 215 to create residual shunts; to be deployable with minimal and consistent push force (e.g., push force on pusher member 406, which will be described in more detail below); so that the shape before and after deployment is predictable; to be devoid of characteristics that cause chronic or excessive tissue irritation, inflammation, etc.; for visibility during imaging procedures; and/or to resist being pulled through septal wall 207.

Figure 10A:
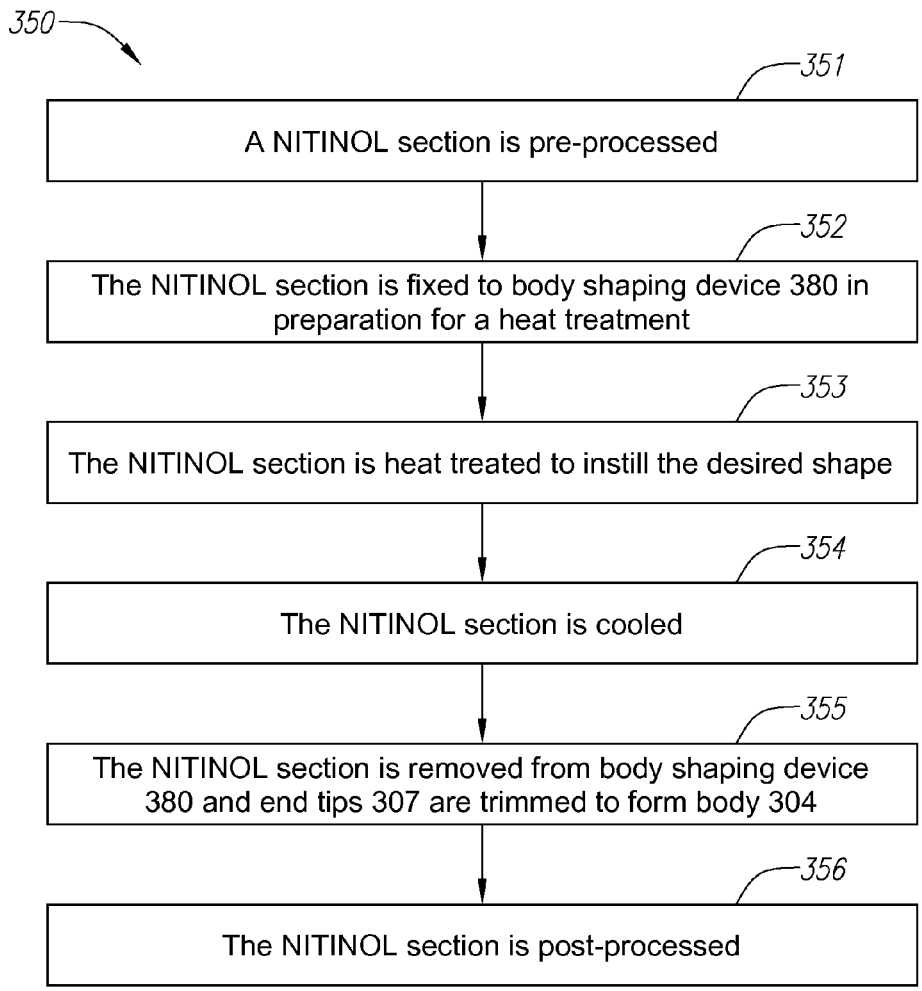
FIG. 10A is a flow diagram depicting one exemplary method of manufacturing another exemplary embodiment of the implantable treatment device.

Also provided herein are methods of manufacturing implant 103. FIG. 10A is a flow diagram depicting one exemplary method 350 of manufacturing an exemplary embodiment of a coil-like implant 103 having body 304, which can be wire, ribbon or the like, composed of NITINOL. First, at 351, a section of NITINOL, from which body 304 can be formed, is pre-processed. Pre-processing 351 can include adding a modified surface region 340 having a desired texture, adjusting body thickness, adjusting the cross-sectional shape of body 304 and the like.

With a ribbon-like implant 103, pre-processing can include etching of the NITINOL section. Methods of etching NITINOL materials are readily understood to one skilled in the art. For instance, a sheet of NITINOL is first etched or grinded or otherwise altered to vary the cross-sectional shape, thickness, surface texture and the like of one or more sections present on the sheet. Etching of the NITINOL sheet can allow for the implementation of numerous different cross-sectional shapes, thicknesses, surface textures and combinations thereof. Afterwards, each section of NITINOL can be cut from the sheet and trimmed as desired.

Figure 10B:
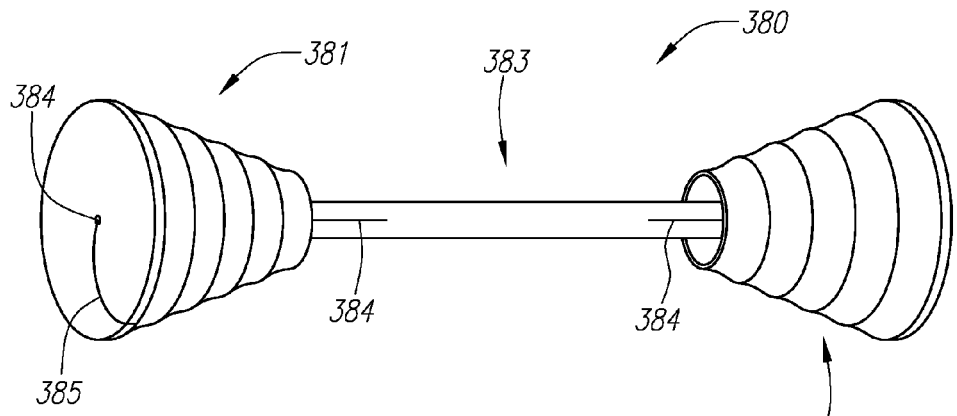
FIG. 10B is a perspective view of an exemplary embodiment of a body shaping device.

At 352, the NITINOL section is fixed to body shaping device 380 in preparation for heat treatment. Heat treatment of NITINOL can instill the desired at rest configuration to body 304 and is well known to those of skill in the art. Accordingly, body shaping device 380 is preferably shaped such that when the NITINOL section is coiled around body shaping device 380, it is in the final desired at rest configuration. One exemplary embodiment of body shaping device 380 is depicted in FIG. 10B. Here, body shaping device 380 is shaped for the exemplary embodiment of implant 103 depicted in FIG. 4A. Body shaping device 380 includes a central body shaping portion 383 corresponding to the shape of central portion 303, and two end body shaping portions 381 and 382 corresponding to the shape of RA portion 301 and LA portion 302, respectively. End body shaping portions 381 and 382 are preferably configured to telescope over central body shaping portion 383 to allow for the inwards manner of coiling of RA/LA portions 301/302 over central portion 303. Central portion 303 includes recesses 384 into which the NITINOL section can be placed to form generally straight sections 305. End body shaping portions 381 and 382 also preferably include recess 385 that can allow for each transition section 331.

Once wrapped around and fixed to body shaping device 380, at 353, the NITINOL section is then preferably heat treated to instill the desired shape. Heat treating can occur at any time and temperature sufficient to instill the desired at rest shape and level of elasticity in implant 103. In one embodiment, which is included as an example only and should in no way be used to limit the inventive subject matter, heat treating can occur at a temperature range of 500-550 degrees Celsius for approximately five minutes.

At 354, the NITINOL section is preferably cooled, e.g., by rapid quenching in room temperature water, then at 355, the NITINOL section is preferably removed from body shaping device 380 and end tips 307 are trimmed, if necessary, to the desired length to form body 304. Finally, at 356, any post-processing is performed, such as the addition of radio-opaque markers, the shaping of end tips 307 and the addition of any desired coatings or blocking material 326.

Figure 11A:
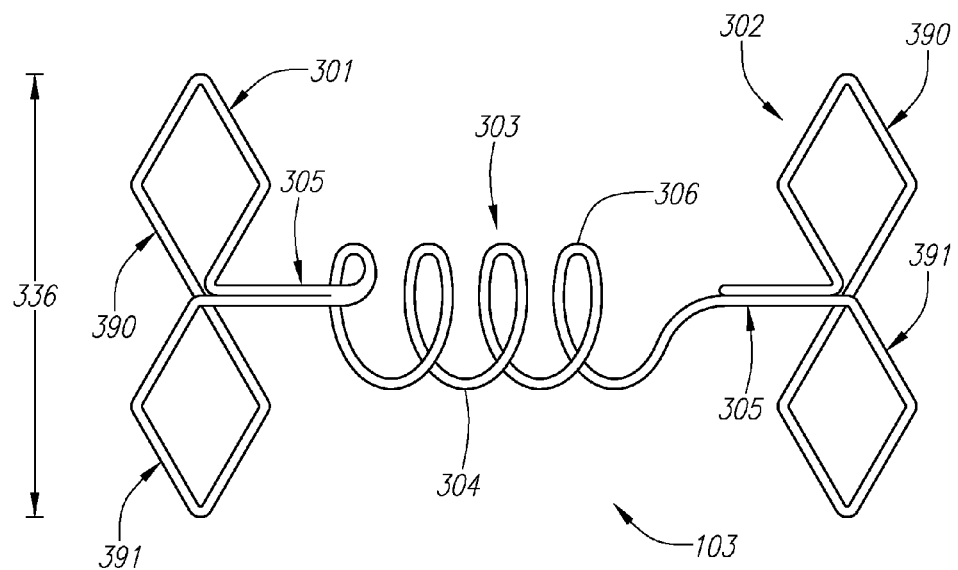
FIGS. 11A-C are perspective views depicting additional exemplary embodiments of an implantable treatment device.
Figure 11B:
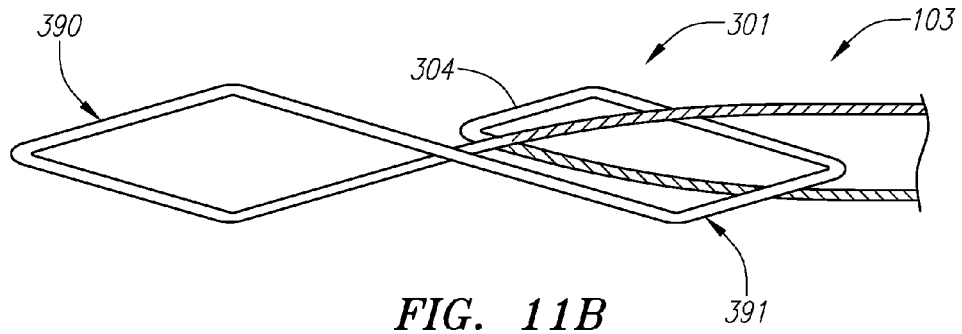
Figure 11C:
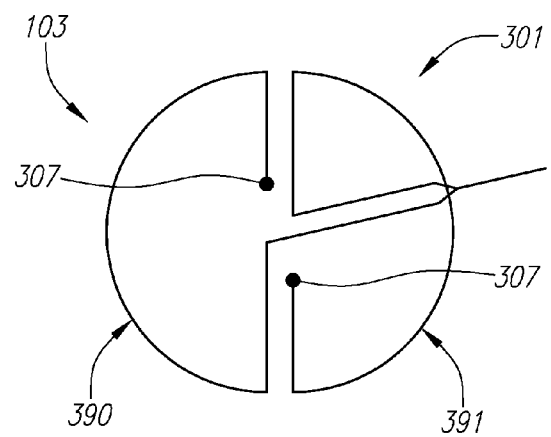

FIGS. 11A-C depict additional exemplary embodiments of implant 103. Specifically, FIG. 11A is a perspective view depicting an exemplary embodiment of implant 103 formed from multiple bodies 304. More specifically, from central portion 303 to RA portion 301 and LA portion 302, body 304 splits into separate wires which are then configured as shaped portions 390 and 391, which in this embodiment have substantially polygonal shapes. The shape and size of polygonal shaped portions 390 and 391 can be configured as desired to facilitate PFO closure. Here, portions 390 and 391 are entirely connected such that implant 103 does not have discrete end tips 307. Polygonal shaped portions 390 and 391 operate similar to coiled segments 306 and are deformable between a housed configuration and an "at rest" deployed configuration as shown here in FIG. 11A. FIG. 11B depicts RA portion 301 in the housed configuration. FIG. 11C depicts another exemplary embodiment where portions 390 and 391 have "D" shapes. Each portion 390 and 391 is not entirely connected and each portion 390 and 391 has an atraumatic end tip 307. It should be noted that body 304 can split into any number of separate portions having any number of configurations. Also, although not shown, implant 103 can include any number of separate bodies 304.

Figure 12:
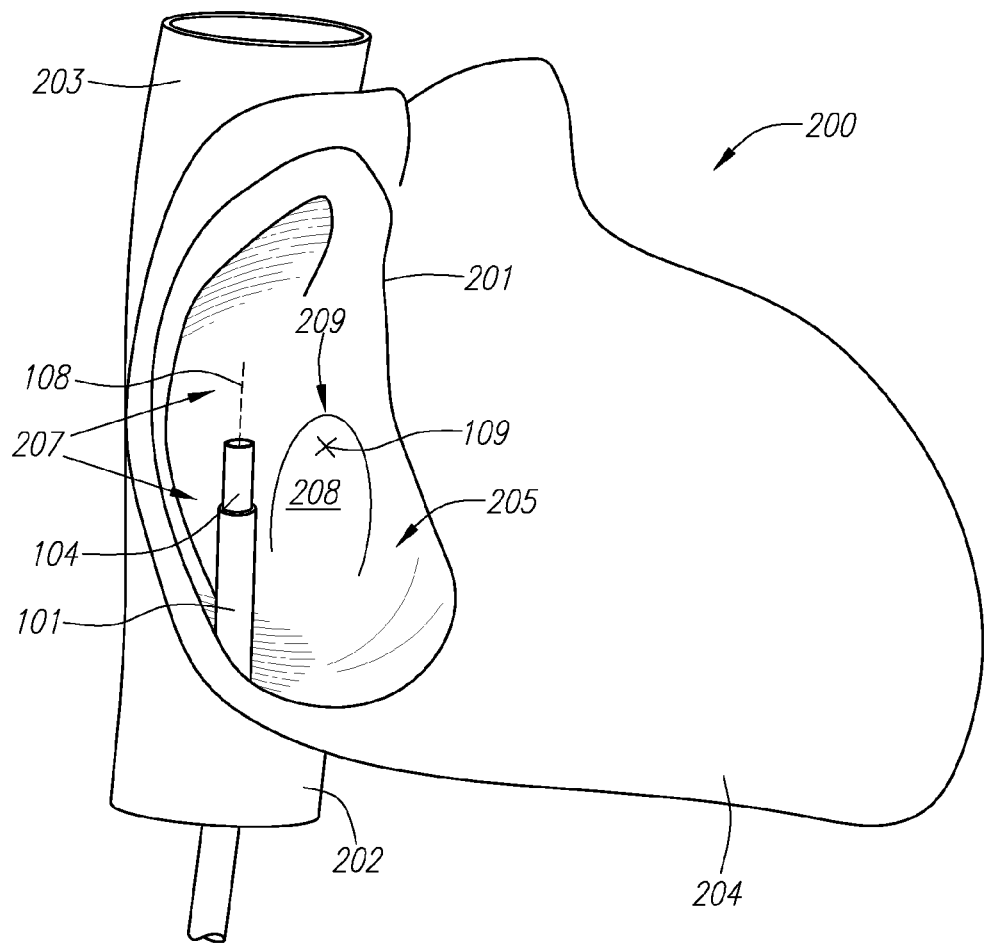
FIG. 12 depicts another exemplary embodiment of the treatment system within a heart.

Turning now to the devices and methods for delivering implant 103, FIG. 12 depicts another exemplary embodiment of treatment system 100 within heart 200. Implant 103 is preferably delivered from right atrium 205, although delivery from left atrium 212 is also possible. Right atrium 205 is preferably accessed via inferior vena cava 202. In this embodiment, implant 103 is delivered from within delivery device 104. To facilitate delivery in this manner, longitudinal axis 108 of delivery device 104 is preferably substantially parallel, i.e., at least close to parallel but not necessarily parallel, to the normal axis 109 of the surface of septal wall 207 into which implant 103 is to be delivered. However, as shown in FIG. 12, longitudinal axis 108 of delivery device 104 is close to perpendicular to this normal axis 109 (shown here extending into the page). To accommodate for this, treatment system 100 is preferably configured for off-axis delivery, which allows the orientation of delivery device 104 to be changed so that the longitudinal axis 108 of delivery device 104 is transverse to the longitudinal axis 107 (not shown) of body member 101.

Figure 13:
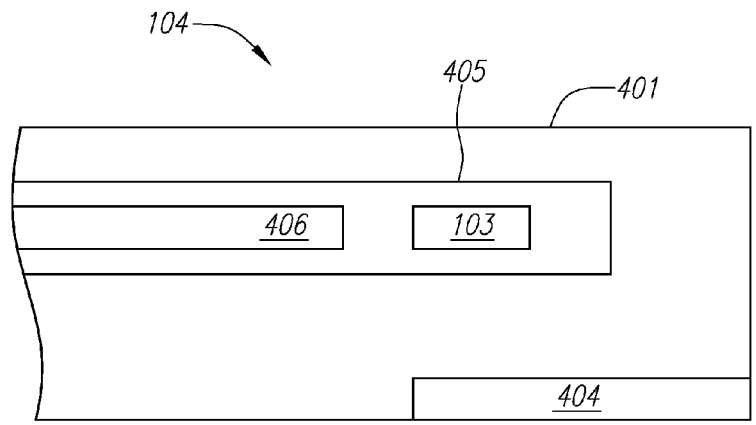
FIG. 13 is a block diagram depicting an exemplary embodiment of a delivery device.

FIG. 13 is a block diagram depicting one exemplary embodiment of delivery device 104 configured for off-axis delivery. Here, delivery device 104 includes an off-axis (OA) delivery member 401. Delivery device 104 is preferably configured to grasp or engage cardiac tissue to support and/or facilitate orientation of delivery member 401. Accordingly, an optional tissue engagement device 404 is included within delivery device 104. Delivery device 104 can also include a needle member 405 for puncturing septal wall 207 and a pusher member 406 for pushing implant 103 from within delivery device 104.

Figure 14A:
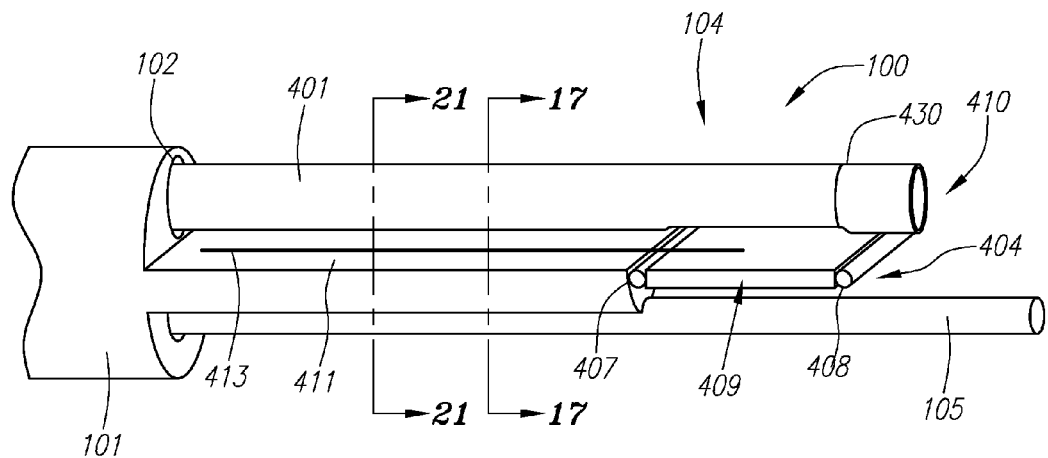
FIG. 14A is a perspective view depicting another exemplary embodiment of the treatment system.

FIG. 14A is a perspective view depicting another exemplary embodiment of treatment system 100, including body member 101, delivery device 104 and stabilization device 105. Here, OA delivery member 401 is an elongate flexible tubular member having open distal end 410. Inner lumen 102 of body member 101 is preferably configured to slidably receive OA delivery member 401, such that OA delivery member 401 can be advanced both proximally and distally. Distal end 410 of OA delivery member 401 is coupled with an elongate support structure 411 of body member 101 via optional grasping device 404. In this embodiment, grasping device 404 includes an arm member 409 coupled with support structure 411 and OA delivery member 401 with hinges 407 and 408, respectively. A biasing element 413 can also be optionally included, to apply a bias force to maintain arm member 409 in the position shown here. Stabilization device 105 is also an elongate member preferably placed in a location to oppose arm member 401.

Figure 14B:
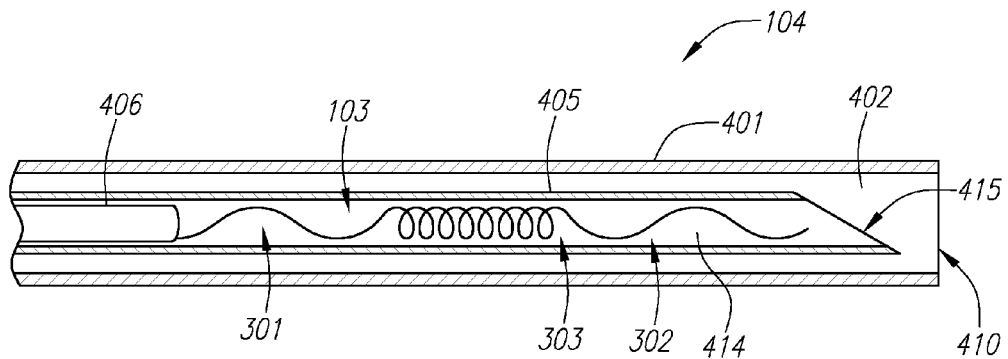
FIG. 14B is a cross-sectional view depicting another exemplary embodiment of the delivery device.

FIG. 14B is a cross-sectional view depicting another exemplary embodiment of OA delivery member 401 with embodiments of needle member 405, pusher member 406 and implant 103 located within lumen 414. Needle member 405 has an open distal end 415 and an inner lumen 414 in which pusher member 406 and implant 103 are slidably received and housed. In this embodiment, implant 103 is deformed to the housed configuration where RA/LA portions 301/302 are relatively straightened but central portion 303 remains in the coiled at rest configuration. As will be discussed in more detail below, delivery of implant 103 is accomplished by first orienting delivery device 104 in the desired orientation transverse to longitudinal axis 107 such that distal end 410 is in proximity with septal wall 207, then advancing needle member 405 through septal wall 207 to create opening 315. After needle member 405 has advanced through septal wall 207 into left atrium 212, pusher member 406 is advanced distally to push LA portion 302 of implant 103 from within lumen 414. Once LA portion 302 is outside lumen 414, LA portion 302 returns to the coiled at rest configuration. Needle member 405 can then be retracted proximally such that LA portion 302 engages septal wall 207 and remains in left atrium 212. As needle member 405 is retracted through septal wall 207, central portion 303 deploys within opening 315. Once needle member 405 is retracted back into lumen 402, OA delivery member 401 can be retracted from septal wall 207, for instance by pulling body member 101 proximally back, thereby allowing RA portion 301 to deploy and engage septal wall 207 in a coiled configuration.

Figure 14C:
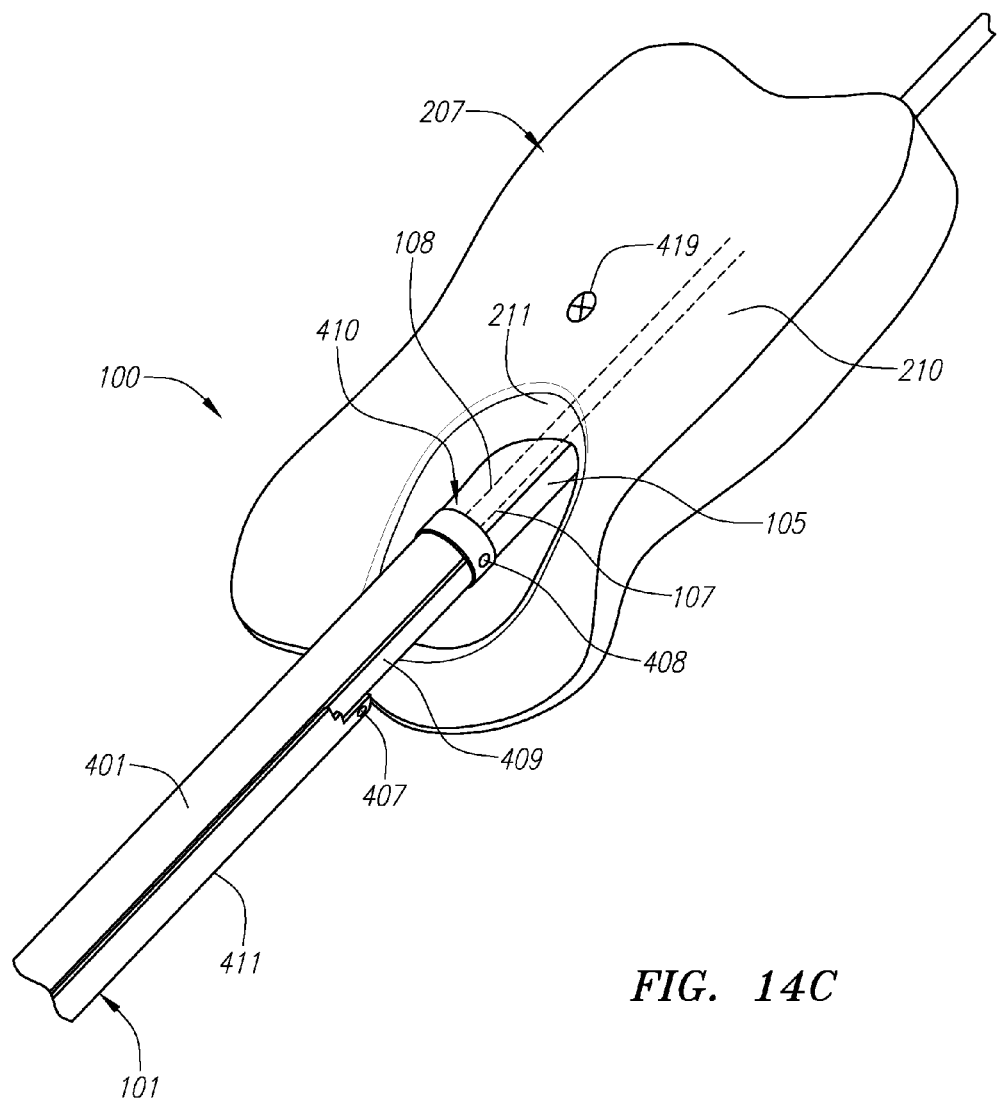
FIGS. 14C-F are perspective views depicting a portion of the septal wall and an additional exemplary embodiment of the treatment system.
Figure 14D:
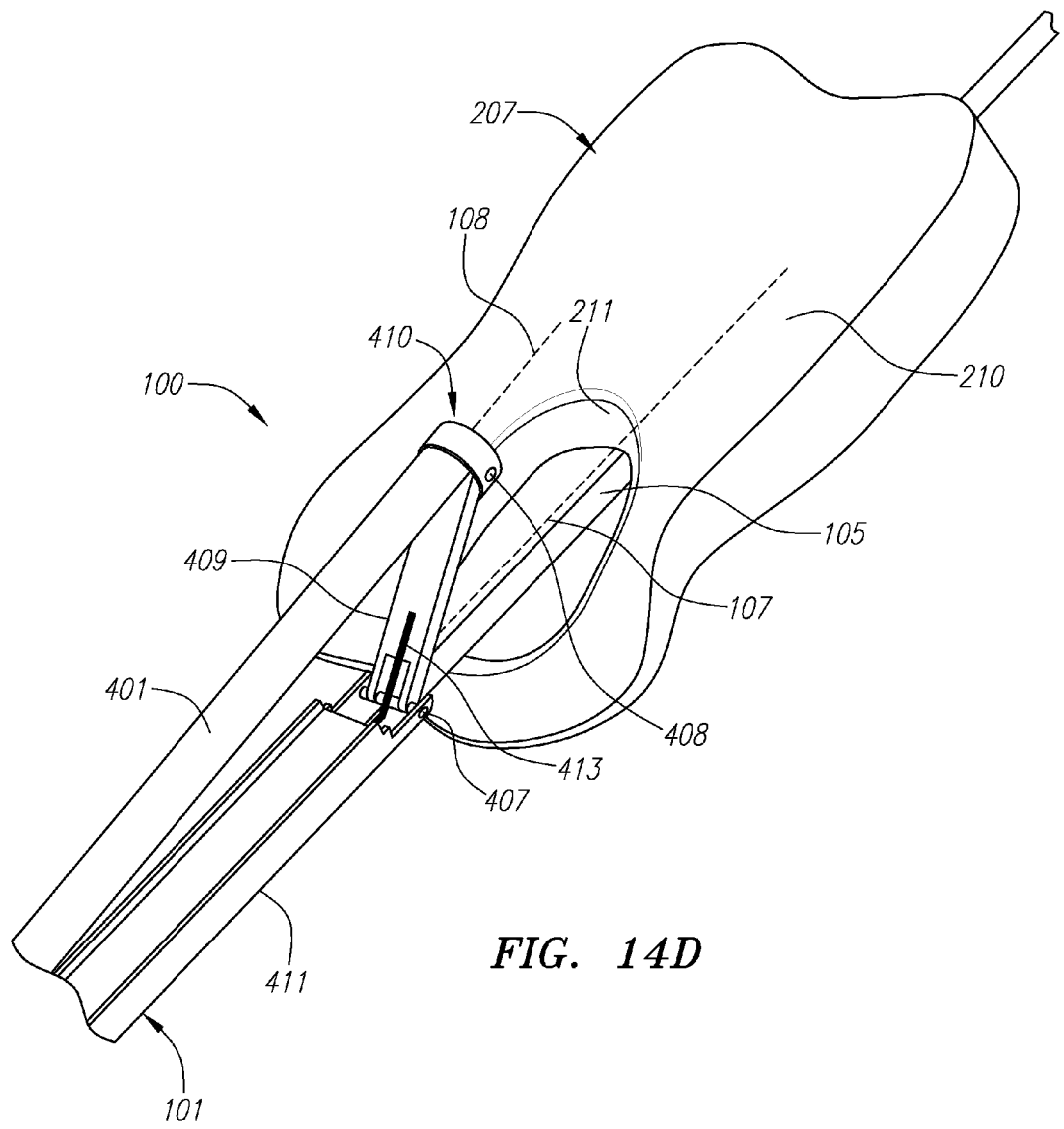
Figure 14E:
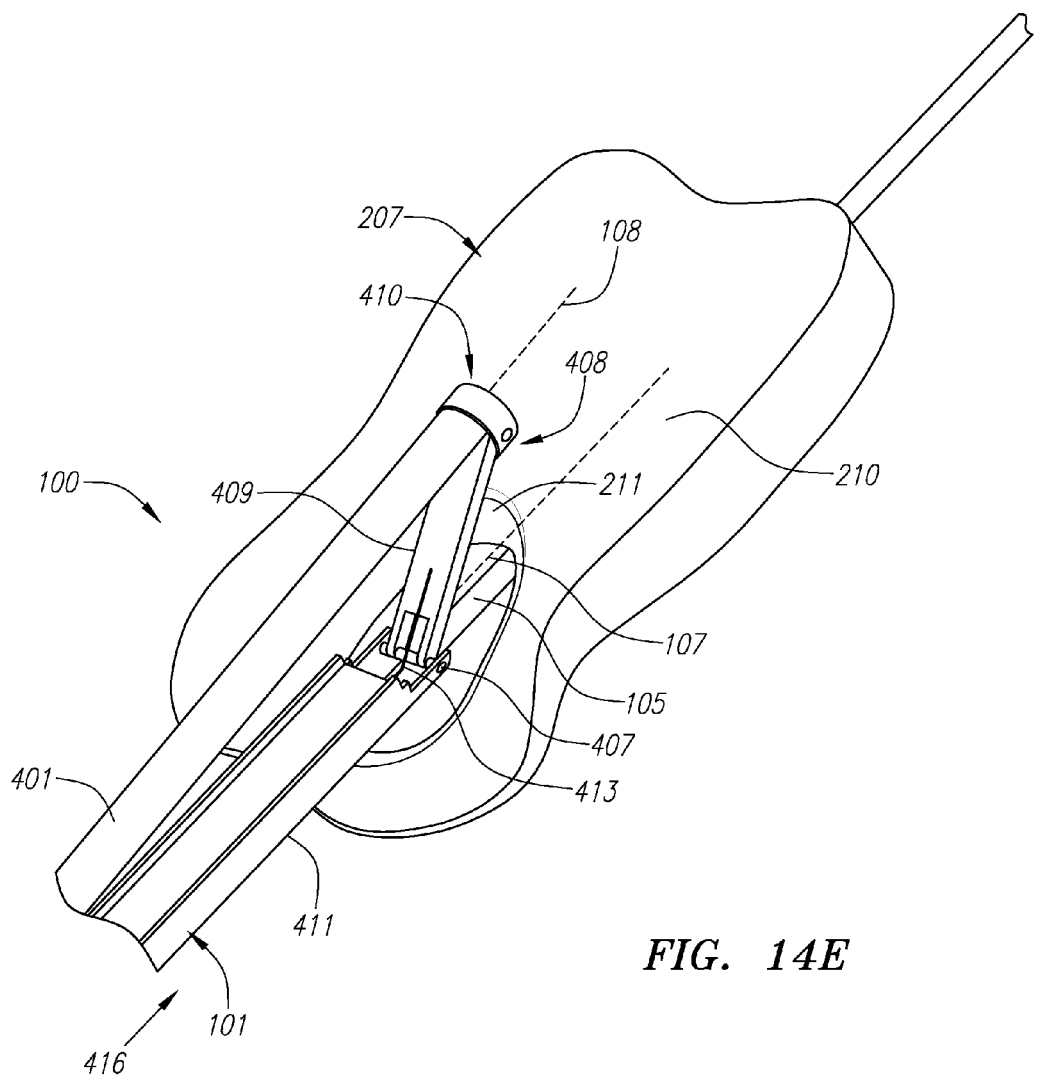

FIGS. 14C-F are perspective views depicting a portion of septal wall 207 and an additional exemplary embodiment of treatment system 100 during use of delivery device 104 prior to insertion of needle member 405. Here, the preferred location for insertion of needle member 405 is indicated by location 419. FIG. 14C depicts treatment system 100 with delivery device 401 in the on-axis position, where the longitudinal axes 107-108 are generally or substantially parallel. Stabilization device 105, the use and structure of which will be described in more detail below, is shown positioned within PFO tunnel 215. In FIG. 14D, OA delivery member 401 has been retracted proximally with respect to body member 101 and in opposition to bias member 413, causing distal end 410 to move away from stabilization device 105 by way of arm member 409 and hinges 407-408. In FIG. 14E, treatment system 100 is advanced distally in direction 416 until the underside surface 417 of arm member 409 abuts limbus 211, at which point OA delivery member 401 can be advanced distally with respect to body member 101 to force arm member 409 back towards stabilization device 105 to clamp, or grasp limbus 211 between arm member 409 and stabilization device 105, which is preferably in a substantially fixed position with respect to arm member 409. By grasping limbus 211 in this manner, treatment system is effectively anchored to septal wall 207.

Figure 14F:
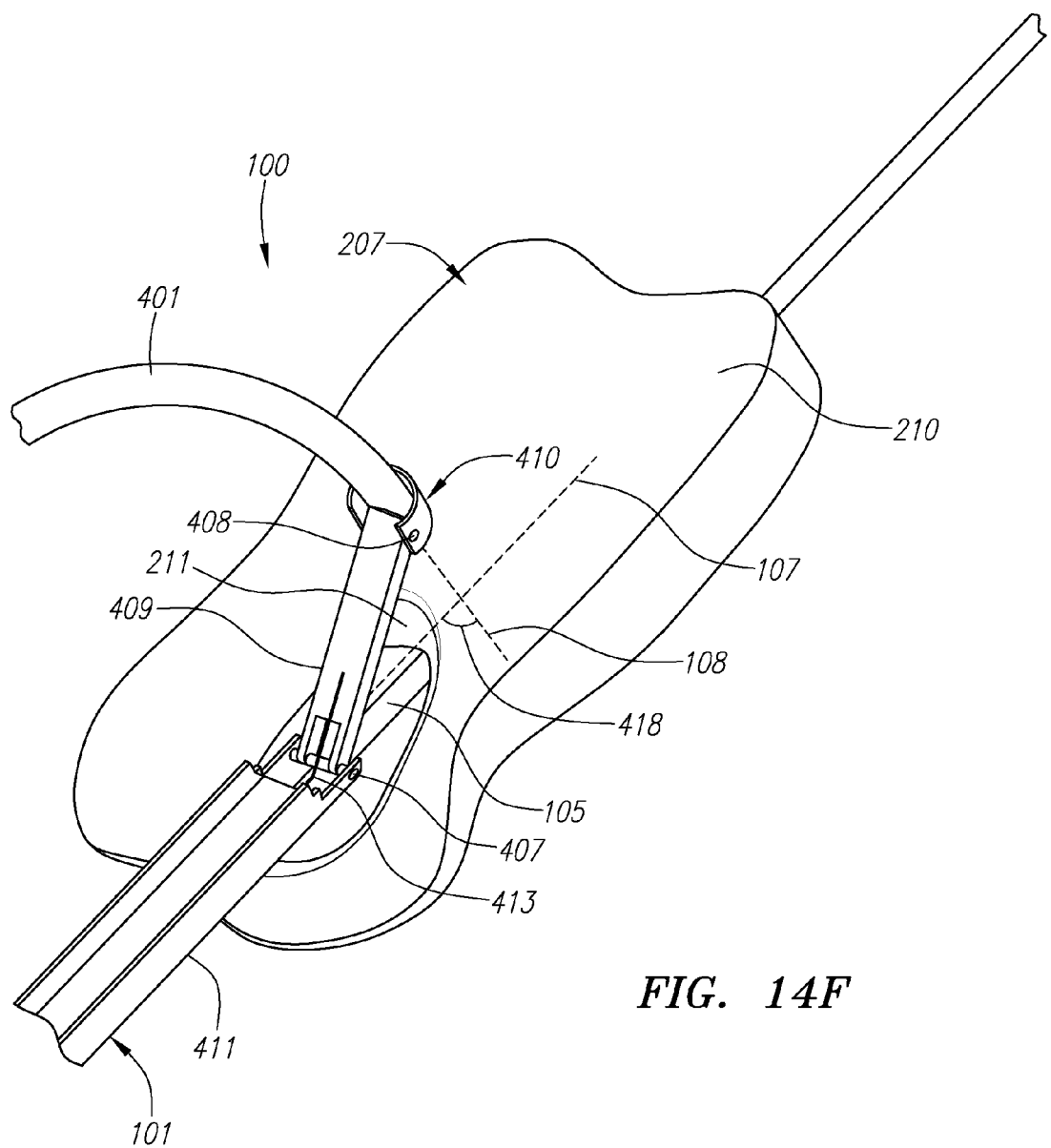

In FIG. 14F, OA delivery member 401 is further advanced distally with respect to body member 101, which causes OA delivery member to deflect, or arc outwards, in order to rotate distal end 410 about hinge 408 into the desired orientation with respect to septal wall 207. Distal end 410 is now preferably in contact with septal wall 207 at the desired needle insertion location 419. As shown here, OA delivery member 401 is in an outwardly arced state. The degree to which OA delivery member 401 arcs outwards can be adjusted by altering the length of OA delivery member 401 present outside of body member 101. Because needle member 405, pusher member 406 and implant 103 all preferably move within OA delivery member 401, the radius of curvature of the arc is preferably kept large enough to allow movement within OA delivery member 401. A very large radius of curvature can result in sharp angles or kinking in OA delivery member 401 that can make movement difficult.

As shown in FIG. 14F, longitudinal axis 108, as measured at distal end 410, is now transverse to longitudinal axis 107. Preferably, the delivery angle 418, which is the angle between longitudinal axis 107 and longitudinal axis 108 as measured at distal end 410, is approximately 90 degrees. Once distal end 410 is in the desired orientation, needle member 405 can be advanced into septal wall 207.

The needle insertion location 419 can be placed in any desired location, but should be chosen based in part on the configuration and size of implant 103 and the degree of overlap between septum primum 214 and septum secundum 210. For instance, in one exemplary embodiment, which is included for illustration only and in no way should be used to limit the inventive subject matter, needle insertion location 419 is placed between 3 and 7 mm from limbus 211. The position of needle insertion location 419 can be determined by the length of arm member 409, which in turn can position distal end 410 using limbus 211 as a point of reference. To allow for added flexibility, the length of arm member 409 can be configured to be adjustable during the implantation procedure. Thus, arm member 409 is preferably configured for at least two functions: (1) to stop travel of body member 101 at limbus 211 by abutting limbus 211 and (2) to position distal end 410 in the desired needle insertion location 419.

Figure 15A:
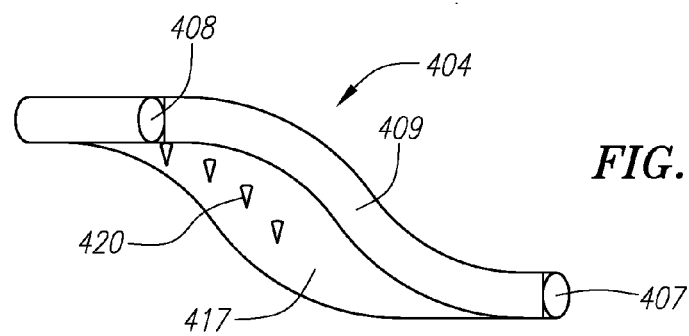
FIGS. 15A-D are perspective views depicting additional exemplary embodiments of the delivery device.

FIGS. 15A-D are perspective views depicting additional exemplary embodiments of grasping device 404 in a pulled back position. In FIG. 15A, arm member 409 is configured to engage limbus 211 with a contoured undersurface 417 that accommodates the shape of limbus 211 in order to facilitate grasping or engagement. Undersurface 417 can also be textured as desired to increase surface friction, or made lubricious to assist in friction-free centering, and, as shown here, undersurface can include abutments 420 configured to fixably grasp limbus 211. Also, it should be noted that any type of hinges 407-408 can be used including, but not limited to, the swivel-type hinges depicted here.

Figure 15B:
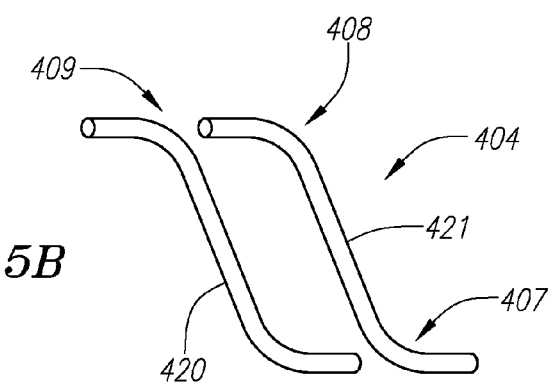
Figure 15C:
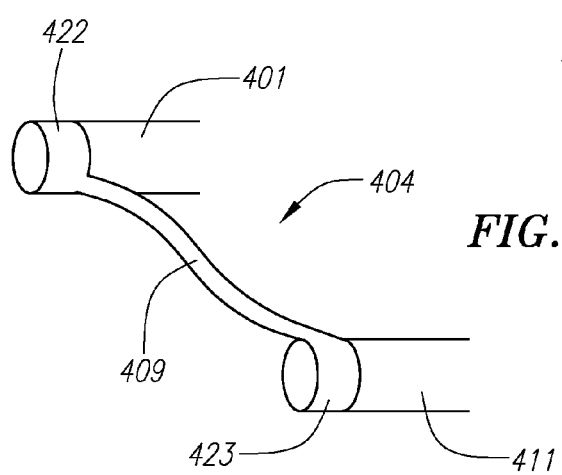

FIGS. 15B-C depict exemplary embodiments of grasping device 404 where hinges 407 and 408 are integrated into arm member 409. In FIG. 15B, arm member 409 includes two elastic wires 420 and 421 each configured to flex at hinge positions 407 and 408, e.g., by reducing the thickness of the material at the hinge positions. Arm member 409 is preferably biased towards a downwards position, which can allow elimination of any additional biasing element 413. In FIG. 15C, arm member 409 is configured to be both flexible and stretchable and can be composed of an elastomeric or rubber-like material or thin or slotted metal or polymeric material with the appropriate modulus. This flexibility and stretchability facilitates the conformance of arm member 409 to limbus 211. Here, arm member 409 includes tubular portions 422 and 423 for coupling arm member 409 with OA delivery member 401 and support structure 411, respectively.

Figure 15D:
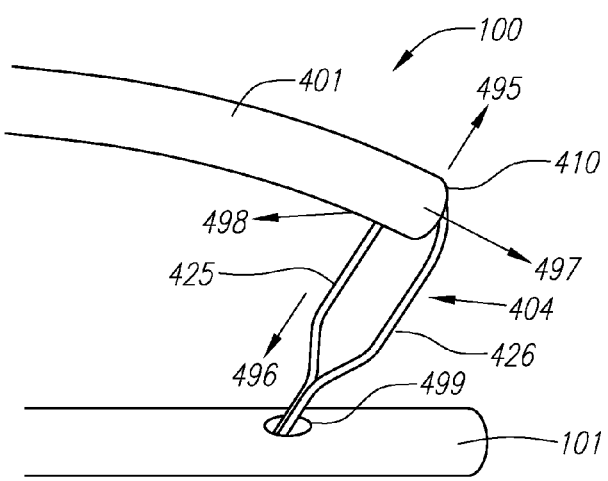

FIG. 15D is a perspective view depicting yet another exemplary embodiment of grasping device 404. Here, arm member 409 again includes two flexible wires 420 and 421 that can be coupled with OA delivery member 401. Like the embodiment described with respect to FIG. 15B, hinges 407 and 408 can be integrated into wires 420 and 421, which can be biased towards a downwards position. As shown in FIG. 15D, wires 425 and 426 are preferably routed through aperture 499 into a lumen 102 within body member 101 and to the proximal end of body member 101, where they can be independently adjusted to control, or steer, OA delivery member 401. For instance, distal movement of both wires 425 and 426 moves distal end 410 of OA delivery member 401 in direction 495 and proximal movement of both wires 425 and 426 moves distal end 410 of OA delivery member 401 in direction 496, as OA delivery member 401 permits. Distal advancement of wire 425 with respect to wire 426, alone or in combination with proximal movement of wire 426 with respect to wire 425, moves distal end 410 in lateral direction 497, while reverse movement moves distal end 410 in lateral direction 498, as OA delivery member 401 permits.

Figure 16A:
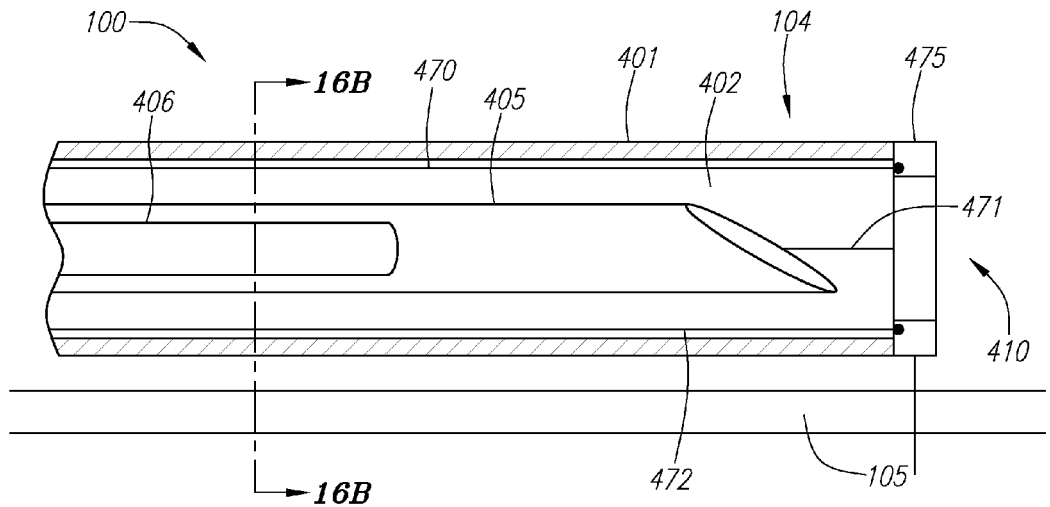
FIGS. 16A-B are cross-sectional views depicting additional exemplary embodiments of the treatment system.
Figure 16B:
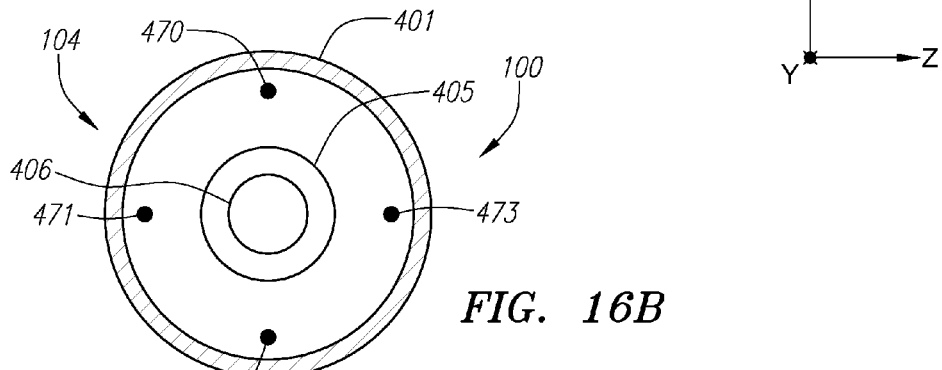

FIGS. 16A-B are cross-sectional views depicting additional exemplary embodiments of treatment system 100 with delivery device 104. FIG. 16A depicts a longitudinal cross-sectional view of treatment system 100 and FIG. 16B depicts a radial cross-sectional view of treatment system 100 taken along line 16B-16B of FIG. 16A. Here, delivery device 104 includes a steerable OA delivery member 401, which is configured to be freely steerable to position distal end 410 in the desired orientation at needle insertion location 419. Accordingly, distal end 410 is preferably left unconnected with any grasping device 404 (not shown). Preferably, steerability is provided through the use of one or more pull wires 424 coupled with distal end cap 475. In this embodiment, four pull wires 470-473 are equally spaced apart from each other within lumen 402. This configuration allows for manipulation of distal end 410 to any three-dimensional (X, Y, Z) orientation. For instance, pulling wire 470 back proximally with respect to wires 471-473, or pulling wire 472 back proximally with respect to wires 470-471 and 473 allows movement of distal end 410 in the X-Z plane. Pulling wire 471 back proximally with respect to wires 470 and 472-473, or pulling wire 473 back proximally with respect to wires 470-472 allows movement of distal end 410 in the Y-Z plane.

Figure 16C:
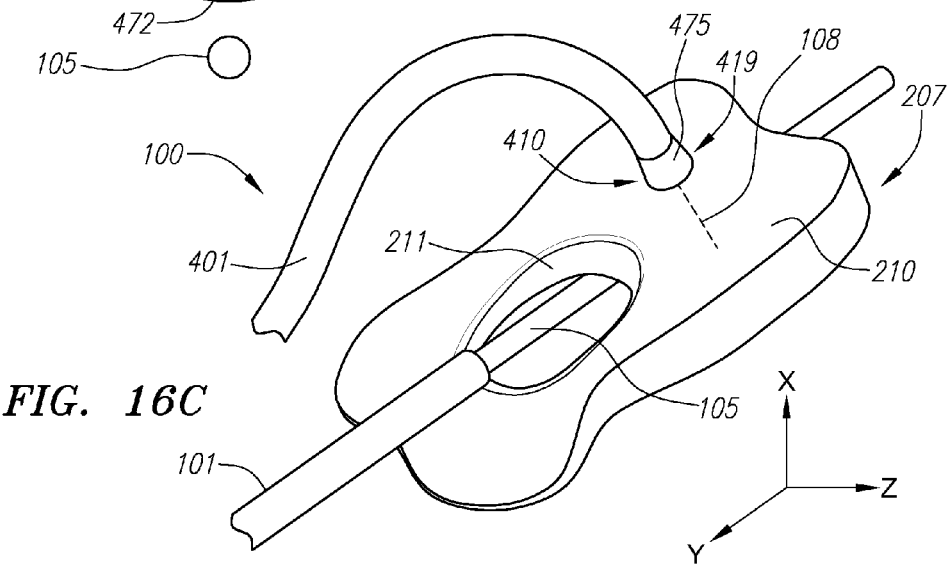
FIG. 16C is a perspective view depicting the embodiment described with respect to FIGS. 16A-B during delivery.

FIG. 16C is a perspective view depicting the embodiment described with respect to FIGS. 16A-B during delivery. Here, distal end 410 has been oriented in its needle insertion location 419 and longitudinal axis 108 lies within both the X-Z and Y-Z planes. The degree of steerability can be altered as desired for each individual application. For instance, the inclusion of additional pull back wires can provide for more finely controllable steerability, while the deletion of any of pull wires 470-473 can eliminate freedom of steerability, but can simplify the overall design of device 104. The design and use of steerable devices is also discussed in parent U.S. patent application Ser. No. 10/847,747, filed on May 7, 2004.

As mentioned above, OA delivery member 401 is preferably configured to allow slidable movement of needle member 405, pusher member 406 and implant 103 within inner lumen 402. Preferably, OA delivery member 401 is configured so as to maintain a sufficient degree of structural integrity and kink resistance, while at the same time providing adequate torque or twist control. In one exemplary embodiment, OA delivery member 401 is composed of a flexible braided metal reinforced polymeric tube configured to provide the desired amount of kink resistance and torque control. In other exemplary embodiments, OA delivery member 401 can be composed of a braided or unbraided polymeric tube. In yet another exemplary embodiment, OA delivery member 401 is composed of a metal tube having apertures located therein to provide added flexibility. For instance, OA delivery member 401 can be a NITINOL slotted tube, with the size and spacing of each slot configured for optimal flexibility, kink resistance and torque control. The apertures are preferably placed in a location corresponding to the portion of OA delivery member 401 that extends or arcs out, while the portion of OA delivery member 401 proximal to this can be left solid without apertures to maintain resilience in OA delivery member 401 and provide resistance to push back from needle member 405 as it penetrates septal wall 207.

Figure 17:
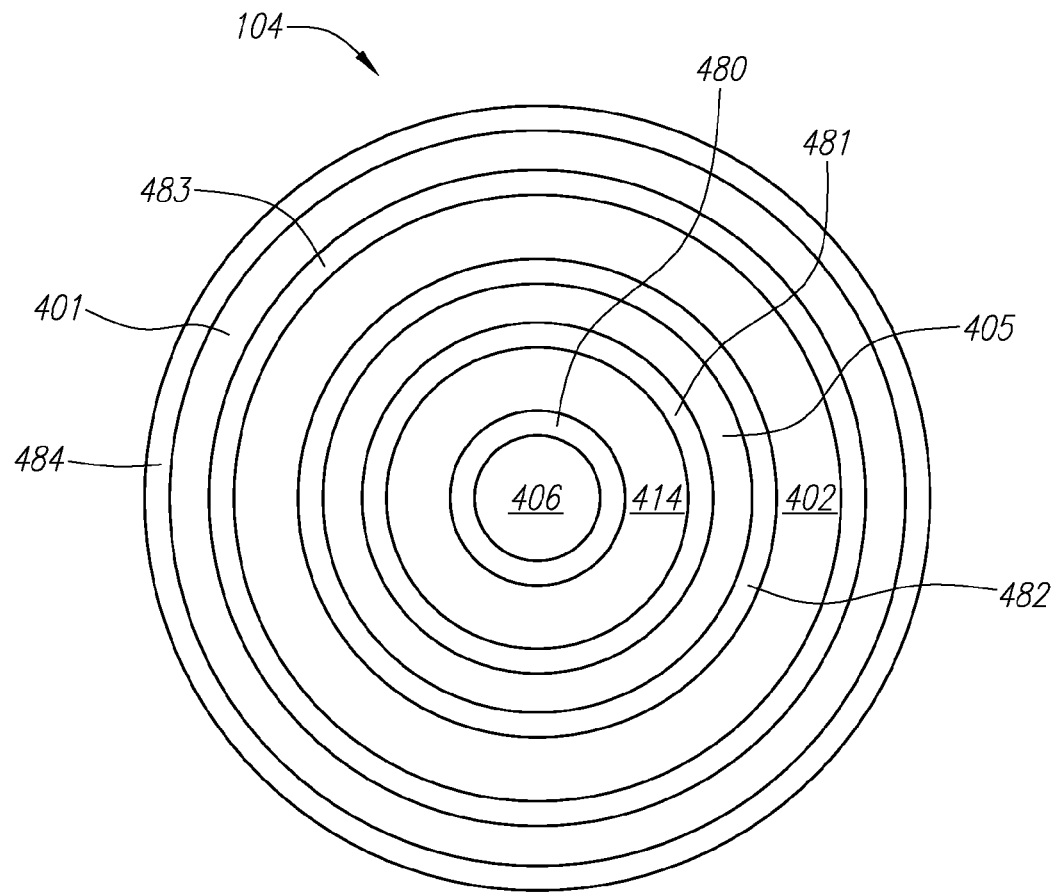
FIG. 17 is a cross-sectional view depicting an exemplary embodiment of the delivery device taken along line 17-17 of FIG. 14A.

Furthermore, OA delivery member 401 can be coated to provide low friction surfaces to facilitate advancement of OA delivery member 401 within body member 101 and the patient's body, as well as to facilitate movement of needle member 405 within lumen 402. Pusher member 406 and needle member 405 can be coated as well. For instance, FIG. 17 is a cross-sectional view depicting an exemplary embodiment of OA delivery member 401 taken along line 17-17 of FIG. 14A. Here, pusher member 406 includes an outer coating 480, needle member 405 includes both an inner coating 481 and an outer coating 482 and OA delivery member 401 includes both an inner coating 483 and an outer coating 484. Coatings 480-484 can be implemented for any purpose desired. For instance, in one embodiment, coatings 480-484 are composed of any material used to lower surface friction, including, but not limited to polymers such as polyethylene (PE), polytetrafluoroethylene, fluorinated ethylene/propylene copolymers, silicones, hydrogels, hydrophilic coatings or polyurethane (PU) and the like. Preferably, a high density PE material is used that is thin enough to provide the desired degree of flexibility while at the same time providing a low friction surface.

Figure 18A:
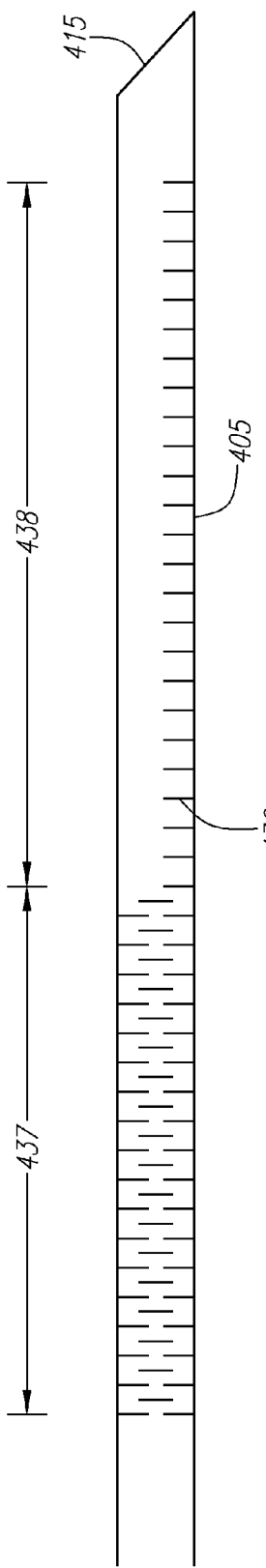
FIG. 18A is a cross-sectional view of an exemplary embodiment of a needle member.

Like OA delivery member 401, needle member 405 and pusher member 406 are also preferably flexible elongate members. FIG. 18A is a cross-sectional view of an exemplary embodiment of needle member 405. Distal end 415 of needle member 405 is preferably substantially sharp enough to penetrate the desired portion of septal wall 207. In this embodiment, distal end 415 is tapered similar to a conventional needle. Also, needle member 405 is preferably flexible enough to move within OA delivery member 401 when deflected for off-axis delivery.

For instance, needle member 405 can include one or more openings, or apertures 436, to increase flexibility. Here, needle member 405 includes multiple apertures 436 in various arrangements. Needle member 405 can be fabricated from any desired material including, but not limited to, NITINOL and stainless steel, and apertures 436 can be formed in any manner including, but not limited to, molding, milling, grinding, laser cutting, EDM, chemical etching, punching and drilling. The design and use of flexible needles is also discussed in parent U.S. patent application Ser. No. 10/847,747, filed on May 7, 2004.

Figure 18B:
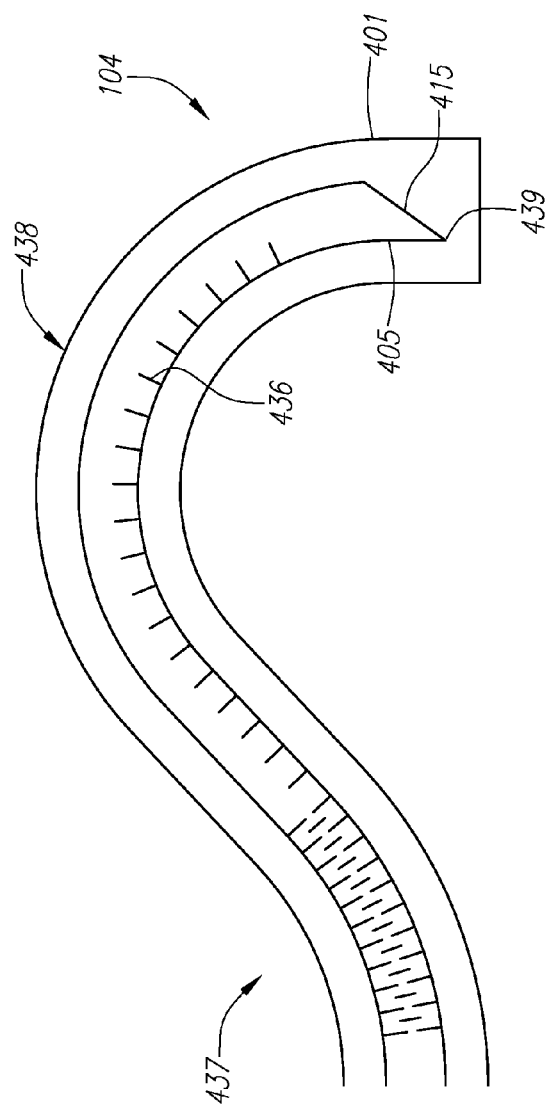
FIGS. 18B-C are cross-sectional views depicting additional exemplary embodiments of a delivery device.

A first region 437 of needle member 405 includes apertures 436 located at various intervals around the circumference of needle member 405. A second region 438, located distal to the first region 437, includes apertures 436 on the lower portion of needle member 405. FIG. 18B is a cross-sectional view depicting an exemplary embodiment of needle member 405 in a deflected state within an exemplary embodiment of OA delivery member 401. Because apertures 436 in region 437 are located around the circumference of needle member 405, region 437 is relatively more flexible than region 438. In region 438, placement of apertures 436 on the lower surface, reduces the possibility that implant 103 will catch or snag an aperture 436 during advancement of needle member 405 from OA delivery member 401. In addition, distal tip 439 of needle member 405 is also preferably aligned on the lower portion of needle member 405 to reduce the possibility that distal tip 439 will impact, catch, snag, or damage OA delivery member 401.

Treatment system 100 can be configured to apply a suction-type force to any surface of septal wall 207 to allow needle member 405 to more easily penetrate the septal tissue without excessive "tenting" of septal wall 207 in response to the pressure applied by needle member 405. For instance, the proximal end of OA delivery member 401 can be coupled with a vacuum or pressure adjustment device configured to lower the air or fluid pressure within OA delivery member 401. The pressure is preferably lowered to a degree sufficient to create a suction-type force between OA delivery member 401 and septal wall 207 thereby keeping septal wall 207 in contact or in proximity with OA delivery member 401 while needle member 405 is advanced into septal wall 207. Also, the suction-type force can be applied through needle member 405 instead of, or in addition to OA delivery member 401.

Treatment system 100 preferably includes one or more sensors to facilitate determination of when needle member 405 has entered left atrium 212. For instance, in one exemplary embodiment, needle member 405 includes a sensor at or near distal end 415. The sensor can be any type of applicable sensor, such as a pressure sensor, thermal sensor, imaging device, acoustic device and the like. In one exemplary embodiment, a pressure sensor is included that is configured to sense the blood pressure change between right atrium 205 and left atrium 212. The pressure sensor can be any type of pressure sensor including, but not limited to, an electrical sensor and a fluid feedback sensor such as a lumen within needle member 405 having an open distal end in fluid communication with the exterior environment. In an alternative exemplary embodiment, distal end 415 of needle member 405 is configured to be visible by an external or internal imaging device, which can then be used to track the position of distal end 415 with respect to septal wall 207.

Figure 18C:
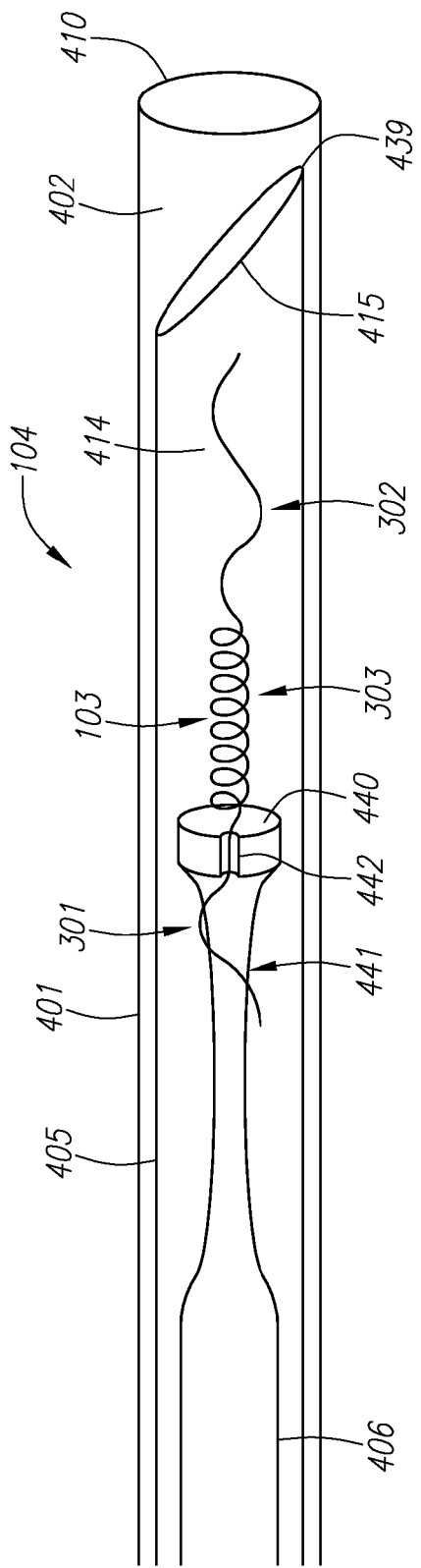

FIG. 18C is a cross-sectional view of another exemplary embodiment of delivery device 104. Here, distal end 440 of pusher member 406 is configured to push against central portion 303 of implant 103 as opposed to end tip 307 of RA portion 301. This reduces the likelihood that RA portion 301 will coil when pushed within lumen 414, which could result in bunching of implant 103 within lumen 414 making delivery more difficult. Because distal end 440 of pusher member 406 is located distal to RA portion 301, pusher member 406 includes a relatively thinner portion 441 that can provide additional room for RA portion 301 within lumen 414 as well as provide added flexibility to pusher member 406. Relatively thinner portion 441 is relatively thinner than distal end 440, which is preferably thick enough to adequately engage central portion 303. Distal end 440 can include a recess 442 to provide enough room for RA portion 301. Recess 442 can also be used to help position implant 103 during delivery. For instance, rotation of pusher member 406 can cause implant 103 to rotate if implant 103 is still routed through recess 442. This can allow the proper rotational orientation of implant 103 before or during delivery into septal wall 207. Distal end surface 443 can be configured in any manner desired to facilitate proper contact and engagement of implant 103.

Figure 19A:
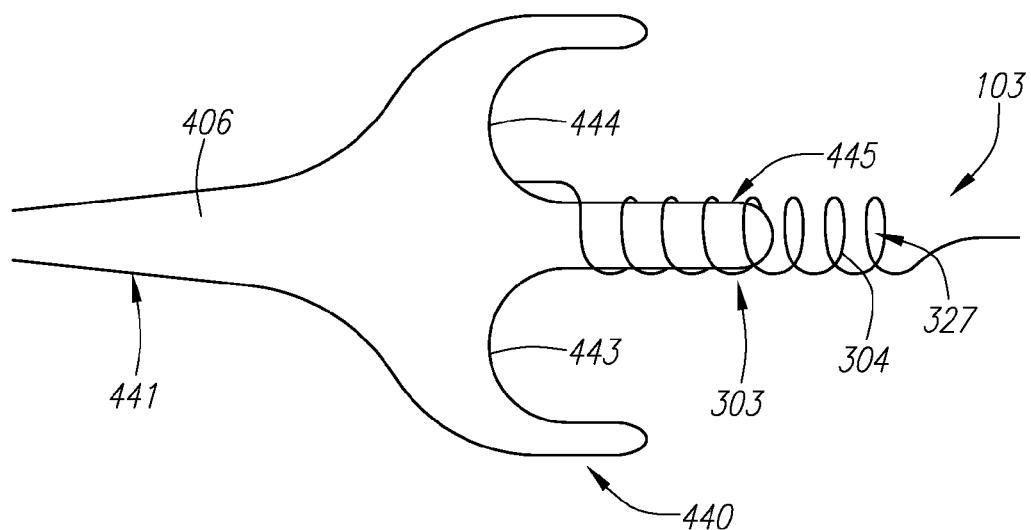
FIGS. 19A-B are cross-sectional views depicting exemplary embodiments of a delivery device and an implantable treatment device.
Figure 19B:
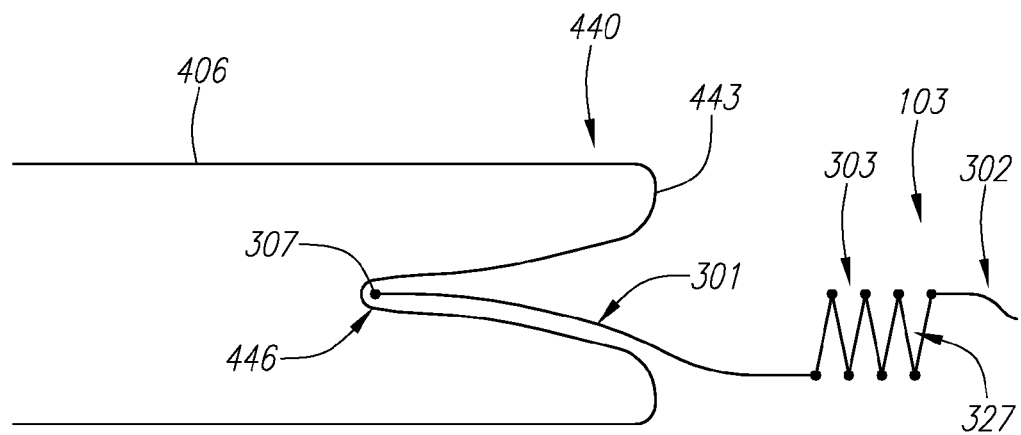

For instance, FIGS. 19A-B are cross-sectional views depicting exemplary embodiments of pusher member 406 and implant 103. In FIG. 19A, distal end surface 443 is contoured with a rounded recessed portion 444 into which a coiled central portion 303 can rest and an elevated portion 445 configured to fit within open interior region 327. As one of skill in the art will readily recognize, the contours of distal end surface 443 are dependent on the type and housed configuration of implant 103, as well as the desired point of contact on implant 103. In FIG. 19B, distal end surface 443 is contoured with a narrow recessed portion 446 into which end tip 307 of RA portion 301 can rest.

Pusher member 406 can also be configured to releasably couple with implant 103. For instance, in one exemplary embodiment, pusher member 406 is tethered to implant 103 with a tether 485 in order to allow implant 103 to be drawn back into needle member 405 if needed, such as in a case of improper deployment. If implant 103 is properly deployed, tether 485 can be released from pusher member 406. In another exemplary embodiment, pusher member 406 can be configured to both push and pull implant 103 while within needle member 405, as depicted in FIGS. 20A-B.

Figure 20A:
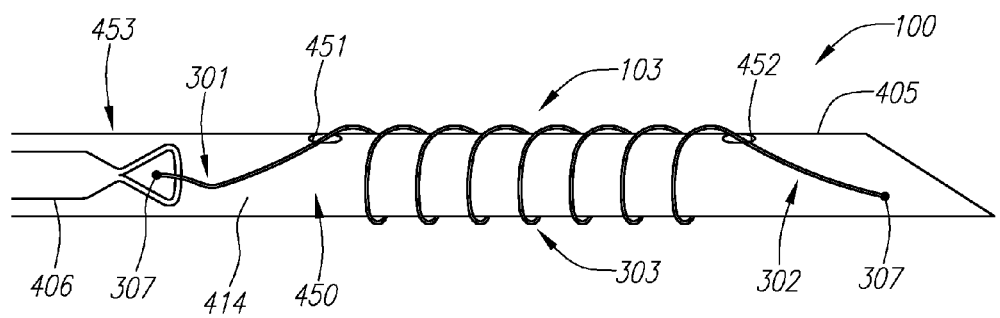
FIGS. 20A-B are schematic views depicting additional exemplary embodiments of a delivery device and an implantable treatment device.
Figure 20B:
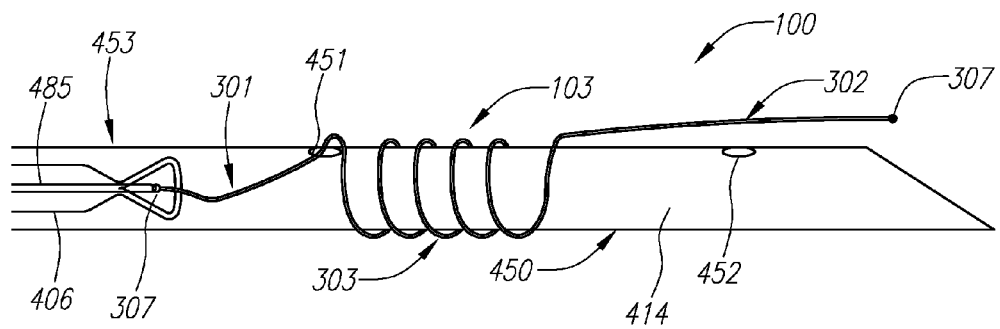

FIGS. 20A-B are schematic views depicting additional exemplary embodiments of needle member 405, pusher member 406 and implant 103. In FIG. 20A, implant 103 is placed over outer surface 450 of needle member 405 and end tips 307 of RA portion 301 and LA portion 302 can be routed through apertures 451 and 452, respectively, and housed within lumen 414. To deliver implant 103, after needle member 405 has traversed septal wall 207 into left atrium 212, pusher member 406 is used to pull implant 103 back proximally to expose end tip 307 of LA portion 302 as depicted in FIG. 20B. To grasp end tip 307, pusher member 406 can include any type of grasping device desired. Here, pusher member 406 includes a clamp-type device 453. Once removed from aperture 452, LA portion 302 can enter the coiled state. As needle member 405 is withdrawn back through septal wall 207, LA portion 302 engages septal wall 207 and cause implant 103 to slide off needle member 405. Pusher member 406 can also be used to push end tip 307 of RA portion 301 to facilitate deployment. In this embodiment, proximally located end tip 307 includes an aperture through which a tether 485 is routed for use as described above.

Figure 21:
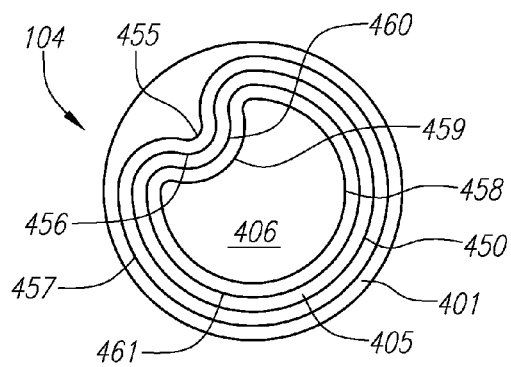
FIG. 21 is a cross-sectional view depicting another exemplary embodiment of a delivery device taken along lines 21-21 of FIG. 14A.

Delivery device 104 can be configured to maintain the proper orientation of OA delivery member 401, needle member 405, pusher member 406 and implant 103 during delivery. FIG. 21 is a cross-sectional view depicting another exemplary embodiment of delivery device 104 taken along lines 21-21 of FIG. 14A where delivery device 104 is configured to use a lock and key technique to maintain proper orientation. Here, the lock and keys are implemented with a combination of abutments and corresponding recesses. For instance, outer surface 450 of needle member 405 includes a recess 456 configured to receive an abutment 455 located on inner surface 457 of OA delivery member 401. Recess 456 can extend longitudinally along needle member 405 for any desired distance to ensure proper orientation even when needle member 405 is advanced and retracted within OA delivery member 401. Similarly, outer surface 458 of pusher member 406 includes a recess 459 configured to receive an abutment 460 located on inner surface 461 of needle member 405. Like recess 456, recess 459 can extend longitudinally along pusher member 406 for any desired distance to ensure proper orientation when pusher member 406 is advanced and retracted. As discussed above with respect to FIGS. 18A-B, pusher member 406 can include recess 442 to accommodate for the presence of RA portion 301. This recess 442 can also maintain implant 103 in the proper orientation with respect to pusher member 406.

The distances that OA delivery member 401, needle member 405 and pusher member 406 are moved proximally and distally with respect to body member 101, can be relatively small. Manual movement of these components, while possible, can be difficult. Treatment system 100 can include one or more automated systems or devices at the proximal end of body member 101 to facilitate movement of these components and lessen the risk that each component is inadvertently advanced too far or not enough. The automated systems or devices can also be configured to apply the desired amount of force to move each component and sense if too much force is being used, which could be indicative of an error in the delivery process.

To further facilitate movement of OA delivery member 401, needle member 405 and pusher member 406, each can be optionally pre-shaped. For instance, in one exemplary embodiment, one or more of OA delivery member 401, needle member 405 and pusher member 406 can include a curved section that corresponds to the desired deflected arc shape of OA delivery member 401 depicted in FIG. 14F.

It should also be noted that needle member 405 can be excluded from system 100 altogether. Pusher member 406 can deploy implant 103 through a pre-existing hole, or implant 103 can be configured with a substantially sharp end tip 307 for creation of a hole while being deployed by pusher member 406.

Figure 22:
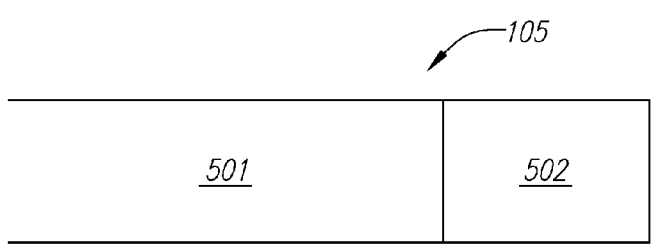
FIG. 22 is a block diagram depicting an exemplary embodiment of a stabilization device.

As described with respect to FIG. 1, treatment system 100 can optionally include stabilization device 105. FIG. 22 is a block diagram depicting an exemplary embodiment of stabilization device 105 within treatment system 100. Here, stabilization device 105 is preferably configured to stabilize treatment system 100 during delivery of implant 103. Stabilization device 105 can have any configuration desired in accordance with the needs of the application. For instance, stabilization device 105 can be configured as a body routed through PFO tunnel 215 or any portion of the patient's vasculature, such as superior vena cava 203. Stabilization device 105 preferably includes an elongate stabilization member 501 and can optionally include grasping device 502, which is preferably configured to grasp nearby tissue in order to facilitate stabilization.

Figure 23A:
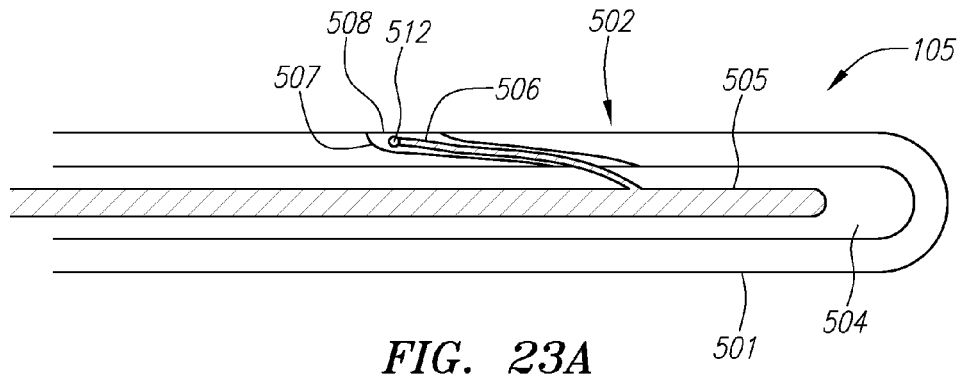
FIGS. 23A-C are cross-sectional views depicting additional exemplary embodiments of a stabilization device.
Figure 23B:
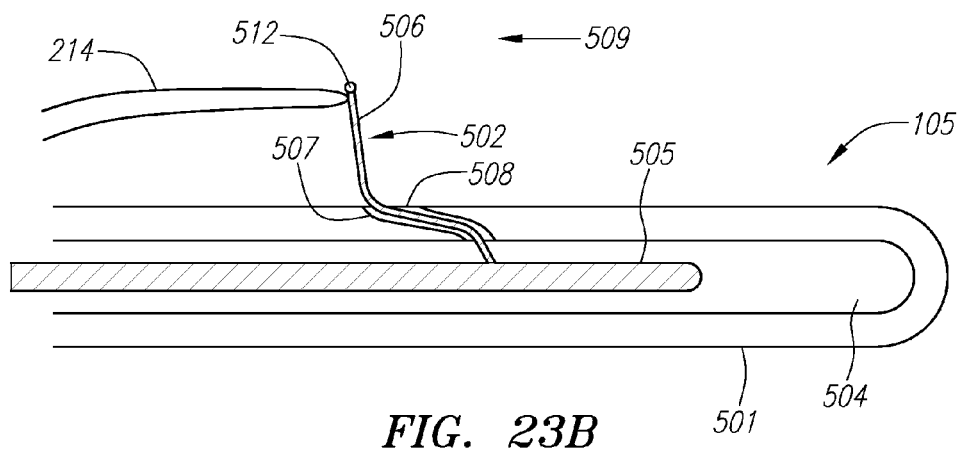
Figure 23C:
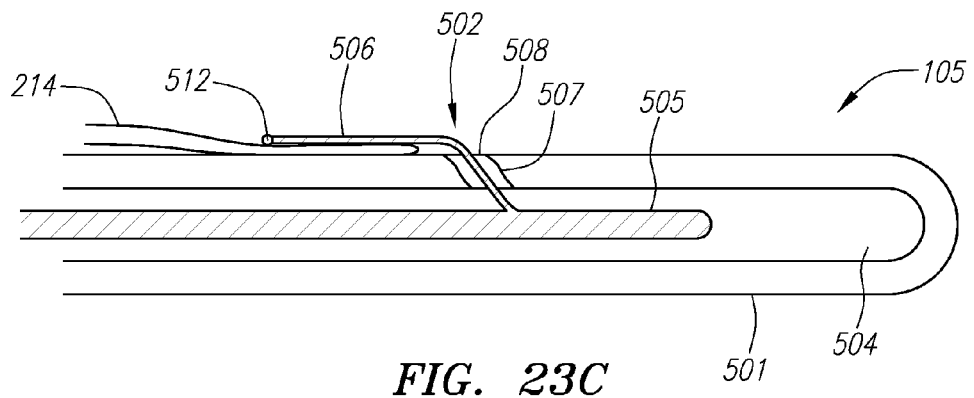

FIGS. 23A-C are cross-sectional views depicting additional exemplary embodiments of stabilization device 105 being used to in an exemplary method of stabilizing treatment system 100. Here, stabilization member 105 is configured as an elongate member including an outer tubular sheath 501 having an inner lumen 504 configured to slidably receive inner elongate pull member 505. Outer tubular sheath 501 and inner pull member 505 are preferably semi-rigid, having enough rigidity to stabilize treatment system 100 while at the same time having enough flexibility to allow movement and manipulation within the patient's vasculature and heart 200. In these embodiments, stabilization device 105 is preferably configured to be routed from right atrium 205 through PFO tunnel 215 into left atrium 212, where grasping device 502 can be used to cover a portion of septum primum 214 and anchor stabilization device 105 thereto.

The nature of the tissue forming septum primum 214 can be irregular, for instance including overlapping folds, variations in tissue thickness and variations in distensibility, each of which can cause septum primum 214 to move, or tent, when needle member 405 is advanced through. The inclusion of grasping device 502 can also provide the additional advantage of holding septum primum 214 in place and reducing the risk of tenting.

Grasping device 502 preferably includes a flexible grasping element 506 coupled with inner pull member 505. Here, grasping element 506 is configured as a rectangular element. Outer tubular sheath 501 preferably includes lumen 507 having open distal end 508, from which grasping element 506 can be deployed. Lumen 507 can be configured with contoured sidewalls to facilitate deployment of grasping element 506. To deploy grasping element 506, inner member 505 can be pulled in a proximal direction with respect to outer sheath 501, causing grasping element 506 to advance through lumen 507 and out of distal end 508. Grasping element 506 can optionally include an atraumatic end 512, which in this embodiment is a radio-opaque element, which may be gold or platinum. In this embodiment, grasping element 506 is configured as a deformable, pre-shaped element having three main configurations.

FIG. 23A depicts grasping element 506 in a first configuration housed within lumen 507. This configuration is preferably used while treatment system 100 is moved through the patient's vasculature and as well as when stabilization device 105 traverses PFO tunnel 215, as depicted here. FIG. 23B depicts grasping element 506 in a second configuration partially deployed from within lumen 507. Once stabilization device 105 is advanced through PFO tunnel 215 and out of PFO exit 218, grasping element 506 is preferably deployed to this configuration by pulling inner member 505 proximally with respect to outer sheath 501. In this configuration, grasping element 506 can be used to catch the edge of septum primum 214 as stabilization device 105 is pulled slightly back in proximal direction 509. FIG. 23C depicts grasping element 506 in a third, fully deployed configuration, after inner member 505 has been pulled back further. Grasping element 506 can optionally include a recess configured to engage an abutment on outer sheath 501 in this configuration, which is preferably used to more fully grasp or engage septum primum 214 to anchor stabilization device 105 thereto.

Once the delivery procedure is complete, inner member 505 can be advanced distally with respect to outer sheath 501 to draw grasping element 506 back within lumen 507. Any component of treatment system 100 adequately coupled with stabilization device 105 is thereby also anchored to septum primum 214. One of skill in the art will readily recognize that this and similar embodiments of stabilization device 105 can be used to engage any tissue flap or edge desired, not solely septum primum 214.

Grasping device 502 can be configured in any manner desired in accordance with the needs of the application. FIGS.

Figure 24A:
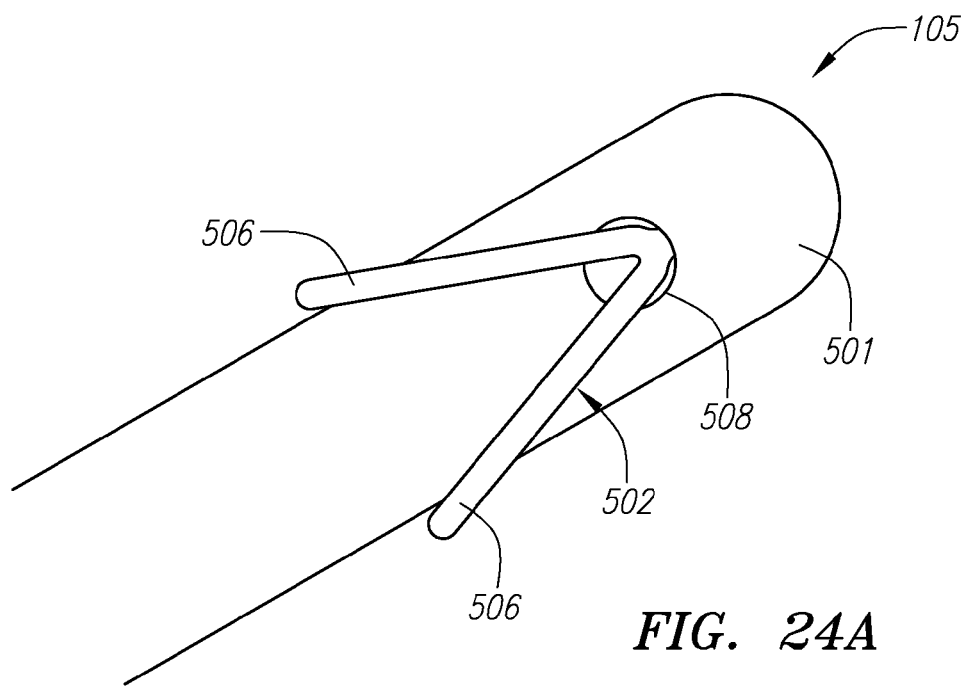
FIGS. 24A-B are perspective views depicting additional exemplary embodiments of a stabilization device.
Figure 24B:
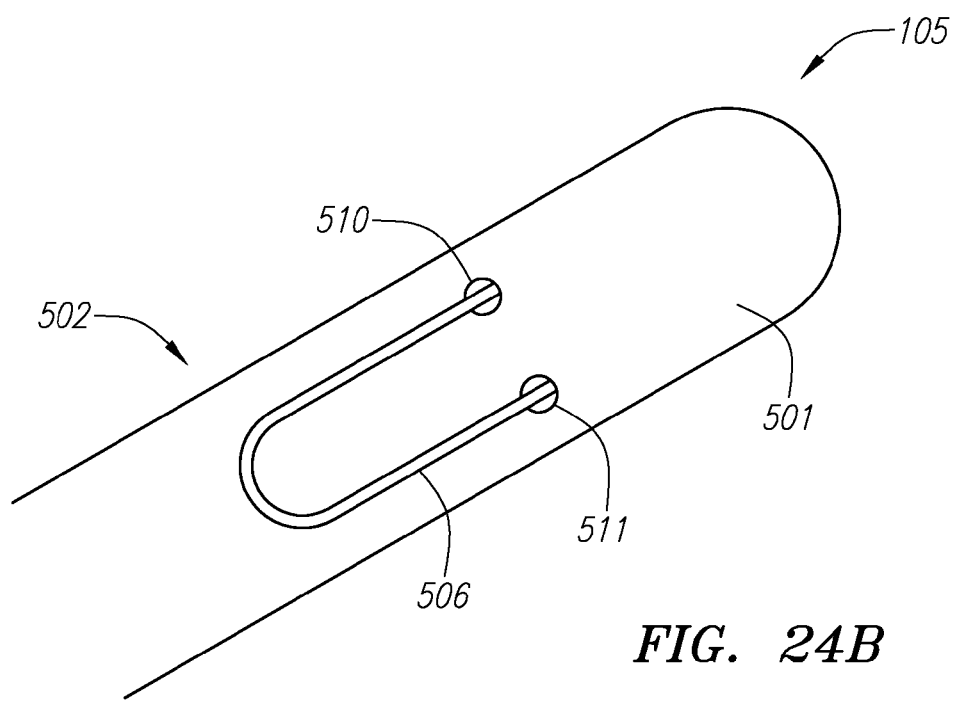

24A-B are perspective views depicting additional exemplary embodiments of stabilization device 105 with grasping device 502. In FIG. 24A, grasping device 502 includes multiple grasping elements 506 for grasping over a wider area. In FIG. 24B, grasping device 502 includes a wire-like grasping element 506. Here, grasping element 506 is looped into lumen 507 (not shown) via apertures 510 and 511, which communicate with lumen 507.

Figure 25A:
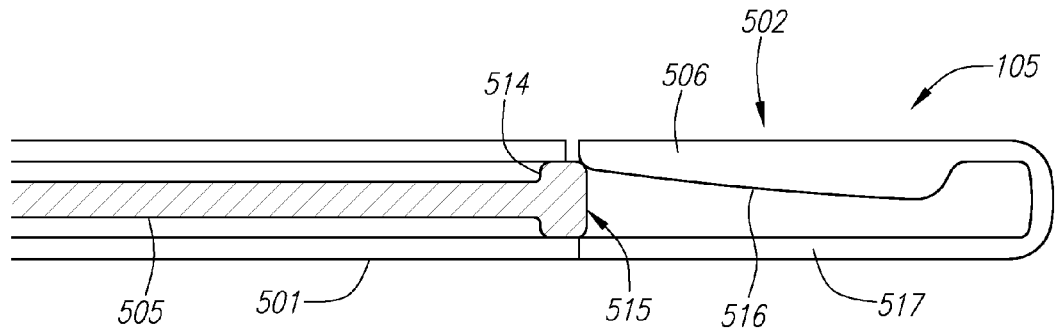
FIGS. 25A-D are cross-sectional views depicting additional exemplary embodiments of a stabilization device.
Figure 25B:
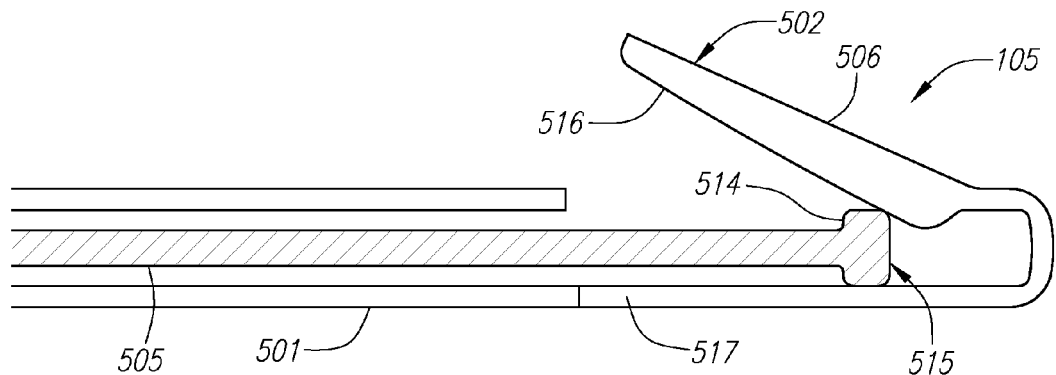
Figure 25C:
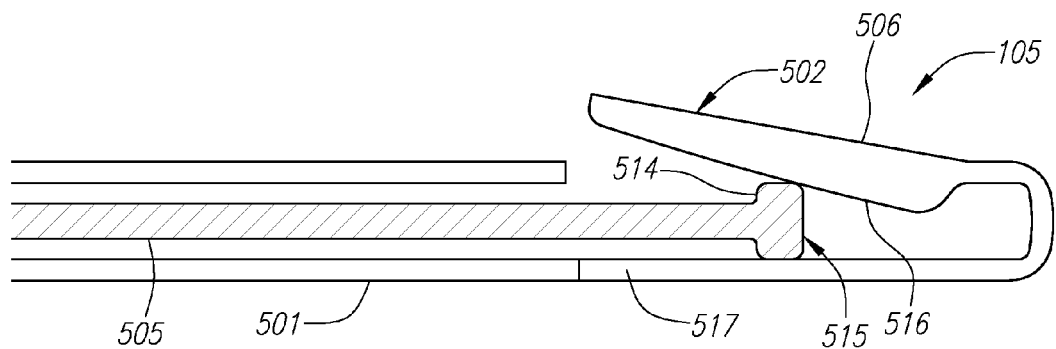
Figure 25D:
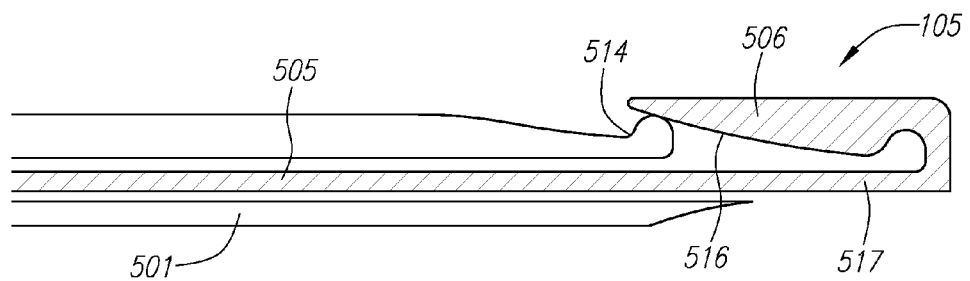

FIGS. 25A-D are cross-sectional views depicting additional exemplary embodiments of stabilization device 105. Here, grasping element 506 has a flap-like shape with tapered inner surface 516 and is located on distal end member 517 of outer sheath 501. Inner member 505 includes an abutment 514 on distal end portion 515 and is configured to push against and apply a force to grasping element 506. FIG. 25A depicts grasping element 506 in the first, housed configuration. To deploy grasping element 506 to the second configuration for catching septum primum 214, inner member 505 is advanced distally with respect to outer sheath 501 as depicted in FIG. 25B. Because of tapered inner surface 516, the more inner member 505 is advanced distally, the more outwards deflection of element 506 will occur. To more fully grasp septum primum 214, inner member 505 (and body member 101, if necessary) is retracted proximally by the desired amount, as depicted in FIG. 25C. Manufacture of this embodiment can be made relatively simple. For instance, distal end member 517 and grasping element 506 can be formed by laser or EDM cutting a NITINOL tube. In FIG. 25D, distal end member 517 is located on distal end of inner member 505 and abutment 514 is located on sheath 501.

Figure 26A:
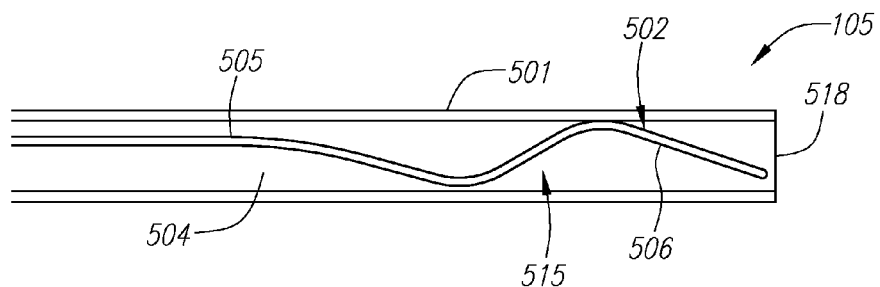
FIGS. 26A-C are cross-sectional views depicting additional exemplary embodiments of a stabilization device.
Figure 26B:
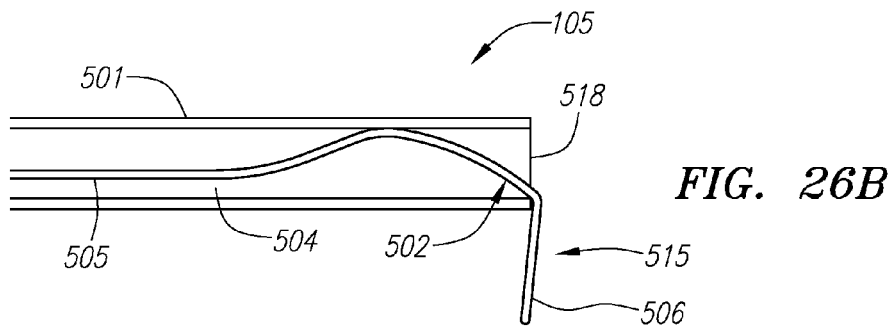
Figure 26C:
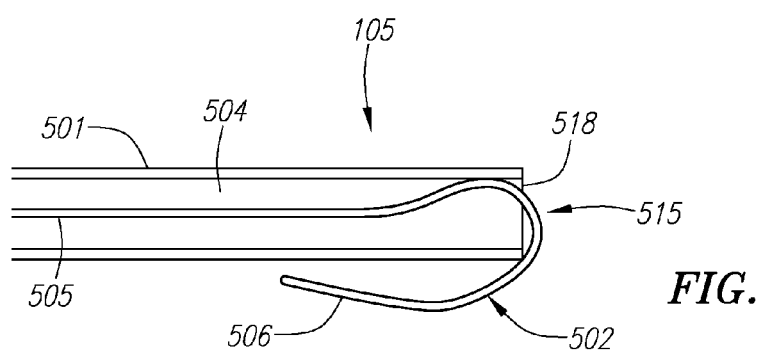

FIGS. 26A-C are cross-sectional views of additional exemplary embodiments of stabilization device 105. Here, outer sheath 501 preferably includes an open distal end 518, from which grasping device 502 can be deployed. Grasping element 506 is preferably located on distal end portion 515 of inner member 505 and can be formed of a deformable elastic material such as stainless steel, NITINOL, shape memory polymers and the like. Grasping element 506 is preferably configured to be slidable within inner lumen 504 and is preferably pre-shaped, such as by heat-treating NITINOL, so that grasping element 506 can assume a desired shape when advanced from inner lumen 504. In FIG. 26A, grasping element 506 is depicted in the first, housed configuration within inner lumen 504. In FIG. 26B, inner member 505 has been advanced distally to deploy grasping element 506 in the second configuration for catching septum primum 214. In FIG. 26C, inner member 505 has been advanced further distally to place grasping element 506 in the third configuration for grasping septum primum 214. Embodiments of stabilization device 105 where grasping device 502 can be deployed by pushing grasping device 502 out from within inner lumen 504, such as that described with respect to FIGS. 26A-C, will be referred to herein as "push out" embodiments.

Figure 27A:
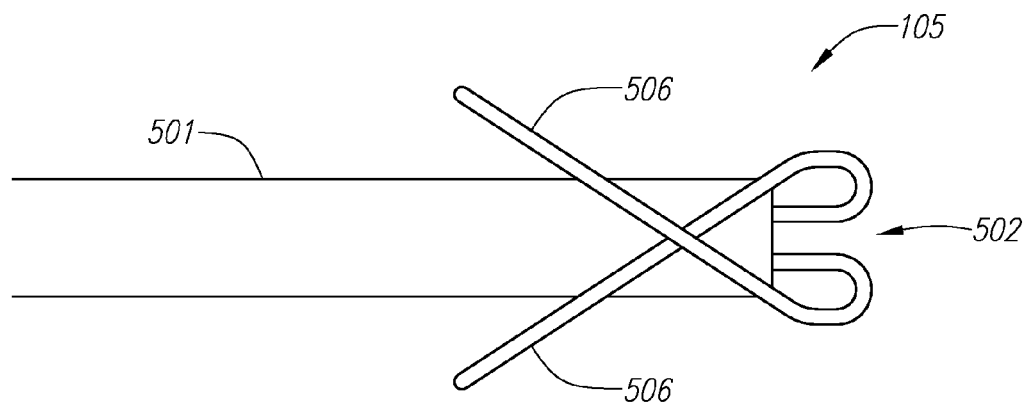
FIG. 27A is a perspective view depicting an additional exemplary embodiment of a stabilization device.
Figure 27B:
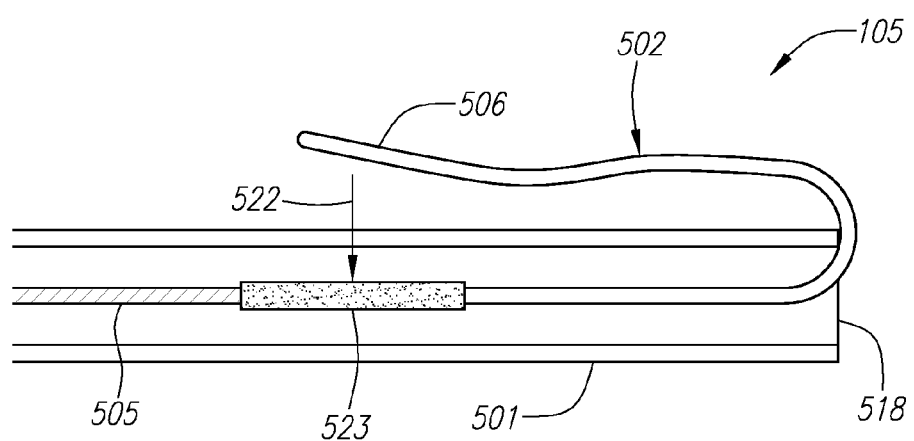
FIG. 27B is a cross-sectional view depicting another exemplary embodiment of a stabilization device.

FIG. 27A is a perspective view depicting an additional exemplary embodiment of stabilization device 105 having a "push-out" grasping device 502. Here, grasping device 502 is shown in the fully deployed third configuration having two grasping elements 506. It should be noted that grasping device 502 can include any number of grasping elements 506. Here, each grasping element 506 overlaps so as to provide additional grasping force at location 419 where needle member 405 insertion occurs. FIG. 27B is a cross-sectional view depicting another exemplary embodiment where grasping element 506 is configured to attract to a magnetic force 522 provided by magnet 523 coupled with inner member 505. Once deployed, the magnetic force is preferably great enough to penetrate outer sheath 501 and septum primum 214 and attract elements 506 to provide additional grasping force. Of course, magnet 523 can be placed in any desired location, for instance, on outer sheath 501 at distal end 518 or on grasping element 506, in which case inner member 505 could be configured to attract to the magnetic force, or any combination thereof.

It should be noted that, in order to provide additional surface friction, additional abutments can be included on grasping element 506 and/or the surface of grasping element 506 can be etched or coated or otherwise textured.

As discussed with respect to FIG. 1, treatment system 100 can include centering device 106 to facilitate proper placement of implant 103. Centering device 106 can be configured to align delivery device 104 in the desired location with respect to the center of PFO tunnel 215. Although the term "centering" is used, it should be understood that centering device 106 can be configured to align delivery device 104 in any location, not necessarily the center of PFO tunnel 215.

Figure 28A:
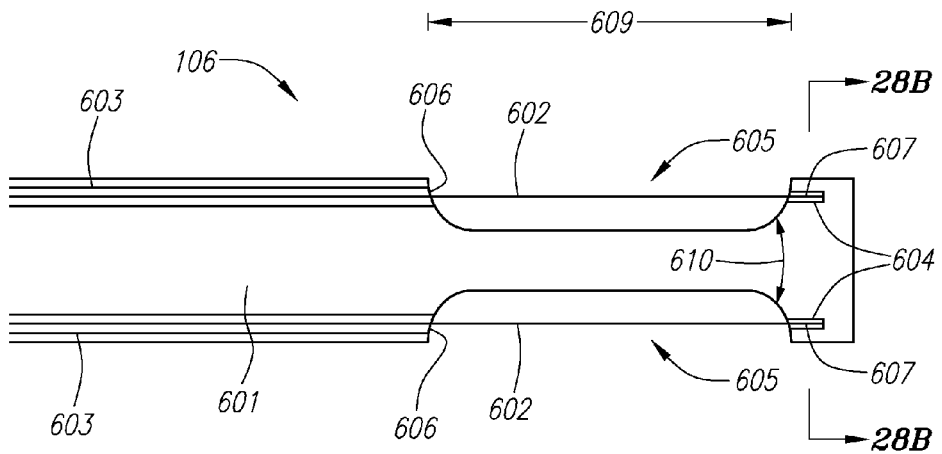
FIGS. 28A-C are cross-sectional views depicting additional exemplary embodiments of a centering device.
Figure 28B:
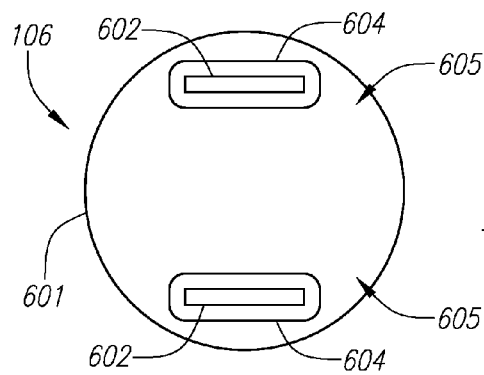
Figure 28C:
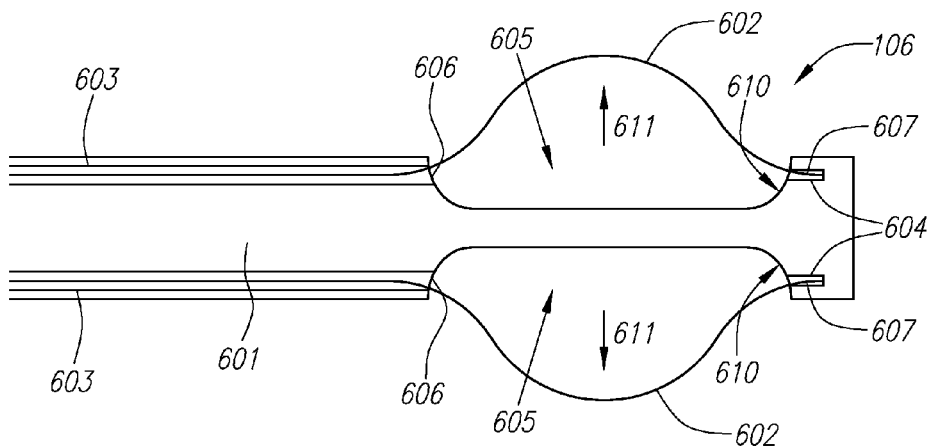

FIGS. 28A-C are cross-sectional views depicting additional exemplary embodiments of centering device 106. In this embodiment, centering device 106 includes an elongate centering support member 601 having two elongate flexible positioning members 602, referred to herein as centering arms 602, located on opposite sides of and extending along the length of support member 601. Support member 601 can include two lumens 603, each configured to slidably receive a centering arm 602. Each lumen 603 preferably has an open distal end 606 which opens to an open or recessed portion 605 of support member 601. Each centering arm 602 preferably extends through this recessed portion 605 and into seat 604 preferably configured to receive distal end 607 of each centering arm 602. Seat 604 is preferably located in recessed portion 605 in a position opposite to lumen 603.

FIG. 28A depicts centering arms 602 at rest within recessed portion 605 along the sides of support member 601. FIG. 28B is a cross-sectional view of centering device 106 taken along line 28B-28B of FIG. 28A. As depicted here, centering arms 602 are preferably configured as rectangular wire bands, although any configuration can be used as desired. Advancement of centering arms 602 in a distal direction causes distal end 607 to contact seat 604 and forces centering arms 602 to extend outwards from recessed portion 605 as depicted in FIG. 28C. Configuration of centering arms 602 as bands helps ensure that arms 602 extend directly away from support member 601 in direction 611.

Figure 28D:
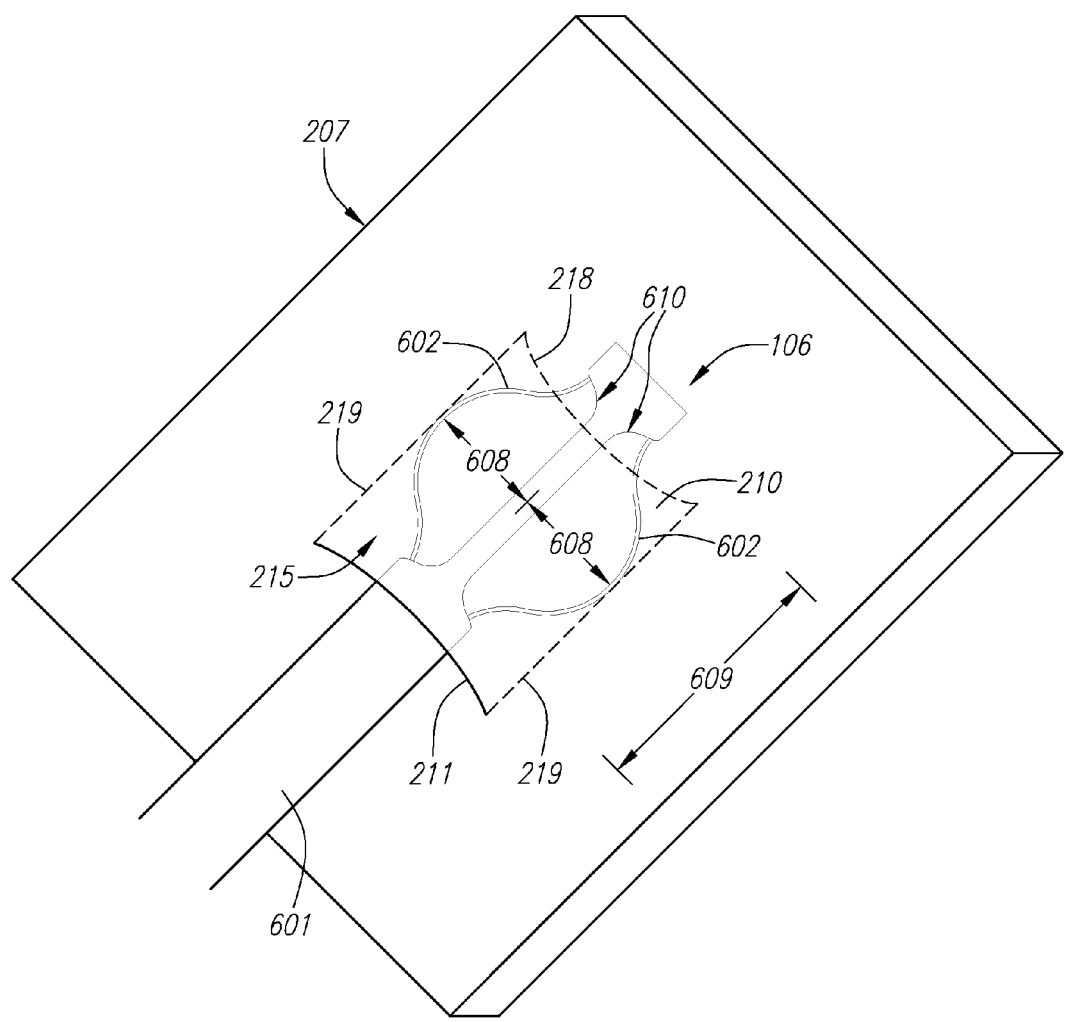
FIG. 28D is a schematic view depicting another exemplary embodiment of a centering device within a septal wall.

When centering device 106 is placed within PFO tunnel 215, centering arms 602 can be extended until coming into contact with sidewalls 219, as depicted in FIG. 28D, which is a perspective view of centering device 106 within PFO tunnel 215. Here, sidewalls 219 and PFO exit 218 are shown as dashed lines to indicate their presence underneath septum secundum 210. When centering arms 602 are each advanced the same amount until contact with both sidewalls 219 is made, the extension distance 608 of each arm 602 will likewise be the same amount and support member 601 will be forced into a centered position within PFO tunnel 215.

In this manner, centering device 106 can be centered within PFO tunnel 215 and can be used as a reference point for delivering implant 103. Preferably, centering device 106 is coupled with delivery device 104, so that centering of centering device 106 will also cause centering of delivery device 104. Preferably, once implant 103 is delivered, centering arms 602 are retracted proximally into lumens 603 and centering device can then be retracted through PFO tunnel 215. Surface 610 of recessed portion 605 is preferably curved, or tapered, to reduce the risk that support member 601 will catch or become hung up on any tissue in or around PFO tunnel 215.

Here, the extended portions of centering arms 602 are shown as being located entirely within PFO tunnel 215. One of skill in the art will readily recognize that variation of length 609 of recessed portion 605 will cause the extended portion of centering arms 602 to vary accordingly.

Support member 601 and centering arm 602 can each be composed of any desired material in accordance with the needs of the application. Preferably, support member 601 is composed of a flexible polymer, such as polyimides, polyamides, polypropylene and the like. Preferably, centering arms 602 are composed of a flexible polymer or metal, such as NITINOL, stainless steel and the like.

Figure 29A:
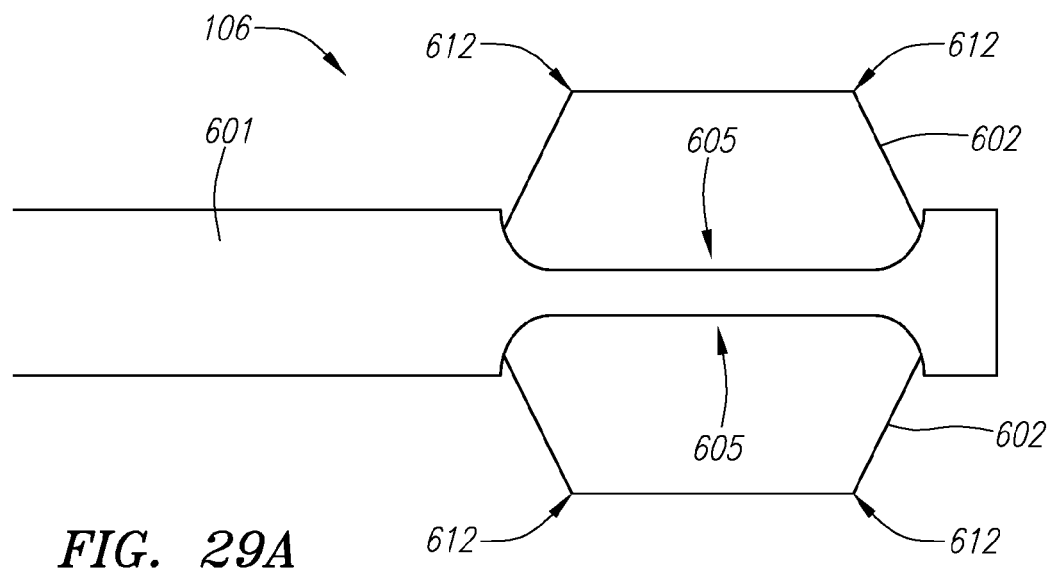
FIGS. 29A-C, 30 and 31 are schematic views depicting additional exemplary embodiments of a centering device.
Figure 29B:
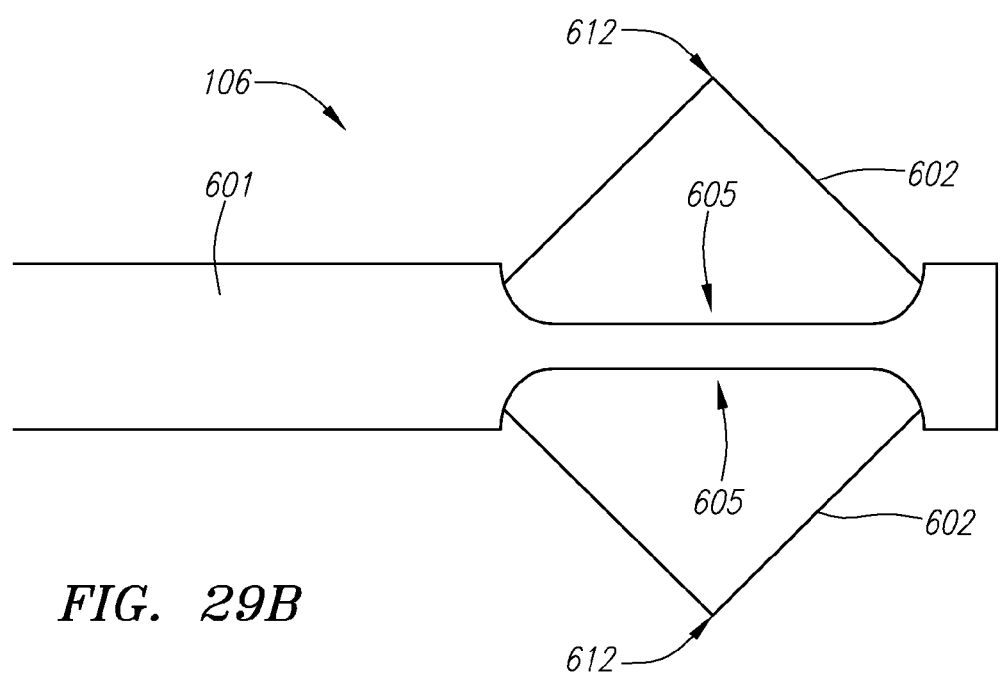

In the embodiment described with respect to FIGS. 28A-D, centering arms 602 have a curved or arcuate shape when extended from support member 601. As the FIGS. 29A-C will show, centering arms 602 can be configured to have any desired shape when extended. FIGS. 29A-B are schematic views depicting additional exemplary embodiments of centering device 106 with centering arms 602 extended in a three-sided and two-sided shapes, respectively. Preferably, portions 612 of centering arms 602 are made thinner than the surrounding portions, so that centering arms 602 have a tendency to flex first in portions 612, allowing these polygonal shapes to be achieved.

Also, arms 602 can be pre-shaped to be biased to assume a desired shape when allowed to expand from recessed portion 605. For instance, in one exemplary embodiment, arms 602 are composed of NITINOL and are heat-treated for pre-shaping. One of skill in the art will readily recognize, in light of this disclosure, that variation of the thickness of arms 602 and pre-shaping can allow an almost limitless number of shapes to be achieved, having curved portions, straight portions and any combination thereof which can be symmetric or asymmetric.

Figure 29C:
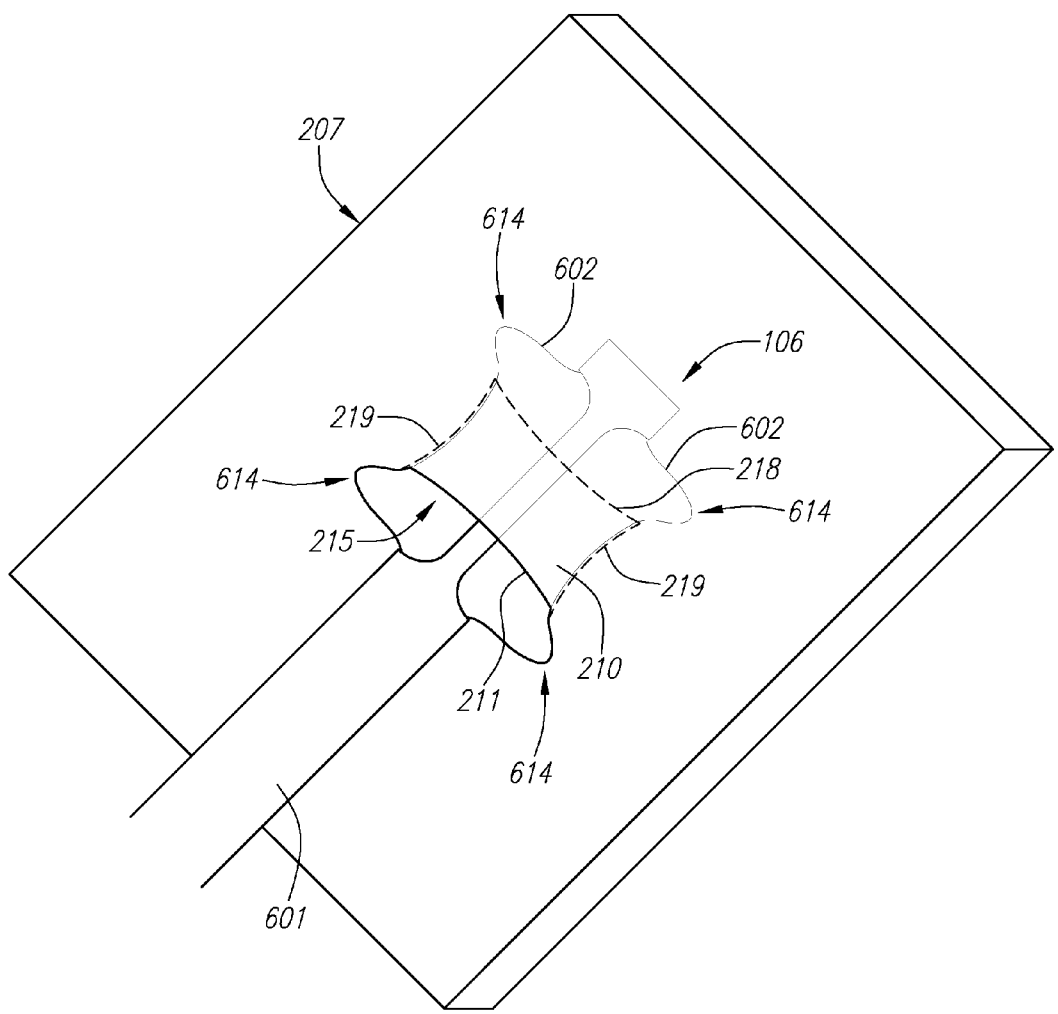

As mentioned above, in some cases, sidewalls 219 of PFO tunnel 215 are not equidistant along the length of PFO tunnel 215, causing PFO tunnel 215 to diverge or converge from PFO entrance 217 to PFO exit 218. Divergence or convergence of PFO tunnel 215 can cause centering device 106 to slip out from PFO tunnel 215 when arms 602 are extended. FIG. 29C is a schematic view depicting another exemplary embodiment of centering device 106 where each centering arm 602 is configured to extend with two outcroppings 614. These outcroppings 614 can be placed outside PFO tunnel 215 to prevent centering device 106 from slipping out of PFO tunnel 215. Outcroppings 614 can be formed by making that portion of centering arm 602 relatively thicker than the surrounding portions, making outcropping 614 less likely to flex. A desired radius of curvature in centering arms 602 can be implemented by pre-shaping, or by gradually varying the thickness and/or width of centering arms 602, where a relatively thinner portion will correspond to a relatively larger rate of curvature.

Figure 30:
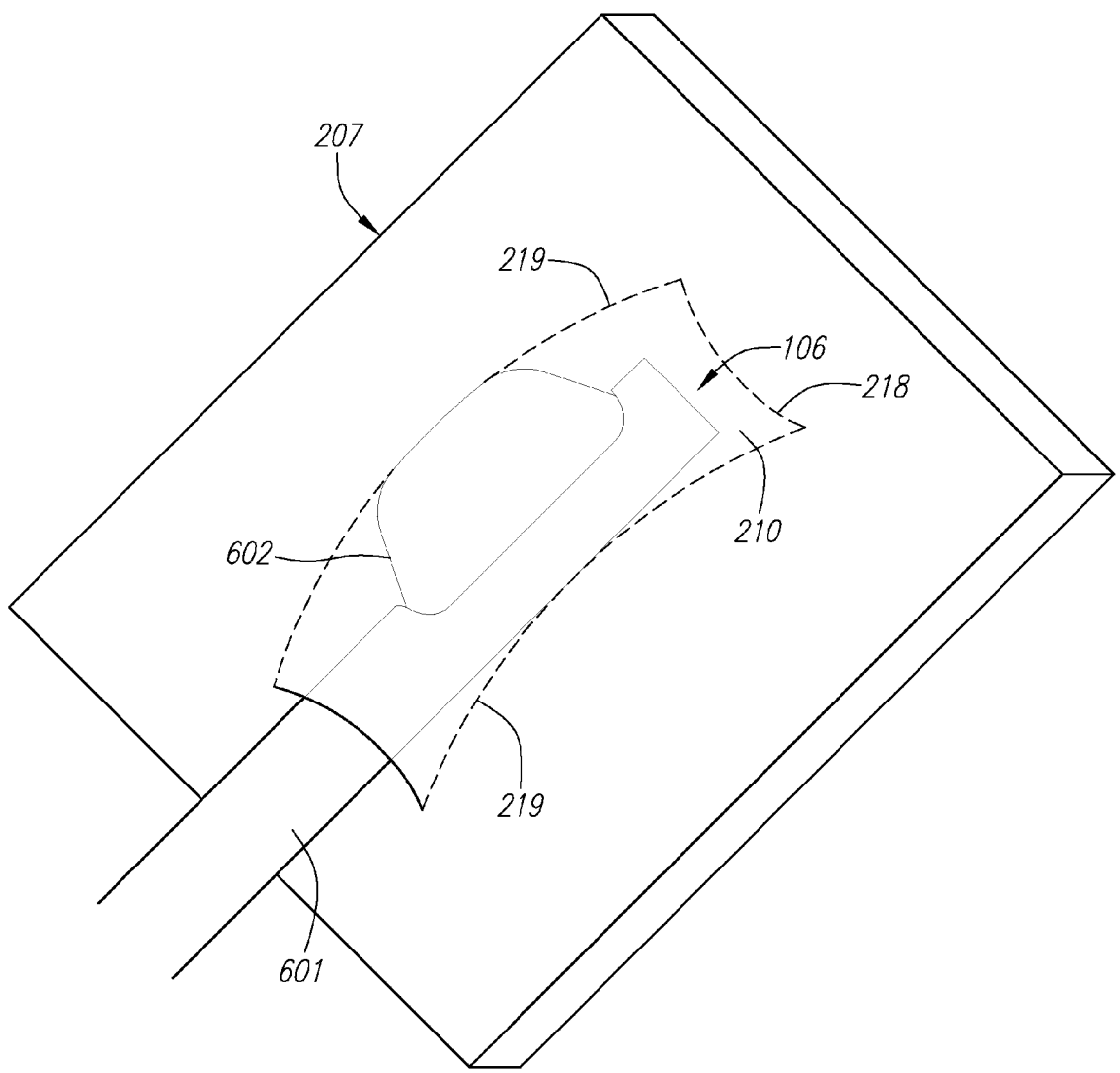

It should be noted that centering device 106 can include any number of one or more arms 602 for centering/positioning purposes. FIG. 30 is a schematic view depicting another exemplary embodiment of centering device 106 having one centering arm 602 extended within PFO tunnel 215. In this embodiment, PFO tunnel 215 is curved to one side and centering arm 602 is positioned on the opposite side. Centering arm 602 can then be extended a predetermined distance to position centering device 106 in the desired location.

In another exemplary embodiment, centering device 106 includes multiple arms 602 configured for use independently of each other to allow the user to have increased control over the position of centering device 106 within PFO tunnel 215. For instance, the user can adjust two opposing arms 602 to center device 106 between sidewalls 219 within tunnel 215, and then adjust a third arm 602 to position device 106 as desired relative to septum secundum 210 and septum primum 214. In another case, the user can use three or more arms 602 for centering based on the tunnel type or anatomy.

Figure 31:
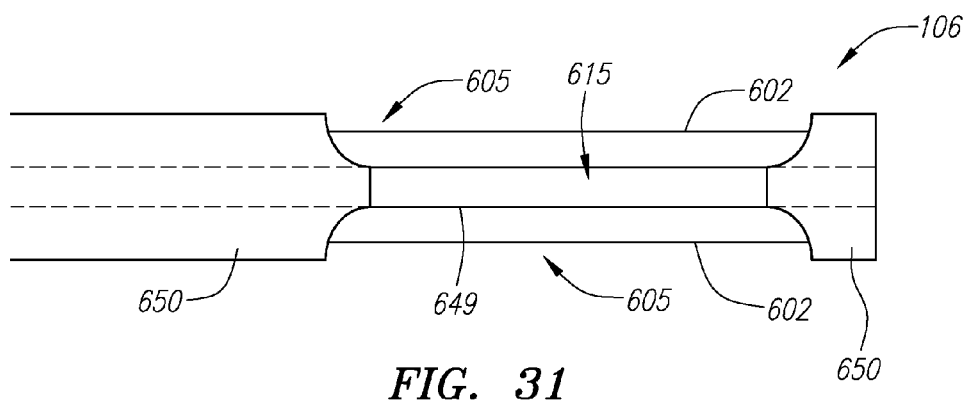

In some embodiments, it can be desirable to keep centering device 106 within PFO tunnel 215 while needle member 405 is advanced through septal wall 207. To reduce the risk that needle member 405 will contact centering device 106 during this procedure, support member 601 can be configured to deflect needle member 405. FIG. 31 is a schematic view depicting an exemplary embodiment of centering device 106 where support member 601 is a rigid cylindrical member 649 having a smooth, or polished, surface 615 between lumen 603 and seat 604 (as shown in FIG. 28A), which are formed in rigid extrusions 650 which are preferable metal and located on member 649. Here, if sharpened distal end 415 of needle member 405 comes into contact with support member 601, it is more likely to be deflected from rigid cylindrical member 649.

Figure 32A:
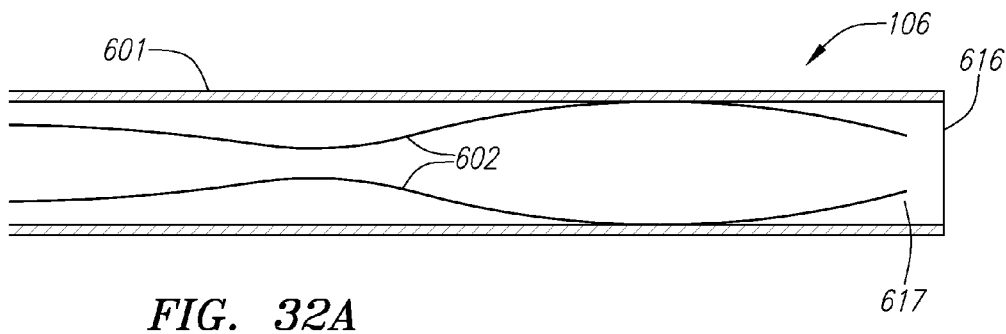
FIGS. 32A-B are cross-sectional views depicting additional exemplary embodiments of a centering device.
Figure 32B:
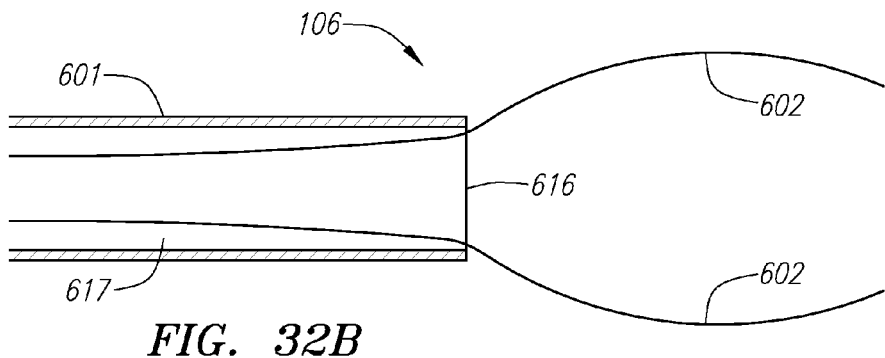

FIGS. 32A-B are cross-sectional views depicting additional exemplary embodiments of centering device 106 where support member 601 includes an open distal end 616 from which one or more pre-shaped centering arms 602 can be extended. Centering arms 602 are preferably pre-shaped to the extended position allowing elimination of seat 604 and recessed portion 605. Centering arms 602 are preferably deformable from a first configuration to allow housing within inner lumen 617 of support member 601 as depicted in FIG. 32A. In FIG. 32B, centering arms 602 are shown deployed from inner lumen 617 in their extended second configuration. Although in FIGS. 32A-B, centering arms 602 are shown as separate elements, the proximal end of the pre-shaped portion of each arm 602 can be coupled together on a common elongate shaft.

Figure 32C:
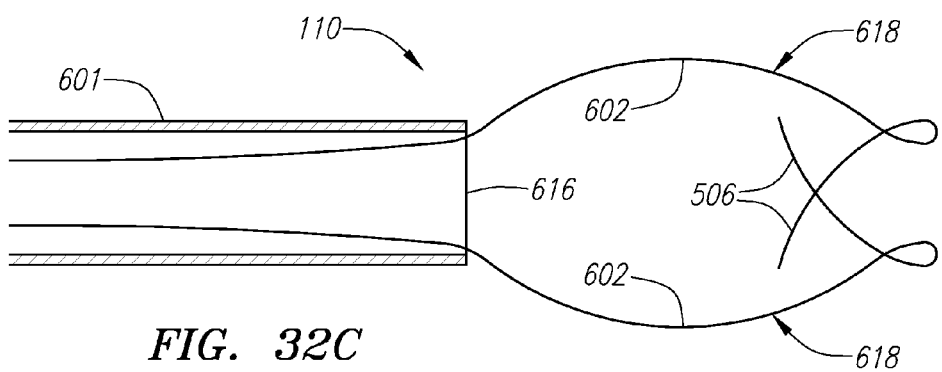
FIG. 32C is a cross-sectional view depicting another exemplary embodiment of a centering device with an exemplary embodiment of a stabilization device.

It should be noted that the functionality of the various embodiments described herein can be combined and integrated together to reduce the number of components in treatment system 100, simplify the design of treatment system 100 and so forth. For instance, FIG. 32C depicts an exemplary embodiment of treatment system 100 where the embodiments described with respect to FIGS. 27A and 32A-B have been integrated together to form device 110. Here, centering arms 602, similar to that depicted in FIGS. 32A-B each include grasping element 506 of stabilization device 105, similar to that depicted in FIG. 27A, located distal to the centering portion 618. Here, centering device 106 is used for centering and stabilization, allowing the elimination of a separate stabilization device 105 from system 100.

For stabilization and centering, support member 601 is preferably advanced through PFO exit 218. Once in left atrium 212, centering arms 602 can be advanced distally to deploy grasping elements 506 from the first, housed configuration, to the second and third configurations for catching and grasping septum primum 214. Once septum primum 214 is grasped, support member 601 can be retracted proximally with respect to centering arms 602 in order to deploy centering portions 618 of each arm 602. The centering portions 618 can then expand outwards and center device 106, thereby preferably also centering body member 101 and delivery device 104, while at the same time maintaining a grasp of septum primum 214.

Figure 32D:
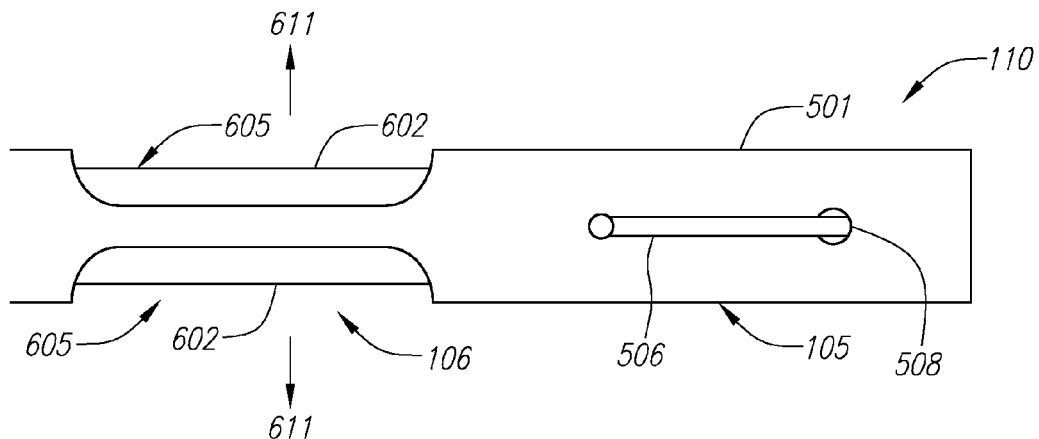
FIG. 32D is a schematic view depicting another exemplary embodiment of a centering device with an exemplary embodiment of a stabilization device.

FIG. 32D is a schematic view depicting another exemplary embodiment of treatment system 100 where centering device 106 and stabilization device 105 have been integrated together. Here, stabilization member 501 includes two lumens 603 and seats 604 (not shown), and recessed portions 605 for use with centering arms 602. After stabilization with device 105, centering arms 602 can be extended in directions 611 to center or otherwise place combined device 110 in the desired position.

Figure 33A:
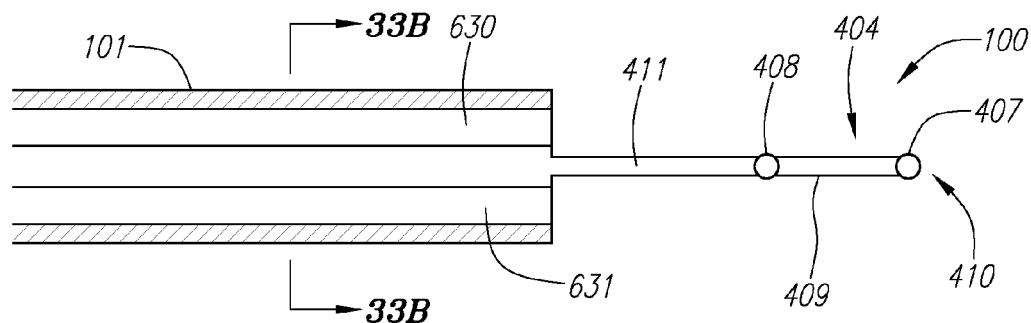
FIG. 33A is a longitudinal cross-sectional view of an exemplary embodiment of a treatment system.
Figure 33B:
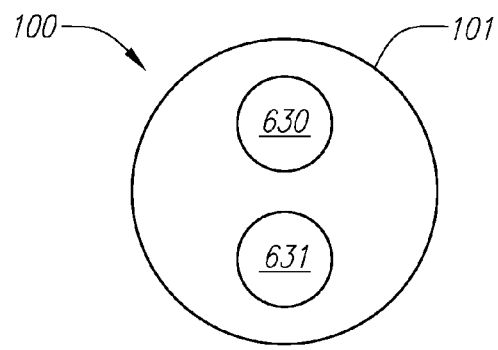
FIG. 33B is a radial cross-sectional view of another exemplary embodiment of a treatment system taken along line 33B-33B of FIG. 33A.

As discussed with respect to FIG. 1, delivery device 104, stabilization device 105 and centering device 106 are each preferably used in conjunction with body member 101. Body member 101 can be configured in any manner desired in accordance with the needs of the application. FIGS. 33A-B are cross-sectional views depicting another exemplary embodiment of treatment system 100 where body member 101 includes two lumens 630 and 631. FIG. 33A is a longitudinal cross-sectional view and FIG. 33B is a radial cross-sectional view taken along line 33B-33B of FIG. 33A. Preferably, lumen 630 is configured to slidably receive delivery device 104, while lumen 631 is configured to slidably receive either stabilization device 105 or an optional guidewire to facilitate routing body member 101 through the patient's vasculature. The guidewire can be placed in lumen 631 until body member 101 is in the desired position within the patient, at which time the guidewire can be removed and stabilization device 105 can be inserted. Also, centering device 106 is preferably integrated with stabilization device 105, such as in the embodiment described with respect to FIG. 32D, in order to provide treatment system with both stabilization and centering capability. In order to prevent rotation of elongate body member 101 around stabilization device 105 during delivery, stabilization device is preferably fixably coupled with either body member 101 or delivery device 104.

FIGS. 34A-C are cross-sectional views depicting another exemplary embodiment of treatment system 100 where body member 101 includes four lumens 630-633 as well as centering arms 602. Here, FIG. 34A is a first longitudinal cross-sectional view, FIG. 34B is a radial cross-sectional view taken along line 34B-34B of FIG. 34A and FIG. 34C is a second longitudinal cross-sectional view taken along line 34C-34C of FIG. 34A. Preferably, lumen 630 is configured to slidably receive delivery device 104, while lumen 631 is configured for any purpose, including reception of stabilization device 105, a guidewire, dye infusion and the like. FIG. 34B depicts centering arms 602 within lumens 632-633 and FIG. 34C depicts centering arms 602 located within lumens 632-633, recessed portions 605 and seats 604. Here, recessed portions 605 and seats 604 are located distal to grasping device 404 on elongate support section 411. The distal portion of support section 411 can be placed within PFO tunnel 215 where centering arms 602 can be deflected for centering prior to deployment of implant 103 in left atrium.

FIGS. 35A-B are cross-sectional views depicting another exemplary embodiment of treatment system 100 where body member 101 includes three lumens 630, 632 and 633 as well as centering arms 602. Here, FIG. 35A is a longitudinal cross-sectional view and FIG. 35B is a radial cross-sectional view taken along line 35B-35B of FIG. 35A. In this embodiment, distal end 112 of body member 101 includes an atraumatic tip 640, which in this embodiment is a floppy tip. Here, with the aid of atraumatic tip 640, body member 101 is configured to be advanceable within the patient's vasculature without the aid of a guidewire. Accordingly, no additional lumen 631 is included for use with a guidewire. Also in this embodiment, stabilization device 105 has been optionally omitted, allowing body member 101 to achieve a relatively smaller radial cross-section size. In another exemplary embodiment, atraumatic tip 640 is omitted and body member 101 is configured to be slidably advanced through a tubular guide catheter placed within the patient's vasculature.

Figure 36A:
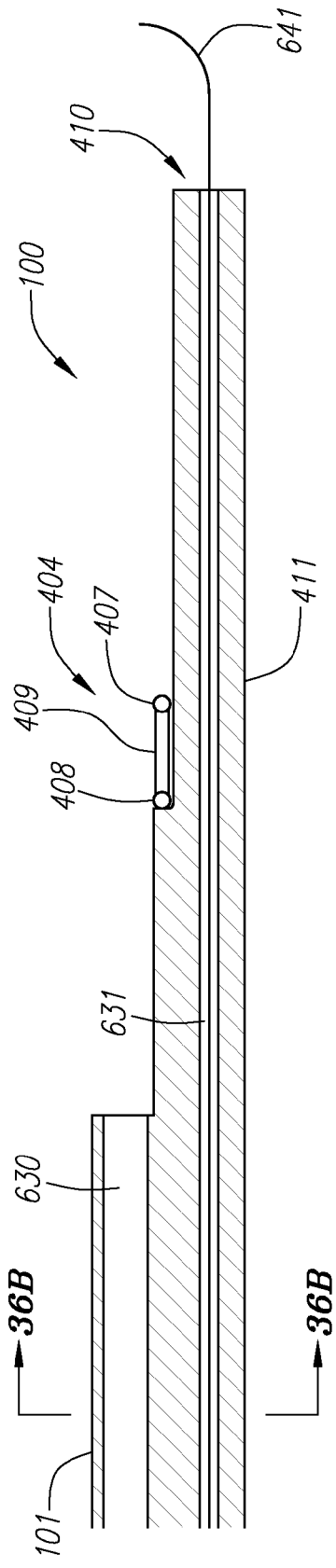
FIG. 36A is a longitudinal cross-sectional view of an exemplary embodiment of a treatment system.
Figure 36B:
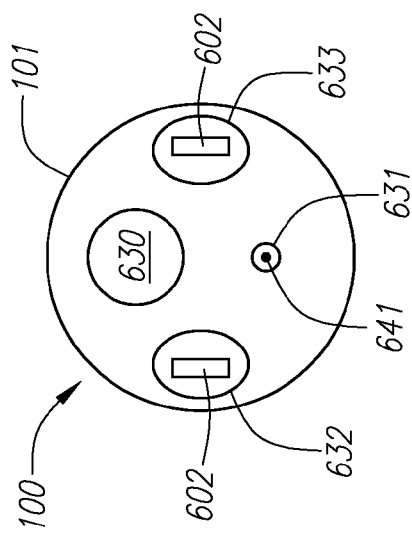
FIG. 36B is a radial cross-sectional view of another exemplary embodiment of a treatment system taken along line 36B-36B of FIG. 36A.

FIGS. 36A-B are cross-sectional views depicting another exemplary embodiment of treatment system 100 where body member 101 includes four lumens 630-633 as well as centering arms 602. Here, FIG. 36A is a longitudinal cross-sectional view and FIG. 36B is a radial cross-sectional view taken along line 36B-36B of FIG. 36A. This embodiment is similar to the embodiment described with respect to FIGS. 34A-C except here, lumen 631 is configured for use with guidewire 641 only, which can be the same size as or relatively thinner than stabilization device 105, allowing the radial cross-section size of lumen 631 and body member 101 to be reduced.

Figure 37A:
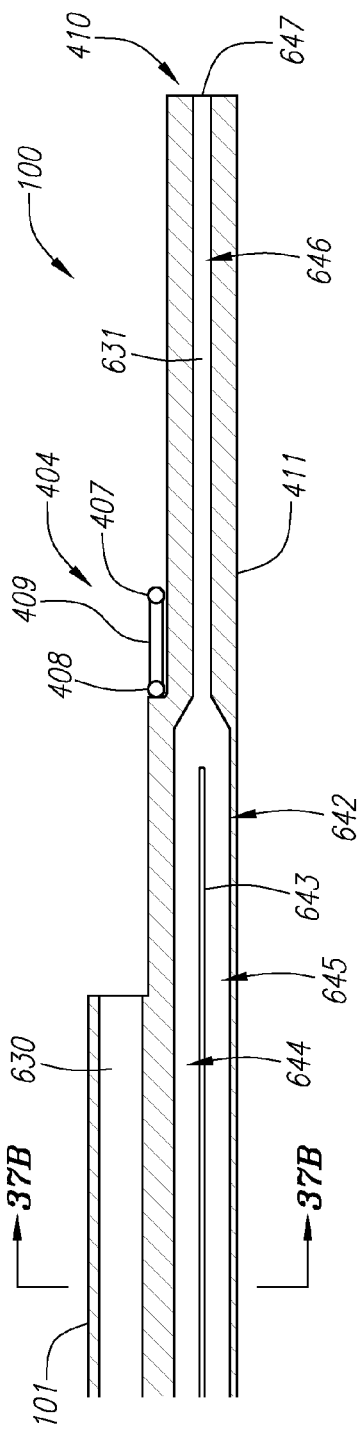
FIG. 37A is a longitudinal cross-sectional view of an exemplary embodiment of a treatment system.
Figure 37B:
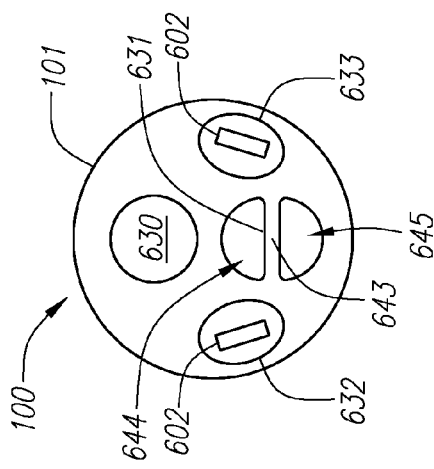
FIG. 37B is a radial cross-sectional view of an exemplary embodiment of a treatment system taken along line 37B-37B of FIG. 37A.

FIGS. 37A-B are cross-sectional views depicting another exemplary embodiment of treatment system 100 where body member 101 includes four lumens 630-633 as well as centering arms 602. Here, FIG. 37A is a longitudinal cross-sectional view and FIG. 37B is a radial cross-sectional view taken along line 37B-37B of FIG. 37A. This embodiment is similar to the embodiment described with respect to FIGS. 35A-C except here, lumen 631 is configured to facilitate exchange of stabilization device 105 and guidewire 641. Proximal portion 642 of lumen 631 includes a divider 643 to separate lumen 631 into a first portion 644 for stabilization device 105 and a second portion 645 for guidewire 641. Distal portion 646 of lumen 631 is preferably tapered to minimize the radial cross-section size of lumen 631. Exchange between stabilization device 105 and guidewire 641 is facilitated because both can reside within proximal portion 642 at the same time, with the desired one of stabilization device 105 or guidewire 641 being advanced distally through open distal end 647 for use.

It should be noted that in each of the embodiments described with respect to FIGS. 33A-37B, functionality can be added or removed as desired, while still remaining within the scope of treatment system 100. For instance, treatment system 100 can be further configured for dye infusion, pressure sensing, imaging, drug delivery, ablation, the use of occlusive devices such as balloons and stents, facilitating the implantation of coronary sinus pacing or defibrillation leads, the use of a stylet and the like. These and other additional types of functionality can be added in any manner, including, but not limited to the addition of one or more lumens 102, or the use of the existing lumens 102, integration directly into body member 101, or the addition of one or more extra body members 101.

In addition, treatment system 100 can include multiple delivery devices 104 for delivery of multiple implants 103, multiple stabilization devices 105 for stabilization on multiple tissue surfaces, multiple centering devices 106 and multiple body members 101 as desired. If treatment system 100 is used to access septal wall 207 via inferior vena cava 202, the maximum radial cross-section size of body member 101 is preferably 13 French or less, although it should be noted that any size body member 101 can be used in accordance with the needs of the application. Body member 101 can be constructed from any material as desired, but is preferably constructed from a flexible polymer such as polyethylene, polypropylene, nylon and the like.

Furthermore, it should be noted that any component or component portion within treatment system 100 can be configured to facilitate any type of imaging, including, but not limited to, internal and external ultrasound imaging, optical imaging, magnetic resonance imaging (MRI), and fluoroscopy. For instance, radio-opaque portions can be used to increase the visibility in fluoroscopic applications while echolucent coatings can be used to increase visibility in ultrasound applications. As an example, in one exemplary embodiment OA delivery member 401 can be entirely radio-opaque, or can include portions that are radio-opaque, such as on distal tip 430 of FIG. 14A.

Also described herein are methods 700 and 800 of treating PFO tunnel 215, preferably by at least partially closing PFO tunnel 215. Methods 700 and 800 are preferably used with treatment system 100, but can be used with any medical system as desired. For ease of discussion, method 700 will be described with respect to treatment system 100 and method 800 will be described without reference to a particular treatment system, although it should be understood that methods 700 and 800 can be used with or without treatment system 100. Generally, the steps of methods 700 will vary, in part, on the actual configuration of implant 103, the number of implants 103 to be delivered, the location in which each implant 103 is to be delivered, the use of guidewire 641 or a guide catheter and the optional use of stabilization device 105 and/or centering device 106 or any combination thereof.

Figure 38A:
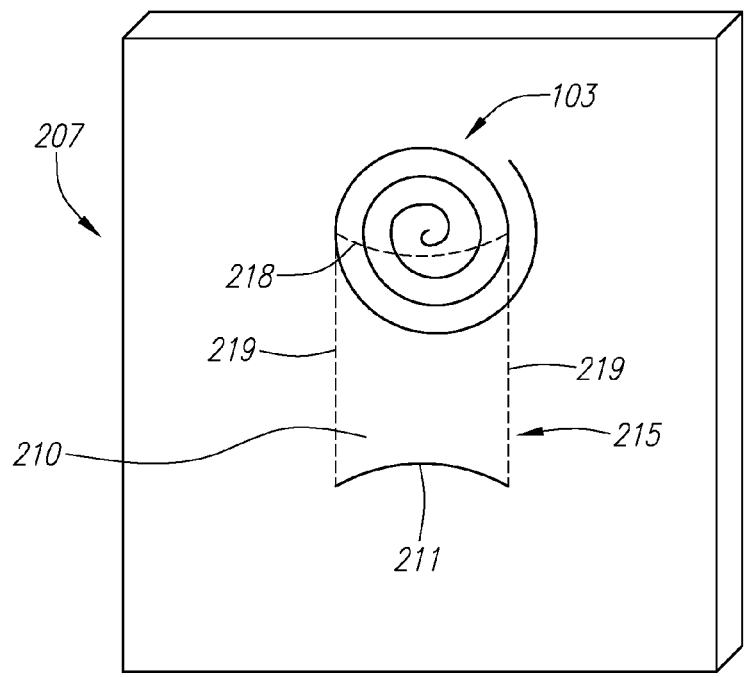
FIGS. 38A-E are cross-sectional views of a septal wall depicting exemplary embodiments of the implantable treatment device.
Figure 38B:
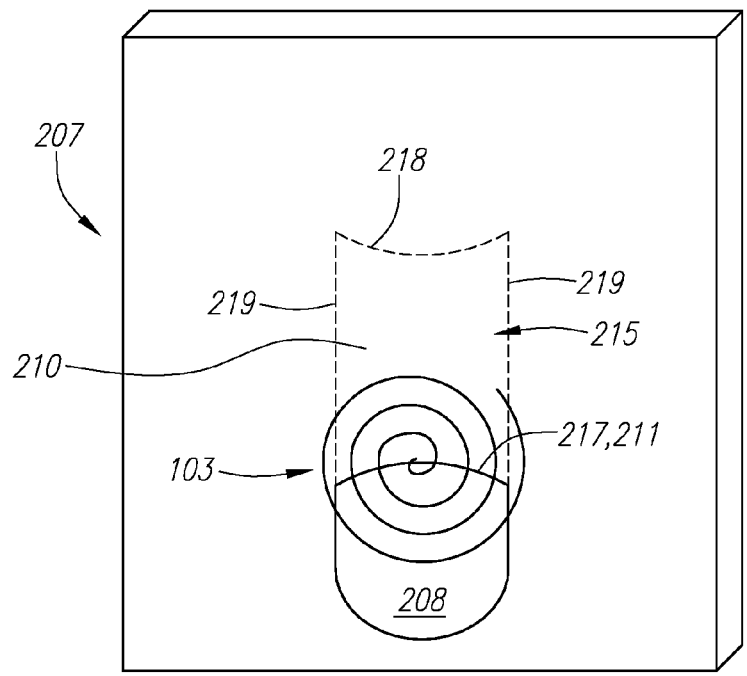
Figure 38C:
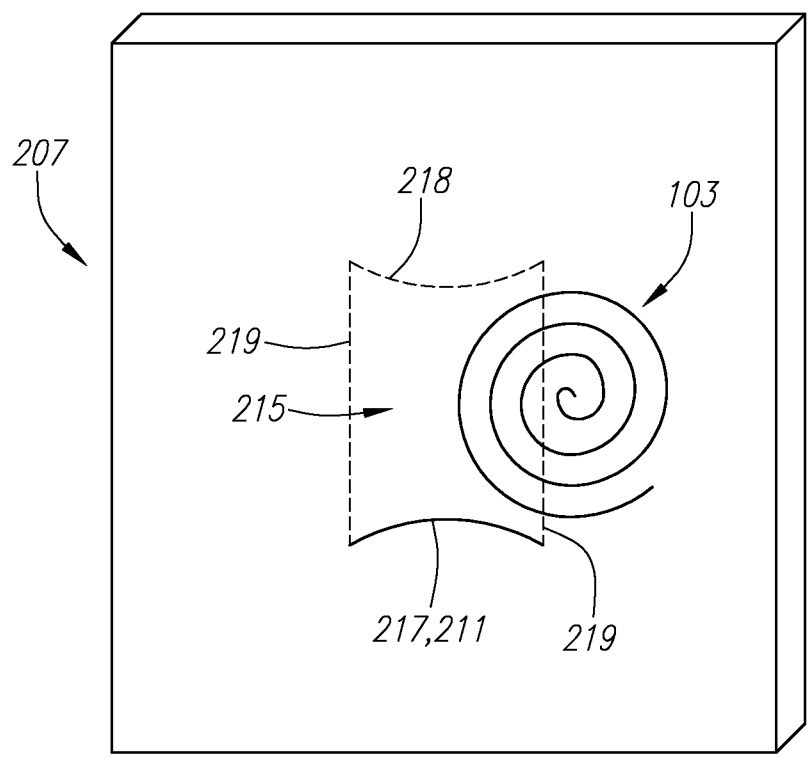

In FIG. 4E, implant 103 is delivered through both septum primum 214 and septum secundum 210. It should be noted, however, that implant 103 can be delivered in any location desired. FIGS. 38A-C are cross-sectional views of septal wall 207 depicting exemplary embodiments of implant 103 in just several of the many alternate locations that can be used. In FIG. 38A, implant 103 has been delivered through the upper portion of septum secundum 210 adjacent to PFO exit 218. In FIG. 38B, implant 103 has been delivered through the lower portion of septum primum 214, adjacent to PFO entrance 217 and near (or in) fossa ovalis 208. In FIG. 38C, implant 103 has been delivered through septal wall 207 adjacent to sidewall 219, septum primum 214 and septum secundum 210.

Figure 38D:
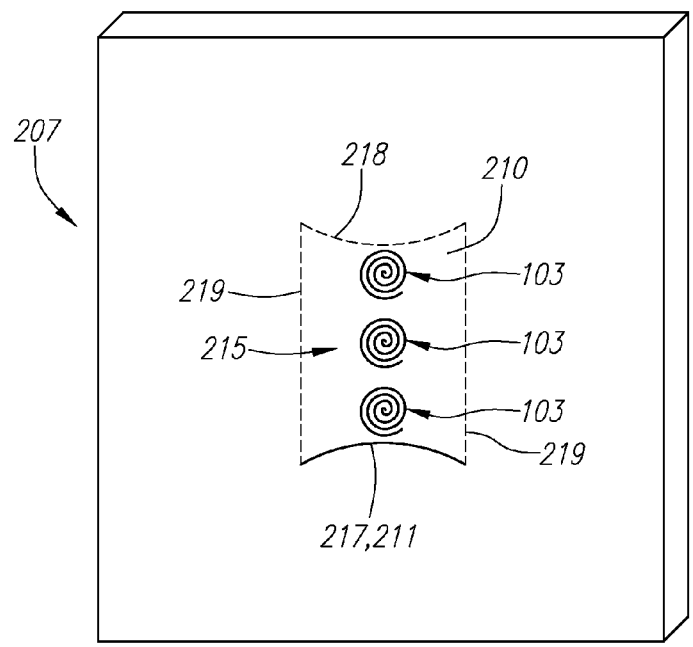
Figure 38E:
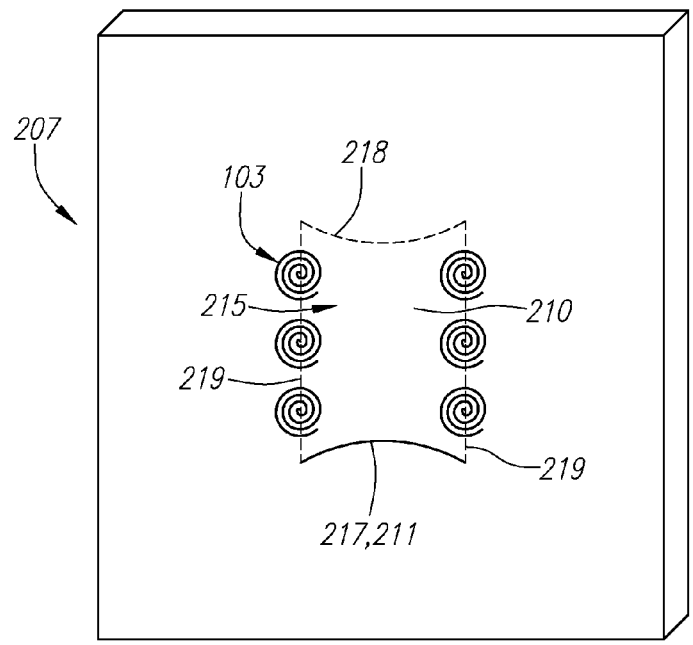

Also, as many implants 103 can be used in any arrangement as desired. FIGS. 38D-E are views of septal wall 207 depicting exemplary embodiments of multiple implants 103 in just several of the many alternate arrangements that can be used. In FIG. 38D, three implants 103 have been delivered through both septum primum 214 and septum secundum 210. In FIG. 38E, six implants 103 have been delivered through septal wall 207 adjacent to both sidewalls 219, septum primum 214 and septum secundum 210.

Although there are many different implementations and variations of method 700, for ease of discussion, method 700 will be described herein as using one implant 103, delivered through both septum primum 214 and septum secundum 210, using an exemplary embodiment of treatment system 100 similar to that described above with respect to FIGS. 33A-B, where body member 101 is configured for use with stabilization device 105 having centering device 106 integrated thereon.

Figure 39A:
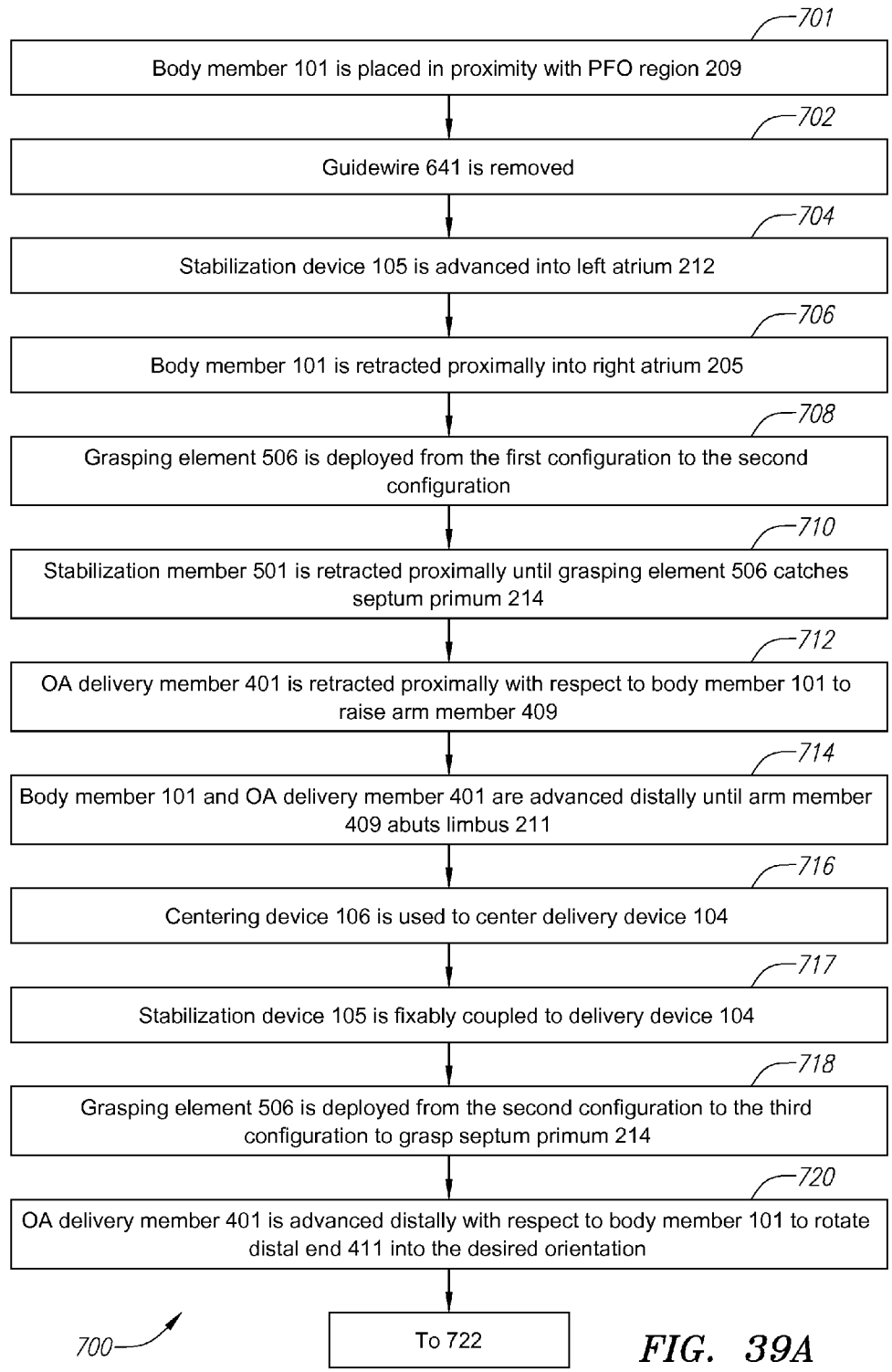
FIGS. 39A-B are flow diagrams depicting an example of a method of treating a septal defect.
Figure 39B:
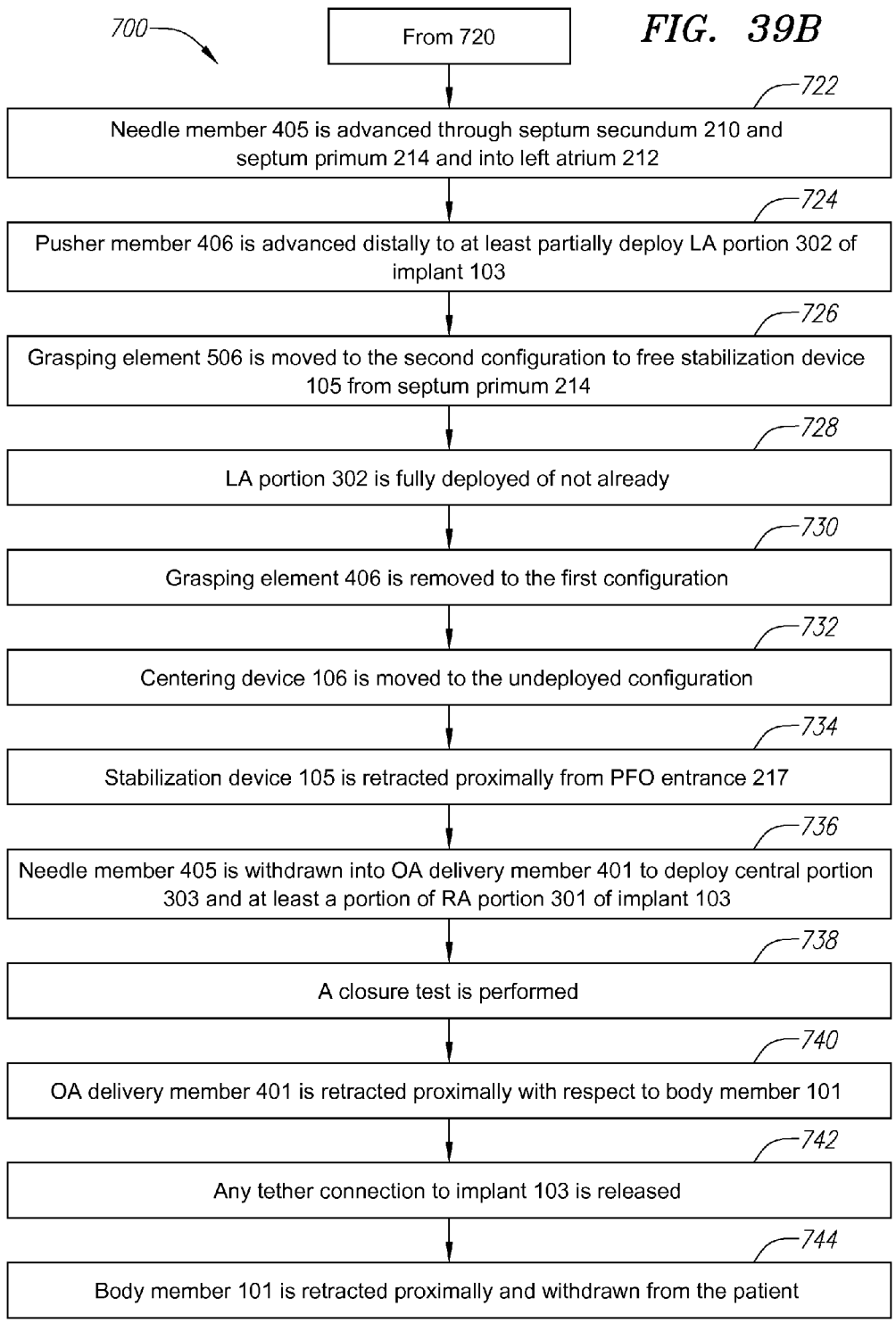

FIGS. 39A-B are flow diagrams depicting an example of method 700. First, at 701, body member 101 is placed in proximity with PFO region 209. As mentioned above, implant 103 can be delivered from left atrium 212 or right atrium 205. Preferably, implant 103 is placed into proximity with PFO region 209 by advancing body member 101 from the femoral vein to right atrium 205 in a conventional manner. For instance, in one example, a needle is inserted into the femoral vein and a guidewire is advanced through the needle into the femoral vein. The needle can then be removed and an access sheath can be routed over the guidewire, which can also then be removed. A J-tip guidewire, such as a 0.035"/0.038" guidewire, can be routed through the patient's vasculature into inferior vena cava 202 and right atrium 205. From there, the guidewire can be routed through PFO tunnel 215 and into left atrium 212. Next, an exchange sheath or multi-purpose guide can then be advanced over the J-tip guidewire into left atrium 212, at which point the J-tip guidewire can be removed. A relatively stiffer guidewire 641 can then be advanced through the exchange sheath or multi-purpose guide and into left atrium 212 and optionally the pulmonary vein, which can act as an anchor for the guidewire. Body member 101 can then be advanced over the guidewire 641 into proximity with PFO region 209, preferably through PFO tunnel 215 and into left atrium 212. In addition, a catheter or guidewire having a sizing device, such as a balloon, can be placed within PFO tunnel 215 to measure the size of PFO tunnel 215, for use in choosing a placement location, implant size, etc.

At 702, guidewire 641, if present, can be removed. At 704, stabilization device 105 is preferably advanced through lumen 631 and into left atrium 212. At 706, body member 101 can be retracted proximally into right atrium 205. Preferably, stabilization device 105 includes a stabilization member 501 and grasping device 502 with grasping element 506. At 708, grasping element 506 can be deployed from the first housed configuration to the second configuration for catching tissue, which, in this example, is preferably septum primum 214.

Next, at 710, stabilization member 501 is preferably moved distally until grasping element 506 catches septum primum 214. Then, at 712, OA delivery member 401 can be retracted proximally with respect to body member 101 to raise arm member 409. At 714, body member 101 and OA delivery member 401 are advanced distally until arm member 409 abuts limbus 211. At 716, centering device 106 can be used to center delivery device 104, preferably by deflecting centering arms 602. Once centered, if not already done so, at 717 stabilization device 105 can be fixably coupled to delivery device 104 (e.g., with a rotating hemostasis valve or Tuohy-Borst valve and the like). Next, at 718, grasping element 506 can be further deployed to the third configuration to grasp septum primum 214 and lock stabilization device 105 to septum primum 214. Alternatively, either 716, 717, 718 or any combination thereof can be implemented prior to 712. Also, 716-718 can be implemented in any order desired with respect to each other.

Once stabilized, centered and locked in place, OA delivery member 401 is preferably advanced distally with respect to body member 101 to rotate distal end 410 into the desired orientation with surface 320 of septum secundum 210. At 722, needle member 405 can be advanced through septum secundum 210 and septum primum 214 and into left atrium 212. Then, at 724, pusher member 406 can be advanced distally to at least partially deploy LA portion 302 of implant 103 from distal end 415 of needle member 405. In embodiments where centering arms 602 are in their deflected state for centering, it is possible for needle member 405 to pass between centering arms 602 and stabilization member 501 when inserted, based on needle insertion location 419. To avoid capture of implant 103 between centering arms 602 and stabilization member 501, centering arms 602 can be retracted proximally back into elongate body 101 thereby removing them from seats 604 and preventing implant 103 from being trapped between centering arms 602 and stabilization member 501. Next, at 726, grasping element 506 can be moved to the second configuration to free stabilization device 105 from septum primum 214. Alternatively, 726 can be performed before 724 if desired.

Then, at 728, LA portion 302 can be fully deployed if not already. At 730, grasping element 506 can be removed to the first configuration, housed within stabilization member 501. Next, at 732, centering device 106 can be moved to the undeployed configuration if not already, preferably by collapsing centering arms 602, after which stabilization device 105 can be retracted proximally from PFO entrance 217 at 734. At 736, needle member 405 can be withdrawn into OA delivery member 401 to deploy central portion 303 of implant 103 and at least a portion of RA portion 301. Here, at 738, an optional closure test can be performed to confirm at least partial closure, and preferably substantially complete closure, of PFO tunnel 215. Any desired closure test can be performed including, but not limited to, the introduction of gaseous bubbles simultaneously with imaging using contrast enhanced transcranial doppler (CE-TCD), intracardiac echocardiography (ICE) and the like, or the infusion of a radio-opaque dye imagable via fluoroscopy. The test may be performed by pulling back OA delivery member 401 as far as necessary to deploy RA coil 301 and then test while device is at PFO entrance.

At 740, OA delivery member 401 can be retracted proximally with respect to body member 101 to complete deployment of RA portion 301, release limbus 211 and place OA delivery member 401 in the original position. If the desired degree of closure is confirmed, then any tether connection to implant 103 can be released at 742. Finally, at 744, body member 101 can be retracted distally and withdrawn from the patient.

Figure 40:
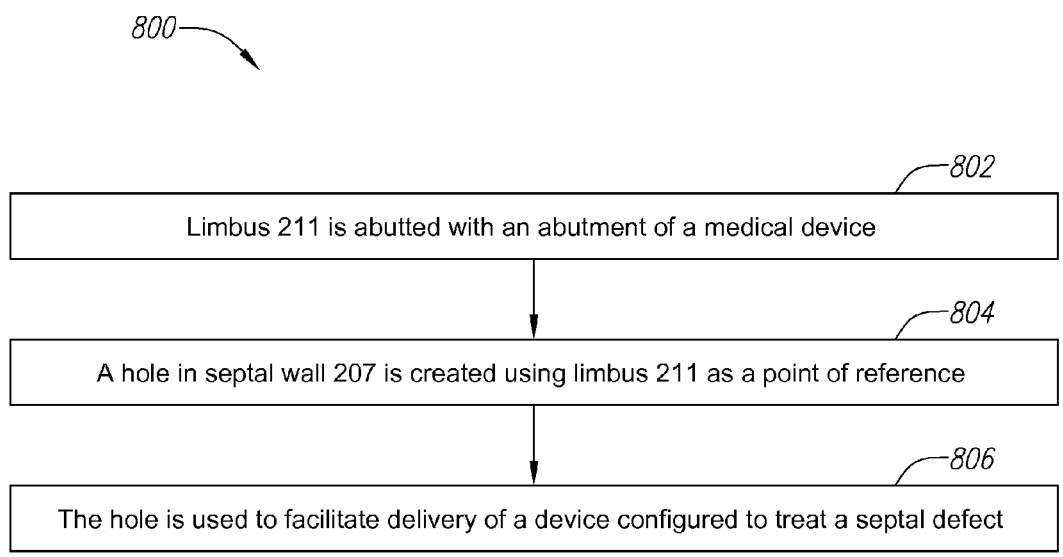
FIG. 40 is a flow diagram depicting another exemplary method of treating a septal defect.

FIG. 40 depicts another exemplary method 800 of treating a septal defect. At 802, limbus 211 is abutted with an abutment of a medical device. Preferably, limbus 211 is engaged with the medical device and optionally grasped such that the medical device is anchored to limbus 211. Then, at 804, a hole in septal wall 207, preferably in septum secundum 210, is created using limbus 211 as a point of reference. For instance, the hole can be created at a fixed or adjustable distance from limbus 211. At 806, the hole is used to facilitate delivery of a device configured to treat a septal defect. In one example, the device is deployed through the hole such that it causes at least partial closure of the septal defect. In this example of method 800, limbus 211 is abutted and used as a reference. In another example of method 800, the edge of septum primum 214 is abutted and used as a reference. In other examples of method 800, one or both sidewalls 219 and/or fossa ovalis 208 are abutted and used as points of reference.

Figure 41A:
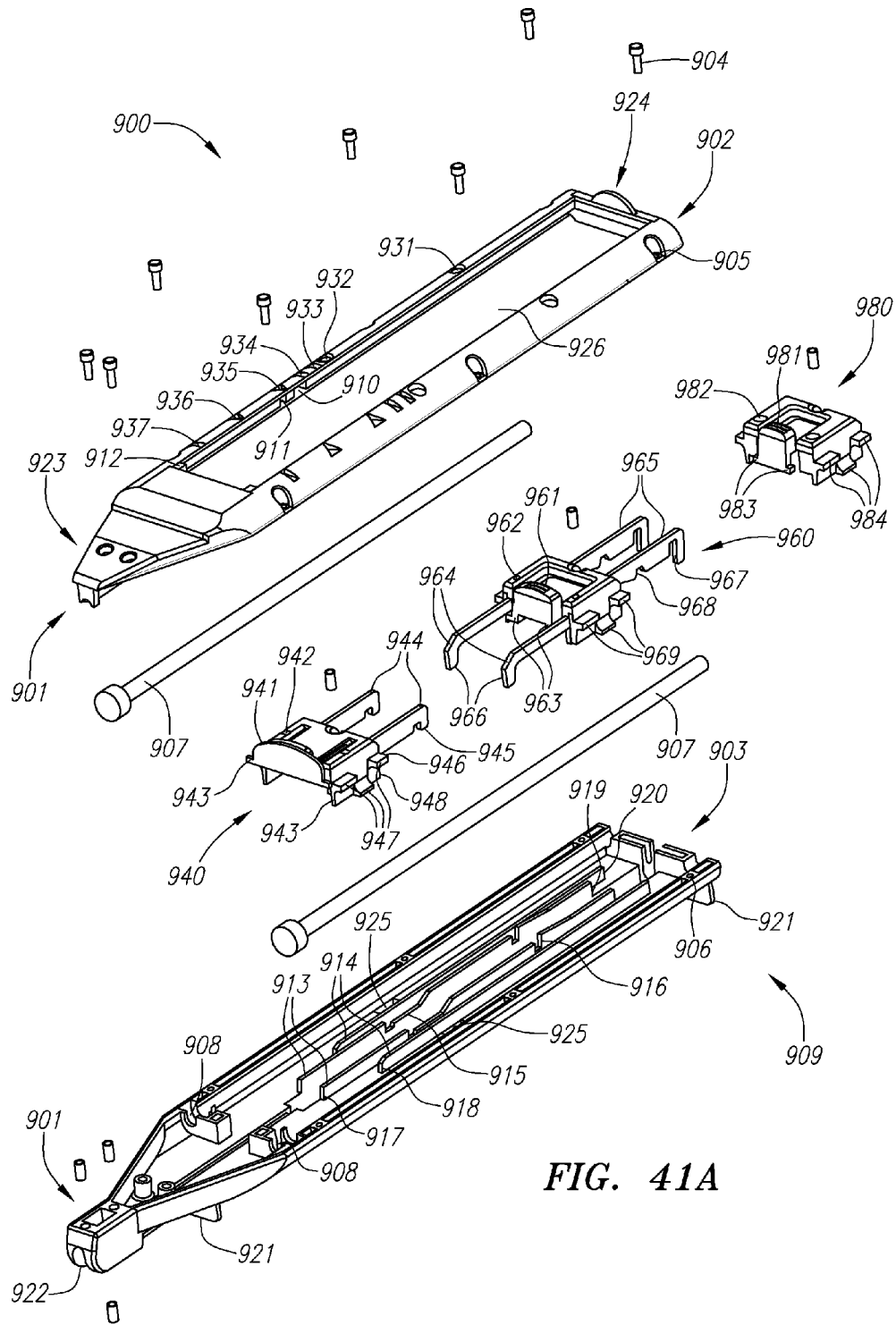
FIG. 41A is an exploded perspective view depicting an exemplary embodiment of a proximal control device.

Control of system 100 can be accomplished with the use of a proximal control device, or proximal controller, 900. FIG. 41A is an exploded view depicting an exemplary embodiment of a proximal control device 900. In this embodiment, proximal controller 900 is preferably used to control delivery device 104 when configured for off-axis delivery, for example, in embodiments where delivery device 104 is configured in a manner similar to that described with respect to FIGS. 14A-F. Proximal controller is shown here in a preferred upright position. To facilitate description of the location of the various elements of controller 900, reference will be made to elements being above or beneath other elements, referring to their respective locations when controller 900 is oriented as shown in FIG. 41A.

Although not limited to such, proximal controller 900 will be described in the context of use with an embodiment of body member 101 and delivery device 104 similar to that described with respect to FIGS. 14A-F. Like the embodiment described with respect to FIGS. 14A-F, delivery device 104 includes OA delivery device 401, needle member 405 and pusher member 406. However, this embodiment does not include stabilization device 105 or centering device 106, although proximal controller 900 can certainly be configured to control those devices as well.

In the embodiment depicted in FIG. 41A, proximal controller 900 includes a housing 901 divided into two parts, an upper portion 902 and a lower portion 903, which are preferably coupled together. Portions 902 and 903 can be coupled together in any manner. Here, portions 902 and 903 are coupled together with a plurality of screws 904 that are routed through apertures 905 in upper portion 902 and interface with threaded chambers 906 within portion 903. Housing 901 also has a distal end 923 and a proximal end 924. Distal end 923 is preferably fixably coupled with body member 101.

Proximal controller 900 includes two guide rails 907 and a user interface 909 including three slidable actuators 940, 960, and 980 configured to slide along guide rails 907. Guide rails 907 are preferably rigid members with a smooth surface to allow for low surface frictional resistance to the movement of actuators 940, 960, and 980. When portions 902 and 903 are coupled together, guide rails 907 are preferably held in place by restraining seats 908 located in both portions 902 and 903 (seats 908 are obscured and not shown in upper portion 902). Also, actuators 940, 960, and 980 are maintained sequentially within housing 901 and can be controllably moved, or slid, along guide rails 907.

In this embodiment, control of each actuator 940, 960, 980 is accomplished by way of depressible buttons 941, 961 and 981, respectively. Access to actuators 940, 960 and 980 is achieved through opening 926 in upper housing portion 902. One of skill in the art will readily recognize that other forms of controlling actuators 940, 960, 980 can be used.

Each of actuators 940, 960, 980 is preferably coupled with a portion of delivery device 104. In this embodiment, actuator 940 is coupled with OA delivery member 401, actuator 960 is coupled with needle member 405 and actuator 980 is coupled with pusher member 406. To facilitate the description herein, actuator 940 will be referred to as OA actuator 940, actuator 960 will be referred to as needle actuator 960 and actuator 980 will be referred to as pusher actuator 980. Of course, any of actuators 940, 960, and 980 can be coupled with any portion of delivery device 104, or any other portion of system 100, as desired.

Preferably, proximal controller 900 is configured such that the movement of actuators 940, 960, and 980 with respect to each other can be controlled, or guided, at appropriate stages during an implantation procedure. At certain stages, movement of the various actuators 940, 960, and 980 is fully independent of the positions of one or more of the remaining actuators 940, 960, and 980. Conversely, at certain stages, movement of the various actuators 940, 960, and 980 is dependent on the positions of one or more of the remaining actuators 940, 960, and 980 and movement can be restricted to certain directions or prevented entirely. Also, controller 900 is preferably configured such that the movement of actuators 940, 960, 980 with respect to the anatomy of the subject can be controlled, or guided, at appropriate stages during the procedure. These features can reduce the risk that the user improperly operates system 100 while within the body of the subject, such as by prematurely releasing implant 103.

In this embodiment, control is also provided by a network of mechanical tabs, slots, abutments, surfaces and/or ribs which can act in conjunction to control and lock the movement of each actuator 940, 960 and 980. Before describing the operation of controller 900, each portion of controller 900 will be described in greater detail.

Upper housing portion 902 includes three slots 910, 911 and 912 (shown here partially obscured) located on both sides of opening 926. Housing portion 902 also includes multiple guide markings 931-937 which can correspond to one of guide markings 942, 962 and 982 located on each of actuators 940, 960 and 980, respectively. In this embodiment, guide markings 931-932 have a circular shape and correspond to circular marking 982 on pusher actuator 980, guide markings 935-936 have a triangular shape and correspond to triangular marking 962 on needle actuator 960, and guide markings 933, 934, and 937 have a rectangular shape and correspond to rectangular marking 942 on OA actuator 940.

Lower housing portion includes two sets of ribs, inner ribs 913 and outer ribs 914. Ribs 913-914 extend upwards from the base of lower housing portion 903. Inner ribs 913 each include two slots 915 and 916. The distal ends 917 of ribs 913 are located distal to the distal ends 918 of ribs 914. The proximal ends 919 of ribs 913 are also located distal to the proximal ends 920 of ribs 914. Located beneath and to the outside of ribs 914 are a set of abutments 925 for abutting OA actuator 940.

An aperture 922 is located at the distal end of lower housing portion 903 and is configured to allow routing of body member 101 therethrough. Lower housing portion 903 also includes a base 921 upon which it can rest and remain stable during the implantation procedure.

OA actuator 940 includes a set of outwardly extending tabs 943 located at the base of button 941. OA actuator 940 also includes two proximally located rails 944 each having two similarly shaped slots 945 and 946 (not shown) located therein. Slot 945 is located proximal to slot 946 and both are located in the bottom portion of rails 944. On both sides of OA actuator 940 are a set of guide rail abutments 947 that facilitate, or guide, the movement of OA actuator 940 along each guide rail 907. Below guide rail abutments 947 on each side is a proximally located tab 948 for abutting abutments 925.

Needle actuator 960 includes a set of outwardly extending tabs 963 located at the base of button 961. Needle actuator 960 also includes two distally located rails 964 and two proximally located rails 965. The distal end of each distal rail 964 includes a downwardly oriented chamfer 966, which can be used to force OA actuator 940 into a locked position in the case where the user has not fully done so. Distal rails 964 are spaced apart at a greater distance than proximal rails 944 (on OA actuator 940) to allow both sets of rails 944 and 964 to slide distally and proximally in a relatively unimpeded manner. OA proximal rails 944 are aligned with tabs 963 on needle actuator 960 and are configured to interact with tabs 963. Needle actuator 960 is configured to slide along rails 944 with tabs 963 in position to interact with slots 945-946. Likewise, OA actuator 940 is also configured to slide along needle actuator rails 964 and to abut chamfer 966 if needed.

Needle actuator proximal rails 965 each include two slots 967 and 968, both of which are located in the bottom portion of rails 965. The proximal surfaces of slots 967 extend further downwards than the other surfaces on rails 965 to provide a locking function that will be described in more detail below. On either side of needle actuator 960 are a set of guide rail abutments 969 that facilitate, or guide, the movement of needle actuator 960 along each guide rail 907.

Pusher actuator 980 includes a set of outwardly extending tabs 983 located at the base of button 981. Tabs 983 are aligned with needle proximal rails 965 and are configured to interact with slots 967-968. Pusher actuator 980 is also configured to slide over proximal rails 965 to allow the interaction of tabs 983 with slots 967-968. On either side of pusher actuator 980 are a set of guide rail abutments 984 that facilitate, or guide, the movement of pusher actuator 980 along each guide rail 907.

Figure 41B:
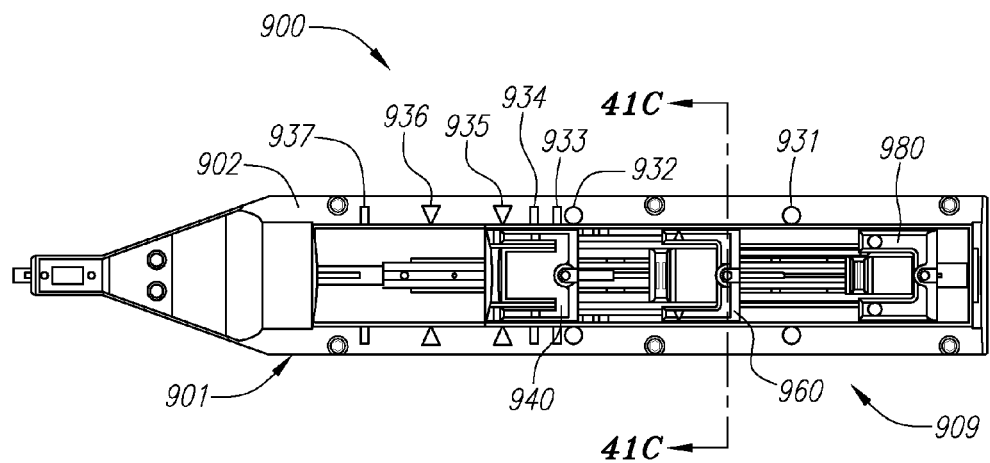
FIG. 41B is a top down view depicting another exemplary embodiment of a proximal control device.
Figure 41C:
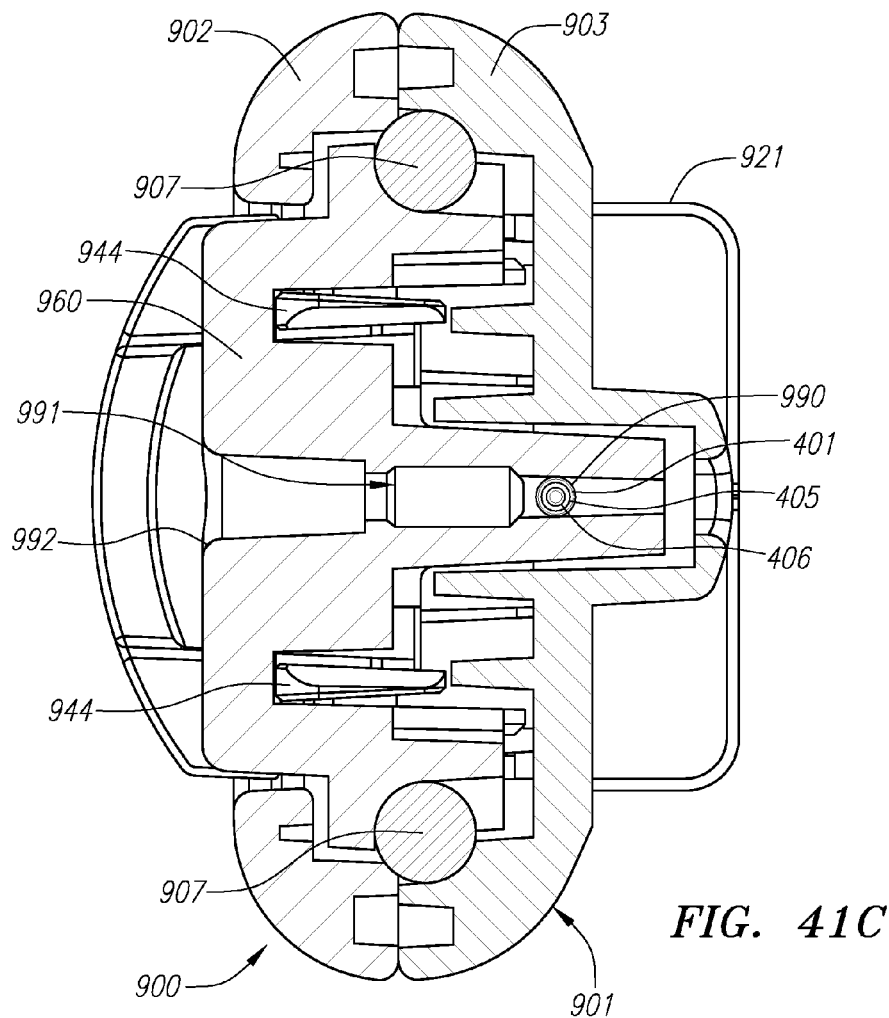
FIG. 41C is a cross-sectional view taken along line 41C-41C of FIG. 41B depicting another exemplary embodiment of a proximal control device.

FIG. 41B is a top down view depicting this exemplary embodiment of controller 900 in an assembled state. Here, each actuator 940, 960 and 980 is shown in a position within housing 901. FIG. 41C is a cross-sectional view of controller 900 taken along line 41C-41C of FIG. 41B. This cross-sectional view depicts needle actuator 960 within housing 901, in addition to needle member 405 with pusher member 406.

Here, needle member 405 is coupled with and surrounded by a sleeve 990, which is preferably formed of a rigid material, such as stainless steel and the like, and preferably smooth to decrease surface friction. A set screw 991 is adjustably located above sleeve 990 in a slot 992 within needle actuator 960. Set screw 991 is preferably adjusted and brought into contact with sleeve 990 to lock sleeve 990 in place within needle actuator 960. One of ordinary skill in the art will readily recognize that any technique can be used to lock sleeve 990 with needle member 405, or otherwise couple needle member 405 with needle actuator 960, including, but not limited to, bonding, welding, clamping, crimping, and the like.

Likewise, OA delivery member 401 and pusher member 406 are also both preferably coupled with their respective actuators 940 and 980, using similar sleeves in combination with set screws. One of skill in the art will readily recognize that numerous different techniques, including adhesives, welding, soldering, mechanical couplings and the like, can be used to lock each actuator 940, 960, and 980 with the respective component of system 100, in this case OA delivery member 401, needle member 405 and pusher member 406.

Turning now to the use of controller 900, an exemplary method of operating controller 900 is described with the aid of FIGS. 42A-I. FIGS. 42A-I are perspective views depicting an exemplary embodiment of controller 900 with actuators 940, 960 and 980 in various positions during the implantation procedure. Because various components of controller 900 can become obscured in the various views and because all components are labeled in FIG. 41A, only visible components are labeled in FIGS. 42A-I.

Figure 42A:
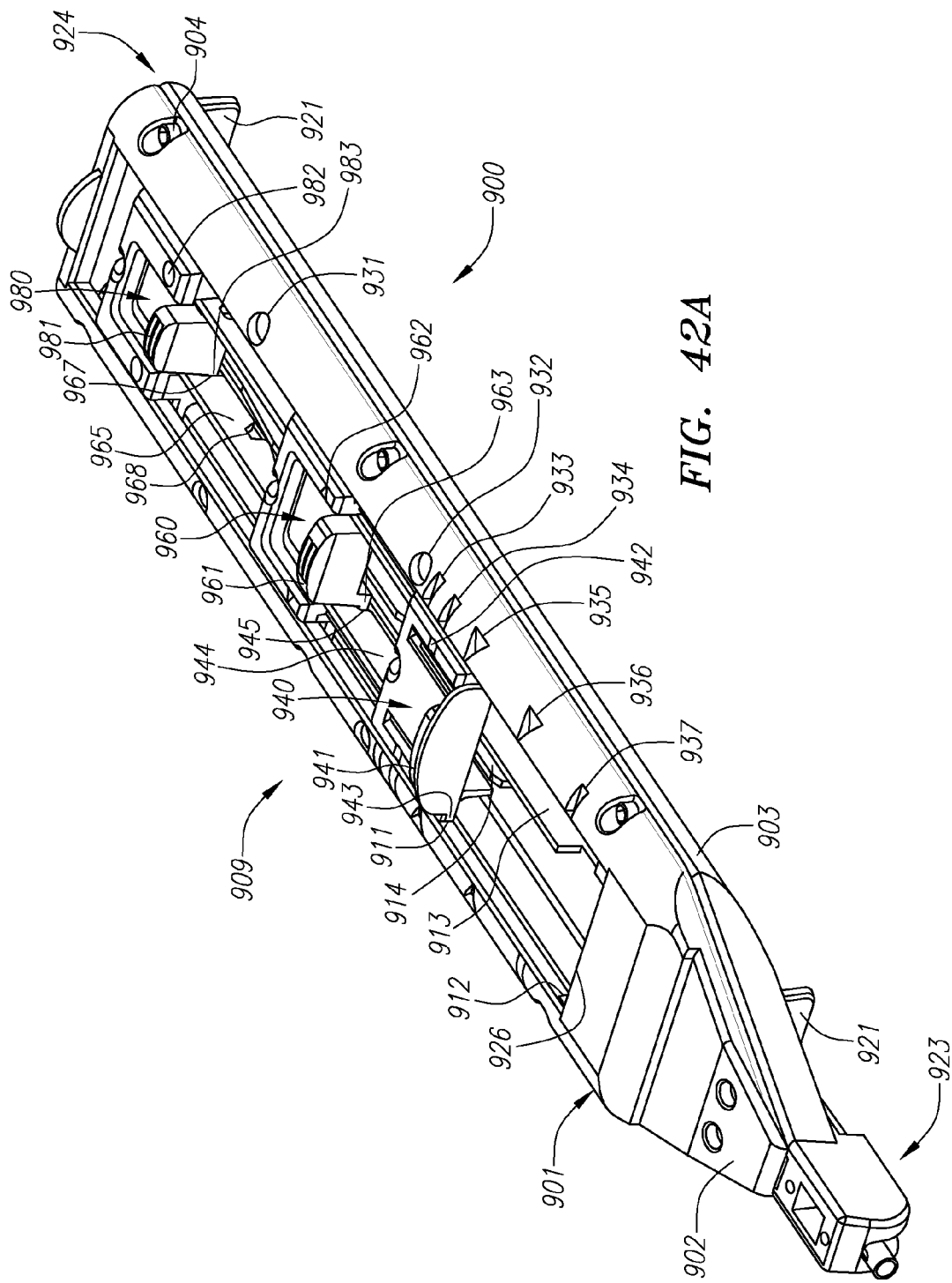
FIGS. 42A-I are perspective views depicting additional exemplary embodiments of a proximal control device.

In FIG. 42A, each of actuators 940, 960, and 980 are shown in start positions, which are suitable positions to be maintained during advancement of body member 101 through the vasculature and into proximity with septal wall 207, preferably within right atrium 205. Here, guide marking 942 on OA actuator 940 is aligned with guide marking 934 on upper housing 902 and tabs 943 on OA actuator 940 are located within slots 911 in upper housing 902. When tabs 943 are located within any of slots 910-912 of upper housing 902, OA delivery device 401 is effectively locked in position with respect to body member 101, which is preferably fixably coupled with housing 901.

Also in this position, tabs 963 on needle actuator 960 are located within slots 945 within OA proximal rails 944. Depression of needle button 961 in this position is prevented by outer ribs 914, which abut tabs 963. This effectively locks actuator 960 in position with respect to OA actuator 940. With regards to pusher actuator 980, tabs 983 are located within slots 967 within needle proximal rails 965. Depression of needle button 981 in this position is prevented by inner ribs 913, which abut tabs 983, effectively locking pusher actuator 980 in position with respect to needle actuator 960, which in turn is locked in position with respect to OA actuator 940. Thus, here, the position of needle actuator 960 and pusher actuator 980 is locked with respect to OA actuator 940 and follows the movement of OA actuator 940.

Figure 42B:
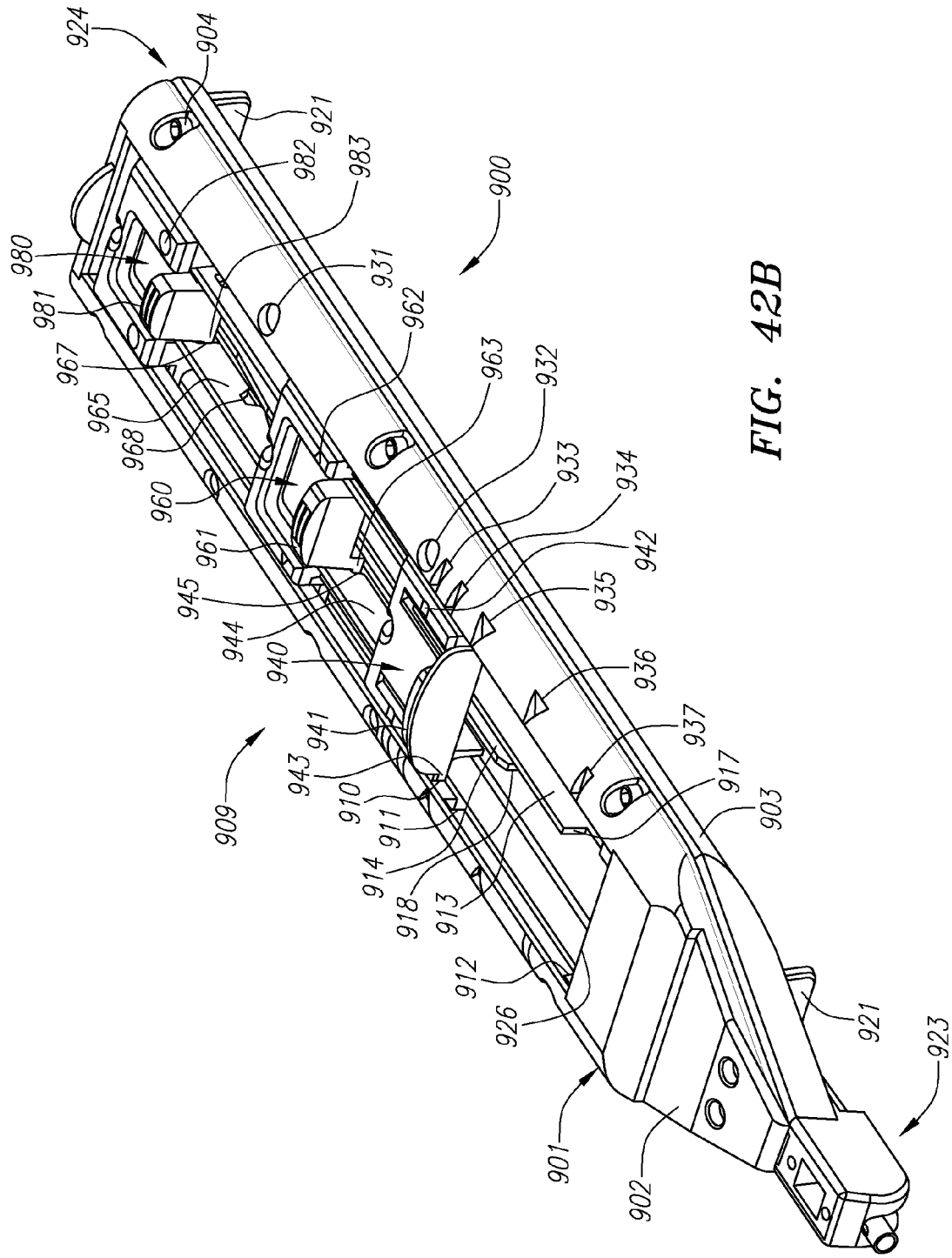

In FIG. 42B, button 941 on OA actuator 940 has been depressed to disengage tabs 943 from slots 911 and allow the proximal transitioning of OA actuator 940 to the position depicted here, at which point button 941 has been released. This raises and proximally moves OA delivery member 401 to raise arm member 409 and place it in position to engage limbus 211, similar to the orientation depicted in FIG. 14D. Here, OA guide marking 942 is aligned with guide marking 933 on housing 902 and OA tabs 943 are located within slots 910 in upper housing 902. OA button 941 remains depressible but the user is prevented from transitioning OA actuator 940 any further proximally than this position by the contact of tabs 948 with abutments 925 on housing portion 903.

Needle actuator 960 and pusher actuator 980 have been transitioned to positions slightly proximal that of the previous position, and remain locked in place with respect to OA actuator 940. Thus, the relative positions of needle member 405 and pusher member 406 have remained locked in place relative to OA delivery member 401, and both needle member 405 and pusher member 406 have been retracted within the subject's anatomy in lockstep fashion with OA delivery member 401. The device is then advanced distally to abut the limbus.

Figure 42C:
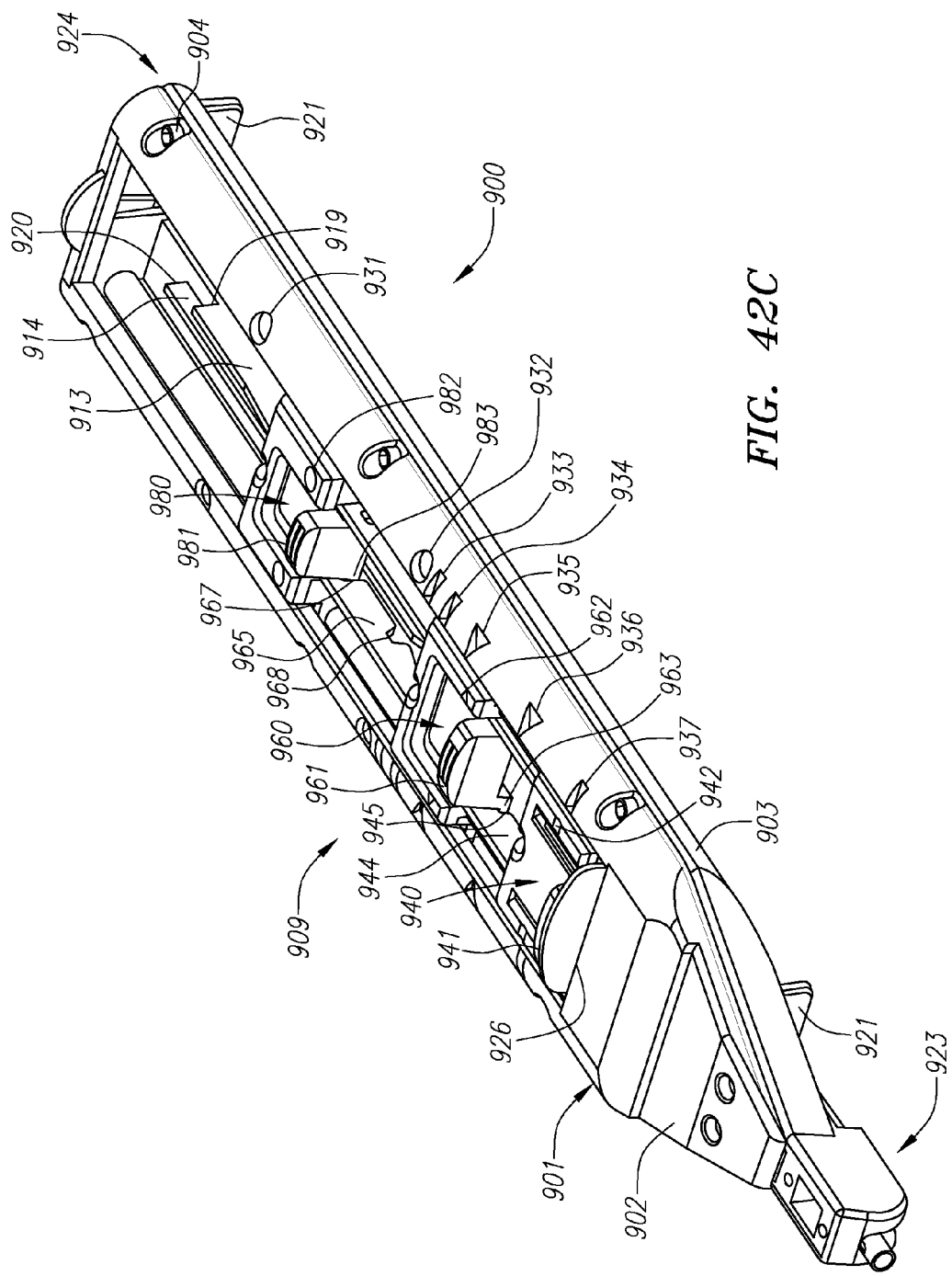

In FIG. 42C, OA actuator 940 has been transitioned distally to advance OA delivery member 401 into contact with septum secundum 210, causing arm member 409 to engage limbus 211 and positioning OA delivery member 401 into an off-axis delivery orientation, similar to the orientation depicted in FIG. 14F. At this point, body member 101 is preferably fixably coupled with the anatomy of the subject by way of grasping device 404. If, during this time, any of actuators 940, 960, and 980 are locked with respect to body member 101, for instance, by locking directly with housing 901 (e.g., OA tabs 943 in slots 910-912) or by locking with OA actuator 940 while locked with housing 901 (e.g., needle tabs 963 in OA slots 945 or pusher tabs 983 in needle slots 968 when needle actuator 960 is locked with respect to OA actuator 940), then that actuator 940, 960, and/or 980 also becomes locked with respect to the anatomy of the subject.

In the position of FIG. 42C, OA guide marking 942 is aligned with guide marking 937 on upper housing 902 and OA tabs 943 are located within slots 912 in upper housing 902. OA button 941 remains depressible but the user is prevented from transitioning OA actuator 940 any further distally than this position by the contact of button 941 with the distal surface of opening 926 on housing portion 902.

Needle actuator 960 and pusher actuator 980 remain locked in position with respect to OA delivery member 401 and have been transitioned to positions distal that of the previous position. Needle button 961 is now depressible because tabs 963 are located distal to distal ends 918 of outer ribs 914. If the user depresses needle button 961, proximal travel of needle actuator 960 is prevented by the proximal surface of slot 945 (which extends further downwards than the distal surface of slot 945) and distal end 918 of outer rib 914, which abut tabs 963. Pusher actuator 980 remains locked in place with respect to OA actuator 940 and needle actuator 960. If a guidewire is being used, it is preferably removed prior to proceeding to the next step.

Figure 42D:
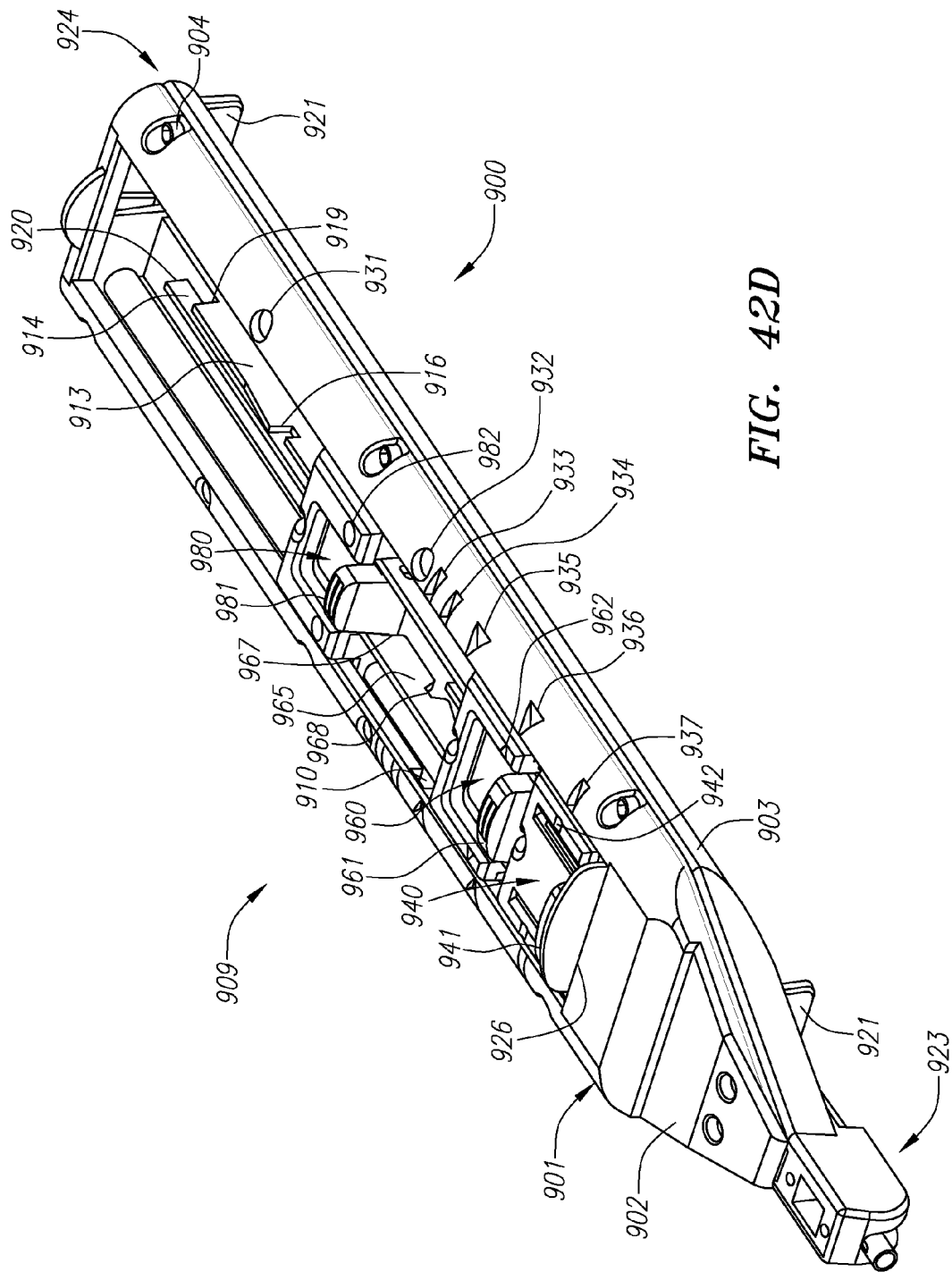

In FIG. 42D, needle actuator 960 has been transitioned distally to advance needle member 405 out of OA delivery member 401 and through septal wall 207, preferably through both septum secundum 210 and septum primum 214. Here, needle guide marking 962 is aligned with guide marking 936 on upper housing 902 and needle tabs 963 are located within slots 946 in OA proximal rails 944. Needle button 961 remains depressible but the user is prevented from transitioning needle actuator 960 any further distally than this position by the presence of OA actuator 940, which remains in the same position as in FIG. 42C. This prevents the user from inadvertently advancing needle member 405 too far into left atrium 212 and causing unwanted tissue damage. Needle distal rails 964 are now located beneath OA tabs 943 and prevent depression of OA button 941, preventing both distal and proximal movement and effectively locking OA actuator 940 in place.

It should be noted that proximal controller 900 can also be configured to automatically advance needle member 405 by the desired amount. For instance, needle member 405 can be spring loaded such that movement of needle actuator 960 to a certain position releases the spring, which provides force sufficient to advance needle member 405 through septal wall 207. Of course, one of skill in the art will readily recognize that other techniques for automatically advancing needle member 405 can be implemented and, accordingly, the systems and methods described herein are not limited to spring-based techniques.

Pusher actuator 980 has been transitioned with needle actuator 960 to a position distal that of the previous position. Specifically, pusher tabs 983 are now located over top of slot 915 in inner ribs 913, enabling the depression of pusher button 981. If the user depresses pusher button 981, proximal travel of pusher actuator 980 is prevented by the proximal surface of slot 967, which extends further downwards than the distal surface of slot 967. Preferably, button 981 is not depressible far enough to force tabs 983 below the bottommost portion of the proximal surface of slots 967, effectively preventing proximal movement of pusher actuator 980.

Figure 42E:
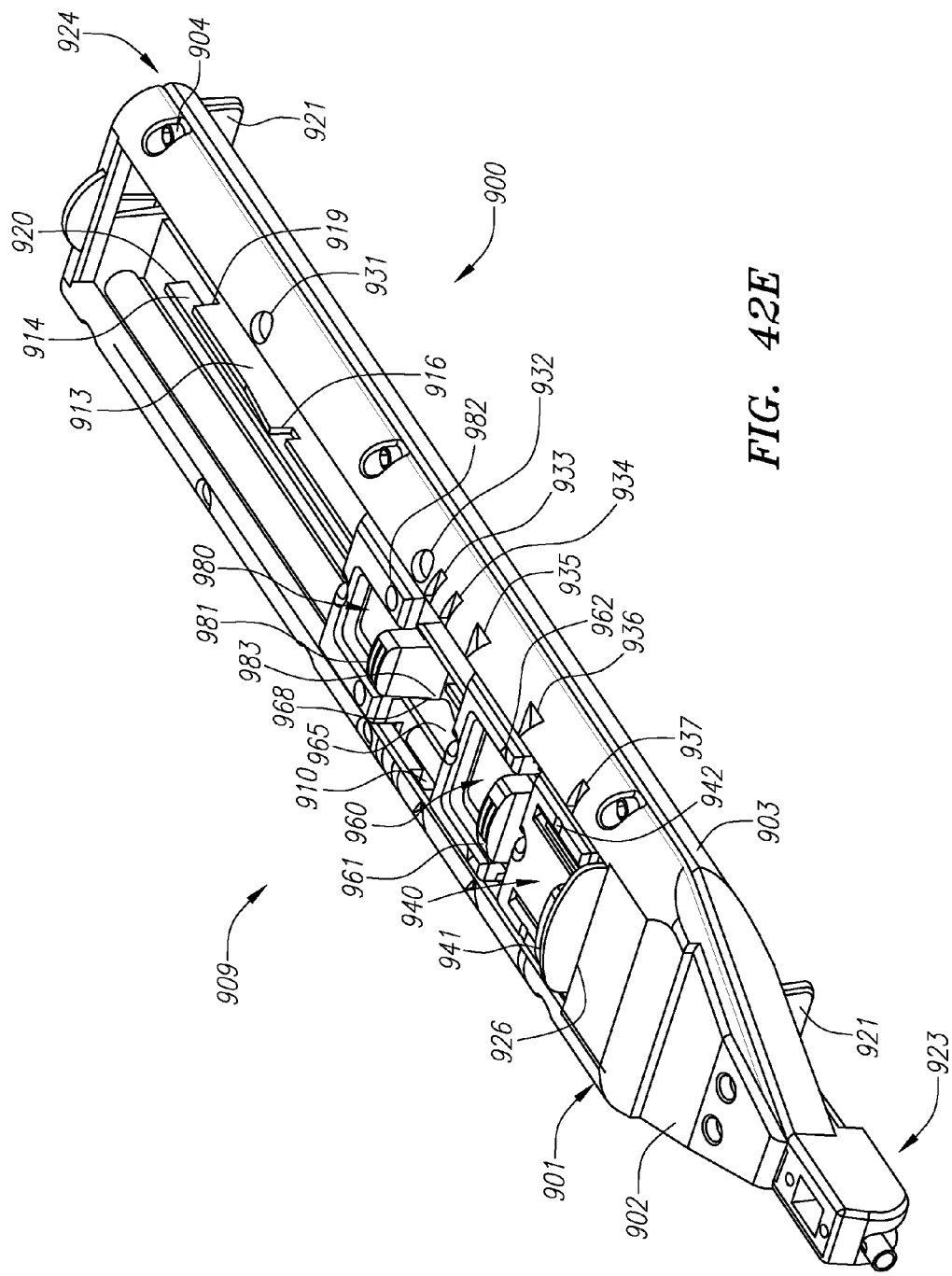

In FIG. 42E, pusher actuator 980 has been transitioned distally to advance LA portion 302 of implant 103 out of needle member 405, which, depending on the specific embodiment of implant 103, allows LA portion 302 to expand within left atrium 212. Here, pusher guide marking 982 is aligned with guide marking 932 on upper housing 902 and pusher tabs 963 have been advanced to the distal end of slots 915 within inner ribs 913 and into slots 968 in needle proximal rails 965. Pusher button 981 remains depressible but the user is prevented from transitioning pusher actuator 980 any further distally than this position by the pusher tabs 963 hitting distal surface of slots 915. As an additional safeguard, distal movement is also prevented by the distal surface of slot 968 in needle proximal rails 965. This distal surface acts in conjunction with inner ribs 913 to block tabs 983 from being advanced and prevent further distal movement of pusher actuator 980. OA actuator 940 and needle actuator 960 remain the same as described with respect to FIG. 42D.

Figure 42F:
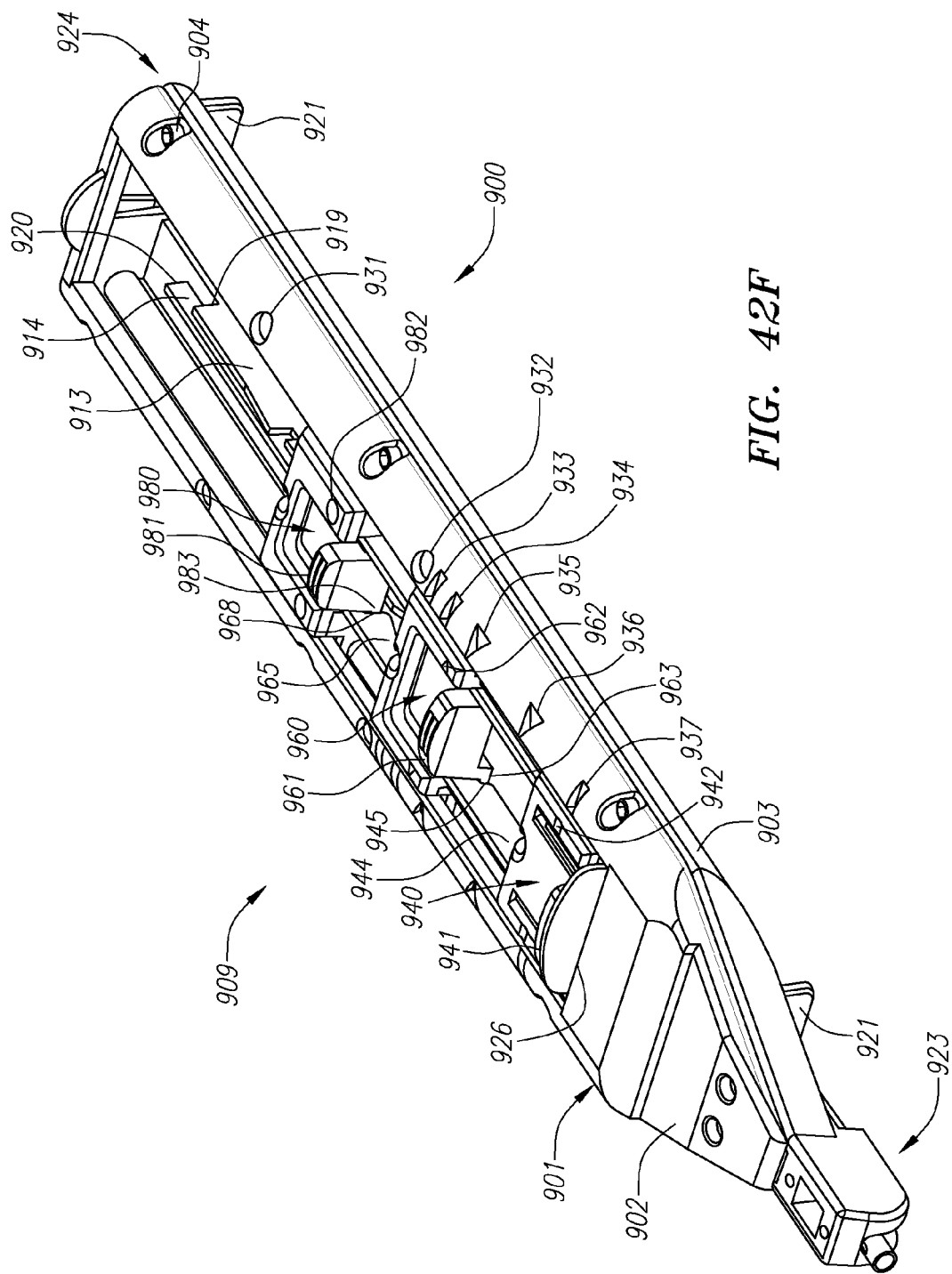

In FIG. 42F, needle actuator 960 has been transitioned proximally to retract needle member 405 from left atrium 212 and back into OA delivery member 401, which preferably pulls LA portion 302 of implant 103 into contact with septum primum 214. Here, needle guide marking 962 is aligned with guide marking 935 on upper housing 902 and needle tabs 963 are located within slots 945 in OA proximal rails 944. Needle button 961 remains depressible but the user is prevented from transitioning needle actuator 960 any further proximally by the proximal surface of slots 945 in OA proximal rails 944. Needle distal rails 964 are no longer beneath tabs 943 and OA button 941 is again depressible.

Pusher actuator 980 remains locked in place with respect to needle actuator 960 and has been transitioned with needle actuator 960 to a position proximal that of the previous position. Specifically, pusher tabs 983 remain within slots 968 but are now located over inner ribs 913 at a position proximal that of slots 915, preventing the depression of pusher button 981 and effectively locking pusher actuator 980 in place with respect to needle actuator 960.

Figure 42G:
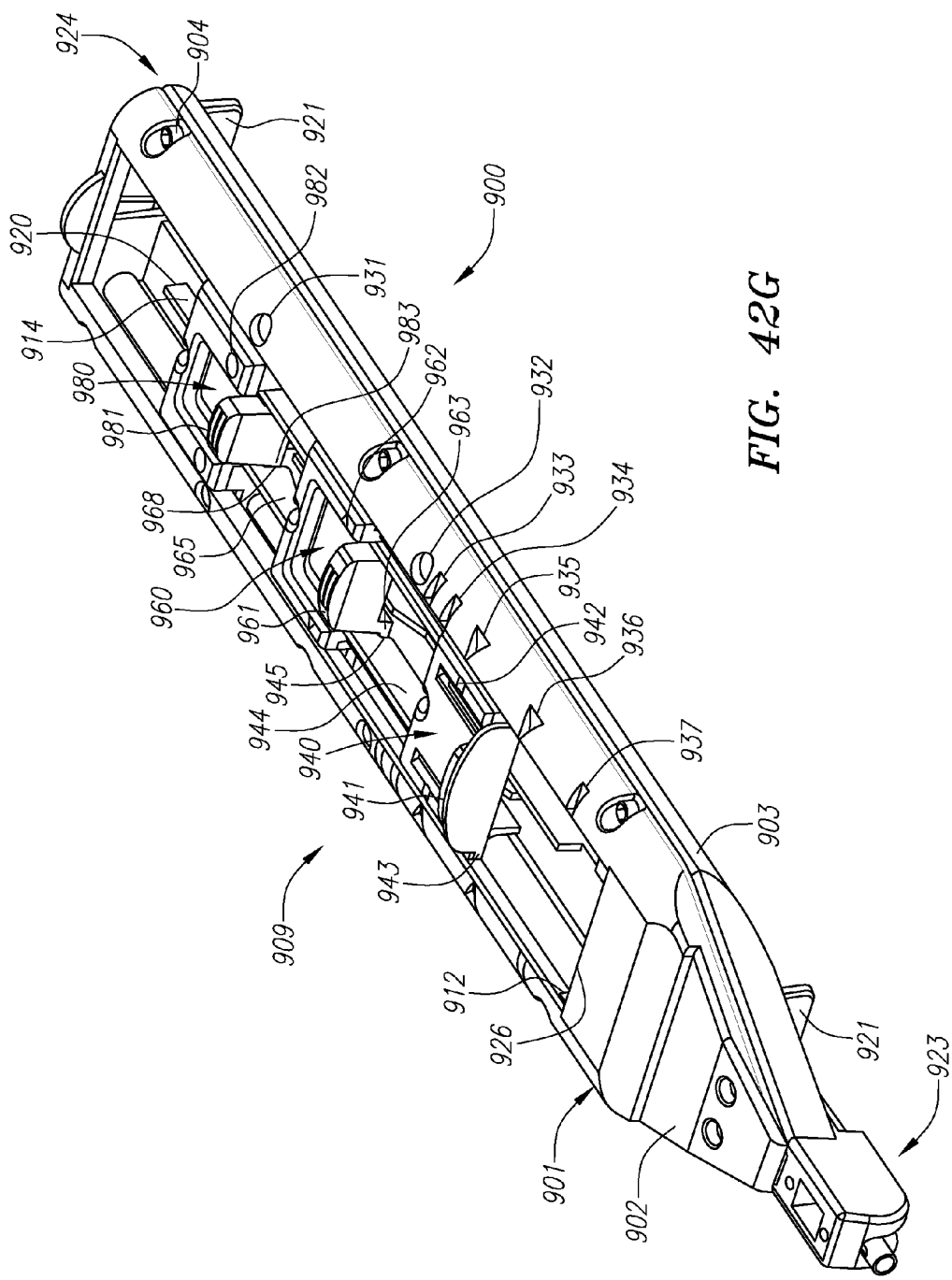

In FIG. 42G, OA actuator 940 has been transitioned proximally to retract OA delivery member 401, removing OA delivery member 401 from the off-axis delivery orientation. Here, OA guide marking 942 is not aligned with any guide marking on upper housing 902 and OA tabs 943 have not yet become seated within any slots in upper housing 902, leaving OA button 941 held in a depressed position by the surface of upper housing 902. Needle actuator 960 and pusher actuator 980 both remain locked in position with respect to OA actuator 940 and move proximally with OA actuator 940 until tabs 983 on pusher actuator 980 contact the proximal surface of slot 916 in inner ribs 913.

In this embodiment, the proximal surface of slot 916 extends further upwards than any other surface on inner ribs 913 and acts to block further travel of actuators 940, 960, and 980. This creates a stopping point in the operation of the device immediately prior to full deployment of implant 103, which, among other things, can allow the user time to image the subject to ensure implant 103 is positioned as desired. Needle button 961 is not depressible at this point due to the presence of outer ribs 914, effectively locking tabs 963 in place within slots 945 on OA proximal rails 944. Pusher button 981 is depressible as tabs 983 are now located over slots 916 in inner ribs 913, although movement in the distal and proximal directions is prevented by the contact of tabs 983 with slots 916. Pusher guide marking 982 is preferably aligned with marking 931 on upper housing 902.

Figure 42H:
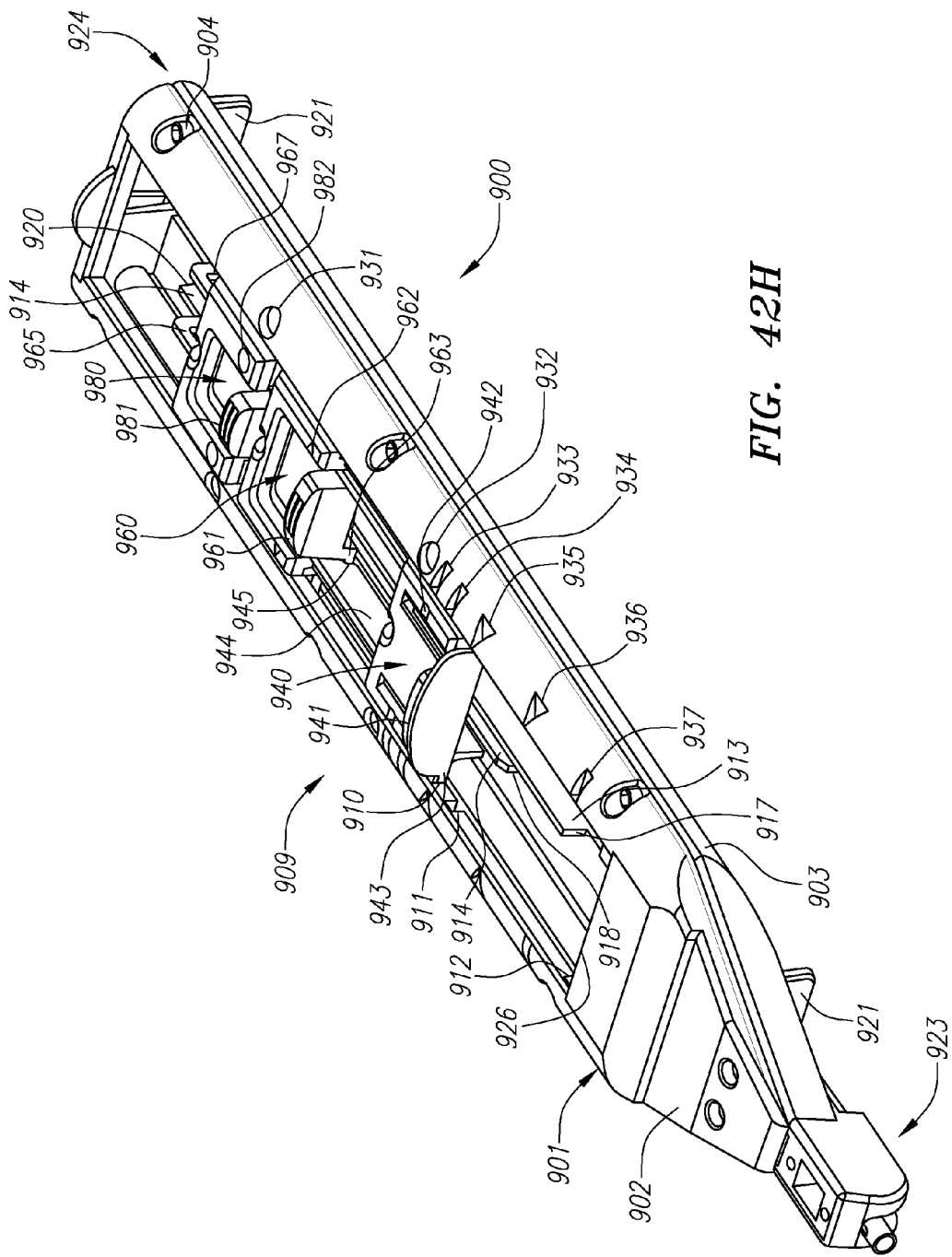

In FIG. 42H, pusher button 981 has been depressed to unlock pusher actuator 980 from needle actuator 960, specifically to unlock tabs 983 from slots 968, allowing OA actuator 940 and needle actuator 960 to be transitioned further proximally. This retracts OA delivery member 401 and needle member 405 with respect to pusher member 406, causing OA delivery member 401 to raise up and disengaging arm member 409 from limbus 211. This also fully exposes implant 103 from within both needle member 405 and OA delivery member 401 and allows RA portion 301 to expand and engage septum secundum 210 (connection to implant 103 may be maintained via the use of a safety device such as a tether and the like).

In this position, OA guide marking 942 is aligned with guide marking 933 on upper housing 902 and OA tabs 943 are seated within slots 910 in upper housing 902. OA button 941 remains depressible but the user is prevented from transitioning OA actuator 940 any further proximally than this position by the contact of tabs 948 with abutments 925 on housing portion 903. Needle actuator 960 remains locked in position with respect to OA actuator 940 and moves proximally with OA actuator 940. Needle button 961 is not depressible due to the outer ribs 914 and is effectively locked in place within slots 945 of OA proximal rails 944. Pusher actuator 980 remains locked in the same position as that depicted in FIG. 42G, although tabs 983 are now located distal to slots 968.

Figure 42I:
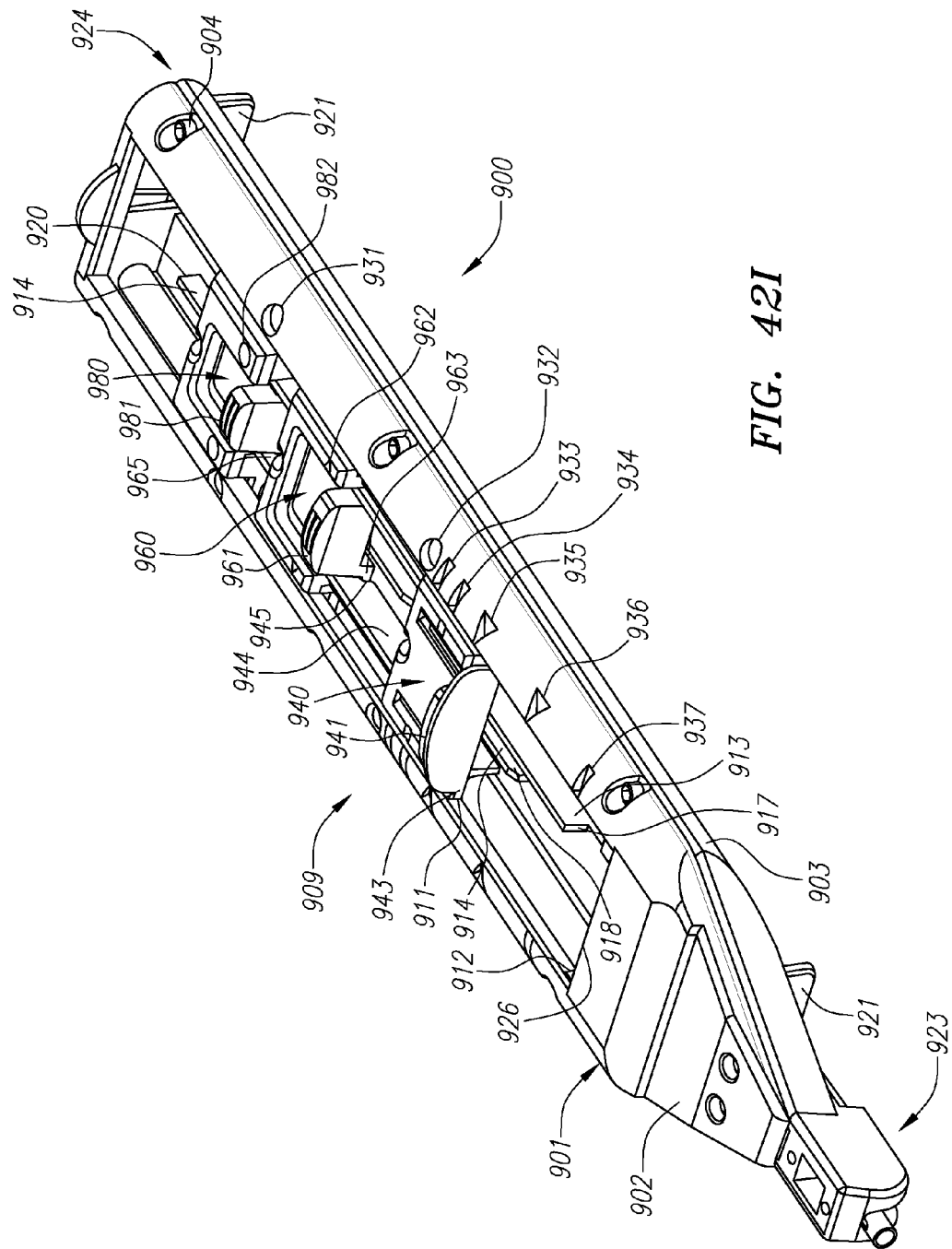

In FIG. 42I, OA actuator 940 has been transitioned distally to lower OA delivery member 401 into the low profile configuration desired for removal of system 100 from within the subject. Before removing system 100, any connection maintained with implant 103 is preferably released. In this position, OA guide marking 942 is aligned with guide marking 934 on upper housing 902 and OA tabs 943 are seated within slots 911 in upper housing 902. OA button 941 remains depressible and movement of OA actuator 940 is not prevented in either direction. Needle actuator 960 remains locked in position with respect to OA actuator 940 and moves distally with OA actuator 940. Needle button 961 is not depressible due to the outer ribs 914 and is effectively locked in place within slots 945. Pusher actuator 980 remains locked in the same position as that depicted in FIG. 42G, although tabs 983 are now located distal to slots 968.

FIGS. 41A-42I depict exemplary embodiments of proximal controller 900 using slidable actuators 940, 960 and 980 for the various elements of system 100. It should be noted that other configurations of proximal controller 900 can also be used to control system 100. FIGS. 43A-B depict an exemplary embodiment of proximal controller 900 where each of the elements of system 100 are controlled via user interface 909 having one main slidable actuator 1001.

FIG. 43A is a perspective view depicting this embodiment fully housed, while FIG. 43B is an internal perspective view depicting this embodiment with a portion of the housing omitted. Here, it can be seen that the main slidable actuator 1001 controls sub-actuators 1002-1004, each coupled with one of OA delivery member 401, needle member 405 and pusher member 406. The order in which sub-actuators 1002-1004 are moved is controlled by multiple springs 1005, each having predetermined spring constants chosen to be different so that springs 1005 act together in a cascading manner to effectuate the desired order of movement of sub-actuators 1002-1004.

Figures 43C, 43D:
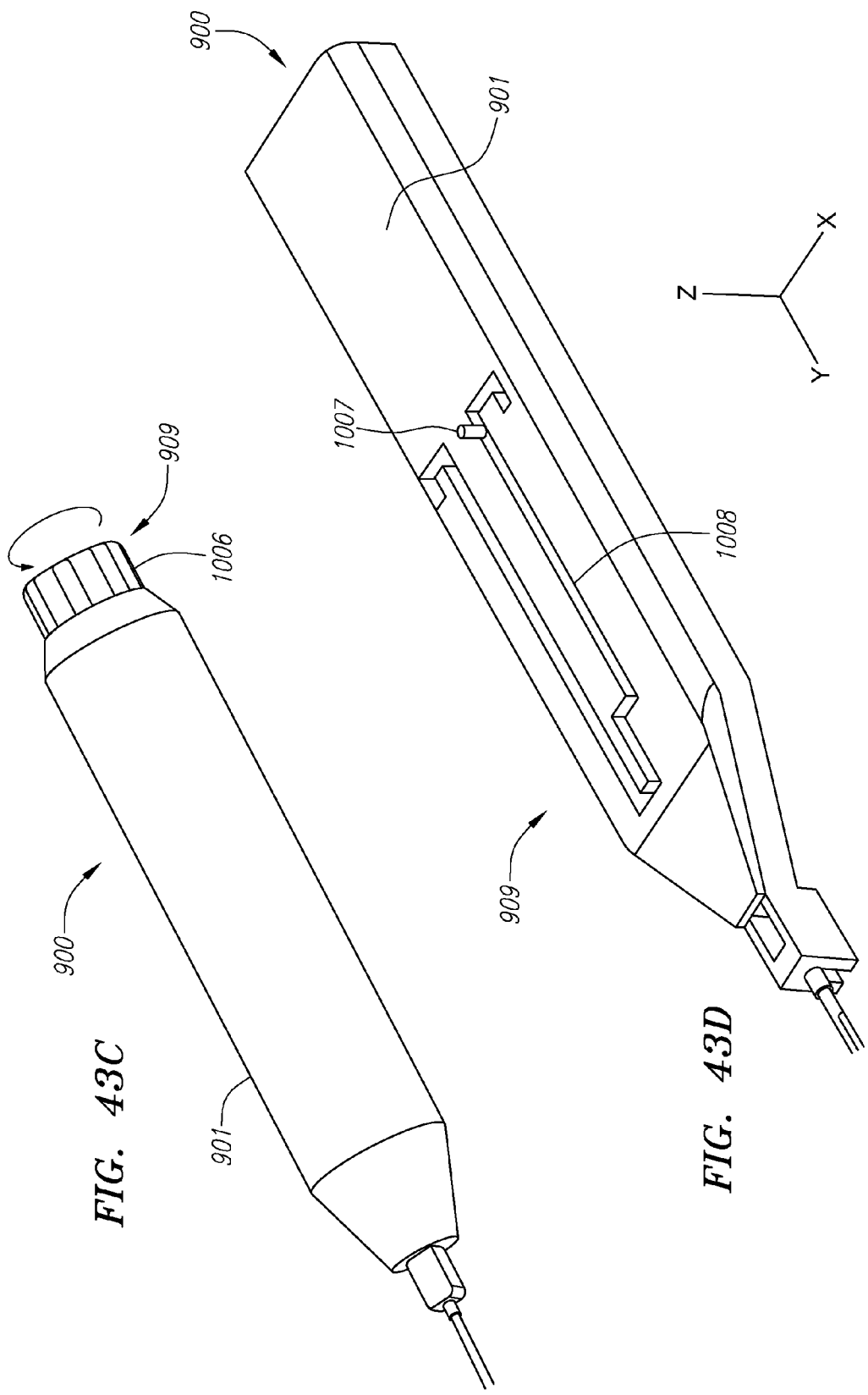
FIGS. 43C-G are perspective views depicting additional exemplary embodiments of a proximal control device.

FIG. 43C is a perspective view depicting another exemplary embodiment of proximal controller 900 where control of the various elements of system 100 is accomplished via user interface 909 having a rotatable knob 1006 located on controller 900's proximal end. In this embodiment, rotation by a certain amount in a certain direction (clockwise or counterclockwise) can equate to movement of a specific element of system 100, such as OA delivery member 401, needle member 405 and pusher member 406, etc. Rotatable knob 1006 can also be depressible to alternate control between the various elements. For instance, each depression can select a different element, or, depression by variable amounts selects corresponding elements.

FIG. 43D is a perspective view depicting yet another exemplary embodiment of proximal controller 900. Here, user interface 909 includes a single lever-like actuator 1007 transitionable through a pathway 1008 to select and move the various elements of system 100. In this embodiment, movement in separate directions equates to different functions of controller 900. For instance, movement of actuator 1007 in the X direction selects a different element of system 100 while movement in the Y direction corresponds to actual movement of the selected element. Preferably, the layout of pathway 1008 is configured to effectuate the proper movement of each element of system 100 in the proper amount at the proper time. Thus, a user can simply continuously advance actuator 1007 through pathway 1008 in a single general direction to achieve proper delivery of implant 103.

Figure 43E:
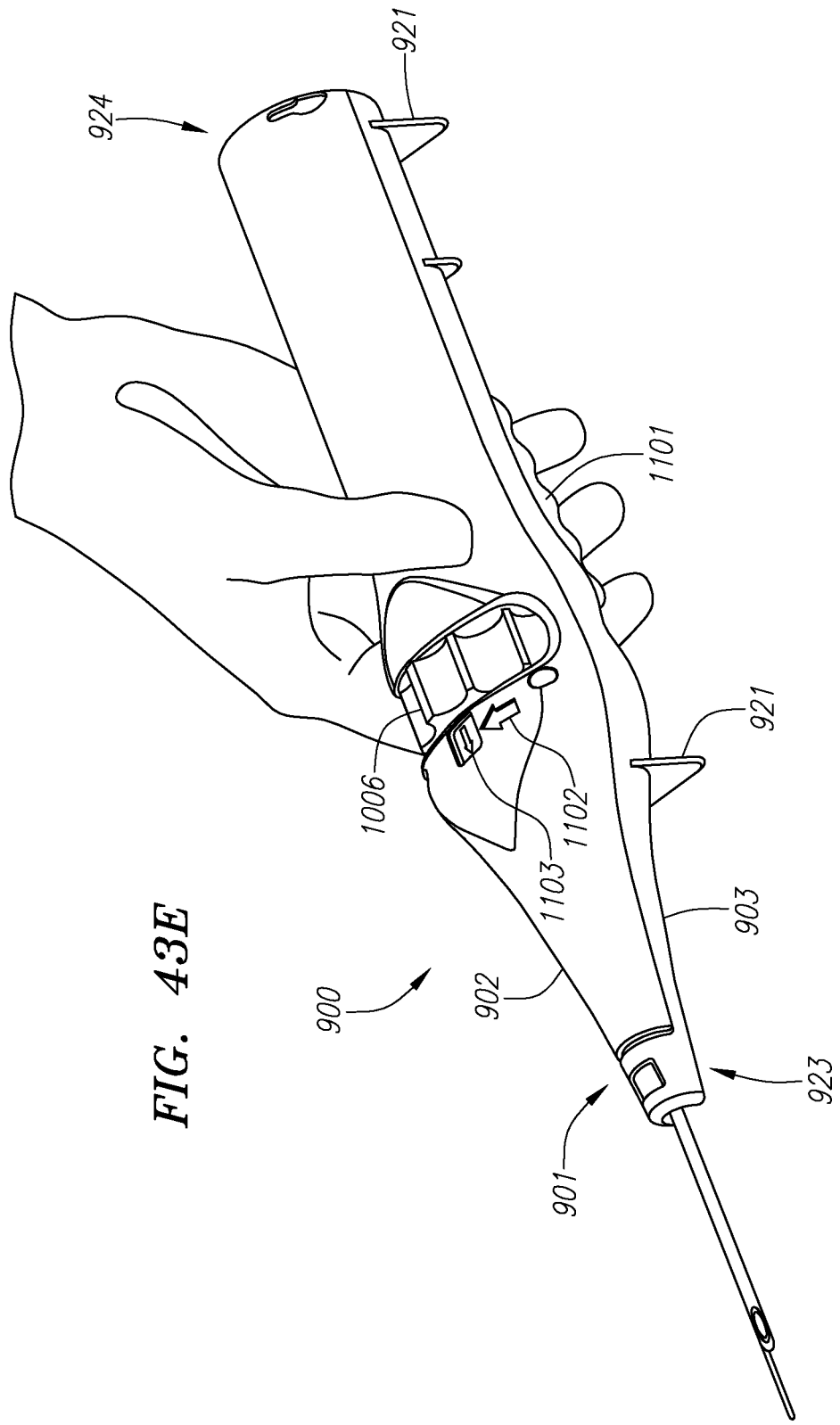

FIG. 43E is a perspective view depicting another exemplary embodiment of proximal controller 900 with rotatable knob 1006 during use by a user. Controller 900 has distal end 923 and proximal end 924 and includes housing 901, having upper and lower portions 902 and 903, respectively. Base 921 can be formed in lower housing 903 as shown. Here, knob 1006 is positioned distal to the grips on handle 1101 in a position such that a user can rotate knob 1006 in either direction (i.e., clockwise or counterclockwise) with his or her finger(s) or thumb. Handle 1101 can be grasped by hand and operated or can be rested on another surface (e.g., the user's leg or a table, etc.) and operated from that position. In this embodiment, the user preferably rotates knob 1006 in only the clockwise direction (from the user's perspective), as indicated by arrows 1102 displayed on device 900. Rotation in one direction increases the ease of operation for the user.

Adjacent to knob 1006 is information display 1103, which can be used to provide information to the user regarding any facet of device operation or the procedure. Display 1103 can have any configuration desired, including, but not limited to a mechanical and/or electronic display. In this embodiment, display 1103 is a window or opening in upper housing 902 through which an imprinted guide can be seen by the user, the guide changeable with rotation of knob 1006 and capable of displaying information regarding what step in the closure procedure the user is currently performing. Optionally, the window can be configured as a lens that magnifies the image for the user.

Figure 43F:
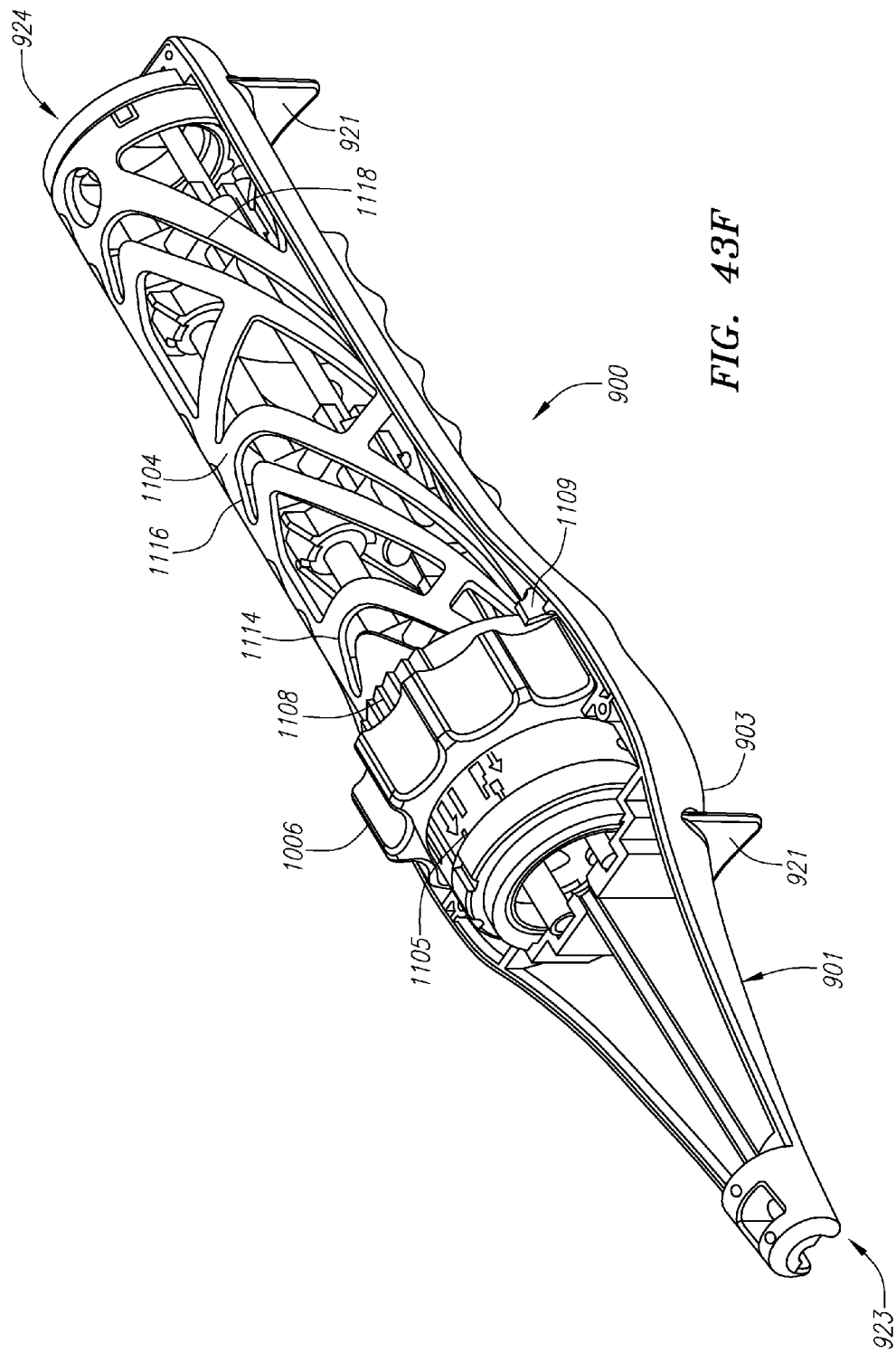

FIG. 43F is a perspective view depicting this embodiment of controller 900 with upper housing 902 removed and not shown. Here, a rotatable guide structure, referred to herein as cam 1104, is visible, which is preferably coupled with and moves in conjunction with rotatable knob 1006. Cam 1104 preferably includes three slots 1114, 1116 and 1118, the function of which will be described below. Also visible is a guide marking surface 1105, which includes the guides visible on display 1103 (shown in FIG. 43E). Rotatable knob 1006 includes a plurality of ratchets 1108 configured to interface with deflectable abutment 1109.

Figure 43G:
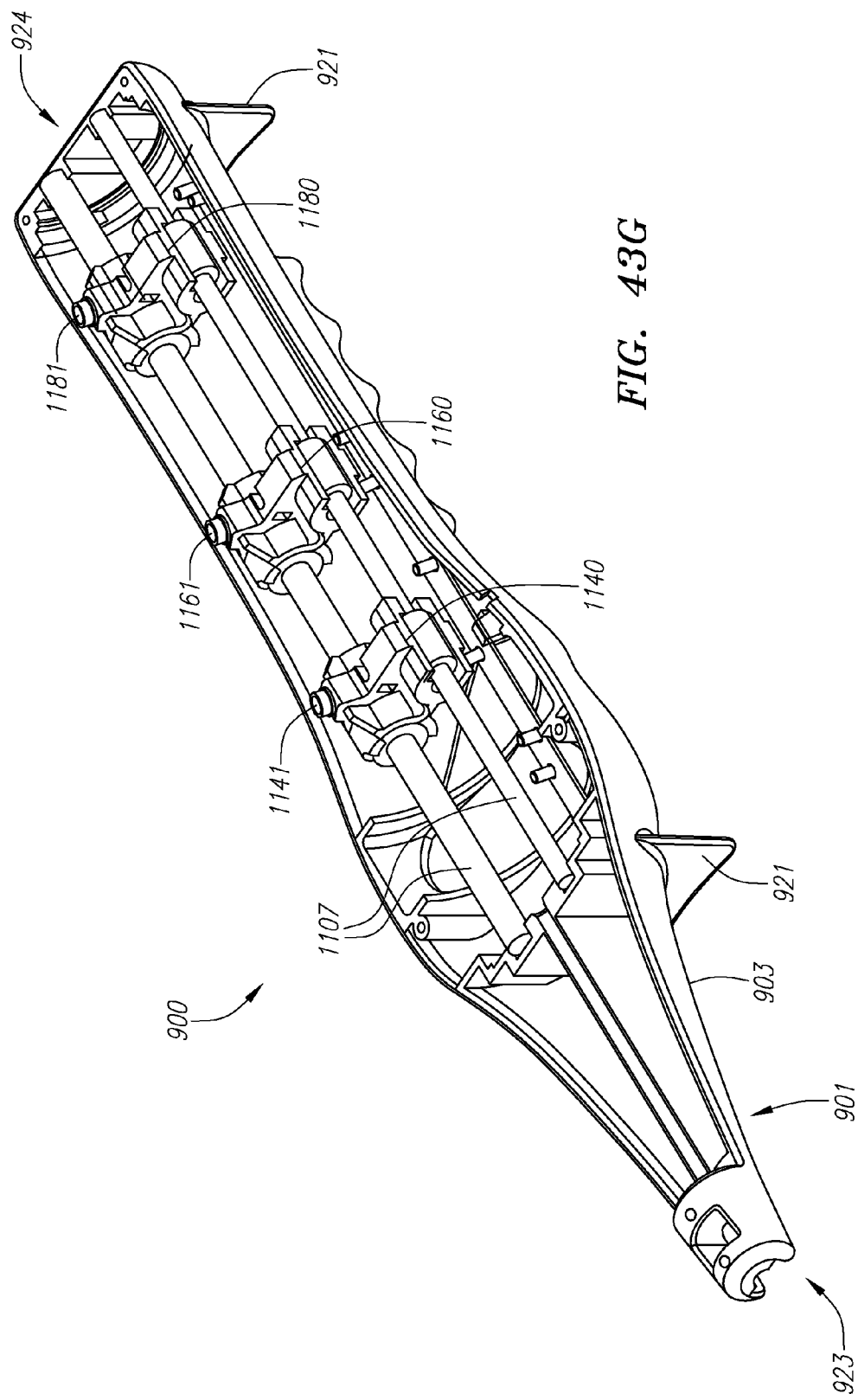

FIG. 43G is a perspective view depicting this embodiment with knob 1006 and rotatable cam 1104 removed from housing 901 and not shown. Here, an OA delivery member actuator 1140, a needle member actuator 1160, a pusher member actuator 1180 and guide rails 1107 can be seen. OA delivery member actuator 1140, needle member actuator 1160, and pusher member actuator 1180 are coupled with OA delivery member 401, needle 405 and pusher member 406, respectively (not shown), and configured to actuate longitudinal movement of members 401, 405 and 406 based on rotation of knob 1006.

Each actuator 1140, 1160 and 1180 can include an interface 1141, 1161 and 1181, respectively, that interfaces with one of the respective slots 1114, 1116 and 1118 (shown in FIG. 43F). In this embodiment, interfaces 1141, 1161 and 1181 are rotatable wheels configured to ride along the surface of slots 1114, 1116 and 1118, respectively, causing each actuator 1140, 1160 and 1180 to slide proximally or distally over guide rails 1107. One of skill in the art will readily recognize that any low friction interface, such as rotatable wheels, ball bearings and the like, can be used to slide or otherwise move within slots 1114-1118. Rotatable cam 1104 can also include one or more reinforcing bridge member (not shown) coupled with cam 1104 at multiple positions along its length to prevent the rotational torque from causing the width of slots 1114, 1116 and 1118 to vary and increase friction on interfaces 1141, 1161 and/or 1181.

Figures 1, 43H:
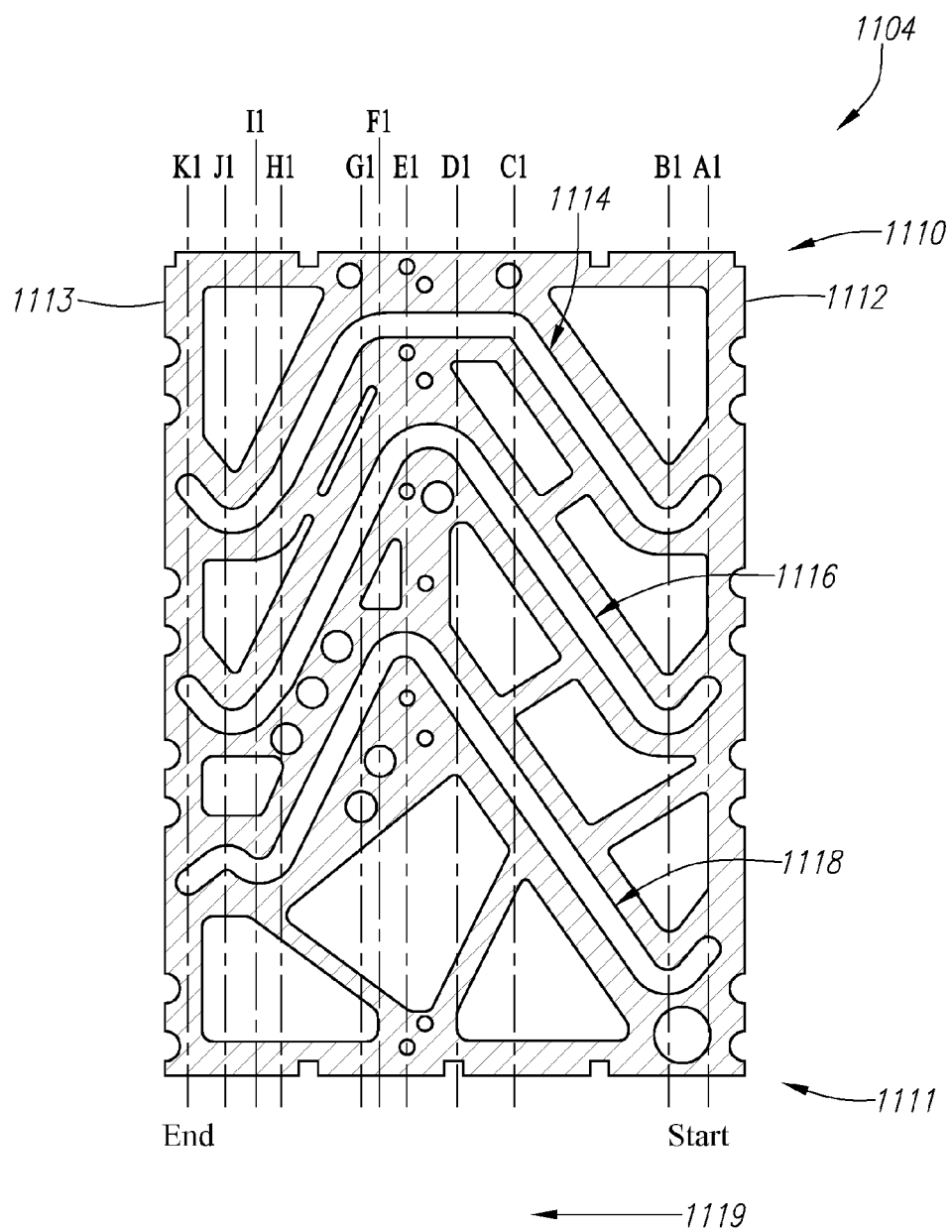
Figures 2, 43H:
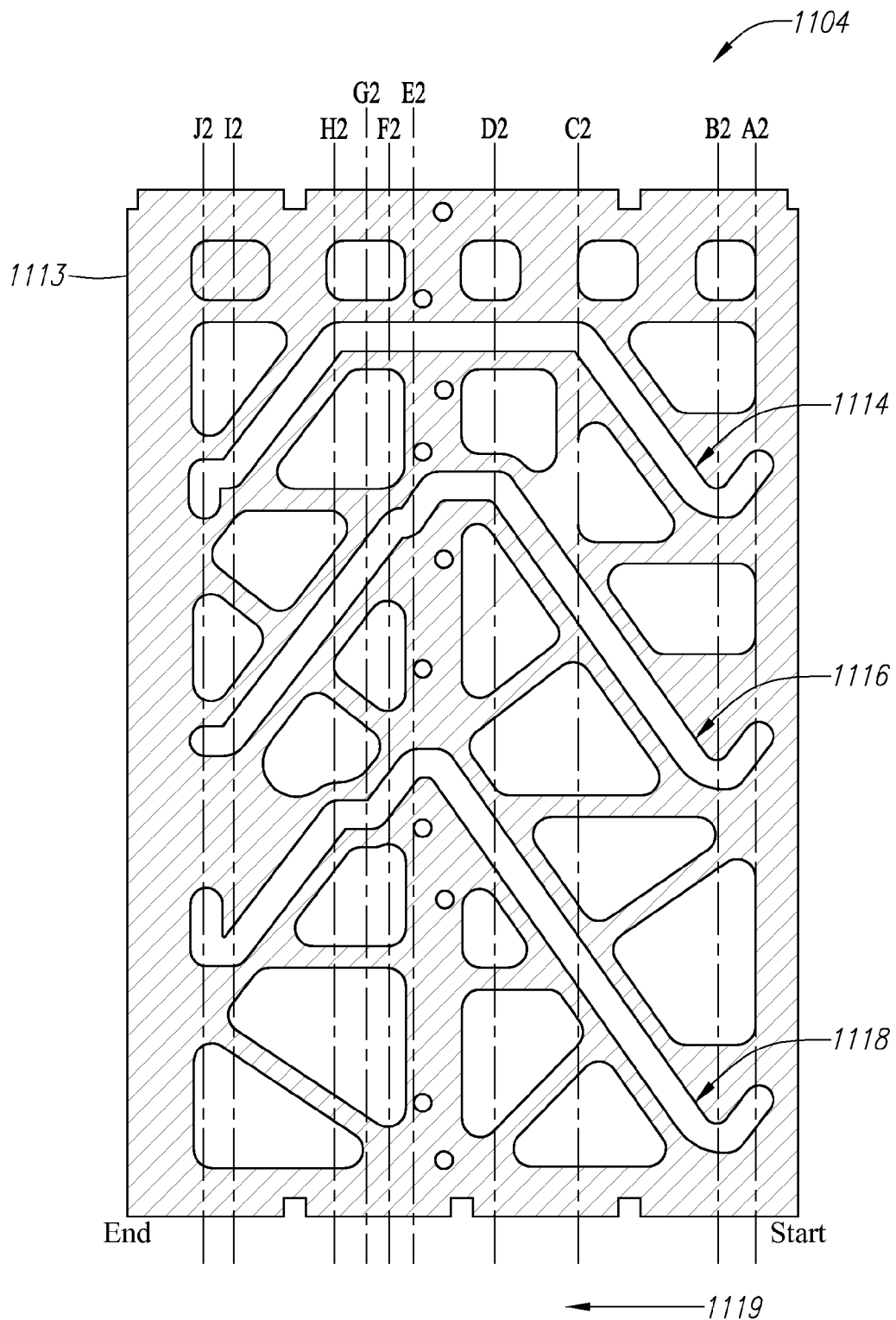
Figures 3, 43H:
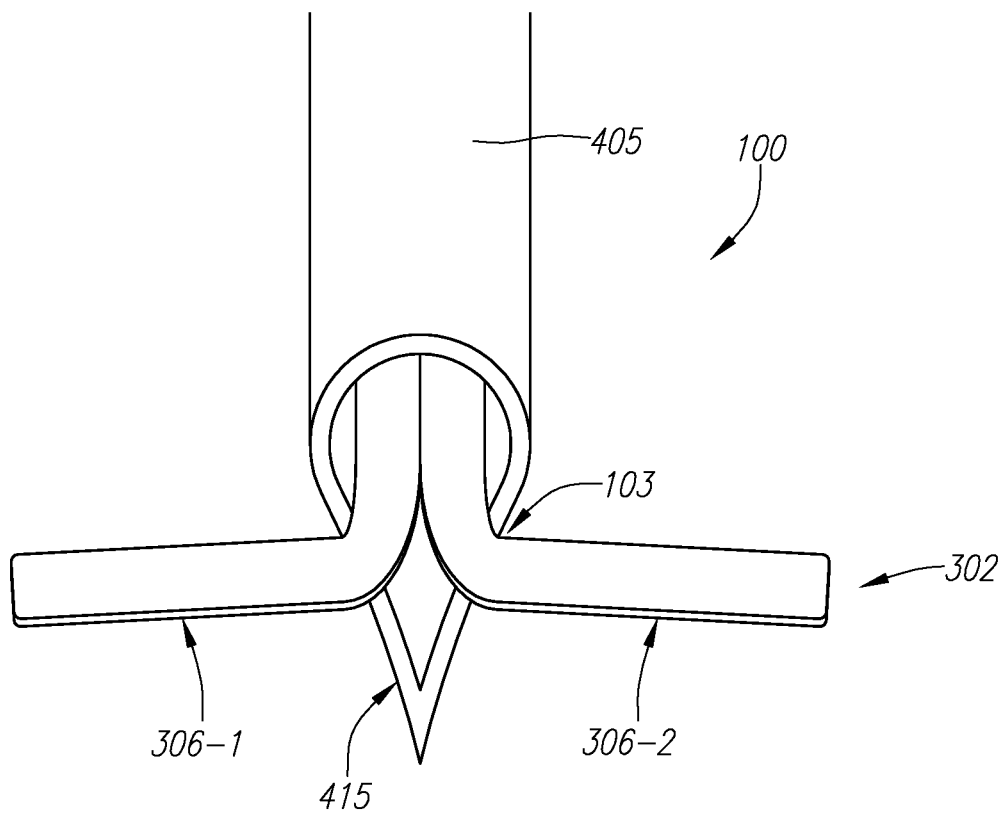

FIG. 43H-1 and FIG. 43H-2 are schematic views of exemplary embodiments of rotatable cam 1104, shown in a flat, unrolled perspective to more clearly illustrate the configuration of slots 1114, 1116 and 1118 and their relation to movement of actuators 1140, 1160 and 1180. In these two figures, cam 1104 has a distal end 1110, a proximal end 1111 and opposite sides 1112 and 1113, which are adjacent when cam 1104 is in a cylindrical configuration. As cam 1104 is rotated in a clockwise direction, interface wheels 1141, 1161 and 1181 travel in slots 1114, 1116 and 1118, respectively, in direction 1119.

The embodiment shown in FIG. 43H-1 will be described first. Reference lines A1-K1 extend longitudinally along cam 1104 and will be used to describe the position of actuators 1140, 1160 and 1180 with respect to the corresponding step in an exemplary embodiment of the closure procedure, making reference to portions of system 100 and the patient's anatomy that are not shown.

At the outset of the closure procedure, interface wheels 1141, 1161 and 1181 are all preferably located in their respective slots 1114-1118 at reference line A1. These positions correspond to a low profile arrangement of members 401, 405 and 406 suitable to be maintained during advancement of body member 101 through the vasculature and into proximity with septal wall 207, preferably within right atrium 205. Once in proximity with septal wall 207, knob 1006 can be rotated to bring wheels 1141, 1161 and 1181 to a position along reference line B1 in the respective slots 1114-1118. These B1 positions are all proximal to the respective A1 positions. OA actuator 1140 has moved proximally and actuated the raising and proximal movement of OA delivery member 401 to raise arm member 409 and place it in position to engage limbus 211, similar to the orientation depicted in FIG. 14D (e.g., a secundum capture position).

Needle actuator 1160 and pusher actuator 1180 have moved proximally as well, such that all three members 401, 405 and 406 remain in the same positions with respect to each other. It should be noted that the use of actuators 1140, 1160 and 1180 interfacing with predefined slots 1114-1118 in the manner described here eliminates the need to lock each member 401, 405 or 406 with respect to another member, since the relative position of each member 401, 405 and 406 is controlled by the radial position of knob 1006 (and cam 1104).

After body member 101 has been advanced distally such that arm member 409 abuts limbus 211, knob 1006 is preferably rotated to the position of reference line C1. This rotation transitions OA actuator 1140 distally causing OA member 401 to enter an off-axis delivery orientation, similar to the orientation depicted in FIG. 14F. Based on the length and shape of arm member 409 and the thickness of limbus 211, it is possible for grasping device 404 to clamp down and capture limbus 211 at a position after position B but prior to position C1. In such a case, continued rotation to position C1 does not cause additional downward movement of arm member 409, but does cause OA member 401 to continue into the off-axis delivery orientation. Again, needle actuator 1160 and pusher actuator 1180 have moved distally with OA member 401, but by a slightly greater amount such that members 405 and 406 remain in the same positions with respect to each other but both have advanced within OA member 401, preferably to a point where needle 405 is just inside OA member 401's distal end 410.

One of skill in the art will readily recognize that the slope of slots 1114-1118 can determine the distal/proximal (i.e., longitudinal) rate of movement at which the respective member 401, 405 and 406 will move in relation to the rate of rotation of knob 1006. A relatively more longitudinal (vertical as depicted here) slope corresponds to a relatively greater distance while a relatively more lateral (horizontal as depicted here) slope corresponds to a relatively shorter distance. The rate at which members 401, 405 and 406 are transitioned can be dependent upon the individual application.

Rotation of knob 1006 to reference line D1 causes needle actuator 1160 to transition distally to advance needle member 405 out of OA delivery member 401 and through septal wall 207, preferably through both septum secundum 210 and septum primum 214. As in other embodiments described herein, it should be noted that proximal controller 900 can also be configured to automatically advance needle member 405 by the desired amount. For instance, needle member 405 can be spring loaded such that movement of needle actuator 1160 to a certain position releases the spring, which provides force sufficient to advance needle member 405 through septal wall 207. Of course, one of skill in the art will readily recognize that other techniques for automatically advancing needle member 405 can be implemented and, accordingly, the systems and methods described herein are not limited to spring-based techniques.

Figure 43I:
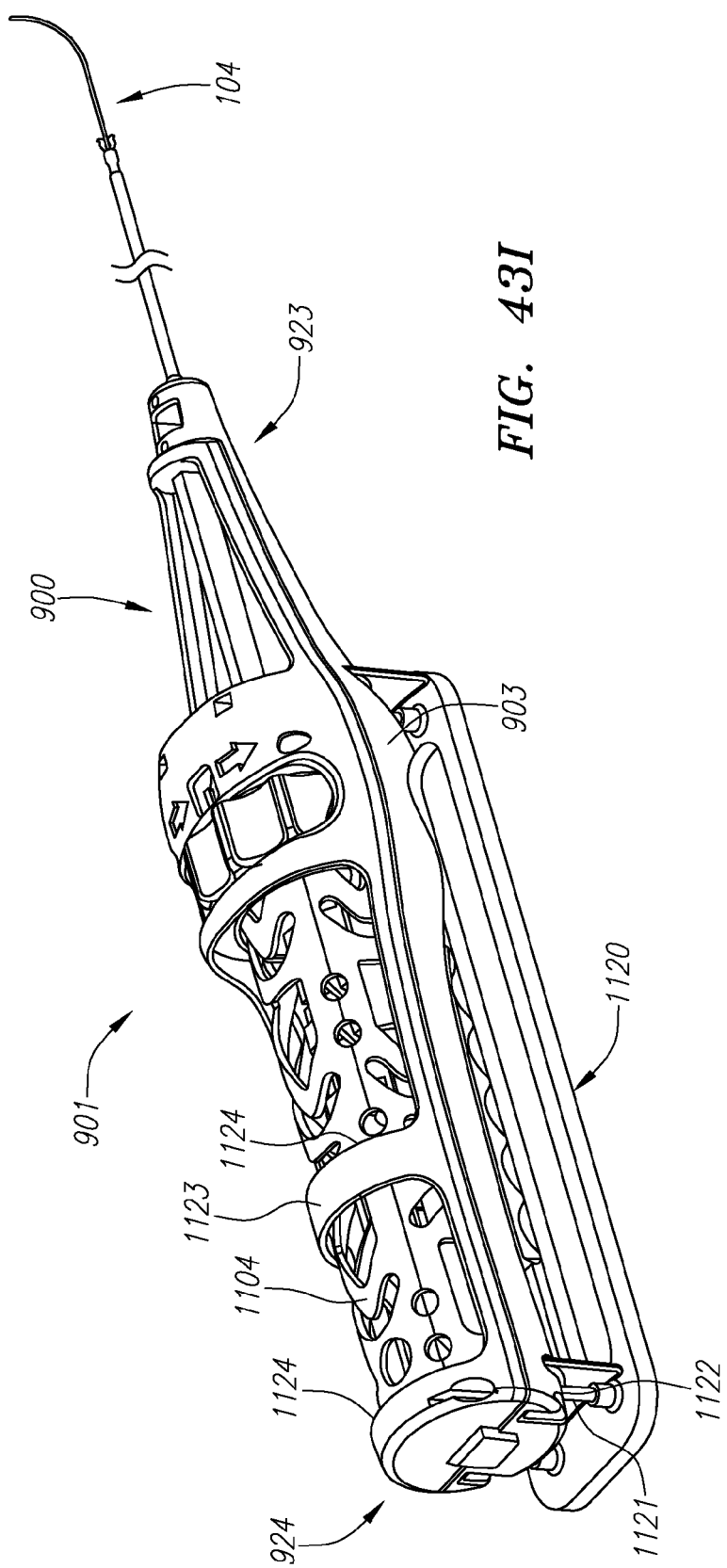
FIG. 43I-J are perspective views depicting additional exemplary embodiments of a proximal control device.

At position D1, pusher actuator 1180 has been transitioned with needle actuator 1160 to a position distal that of the previous position, such that the positions of needle 405 and pusher 406 with respect to each other are the same as in position C1, although both have been transitioned distally together while OA member 401 has not moved. As can be seen in FIG. 43H-I, this is because needle slot 1116 and pusher slot 1118 are sloped in a distal direction from position C1 to position D1, while OA member slot 1114 remains generally lateral. In this embodiment, rotation of knob 1006 to position D1 engages a ratchet 1108 on abutment 1109 (see FIG. 43F) such that knob 1006 can no longer be rotated in the opposite direction as a safeguard measure. Preferably, ratchets 1108 are located, at least, in positions corresponding to positions D1-J1 to provide additional safeguards throughout the procedure.

Rotation of knob 1006 to reference line E1 causes pusher actuator 1180 to transition distally causing pusher member 406 to advance LA portion 302 of implant 103 out of needle member 405, which, depending on the specific embodiment of implant 103, allows LA portion 302 to expand within left atrium 212. OA actuator 1140 remain in the same position as position D1, while needle actuator 1160 is transitioned proximally by a relatively small amount to facilitate deployment of LA portion 302.

Rotation of knob 1006 to reference line F1, first causes needle actuator 1160 to retract proximally while pusher actuator 1180 remains stationary, then causes pusher actuator 1180 to retract proximally as well. This sequential motion can first further deploy LA portion 302 and center portion 303, and then retracts implant 103 to cause LA portion 302 to contact septum primum 214. OA actuator 1140 remains stationary between positions E1 and F1.

Rotation of knob 1006 from position F1 to position G1 causes needle actuator 1160 and pusher actuator 1180 to proximally retract, at least partially, into OA member 401. OA actuator 1140 is proximally refracted by a relatively smaller amount than actuators 1160 and 1180. In this embodiment, implant 103 is preferably coupled with pusher member 406 to prevent complete deployment until desired.

Rotation of knob 1006 from position G1 to position H1 and then on to position I1 causes OA actuator 1140, needle actuator 1160 and pusher actuator 1180 to proximally retract to transition OA delivery member proximally from the OA delivery orientation. Here, pusher 406 is retracted proximally by the greatest amount, while needle 405 is retracted proximally by a slightly less amount and OA member 401 is refracted proximally by a slightly less amount than needle 405. Needle 405 is preferably again fully housed within OA member 401. In this embodiment, central portion 303 of implant 103 is preferably flexible and allows implant 103 to bend prior to being released from pusher 406.

Rotation of knob 1006 from position I1 to position J1 causes pusher actuator 1180 to advance distally while OA actuator 1140 and needle actuator 1160 are refracted proximally and then held in a constant position. This can expose the distal end of pusher 406 and allow RA portion 301 of implant 103 to be released, thereby fully deploying implant 103 (with the exception of any safety devices, such as a tether, that still connect implant 103 to delivery device 104).

Rotation of knob 1006 from position J1 to position K1 distally advances OA actuator 1140 and needle actuator 1160 to positions similar to the start position A1, placing OA member 401 in the low profile position suitable for withdrawal through the anatomy of the subject with needle 405 located within OA member 401. Pusher actuator 1180 has been proximally retracted to cause pusher 406 to retract into OA member 401 for withdrawal from the subject.

Turning now to the embodiment shown in FIG. 43H-2, reference lines A2-J2 extend longitudinally along cam 1104 and will be used to describe the position of actuators 1140, 1160 and 1180 with respect to the corresponding step in an exemplary embodiment of the closure procedure, making reference to portions of system 100 and the patient's anatomy that are not shown. While not required, this embodiment is preferably used to deploy a clip-like implant 103, such as that described in the incorporated '842, '710 and '748 applications (see below). The movement of actuators 1140, 1160 and 1180 between positions A2 and E2 are similar to the movements between positions A1 and E1 described with respect to FIG. 43H-1 and will not be repeated.

At position E2, pusher actuator 1180 has been advanced to its most distal position and needle actuator 1160 has been retracted from its most distal position by a relatively small amount, to ensure full deployment of the LA portion 302 of the clip 103. OA actuator 1140 remains in a relatively constant position from C2 until H2.

Rotation of knob 1006 from position E2 to position F2 moves pusher actuator 1180 proximally while maintaining needle actuator 1160 in a constant relative position. If a beveled needle member is used, this movement preferably causes the clip 103 to be retracted into the beveled portion of the needle such that the needle can facilitate maintenance of a proper orientation of clip 103, i.e., help resist rotation of clip 103 during deployment against the septal wall.

Such a configuration is depicted in FIG. 43H-3, which is a perspective view depicting an exemplary embodiment of clip 103 with LA portion 302 having two arm-like left atrial anchors 1064-1 and 1064-2 in a deflected, deployed state. In FIG. 43H-3, clip 103 is partially deployed from needle member 405 such that arm members 1064-1 and 1064-2 are in close proximity to the beveled distal end 415 of needle member 405, where distal end 415 can maintain clip 103 in the desired orientation. One example of a desired orientation is placement of arm members 1064-1 and 1064-2 such that they extend across the entire native PFO tunnel on the left atrial side of the septum primum.

Rotation of knob 1006 from position F2 to position G2 moves both pusher actuator 1180 and needle actuator 1160 proximally back through the septal tissue the same distance (and at the same rate), preferably to bring LA portion 302 of clip 103 into contact with the septum primum.

Rotation of knob 1006 from position G2 to position H2 moves needle actuator 1160 back proximally while maintaining pusher actuator 1180 in a relatively constant position to bring the needle member 405 into the OA delivery member 401.

Rotation of knob 1006 from position H2 to position I2 moves each of the three actuators 1140, 1160 and 1180 proximally the same distance (and at the same rate), to cause the OA delivery member to exit the OA delivery position and transition to the configuration similar to that depicted in FIG. 14E. At this position, the RA portion 303 of the clip 103 has preferably not deployed yet. The clip can be slightly bent but still preferably retained by the pusher member 406, which preferably engages clip 103 (e.g., such as in the configuration described with respect to FIG. 46C).

Rotation of knob 1006 from position I2 to position J2 preferably does not move any of the actuators 1140, 1160 and 1180, but places OA actuator 1140 and pusher actuator 1180 in positions adjacent longitudinal portions of slots 1114 and 1118 that allow actuators 1140 and 1180 to move proximally and distally, respectively. This allows OA delivery member 401 to fully collapse to the elongate, unraised state when withdrawn through the vasculature.

Once in position J2, the user preferably manually retracts delivery device 104 proximally. Because LA portion 302 is deployed against the septum primum 214 and still attached to pusher member 406, the manual retraction of the delivery device 104 causes OA member 401 and needle member 405 to move proximally with respect to pusher member 406. This causes RA portion 303 of clip 103 to become exposed from within OA delivery member 401 (and needle member 405) where it is no longer restrained and free to deploy. (It should be noted that in other embodiments, pusher member 406 can be configured such that clip 103 is released only upon user actuation of a release mechanism.) RA portion 303 can then deploy against the septum secundum to complete delivery.

FIG. 43I is a perspective view depicting another exemplary embodiment of proximal controller 900 resting on a loading platform 1120 for use in loading implant 103 (not shown) prior to final assembly. Here, upper housing 902 has been replaced with a loading upper housing 1123 having open section 1124 to allow access to cam 1104. Loading platform 1120 is preferably used for loading implant 103 into delivery device 104 and engaging each actuator 1140, 1160 and 1180 with cam 1104. Loading platform 1120 can include one or more pegs 1121 configured to slide within corresponding apertures 1122 in lower housing 903 of controller 900. Pegs 1121 are preferably configured to contact and lift cam 1104 to disengage actuators 1140, 1160, and 1180. Once disengaged, actuators 1140, 1160 and 1180 can be freely moved within cam 1104 and delivery device 104 can be loaded with implant 103.

Figure 43J:
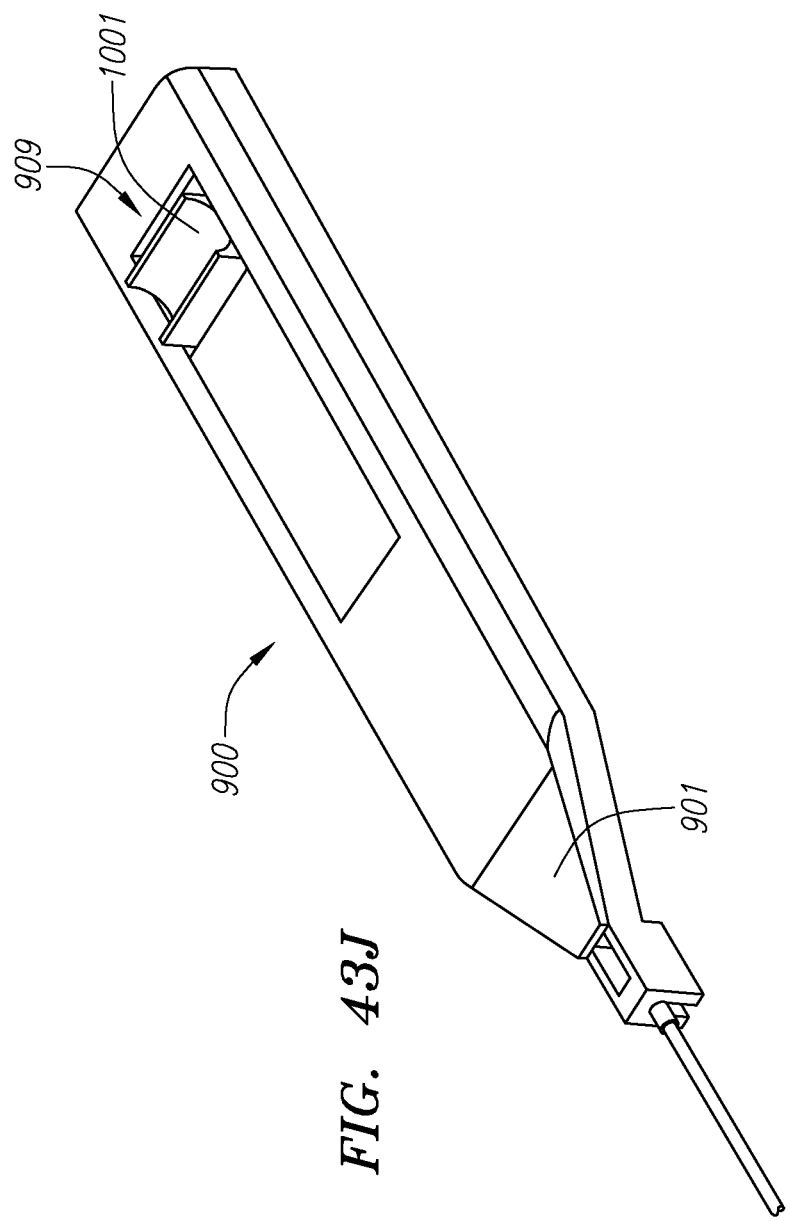

FIG. 43J is a top down view of another exemplary embodiment of proximal controller 900, similar to that described with reference to FIGS. 43A-B. In this embodiment, members 401, 405 and 406 (not shown) are controllable by way of a series of actuators that are translatable distally and proximally by distal and/or proximal movement of a single user interface 1201. FIG. 43K is a top down view of lower housing 903 with actuators 1240, 1260 and 1280 shown therein. Actuators 1240, 1260 and 1280 are coupled with OA member 401, needle member 405 and pusher member 406, respectively. User interface 1201 is coupled with pusher actuator 1280 which in turn is coupled with needle actuator 1260, which is in turn coupled with OA actuator 1240. Two bias members 1208 and 1209 are also shown. Bias member 1208, in this embodiment, is a spring-like member and is coupled between OA actuator 1240 and needle actuator 1260. Bias member 1209 is also a spring-like member and is coupled between needle actuator 1260 and pusher actuator 1280. It should be noted that any member configured to apply a bias can be used for bias members 1208 and 1209, not limited solely to spring-like members.

FIG. 43L is a top down view of lower housing 903 with actuators 1240-1280 removed and FIG. 43M is top down view of actuators 1240-1280. Preferably, actuators 1240 and 1260 each include slots 1204 and 1206, respectively. Pusher actuator 1280 preferably includes a deflectable strut 1212 configured to interface with slot 1206. The distal end of strut 1212 preferably includes an upward-facing abutment 1216 and a downward-facing abutment 1217 located opposite to abutment 1216 (here, abutment 1217 is obscured by strut 1212). Abutment 1216 is preferably configured to interface with slot 1206 of needle actuator 1260, while abutment 1217 is preferably configured to interface with track 1203 in lower housing 903. Likewise, needle actuator 1260 preferably includes a deflectable strut 1210 also having an upward-facing abutment 1214 and a downward-facing abutment 1215 (obscured). Upward-facing abutment 1214 is preferably configured to interface with slot 1204 in actuator 1240, while downward-facing abutment 1215 is preferably configured to interface with track 1203 in lower housing 903. In this embodiment, there are two of each of struts 1210-1212, slots 1204-1206, abutments 1214-1217 and tracks 1203, but it should be noted that more or less of said items can be used depending on the needs of the application.

In this configuration, movement of actuators 1240-1280 is dependent, in part, on the positions of abutments 1214 and 1216 within slots 1204 and 1206 respectively, as well as the position of abutments 1215 and 1217 within track 1203. In addition, bias members 1208 and 1209, depending on the relative bias strengths thereof, will also influence the order of movement of actuators 1240 and 1260, respectively.

Track 1203 and slots 1204 and 1206 are preferably laid out to provide an desired order of movement to each of actuators 1240-1280, either in unison or in relative motion with each other. To operate, a user preferably depresses interface button 1201 and advances user interface 1201, as well as pusher actuator 1280 which is coupled with interface 1201, in a distal direction. As with the other embodiments of controller 900 described herein, the movement of the actuators is dependent on the order of steps in the desired treatment or closure procedure.

In FIG. 43K, actuators 1240-1280 are in positions suitable to place members 401, 405 and 406 in a low profile configuration suitable for advancement within the vasculature. Once in position within the heart, the user can commence the procedure by depressing interface 1201 and sliding it distally. It should be noted that guide markings can be placed on upper hosing 902 to guide the user in how far to advance interface 1201. Distal movement of interface 1201 causes pusher actuator 1280 to move distally, which also forces needle actuator 1260 to advance distally in lockstep fashion, since struts 1212 are prevented from deflecting outward and advancing in slots 1206 by the presence of rail 1202, which abuts downward-facing abutment 1217. Thus, struts 1212 do not move with respect to needle actuator 1260 and downward-facing abutment 1217 slides within track 1203. Conversely, OA actuator 1240 remains stationary because each track 1203 is coincidental with slot 1204 at this position, allowing struts 1210 to deflect and upward-facing abutment to slide forward within slot 1204.

The rate at which each actuator 1240-80 moves can be varied according to the slope of the respective slots and track. Additional abutments, such as abutments 1224 in lower housing 903 shown in FIG. 43L, can be incorporated to prevent further distal motion of the actuators. As mentioned above, bias members 1208 and 1209 can be configured with different relative strengths, for instance, to allow actuators 1240 and 1260 to move in a desired sequence. Furthermore, bias members 1208 and/or 1209 can be configured to cause a particular actuator to move in a direction opposite that in which interface 1201 is being moved. For instance, slot 1206 has a middle section 1207 with a reversed slope that allows needle actuator 1260 to move proximally when the appropriate forces are applied by bias members 1208 and 1209.

Thus, as will be readily apparent to one of skill in the art based on the description herein, the layout of slots 1204-1206, track 1203 and the configuration of bias members 1208-1209 can allow numerous desired combinations of movement of actuators 1240-80 to be achieved. A wide variety of different procedures can be performed with the embodiments of proximal controller described herein, including, but not limited to those in the heart.

It should be noted that proximal controller 900 is not limited to the exemplary embodiments described with respect to FIGS. 41A-43M. Each of these embodiments can be likewise implemented using automated electronic techniques, for instance, such as a rotatable cam controlled by one or more electronic push buttons. These and other techniques that can be used include, but are not limited to, automatic actuation, electronic actuation, robotic actuation, infrared sensor actuation, and other types of manual actuation using levers, depressible buttons, rotatable knobs and dials, switches and the like.

Figure 44A:
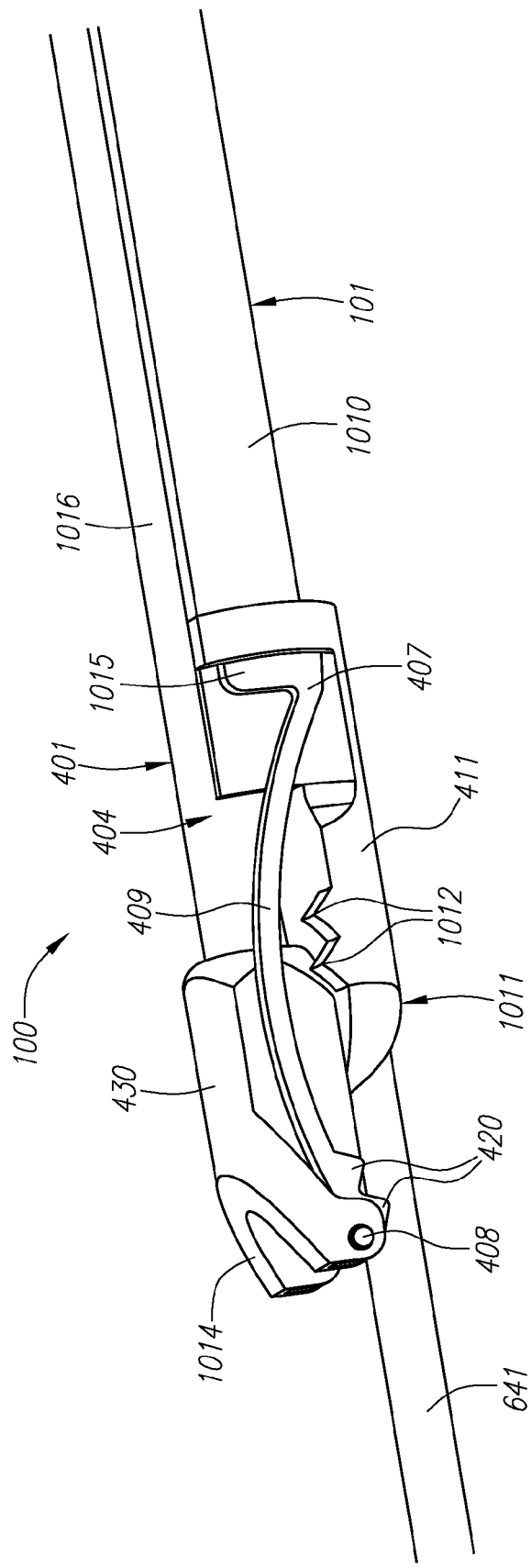
FIG. 44A is a perspective view depicting another exemplary embodiment of a treatment system.

Referring back to configuration of the distal portion of system 100, FIG. 44A is a perspective view depicting another exemplary embodiment of system 100 without inclusion of stabilization device 105 and centering device 106. Here, body member 101 includes tubular body 1010 coupled with distal end tip 1011, which includes elongate support section 411. Guidewire 641 is shown routed through distal end tip 1011. OA delivery member includes distal cap 430 coupled with tubular body 1016.

Any portion of system 100 can be configured to increase the surface friction with septal wall 207. Here, elongate support section 411 of body member 101 includes multiple abutments, or teeth 1012 to aid in engaging the inner wall of tunnel 215, such as the wall of secundum 210. In this embodiment, teeth 1012 are triangularly configured although one of skill in the art will readily recognize that any configuration of teeth 1012 can be used. Also, any surface of system 100 can be configured to increase the surface friction with septal wall 207, such as by the use of abrasive coatings or textures formed without coatings. For instance, a polymeric sheet can be coupled between arm members 409 such that it extends across the gap between arm members 409 and thereby increases the surface friction with septal wall 207 as well as stabilizes the position of each arm member 409 with respect to the other. Any polymeric sheet or strands of polymeric material can be used including (but not limited) to polyester fabrics and the like.

Also in this embodiment, distal cap 430 of OA delivery member 401 is configured to be atraumatic. This reduces the risk of damaging bodily tissue during the implantation procedure or while routing OA delivery member 401 within the subject's vasculature. Here, the portion of distal cap opposite elongate support section 411 has an atraumatic beveled distal surface 1014.

In this embodiment, grasping device 404 includes two arm members 409 having a generally curved shape to accommodate limbus 211. The underside of each arm member 409 includes abutments 420 configured as teeth to aid in engaging septal wall 207. Here, hinge 408 is a swivel-type hinge that allows distal cap 430 of OA delivery member 401 to swivel, or rotate, about arm member 409. Hinge 407 is formed by the intersection of arm member 409 with a base portion 1015. Arm member 409 is configured to flex at this intersection from the at-rest state depicted here. This allows OA delivery member 401 to be raised up and away from body member 101 when proximal force is applied, but also biases OA delivery member 401 to return to the at-rest state, both facilitating engagement with limbus 211 and return of OA delivery member 401 to this low-profile configuration prior to withdrawal from the subject.

If desired, the angle at which OA delivery member 401 is oriented with respect to body member 101 after advancement of OA delivery member 401 into the off-axis position, can be adjusted by varying the lengths of each arm member 409. For instance, if an arm member 409 on the left side were relatively longer than arm member 409 on the right side, when deployed into the off axis configuration OA delivery member 401 would tilt to the left. One of skill in the art will readily recognize that by varying the degree to which the arm members 409 differ in length, one can vary the amount of tilt introduced into OA delivery member 401. This tilt can be used to cause needle 405 to penetrate septal wall 207 at any angle desired or needed for the particular application.

Figure 44B:
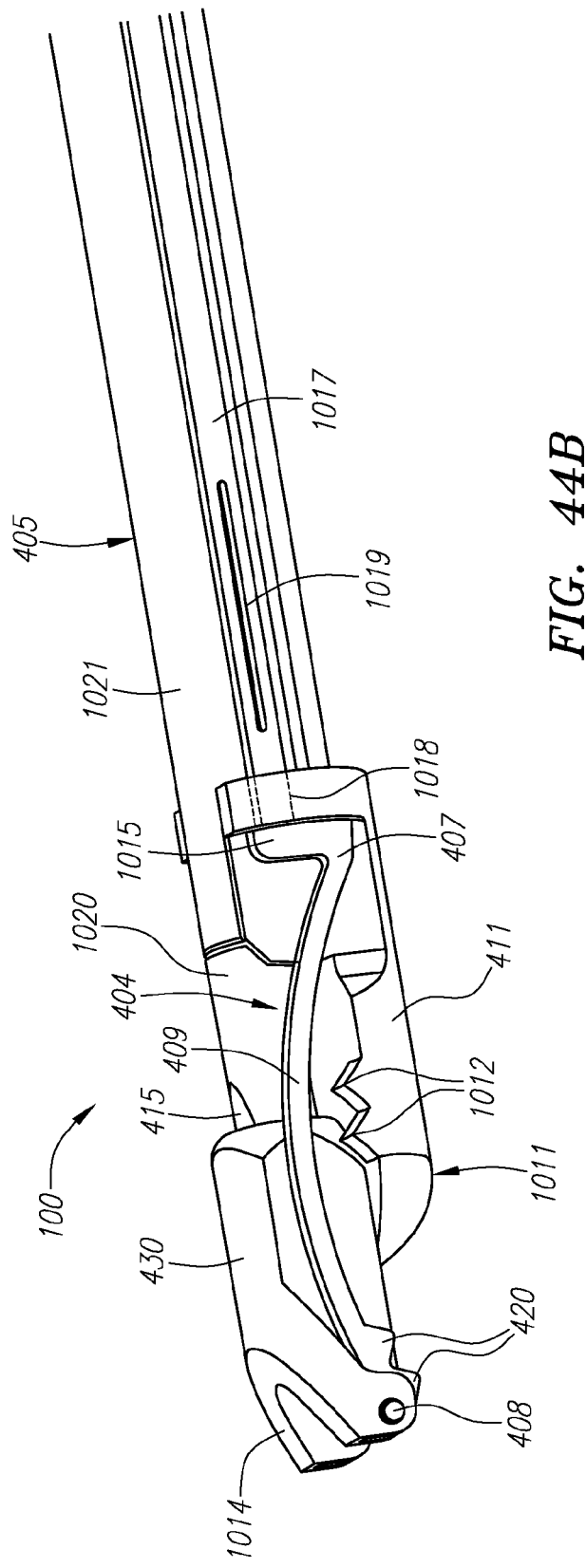
FIG. 44B is an internal perspective view depicting the exemplary embodiment of a treatment system depicted in FIG. 44A.

FIG. 44B is a perspective view depicting this exemplary embodiment of system 100 without guidewire 641, tubular body 1010 of body member 101, and tubular body 1016 of OA delivery member 401 in order to facilitate description of system 100. Visible within OA delivery member 401 is needle member 405 having a rigid distal end portion 1020 and a tubular body 1021. Rigid distal end portion 1020 includes sharp distal tip 415 and is preferably composed of a rigid material such as stainless steel, NITINOL and the like.

Figure 44C:
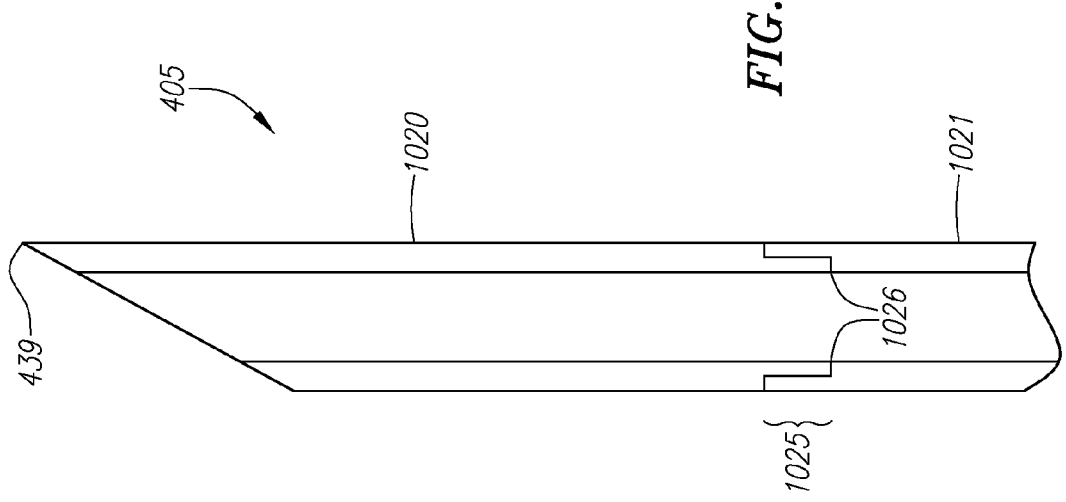
FIG. 44C is a cross-sectional view depicting another exemplary embodiment of a needle member.

FIG. 44C is a cross-sectional view depicting an exemplary embodiment of needle member 405 with rigid distal end portion 1020 and tubular body 1021. Here, the interface region 1025 between portion 1020 and tubular body 1021 is configured to be overlapping. This can increase the strength of the coupling between each portion of needle member 405. In this embodiment, the thickness of the part of portion 1020 and tubular body 1021 in interface region is tapered, in this case in a stepped fashion, such that each portion is complementary to the other. As one of ordinary skill in the art will readily recognize, the stepped interface region 1025 can be reversed such that the most proximal part of portion 1020 is located on the outside of the most distal part of tubular body 1021.

Although not shown, interface 1025 can be further strengthened with the use of a tubular support member surrounding interface 1025. For instance, in one exemplary embodiment, a polymeric tube (e.g., polyester, polyethylene and the like) can be heat shrunk or bonded around the relatively rigid interface 1025 to provide strain relief.

It should be noted that the location of interface region 1025 along the longitudinal axis of needle member 405 can be chosen as desired. In one embodiment, the location of interface region 1025 is close enough to distal tip 415 to have a minimal effect on the flexibility of needle member 405, while at the same time being far enough from distal tip 439 to minimize the risk of any portion of implant 103 or pusher member 406 catching on surface junction 1026 during delivery. The actual location of interface region 1025 is dependent on the size of implant 103, the length of needle member 405 that enters a curved state during delivery, the angle of the sharp beveled surface of needle member 405, as well as other factors.

Referring back to FIG. 44B, also visible is an elongate support portion 1017 and base portion 1015 of grasping device 404. Elongate support portion 1017 is configured to fit within a lumen of body member 101, preferably within tubular body 1010 (not shown). Elongate support portion 1017 provides support and leverage to arm members 409 during use. Elongate support portion 1017 is preferably coupled with tubular body 1010. In this embodiment, elongate support portion 1017 can be adhesively coupled with tubular body 1010 and can include one or more apertures 1019 configured to improve the strength of the adhesive bond and to facilitate the manufacturing process. Preferably, apertures 1019 are configured such that the adhesive, which can be introduced through one or more side ports or slits in tubular body 1010, can distribute within each aperture 1019 during the bonding process. This allows for a stronger bond between section 1017 and tubular body 1010 and also allows for an outlet for any excess adhesive applied during the manufacturing process.

Elongate support section 1017 can routed through a lumen 1018 (shown to be obscured with dashed lines) in distal end tip 1011. This allows the coupling of elongate support section 1017 with body member 101 to further strengthen the coupling of distal end tip 1011 with the remainder of body member 101. It should be noted that any technique, other than ones using adhesives, can be utilized to couple arm members 409 with body member 101.

The various tubular bodies used in system 100, such as tubular body 1010, 1016, and 1021, are preferably composed of flexible, durable, bio-compatible materials including, but not limited to, NITINOL, stainless steel, and polymers such as PEBAX, polyester, polyvinylchloride (PVC), polyethylene, polyetheretherketone (PEEK), polyimide (PI), nylon (with or without reinforcing materials such as braided or coiled stainless steel, kevlar, carbon fiber and the like). Some materials, such as PEEK, can be manufactured with a curve in a desired direction. Preferably, system 100 is manufactured so that the curve of the outer sheath is aligned in a predetermined manner to be consistent with any curved path the respective outer sheath is designed to follow. For instance, needle tubular body 1020, if manufactured from a material displaying a curve, it is preferably aligned such that the curve is oriented similarly to the curved path needle member 405 follows in the exemplary embodiment described with respect to FIG. 18B. Also, needle distal end portion 1020 is preferably coupled with tubular body 1021 such that needle distal tip 439 (not shown in FIG. 44B) is oriented as desired (e.g., on the inside of the curved portion of needle member 405).

Figure 44D:
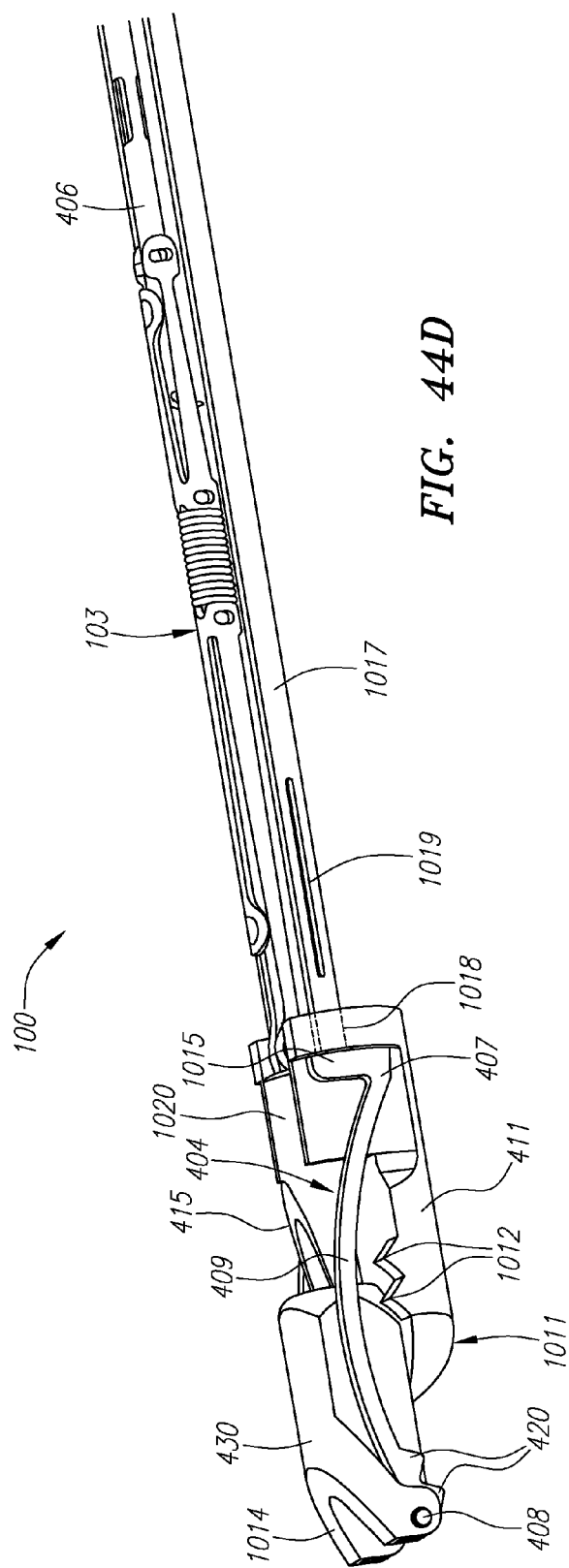
FIG. 44D is an internal perspective view depicting the exemplary embodiment of a treatment system depicted in FIGS. 44A-B.

FIG. 44D is a perspective view of the exemplary embodiment of FIG. 44B but without tubular body 1020 of needle member 405. Here, implant 103 and pusher member 406 are both visible. Implant 103 is configured as a clip, similar to the embodiments described in the incorporated application "Clip-based Systems and Methods for Treating Septal Defects," which is referenced above, and also similar to the embodiments described in (1) U.S. patent application Ser. No. 12/113,842 entitled "Systems and Methods for Accommodating Anatomical Characteristics in the Treatment of Septal Defects" filed May 1, 2008, (2) U.S. provisional patent application Ser. No. 61/054,710, entitled "Wire-like and Other Devices for Treating Septal Defects and Systems and Methods for Delivering the Same" filed May 20, 2008, and (3) U.S. provisional patent application Ser. No. 61/054,748, entitled "Tissue-piercing Implants and Other Devices for Treating Septal Defects" filed May 20, 2008, each of which is fully incorporated by reference herein.

Figure 44E:
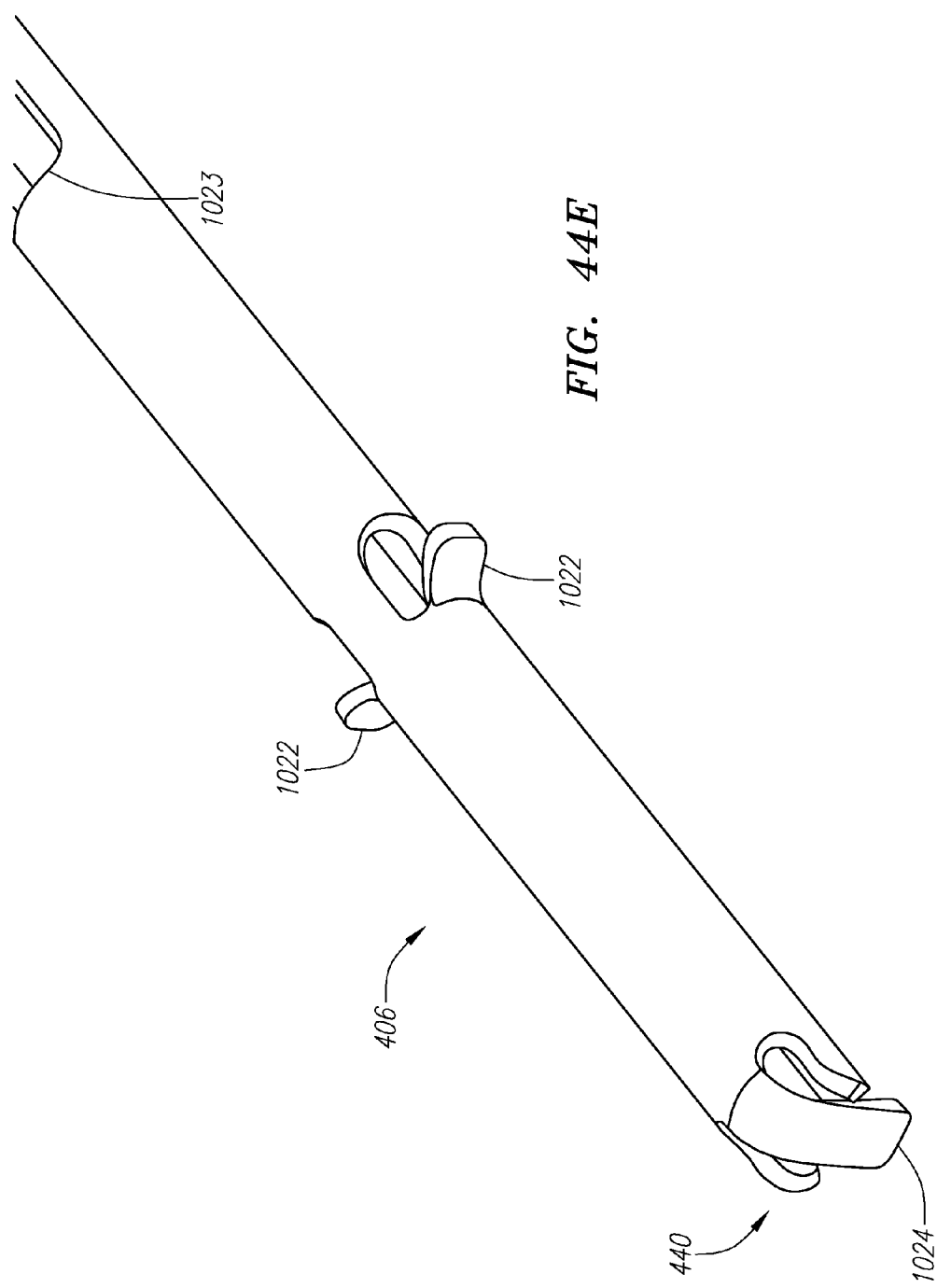
FIGS. 44E-F are perspective views depicting additional exemplary embodiments of a pusher member.

FIG. 44E is a perspective view depicting the distal portion of pusher member 406 in greater detail. Here, pusher member 406 includes tabs 1022 for engaging with apertures on clip 103 and one or more apertures 1023 which increase the flexibility of pusher member 406. The location of apertures 1023 also controls the direction in which pusher member 406 is relatively more flexible. Pusher member 406 also includes a closed distal end 440, which is closed by way of a deflected tab 1024, which also extends past the end of pusher member 406. This allows pusher member 406 to remain configured in a generally tubular manner, but reduces the risk of an open distal end 440 sliding over a portion of implant 103 or of distal end 440 sliding into an open central portion 303 of implant 103, whether configured as a coil, clip or otherwise. Deflected tab 1024 can be used as an alternative to, or in addition to, a blocking member included within central portion 303 of implant 103. A blocking member within implant 103, or at distal end 440 of pusher member 406, can also be a deflected tab, a radiopaque rod, and the like.

Figure 44F:
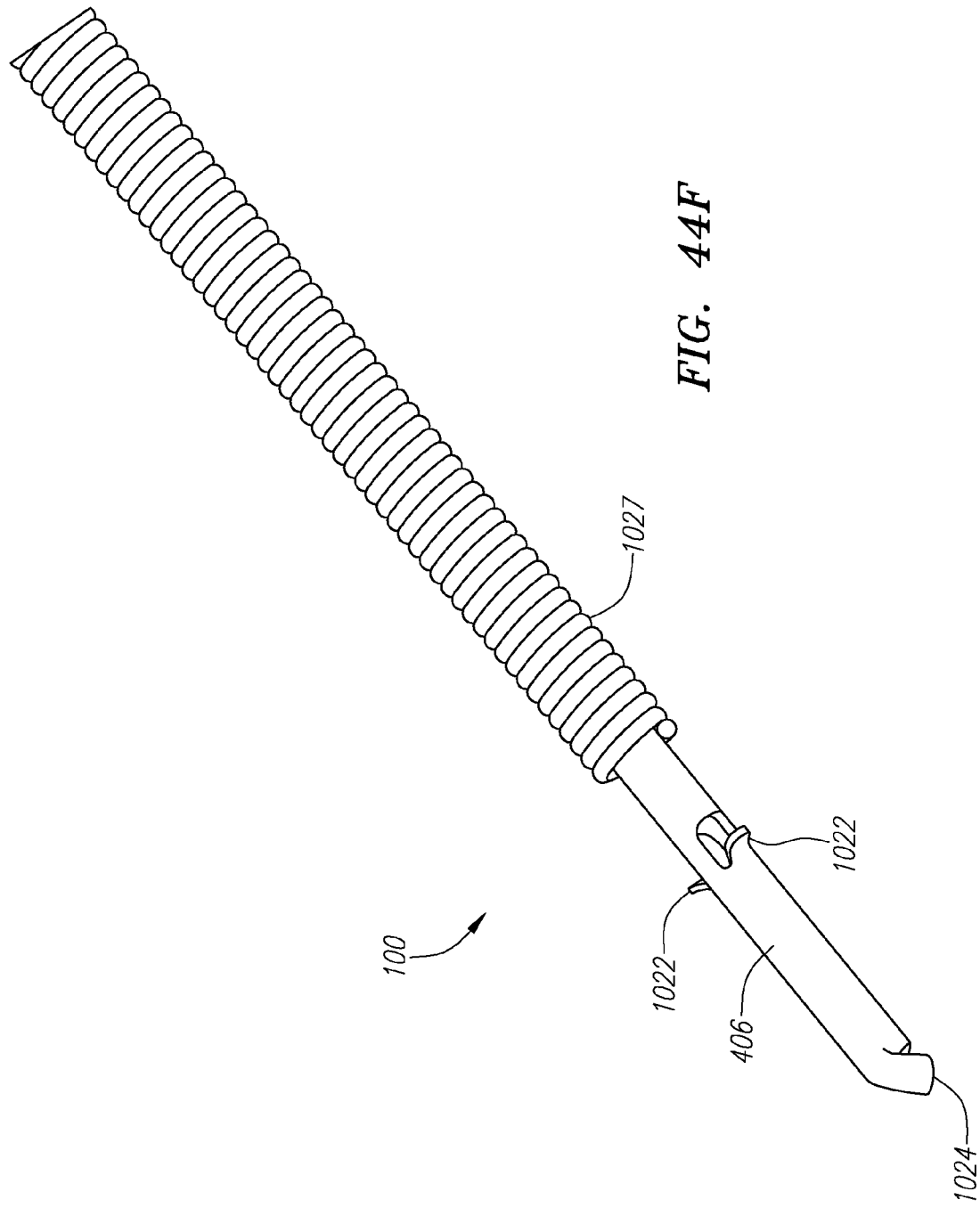

FIG. 44F is a perspective view depicting another exemplary embodiment of system 100 where pusher member 406 is located within an intermediate sheath 1027. Here, intermediate sheath 1027 is configured to reduce the risk of buckling or kinking, by occupying the space between the outer diameter of pusher member 406 and the inner diameter of needle member 405. Intermediate sheath 1027 is preferably flexible and, as depicted here, can be configured in a coil-like manner.

Figure 45A:
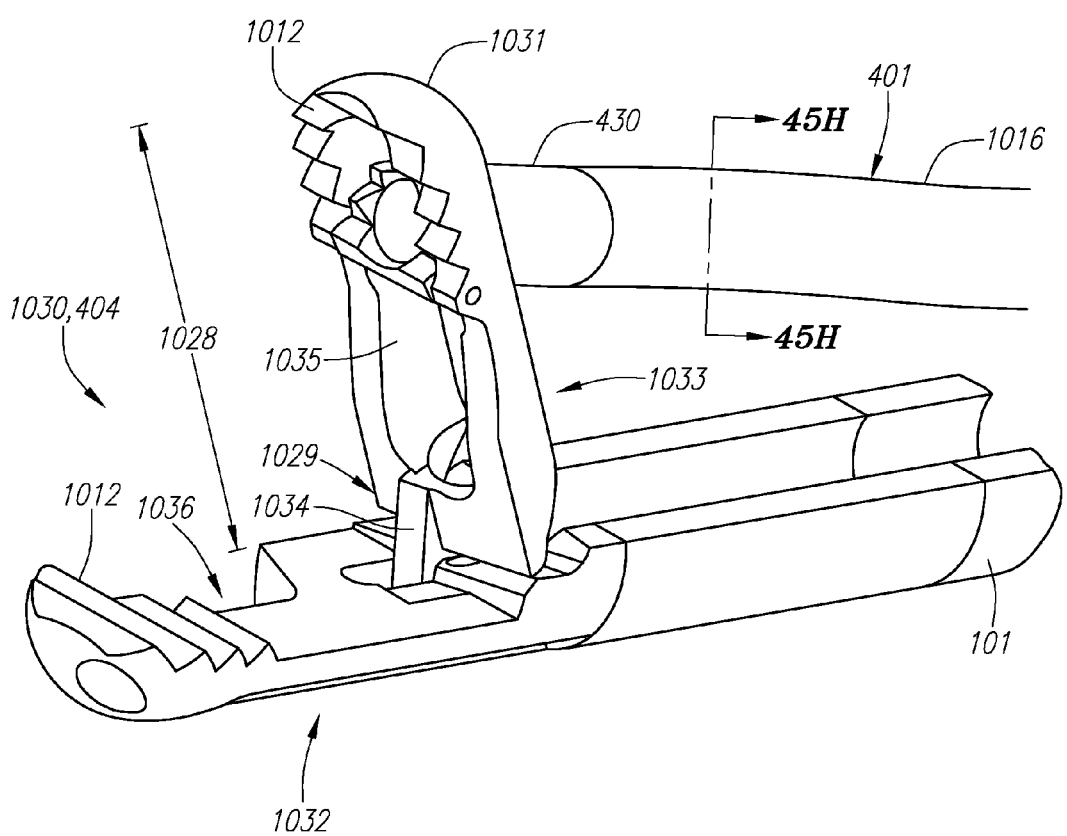

FIG. 45A is a perspective view depicting another exemplary embodiment of system 100. As with all other embodiments described herein, it should be noted that the elements, features and characteristics of this embodiment can be used with any other embodiments described herein. Shown here is OA delivery member 401 having outer sheath 1016. OA delivery member 401 is coupled with distal end tip 430 which in turn is pivotably coupled with distal end section 1030 of body member 101. Here, distal end section 1030 functions as tissue engagement device 404. Distal tips 1031 of distal end section 1030 have a rounded, preferably spherical radius, to maximize the atraumatic characteristics of the device.

Distal end section 1030 includes a lower portion 1032 pivotably coupled with an upper portion 1033. Both portions 1032 and 1033 can include one or more teeth 1012. In the instance where a plurality of teeth 1012 are present, as shown here, teeth 1012 on upper portion 1033 are preferably located in positions complimentary to teeth 1012 located on lower portion 1032 to allow for a greater interface between the two portions 1032-33 and a smaller overall profile. Portions 1032 and 1033 can be constructed from any desired material, including but not limited to NITINOL, stainless steel, polymeric materials or combinations thereof. For instance, in one exemplary embodiment, portions 1032 and 1033 are each constructed from a rigid polymeric material while teeth 1012 are constructed from stainless steel.

Lower portion 1032 and upper potion 1033 can be pivotably coupled together in any manner desired, including use of a living hinge or a hole and rod/strut mechanism (as shown here). Here, the hinge is formed through a single strut 1034 on upper portion 1033, although any number of struts 1034 can be used, as one of skill in the art will recognize the number and placement of struts 1034 can result in increased stability.

In this embodiment, distal tip 430 is also pivotably coupled with upper portion 1033 by way of a hinge (although, again, one of skill in the art will readily recognize the multiple manners in which distal tip 430 can be pivotably coupled with upper portion 1033). Here, distal tip 430 also includes teeth 1012 to provide increased friction with body tissue. Upper portion 1033 includes an open region 1035 in which distal tip 430 preferably partially resides. This allows distal tip 430 to be disposed proximal to distal tip 1031 thereby allowing a greater surface of body tissue to be engaged by distal end section 1030. Also of note is that lower portion 1032 is configured to provide an open region 1036. Open region 1036 is positioned adjacent distal tip 430 and allows needle member 405 (not shown) to pass distal end section 1030. FIG. 45A depicts system 100 with distal end section 1030 in an open position ready to engage body tissue, preferably septum secundum 210 (not shown).

The placement of distal tip 430 in a position proximal to distal end 1031 allows the height of upper portion 1033 in the capture position to be increased, making it more difficult for distal end section 1030 to inadvertently pass into the PFO tunnel. For instance, the distance from base 1029 of upper portion 1033 to the furthest point on the opposite end of upper portion 1033 that engages tissue can be referred to as the clamp distance 1028 of the device. If clamp distance 1028 is too short, distal end section 1030 may not be able to properly engage secundum 210. For instance, the limbus may be too thick to allow any grasping to occur or, alternatively, distal end section 1030 may be able to grasp the limbus, but not with enough force and surface friction to maintain an effective and reliable "lock" on the septum secundum during the course of the procedure. An adequate clamp distance 1028 preferably allows the user to maintain an effective lock on the secundum 210 to prevent non-negligible slippage during the procedure. This is also dependent on the configuration of the surfaces of upper portion 1033 and lower portion 1032, i.e., whether teeth 1012 or some other friction increasing structure, coating or texture is present, and the degree to which surface friction is thereby increased by said friction increasing means.

Preferably, device 404 is configured to achieve a puncture distance, i.e., the distance from the edge of the limbus to the point on the outer surface of the secundum where the needle penetrates, of at least 3 millimeters (mm) in instances where the limbus is relatively thin. Clamp distance 1028 is preferably greater than the puncture distance to allow for adequate secundum tissue to be engaged. In one exemplary embodiment, device 404 is configured to achieve a puncture distance is in the range of 3-7 mm and preferably 3-5 mm. In another exemplary embodiment, device 404 is configured to achieve a puncture distance of approximately 4 mm. Clamp distance 1028 is preferably less than 15 mm. It should be noted that these distances are merely exemplary embodiments, and, in instances where no length is recited in the claims, in no way should the embodiments described herein be construed as limited to any particular length.

Also, upper portion 1033 can be made to extend relatively further distally than lower portion 1032 such that distal tip 430 is located distal to the distal tip 1031 of lower portion 1032. This can facilitate the motion of needle member 405 past lower portion 1032 and allow easier penetration and left atrial access.

It should be noted that upper portion 1033 and lower portion 1032 can be pivoted with respect to each other, or opened, by any amount in accordance with the needs of the application including amounts greater than or equal to 90 degrees. A mechanical stop is preferably included to prevent travel of the upper portion 1033 past the desired position. A stop is also preferably included between distal tip 430 and upper portion 1033 that prevents rotation of distal tip 430 too far forward in a distal direction and thereby maintains the desired orientation with the body tissue.

FIG. 45B is another perspective view depicting system 100, this time with distal end section 1030 in a closed configuration, such as that which would be used while advancing the device through the body vasculature (body member 101, distal end tip 430 and OA delivery member 401 are not shown for clarity).

FIG. 45C is a perspective view depicting another exemplary embodiment of lower portion 1032. In this embodiment, open region 1036 has a bent L shape and teeth 1012 are present on each of two side sections 1037 of lower portion 1032. Open region 1036 allows the passage of needle 405 and the escape of closure device 103 (not shown) after deployment.

FIG. 45D is a perspective view depicting another exemplary embodiment of lower portion 1032. Here, open region 1036 is almost entirely encompassed by side sections 1037 except for a distal escape slit 1040. Side sections 1037 are configured to deflect outwards away from each other thereby opening escape slit 1040 and providing a path through which closure device 103 can pass. Side sections 1037 are made deflectable, in this embodiment, by living hinges 1039.

In both FIGS. 45C and 45D, apertures 1038 are visible. Apertures 1038 can be used for passage of other devices, not limited to a guidewire and the like. Preferably, a guidewire is present in the PFO tunnel before attempting to engage the limbus. Aperture 1038 can be offset from center to allow needle 405 to pass by any guidewire that may be present. Although not shown in FIG. 45A-D, distal end section 1030 also preferably includes a bias member 413 that applies a closure bias between lower portion 1032 and upper portion 1033. This bias member 413 can be any member configured to apply pressure between portions 1032 and 1033 such as a spring, a bent nitinol wire, and the like. In one exemplary embodiment, the rod used as part of the hinge between upper portion 1033 and lower portion 1032 can be configured to allow pivoting motion while at the same time entering a torsioned state upon flexation thereby acting as both a hinge and a bias member 412.

Preferably, lower portion 1032 is configured to minimize surface friction to tissue as lower portion 1032 is advanced into PFO tunnel 215. For instance, one or more of teeth 1012 are preferably angled to have a relatively higher degree of surface friction against tissue when teeth 1012 are translated proximally than when translated distally. This allows lower portion 1032 to be easily advanced into PFO tunnel 215 while at the same time adequately engaging secundum 210 once properly positioned within tunnel 215.

Figure 45E:
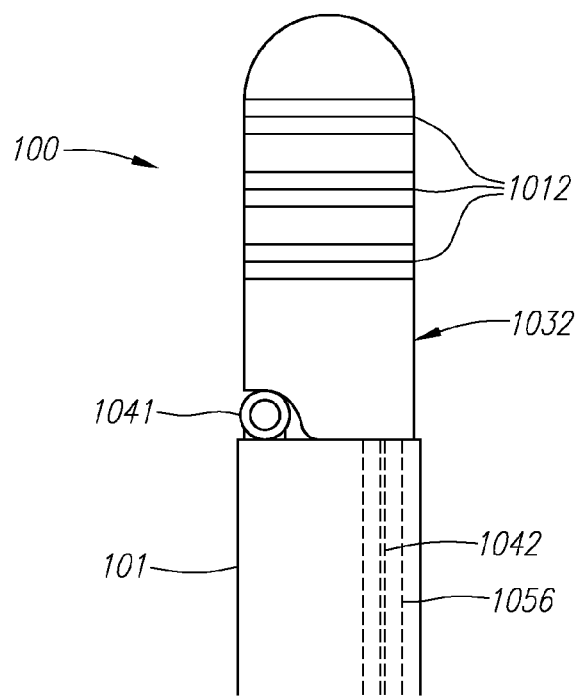
FIGS. 45E-G are top down views depicting additional exemplary embodiments of a treatment system.
Figure 45F:
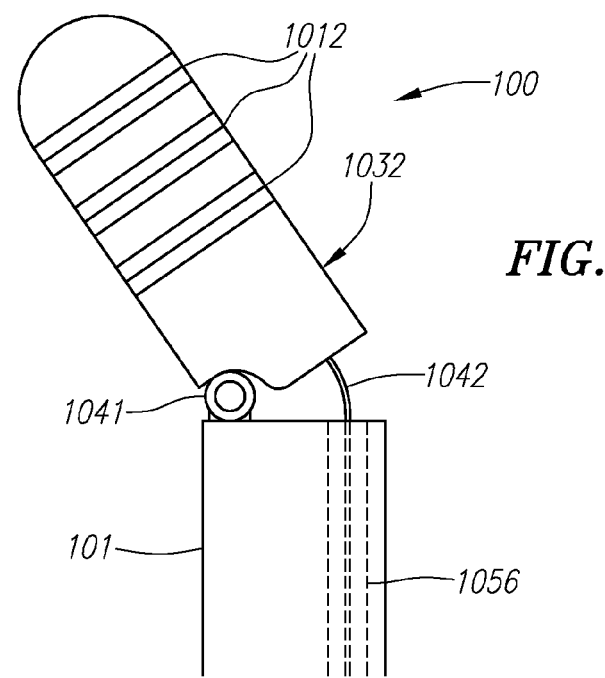

FIG. 45E is a top down view depicting an exemplary embodiment of system 100 having a deflectable lower portion 1032. This deflectable lower portion 1032 can be used instead of open portion 1036 to allow passage of needle member 405 and closure device 103. Here lower portion 1032 is pivotably coupled with body member 101 by way of hinge 1041 which is depicted on the left side of this figure. A push/pull wire 1042, slidably located within lumen 1056, is coupled with lower portion 1032 and allows the user to exert control over the position of lower portion 1032. FIG. 45E depicts lower portion 1032 in an undeflected state, while FIG. 45F depicts lower portion 1032 after it has been deflected about hinge 1041 by exerting a distal force on push/pull wire 1042. A stop (not shown) can be included to stop deflection of portion 1032 at the desired position. Push/pull wire 1042 can also reside external to body member 101 instead of within lumen 1056 in body member 101.

Figure 45G:
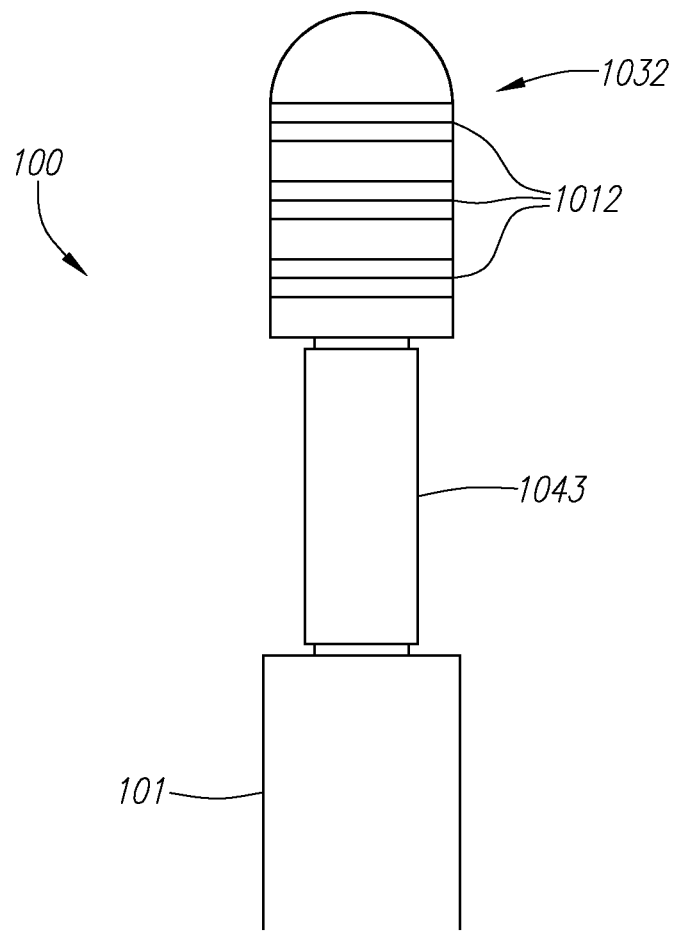

FIG. 45G is a top down view depicting lower portion 1032 in an impact-resistant configuration. In this embodiment, the configuration is achieved through the use of a rotatable outer covering, preferably composed of nitinol, stainless steel, or the like. This rotatable portion 1043 is preferably configured to rotate, or spin, if needle member 405 (not shown) were to come into contact with it. In an alternative embodiment, the low friction configuration can be achieved by the use of a static, generally cylindrical, highly polished or otherwise smoothed metallic section in a similar position on lower portion 1032.

Figure 45H:
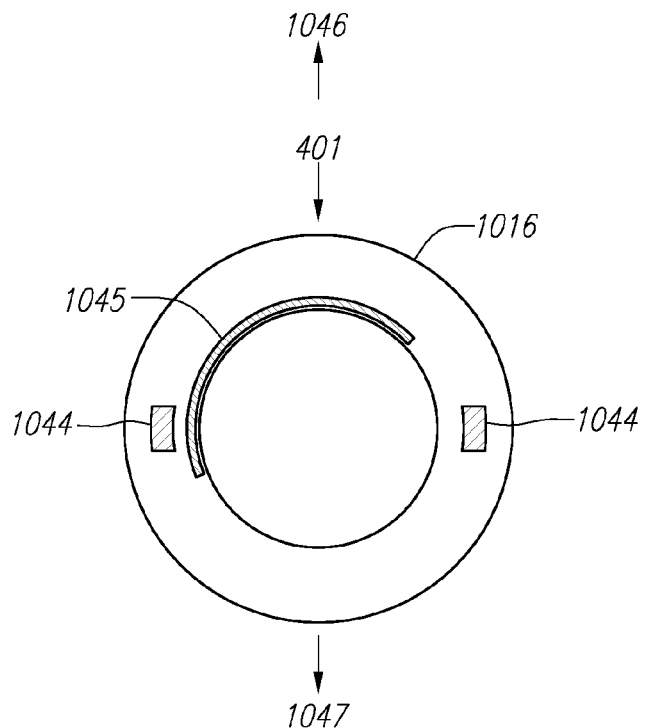
FIG. 45H-I are radial cross-sectional views taken along lines 45H-45H of FIG. 45A depicting additional exemplary embodiments of a delivery device.

FIG. 45H is a radial cross-sectional view taken along lines 45H-45H of FIG. 45A. Shown here is outer tubular sheath 1016 of OA delivery member 401 (the other members of system 100 are not shown for clarity). In this embodiment, outer sheath 1016 includes two reinforcement members 1044 which are disposed longitudinally along the length of sheath 1016, preferably at orientations generally 180 degrees apart. FIG. 45H also shows a segment of coil reinforcement 1045. Coil reinforcement 1045 is preferably disposed within sheath 1016 (as shown) or along an inner or outer surface of sheath 1016 and extends in a coiled fashion around the central axis of OA delivery member 401.

Both reinforcement members 1044 and coil reinforcement 1045 can extend along any length of OA delivery member 401 including the entire length, or any portion of the length in which additional reinforcement is desired. Reinforcement members 1044 and coil reinforcement 1045 can be used together or each individually as desired. In addition, any number of one or more reinforcement members 1044 can be used and any number of one or more coil reinforcements 1045 can be used. Reinforcement members 1044 and coil reinforcement 1045 can be made of any desired reinforcing material such as nitinol, stainless steel, cobalt-chrome alloys and the like. Reinforcement can decrease the tendency of sheath 1016 to stretch, can prevent buckling, kinking or other radial distortion when OA delivery member 401 is bent or deflected (such as during off axis delivery), and can provide a high radiopacity.

Also, use of reinforcement members 1044 can increase the tendency of sheath 1016 to deflect in a given direction. For instance, if reinforcement members 1044 are disposed at opposite sides of sheath 1016 as depicted here, sheath 1016 will be more likely to deflect up or down in directions 1046 and 1047 as shown. This can provide benefit during the delivery procedure by increasing the likelihood of OA delivery member 401 to deflect in a desired direction. Furthermore, sheath 1016, if fabricated from certain polymeric materials recognized by those of skill in the art, can exhibit a natural tendency to deflect in a given direction and this natural tendency can be used with reinforcement members 1044 to provide deflection in a desired direction. In addition, some manufacturing processes (e.g., extrusion and the like) can be used to orient the polymeric chains of sheath 1016 advantageously to provide the desired directionality. Furthermore, a relatively thinner portion of sheath 1016, which extends along the length of sheath 1016 in the desired region, can improve the tendency of sheath 1016 to deflect in a particular direction.

Figure 45I:
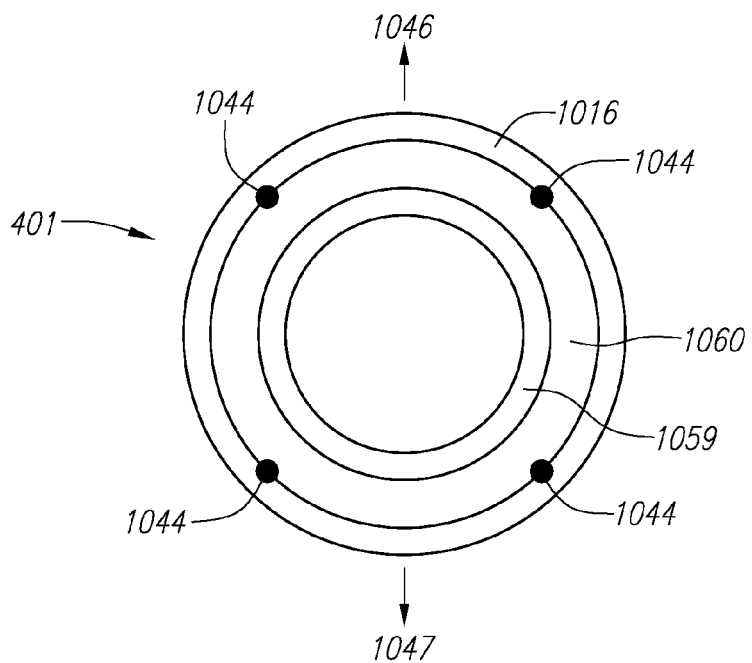

FIG. 45I is a cross-sectional view depicting another exemplary embodiment of OA delivery member 401. Here, OA deliver member 401 can include at least two, preferably three layers. An inner layer 1059 can be composed of nylon (e.g., nylon 6, nylon 12, etc.) or another friction reducing material (e.g., teflon, polyethylene, etc.). A mid-layer 1060 is preferably configured to resist kinking In this embodiment, mid-layer 1060 is a braided stainless steel material, although other materials can be used. One exemplary braid is a sixteen wire braid of ribbon or round wire. The braid density can be approximately eighty wire crossovers per inch (PPI), sometimes referred to as the "pic" count. Here, four reinforcement members 1044 are located between layer 1060 and outer sheath 1016. Outer sheath 1016 can be composed of nylon, teflon, polyethylene or the like. It should be noted that if reinforcement members 1044 are placed between layers 1059 and 1060, layer 1016 can be eliminated.

Figure 46A:
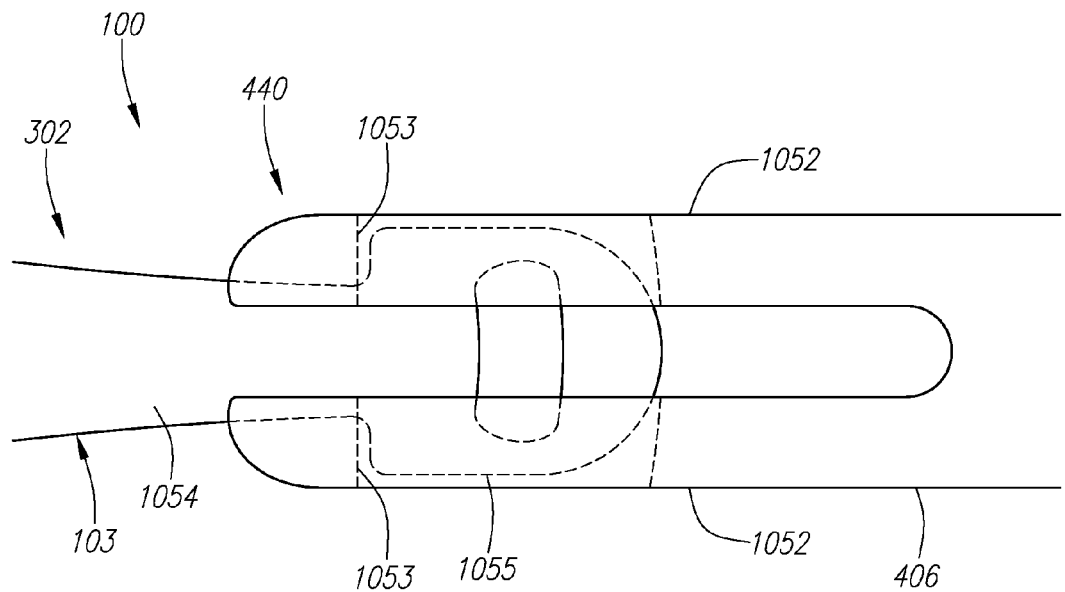
FIG. 46A is a side view depicting another exemplary embodiment of a treatment system.

FIG. 46A is a side view depicting another exemplary embodiment of system 100. Here, pusher member 406 is shown with closure element 103. Pusher member 406 includes two deflectable members 1052 located on its distal end 440. Deflectable members 1052 are each biased to deflect away from each other. Members 1052 each include an aperture 1053 in which implant 103 is configured to interface. In this embodiment, pusher member 406 is configured to operate with a clip-like embodiment of implant 103, although pusher member 406 is not limited to such. This embodiment of implant 103 includes one or more deflectable arm-like members 1054 on RA portion 301 having relatively larger distal ends 1055. Here, distal ends 1055, apertures 1053 and a portion of arm-like members 1054 are shown with dotted lines to indicate obscurement by members 1052. When located within needle member 405 (not shown), deflectable members 1052 are restrained and maintained in the position shown in FIG. 46A.

Figure 46B:
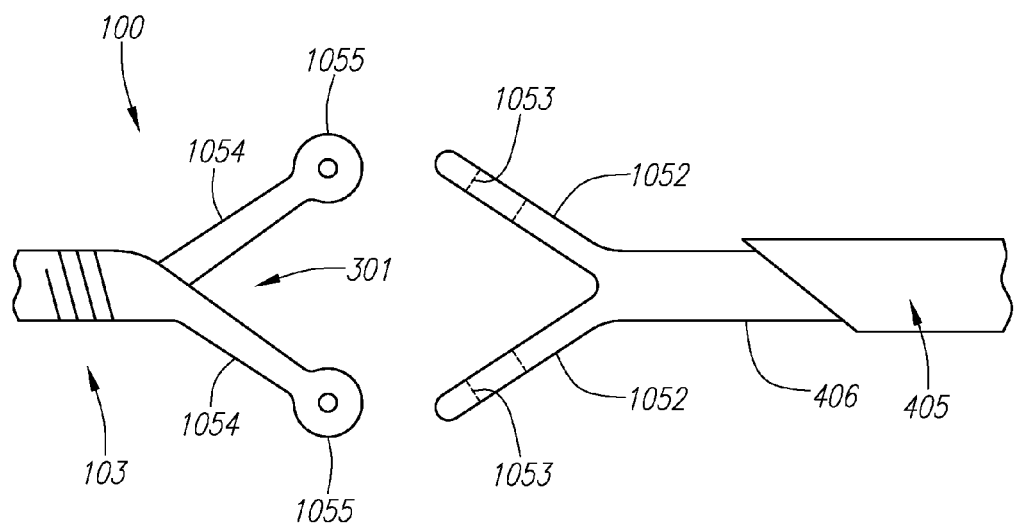
FIGS. 46B-C are perspective views depicting additional exemplary embodiments of a treatment system.

FIG. 46B is a perspective view depicting pusher member 406 after advancement from needle 405. Here, needle 405 no longer restrains members 1052, which then enter the deflected state shown. Upon deflection, members 1054 of implant 103 are free to enter a deflected state configured to engage the septal wall (not shown). Although not shown, an additional tether can be coupled with implant 103 and used to retrieve implant 103 should such retrieval become desirable at a later stage. In order to maintain a high degree of correspondence between motion of pusher 406 and implant 103, apertures 1053 are preferably configured to engage distal ends 1055 with a relatively snug fit, i.e., the amount of free space between distal ends 1055 and the walls of members 1052 around apertures 1053 is preferably minimized.

Figure 46C:
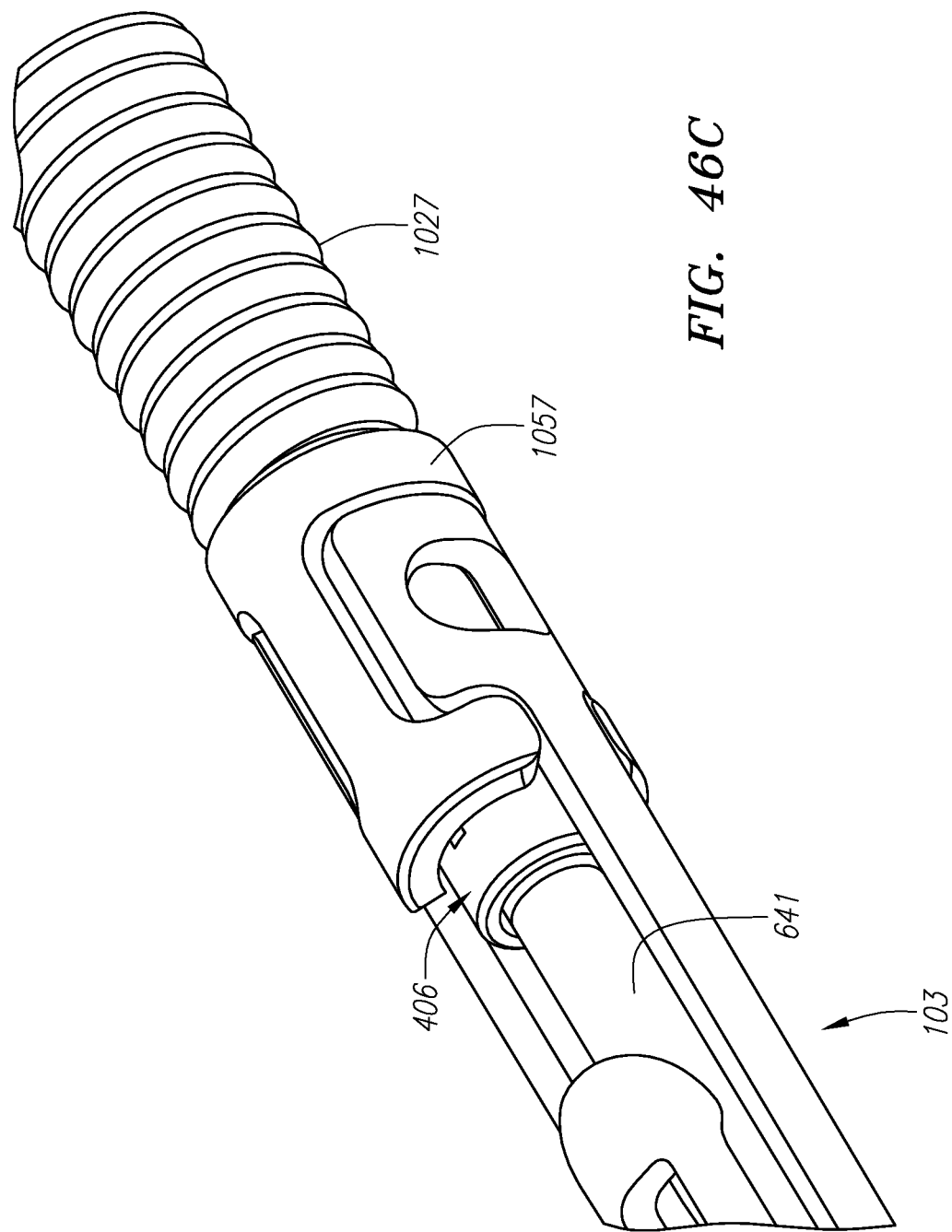

FIG. 46C is a perspective view depicting another exemplary embodiment of system 100 with pusher member 406 and clip-like implant 103. Here, pusher member 406 includes an interface portion 1057 that is configured to interface with clip 103. Portion 1057 is preferably welded or otherwise fixably coupled with the tube-like body of pusher member 406. Portion 1057 can also be part of a solid wire body of pusher 406. The outer diameter of portion 1057 is preferably sized to fit snugly within the inner diameter of needle 405 (not shown). As can be seen, pusher 406 is configured to engage implant 103 while within needle 405 and can be used to advance implant 103 distally and retract implant 103 proximally as desired, similar to the embodiments described with respect to FIGS. 20A-B, 44E-F and 46A-B.

It should be noted that any feature, function, method or component of any embodiment described with respect to FIGS. 1-46C can be used in combination with any other embodiment, whether or not described herein. As one of skill in the art will readily recognize, treatment system 100 and the methods for treating a septal defect can be configured or altered in an almost limitless number of ways, the many combinations and variations of which cannot be practically described herein.

Figure 47A:
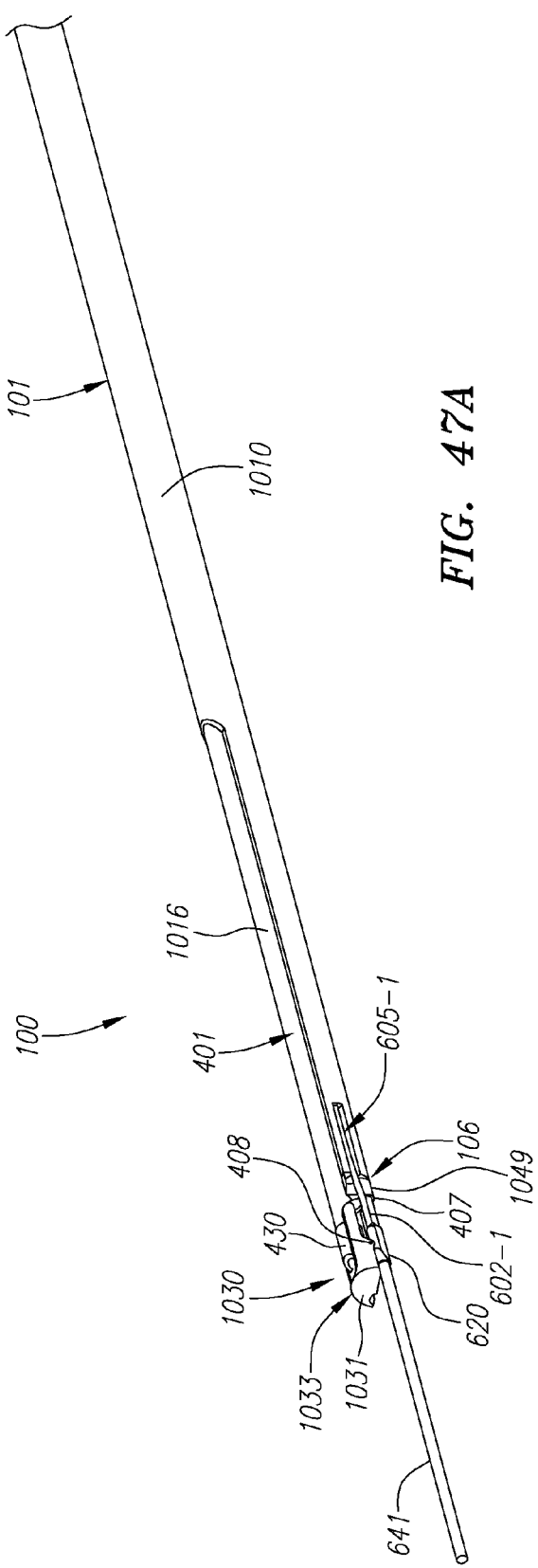
FIGS. 47A-N are perspective views depicting an exemplary embodiment of a treatment system during various stages of use in a PFO closure procedure.

FIG. 47A is a perspective view depicting another exemplary embodiment of PFO treatment system 100, where a centering device 106 is integrated therewith. Body member 101 includes outer sheath 1010 with an inner lumen in which OA delivery member 401 is slidably housed. The distal end of OA delivery member 401 contains distal tip 430 which is pivotally coupled with distal end section 1030 in a manner similar to that described previously. Distal end section 1030, which functions as a tissue engagement device, is, in turn, pivotally coupled with body member 101, specifically at a distal end portion 1049 to outer sheath 1010. Centering device 106 includes centering arms 602-1 and 602-2 (not shown), each of which are configured to deflect from a respective recessed portion 605-1 and 605-2 (not shown) in body member 101. The distal end of centering arms 602 are coupled to a distal hub element 620 (referred to herein as a "tracking element") that includes an inner lumen adapted to track (or slide) over guidewire 641 (or any other elongate component), which is preferably routed through the PFO tunnel. Tracking element 620 preferably has a low friction, rounded design to facilitate passage through the PFO tunnel. Centering arms 602 are each preferably housed within separate lumens 603 (not shown) within body member 101, although it should be noted that centering arms 602 can also be housed in a common lumen in system 100.

Figure 47B:
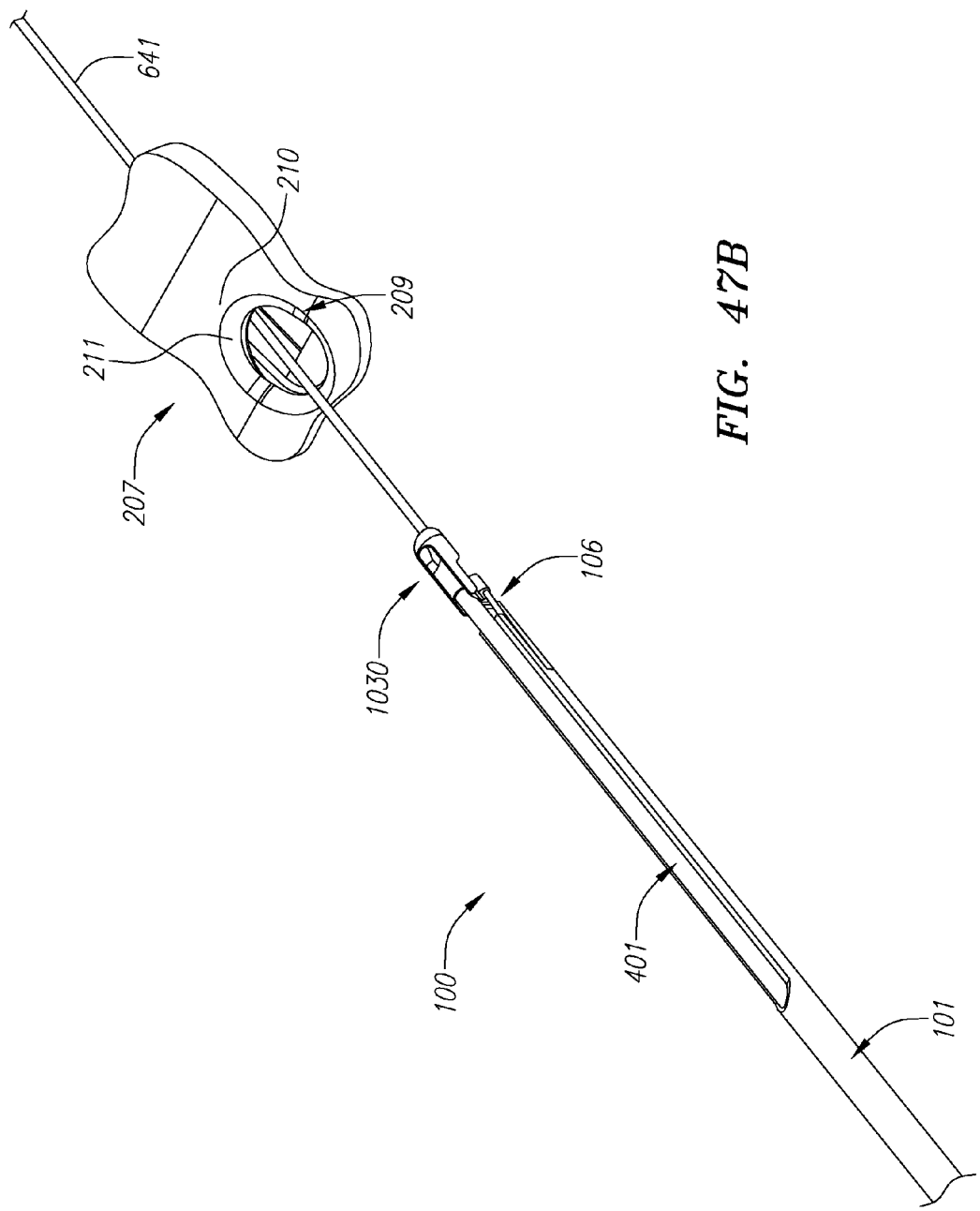
FIG. 47O is an enlarged perspective view depicting region 47O of FIG. 47N.
FIGS. 47P-T are perspective views depicting an exemplary embodiment of a treatment system during various stages of use in a PFO closure procedure.

FIG. 47B is a similar perspective view showing this embodiment of system 100 at the initial stage of a PFO treatment procedure. Here, guidewire 641 is shown extending through a PFO tunnel in an atrial septal wall 207 (here represented by a modeled tissue section). Body member 101 has been advanced into proximity with the PFO region 209 with distal end section 1030 (which can also function as a tissue engagement device) located just inferior to the PFO tunnel opening in the right atrium.

Figure 47C:
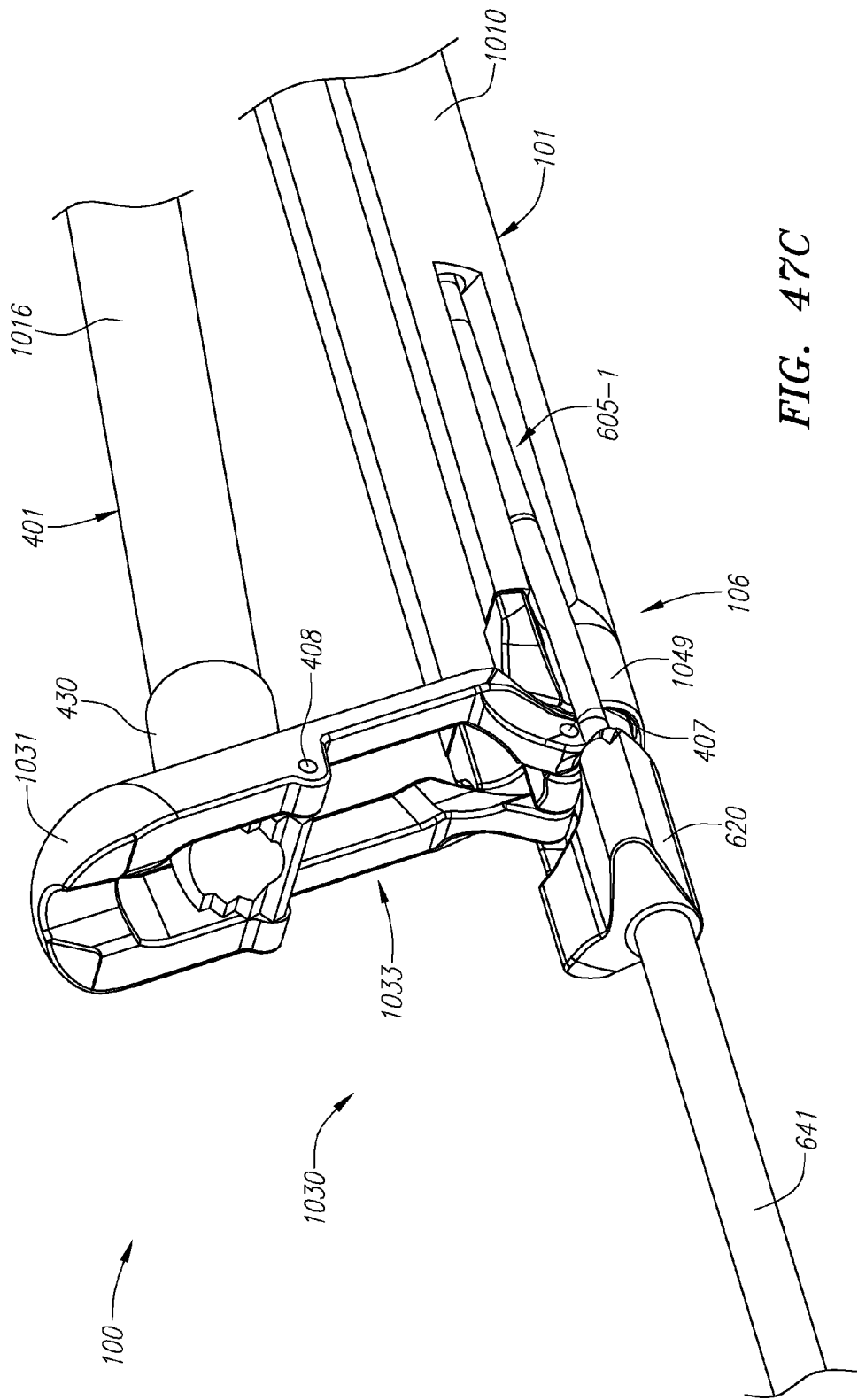
Figure 47D:
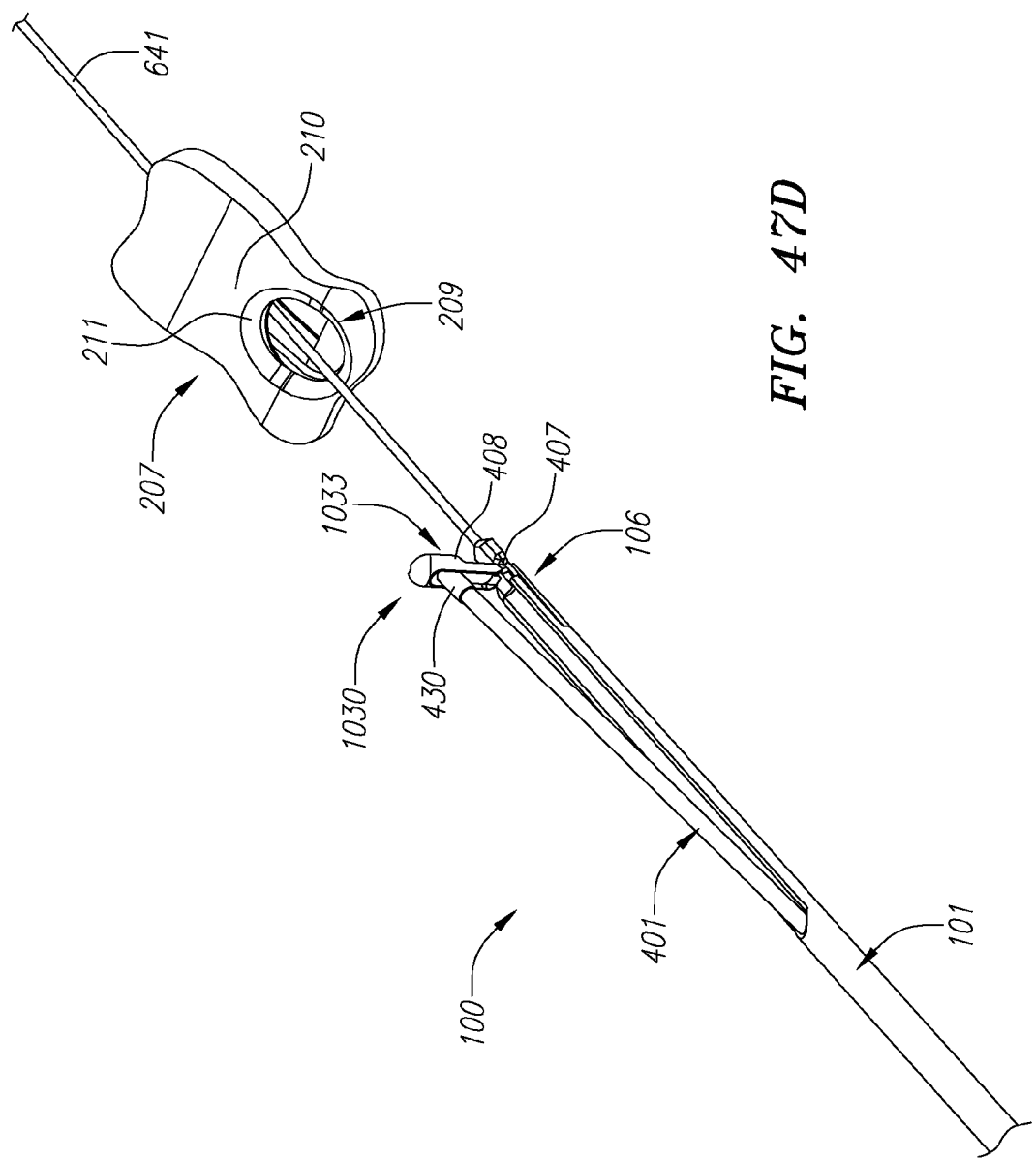

FIG. 47C depicts system 100 with distal end section 1030 in an open state, where upper jaw-like portion 1033 is in a raised position preferably achieved by retraction of OA delivery member 401 in a proximal direction. This position is entered prior to further advancement of body member 101 in order to prepare system 100 to grasp limbus 211 of septum secundum 210 (see FIG. 47D). Hinge 407 is present on the base portion of upper jaw 1033 to allow jaw 1033 to freely pivot back and forth between a raised and lowered state. Hinge 408 allows distal tip 430 and OA delivery member 401 to temporarily maintain a generally forward facing orientation while upper jaw 1033 is raised and lowered.

Figure 47E:
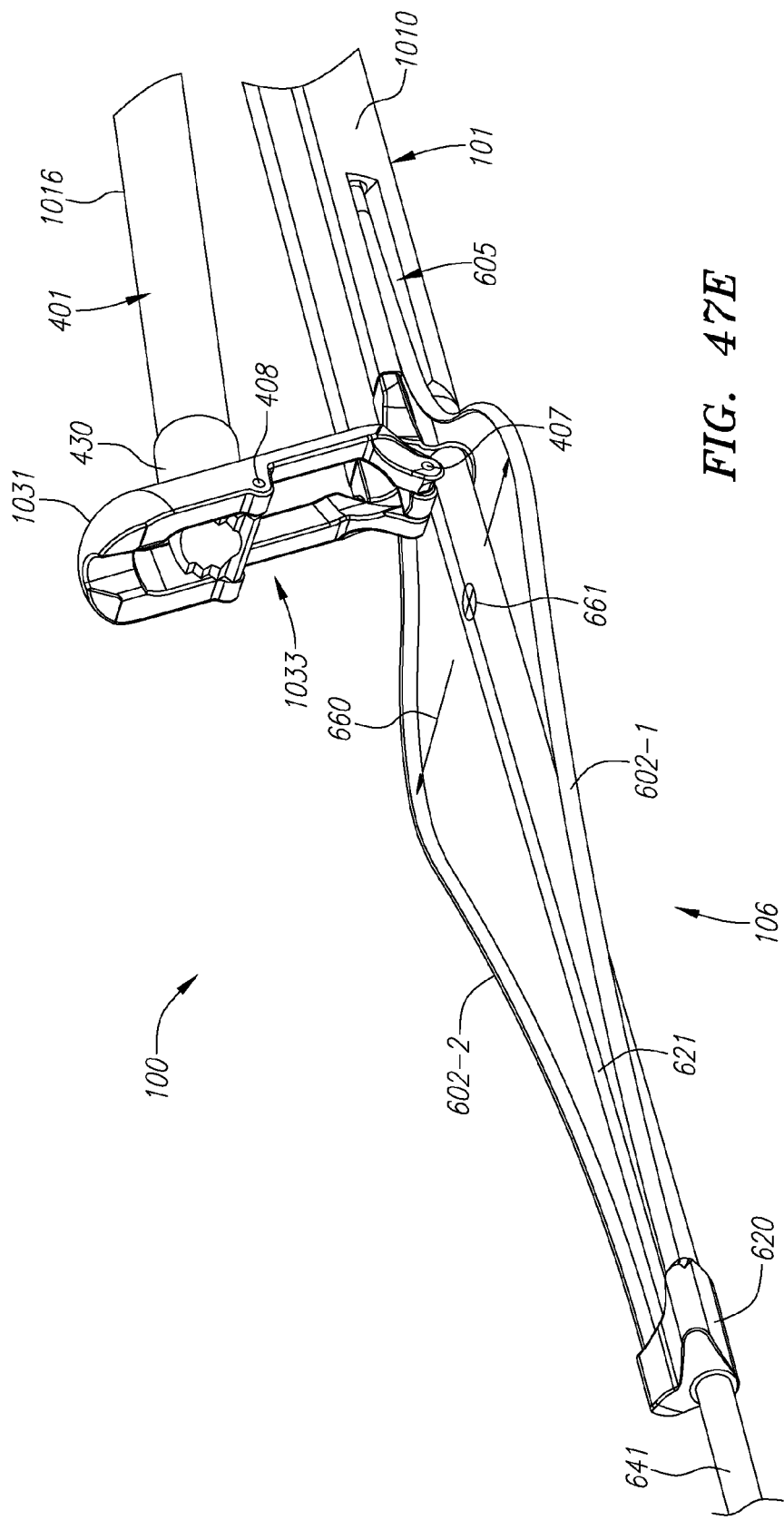

FIG. 47E depicts the next stage of deployment of system 100. Here, centering arms 602-1 and 602-2 have expanded outwards laterally away from the sides of body member 101. This is achieved by the advancement of optional centering core member (or wire) 621 along with centering arms 602 such that tracking element 620 advances distally along guidewire 641. Arms 602 and core member 621 are preferably secured to tracking element 620. Core member 621 provides additional push force on tracking element 620, which allows deployment of centering arms 602 without buckling. Centering arms 602 are biased towards the outwardly extending state, which is curved in the manner depicted here, giving the centering arms 602 a teardrop-like overall profile having a distal taper and a proximal bulge. Advancement of tracking element 620 a sufficient amount distally causes this biased portion of each centering arm 602 to be exposed from within the respective recessed portion 605 of body member 101, allowing centering arms 602 to deflect outwards. Once fully deployed, the widest region of the proximal bulge is preferably coincidental with the desired puncture location through the septal wall. Arrows 660 in FIG. 47E indicate a position in the widest region of the proximal bulge that aligns with the intended puncture site 661. This helps ensure that the puncture location (and subsequently the implantation position for any closure device) is centered with respect to the sidewalls of the PFO tunnel.

Distal advancement of tracking element 620 is preferably limited (e.g., by a distal stop in body member 101 or the proximal controller), at which point continued advancement of centering arms 602 will cause arms 602 to reach their fully outwardly extended position. Centering arms 602 are preferably actively deployed, i.e., forcibly extended outwards through distal advancement of the arms by the user. However, arms 602 can also be passively deployed, i.e., exposure of arms 602 from recesses 605 allows arms 602 to spring outwards autonomously.

Figure 47F:
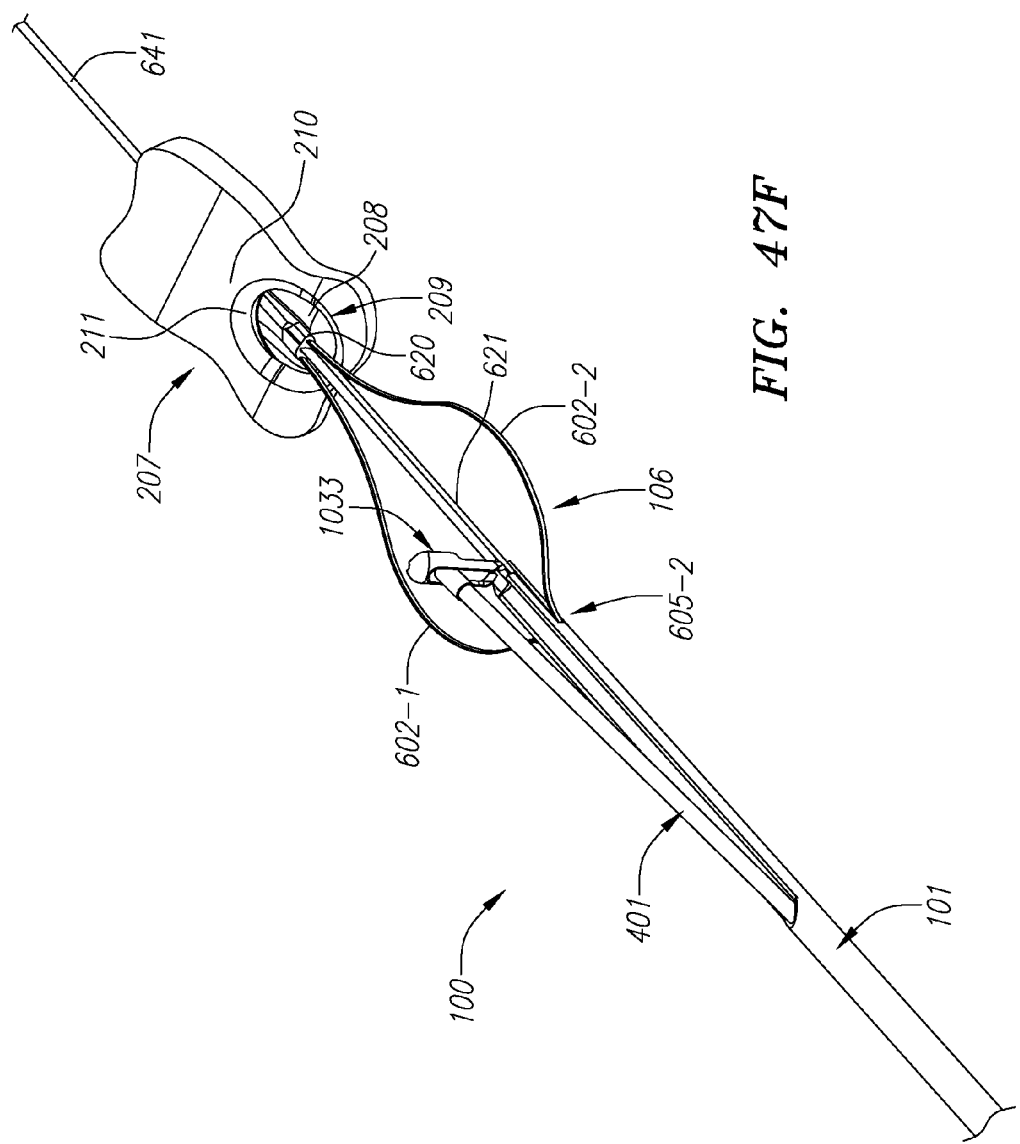

FIG. 47F depicts system 100 after the next step in the procedure, where centering arms 602 have been extended while in a position in proximity with, but inferior to the PFO region 209. Preferably, advancement of body member 101 along guidewire 641 is stopped short of PFO region 209 by an amount sufficient to allow the deployment of centering arms 602 prior to insertion into the PFO tunnel. In the embodiment depicted here, tracking element 620 is located adjacent to the fossa ovalis 208 prior to entering the PFO tunnel and centering arms 602 are fully deployed outwards.

Figure 47G:
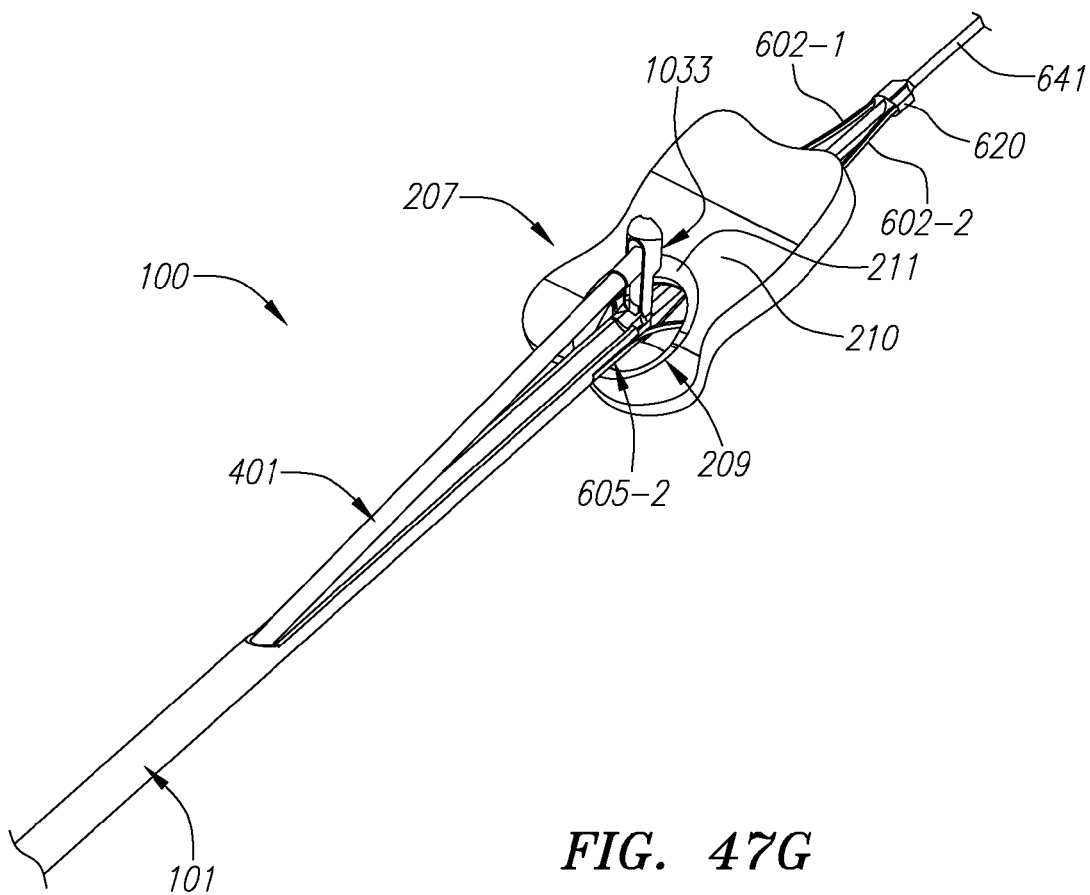

Preferably, after centering arms 602 are fully deployed, body member 101 can be distally advanced until upper jaw 1033 contacts limbus 211 as depicted in FIG. 47G. The length of centering arms 602 is preferably sufficient such that they extend entirely through the PFO tunnel and into the patient's left atrium as depicted here. However, it should be understood that shorter centering arms can be used if desired. Centering arms 602 are preferable configured to expand to a width greater than that of the PFO tunnel, such that as arms 602 are advanced into the PFO tunnel they can partially collapse. Here, centering arms 602 are sufficiently flexible and can distort so as to accommodate narrow tunnels without causing trauma to the septal tissue. In other embodiments where there is no distal stop preventing further distal movement of tracking element 620, partial collapse of centering arms 602 can cause tracking element 620 to move forward distally along guidewire 641, to accommodate the narrowing of the space between arms 602.

Also, centering arms 602 can be deployed while within the PFO tunnel, as opposed to deployment prior to advancement into the PFO tunnel as shown. The use of centering arms 602 helps ensure that upper jaw 1033 contacts limbus 211 in a position aligned along the center of the PFO tunnel. This helps upper jaw 1033 grasp the center of limbus 211 and results in deployment of the implantable device through the center of the PFO tunnel.

Figure 47H:
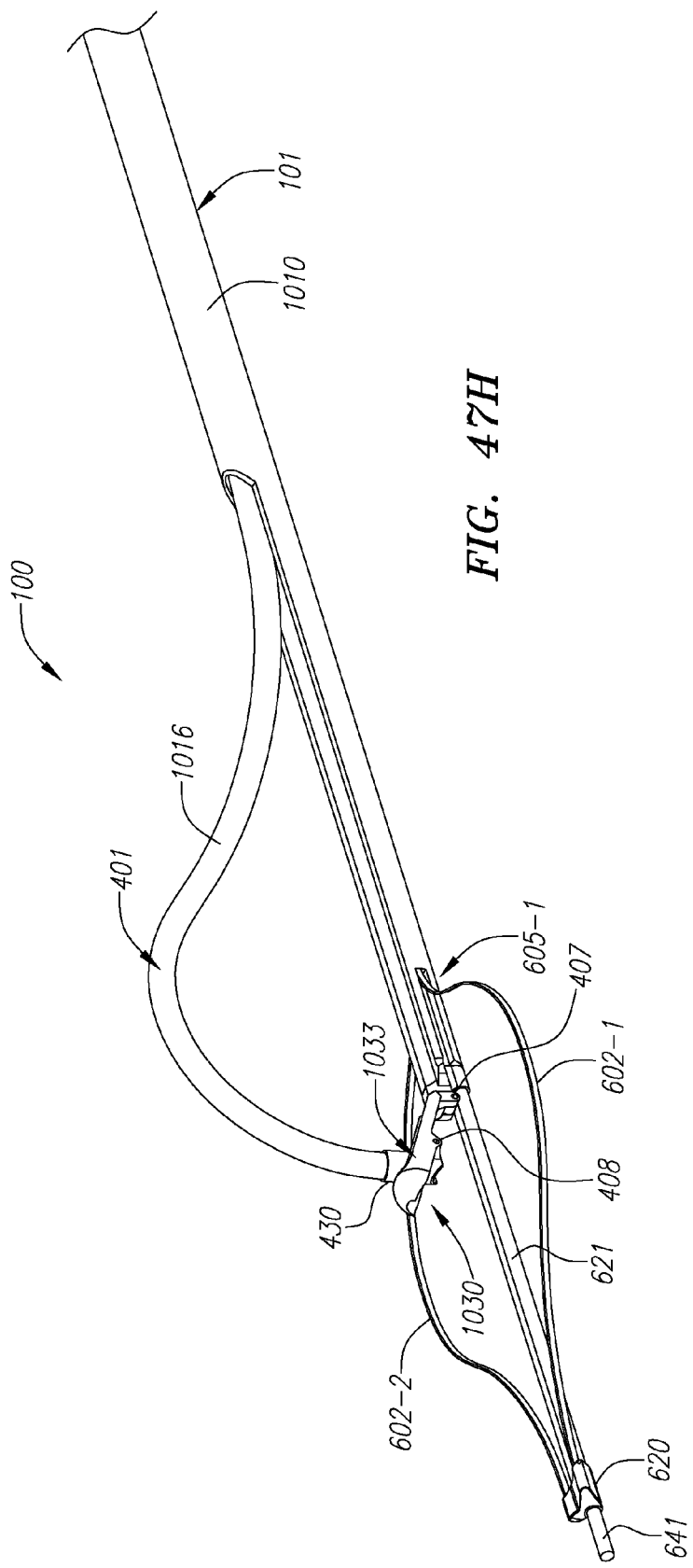
Figure 47I:
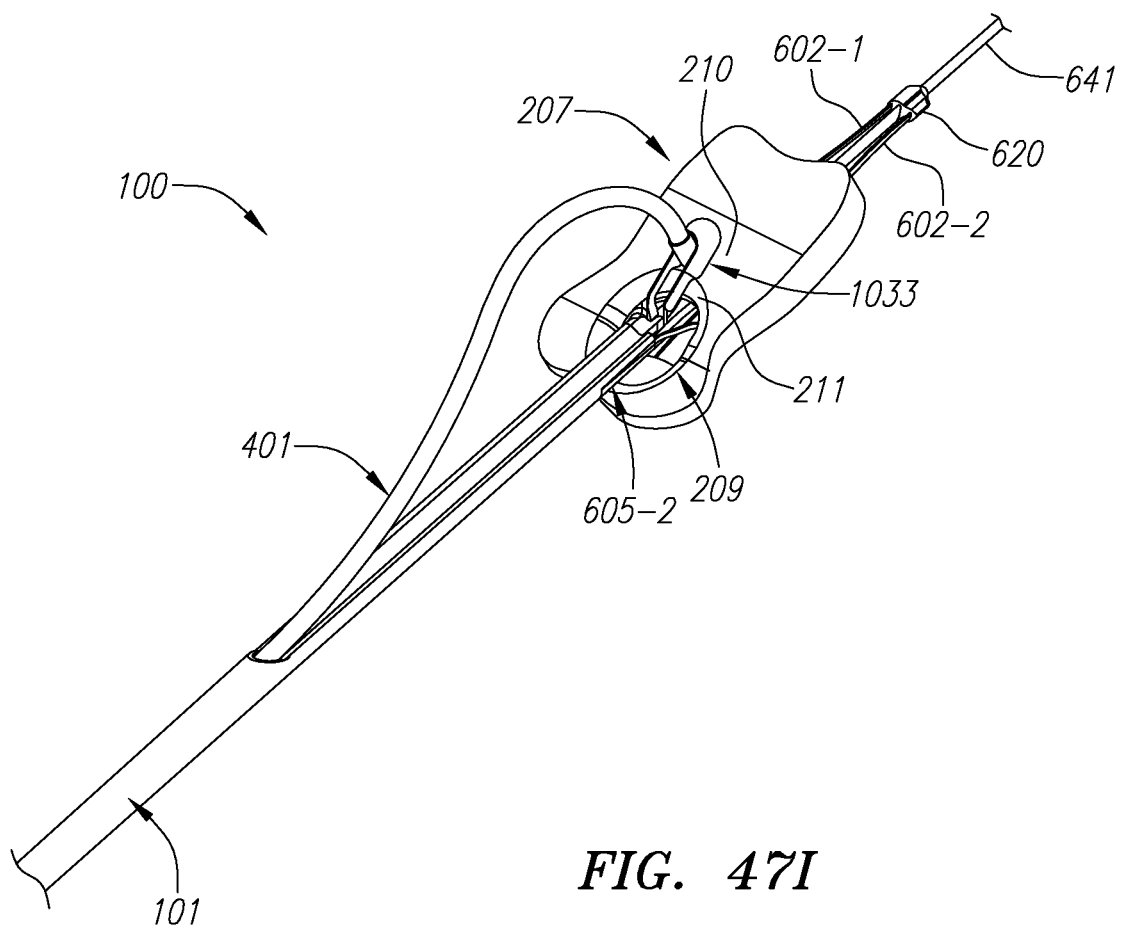

FIG. 47H depicts system 100 after OA delivery member 401 has been advanced distally into an arc-up, or arc-out position, where OA delivery member 401 extends outwards away from body member 101 to alter the orientation of distal tip 430 from facing distally (and lying generally parallel to body member 101) to facing the septal tissue (and lying generally perpendicular to body member 101). FIG. 47I depicts system 100 in this same state except with septal wall 207 shown. The act of advancing OA delivery member 401 distally to cause OA delivery member 401 to arc up also forces upper jaw 1033 downwards against septum secundum 210 and limbus 211, to clamp or grasp the septal tissue and anchor system 100 in place with respect to PFO region 209.

Figure 47J:
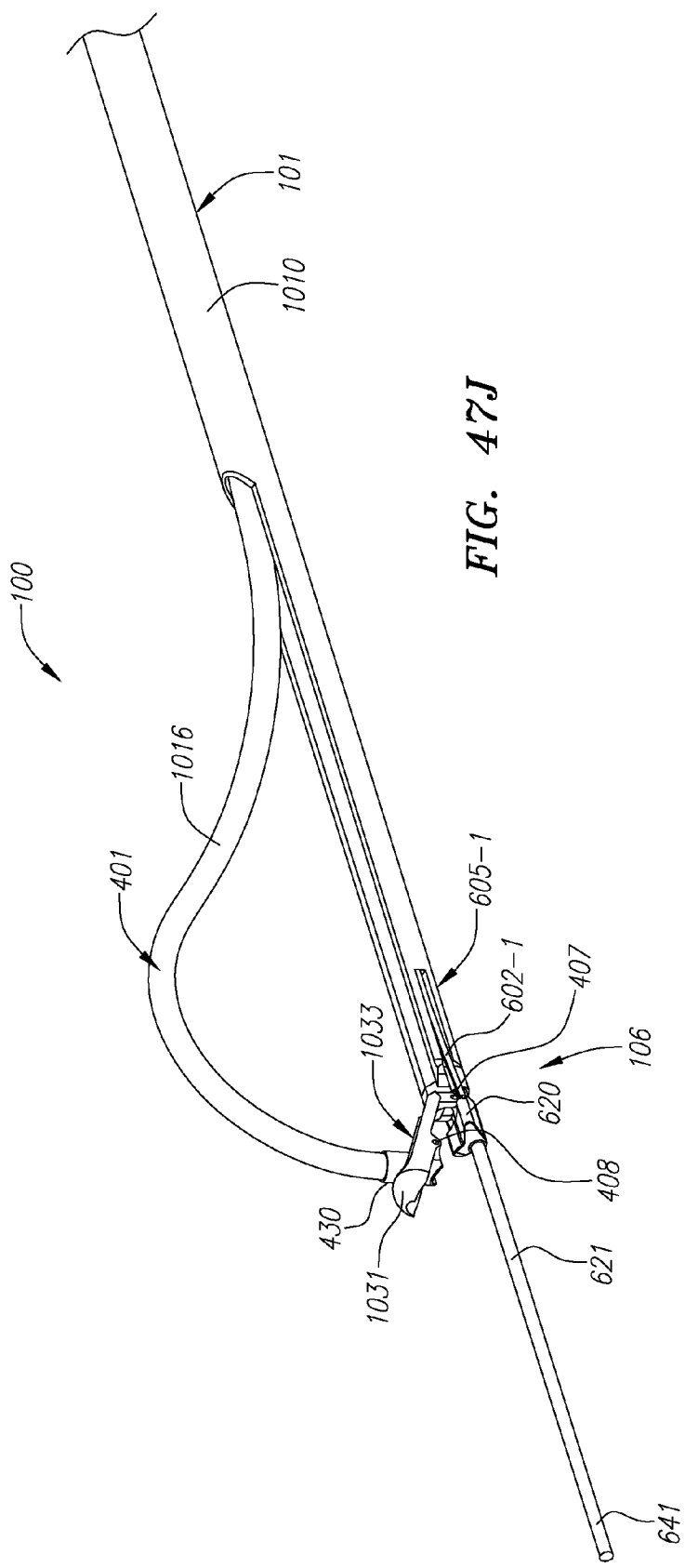

FIG. 47J shows system 100 after refraction of tracking element 620 and centering arms 602 back to the initial, undeployed position. Although the configuration of system 100 can be altered such that centering device 106 can remain deployed during the entirety of the PFO treatment procedure, in this embodiment centering device 106 is retracted at this point to prevent trapping the closure device between the centering arms 602-1 and 602-2. For these reasons, a locking mechanism in the handle prevents advancement of needle member 405 (not shown) until centering device 106 is retracted. This locking mechanism is described with respect to FIGS. 49D-F. The remainder of this exemplary embodiment will be described with reference to a needle like member and an implantable device, but it should be understood that the off-axis delivery and centering features can be used with other treatment methods, such as the use of RF (radio-frequency) closure methods that can entail advancement a piercing element through the septum secundum in a centered location, for the purposes of effecting PFO closure with RF energy.

Figure 47K:
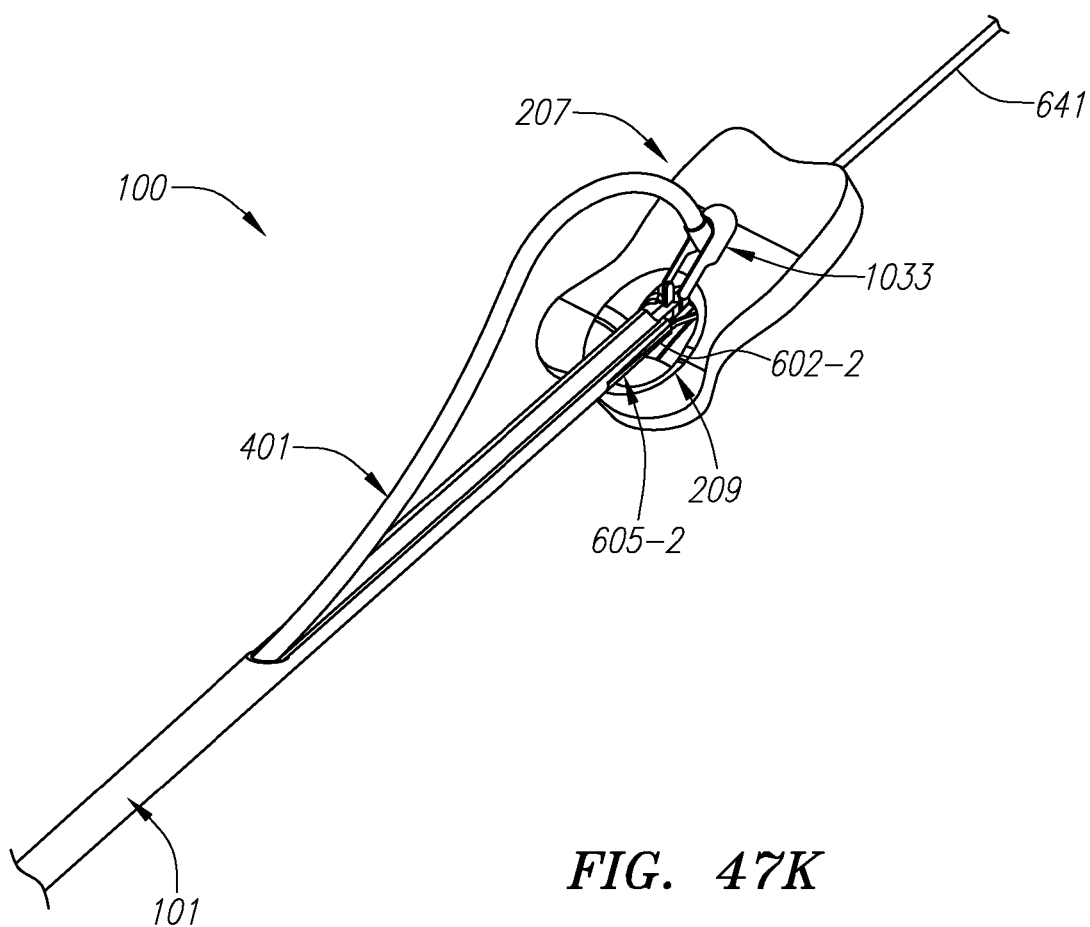
Figure 47L:
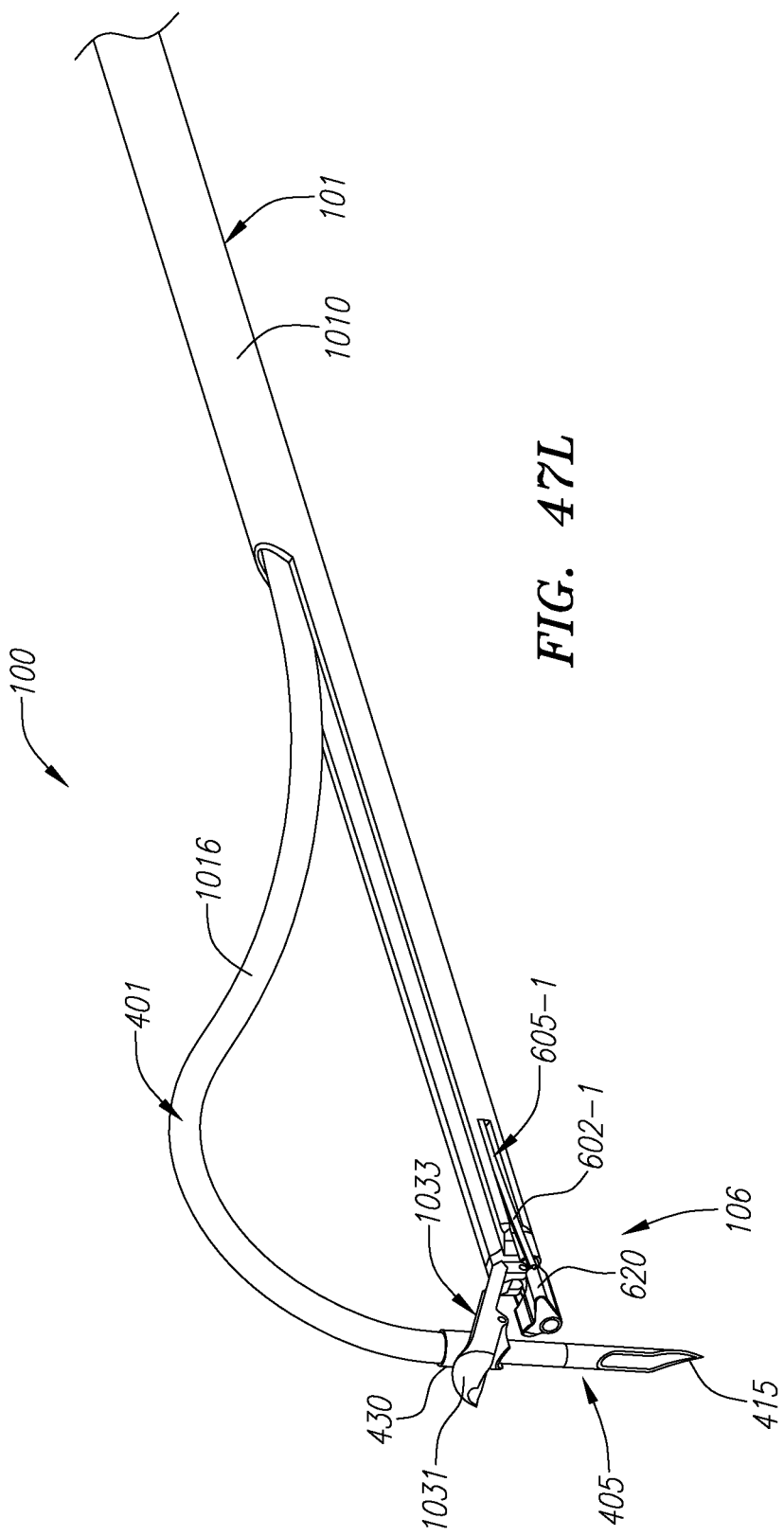
Figure 47M:
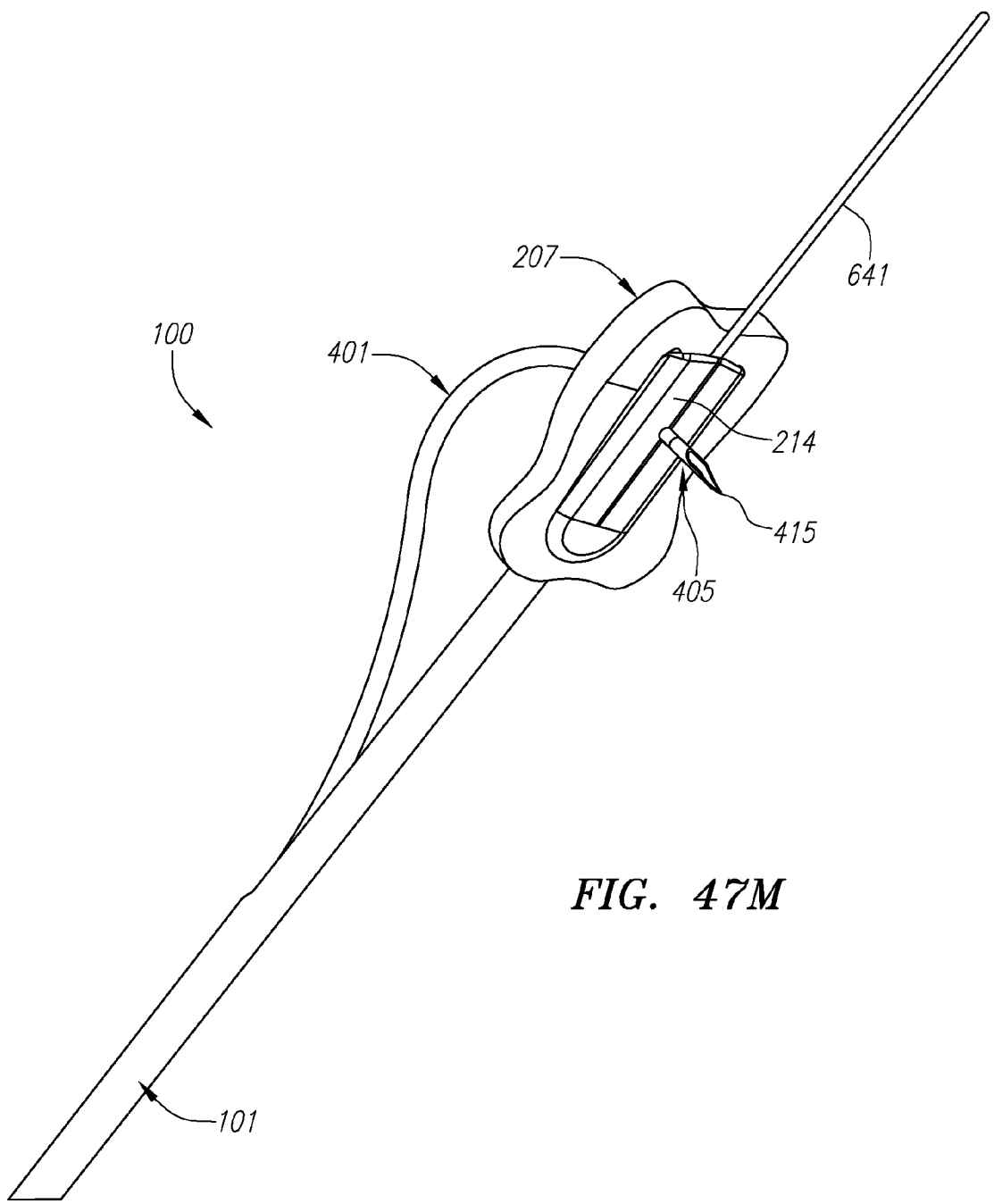

FIG. 47K depicts systems 100 in the same state but with septal wall 207 visible. Guidewire 641 remains extended through the PFO tunnel. FIG. 47L depicts system 100 after advancement of needle member 405 with sharp distal tip 415 from within OA delivery member 401. FIG. 47M shows system 100 in the same state as in FIG. 47L but shows the passage of needle member 405 through septal wall 207 (here including both the septum secundum and septum primum) such that sharp tip 415 lies disposed within the left atrium.

Figure 47N:
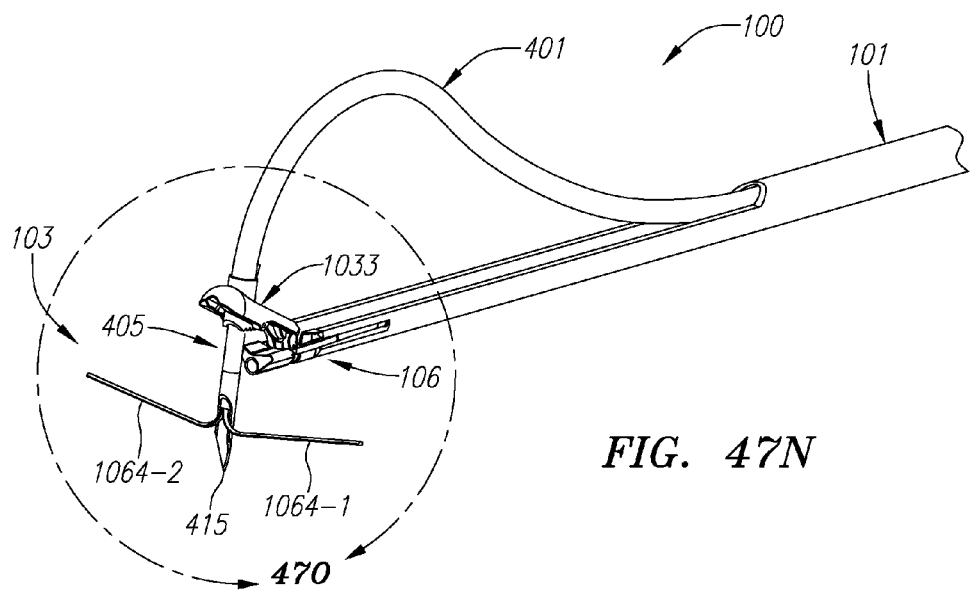

FIG. 47N depicts the next step in the PFO treatment procedure where implantable closure device 103, which in this embodiment is a clip, has been partially advanced from within needle member 405. Here, clip 103 has a configuration similar to that described in U.S. Patent Application Publication No. 2009/0318956 entitled "Wire-Like and Other Devices for Treating Septal Devices and Systems and Methods for Delivering the Same." This application is fully incorporated by reference herein. Clip 103 has left atrial anchor members 1064-1 and 1064-2 which are shown in a deployed state where they have deflected apart from each other.

Figure 47O:
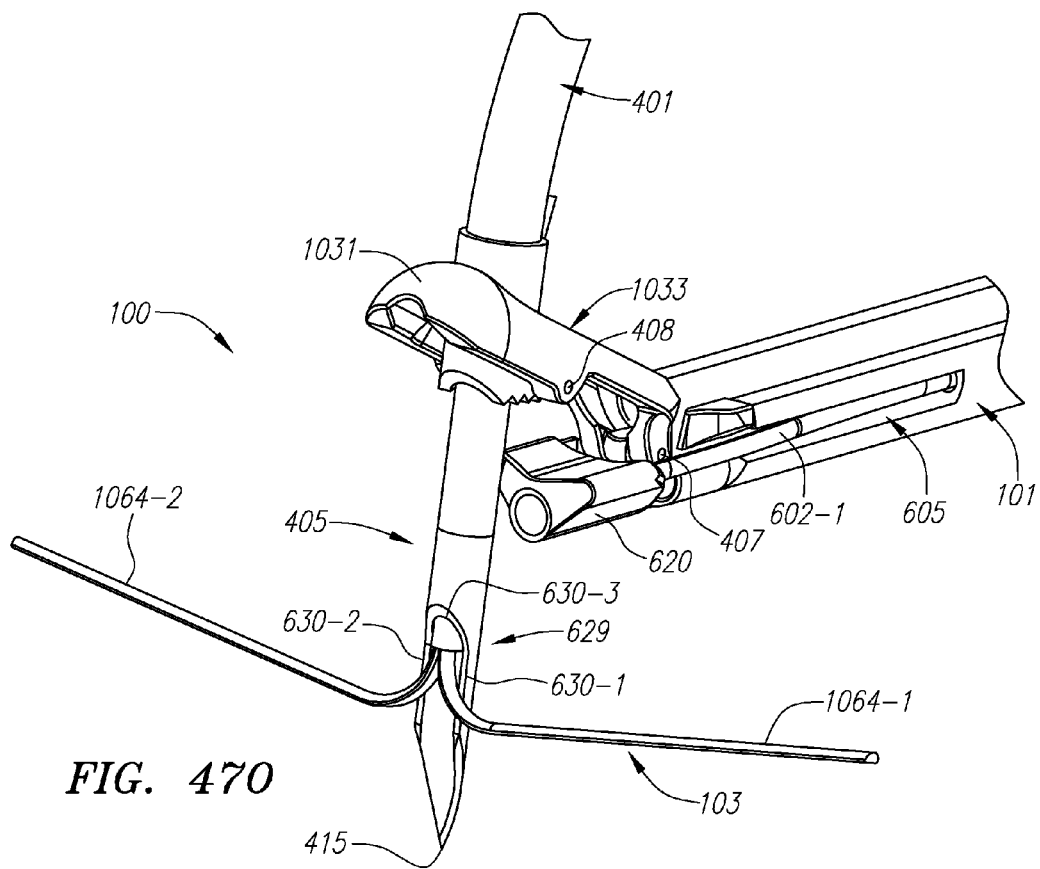

Region 47O of FIG. 47N is enlarged and shown in greater detail in FIG. 47O. Here it can be seen that the distal region of needle member 405 is shaped to allow clip 103 to deploy without resting on the sharp, blade-like edge that terminates needle distal tip 415. Specifically, proximal to the sharp needle edge is a cutaway region 629 that includes two unsharpened edges 630-1 and 630-2 that form a lateral backing on which left atrial anchor members 1064-1 and 1064-2 can rest once advanced from within needle member 405. The backing aligns left atrial anchor members 1064-1 and 1064-2 to ensure they are properly oriented across the width of the PFO tunnel. Edges 630-1 and 630-2 are connected by curved proximal edge 630-3. Edges 630-1 and 630-2 can be flattened, squared off and/or rounded with respect to the adjacent needle side surfaces. While referenced for convenience as a "cutaway" region, this feature can be formed in any manner desired and is not required to be physically cut away from the needle distal tip during assembly. For instance, region 629 can also be referred to as a seat or a buffer region. Alignment between the septal wall and cutaway region 629 is achieved by using a proximal sheath having a directional bend. The sheath is preferably an extruded PEEK tube, which can exhibit a natural directional bend. This proximal sheath of needle member 405 is then properly aligned with the rigid distal end during assembly such that needle member 405 will then tend to bend in one direction, with the rigid distal end oriented to allow the left atrial anchors to be deployed directly lateral (e.g., perpendicular) to the direction of bending. Because of this tendency to bend in one direction, the needle member 405 will naturally align itself within the OA delivery member 401 as the OA delivery member 401 bends in one direction into the arc-up position, as shown in FIGS. 47N-P.

Figure 47P:
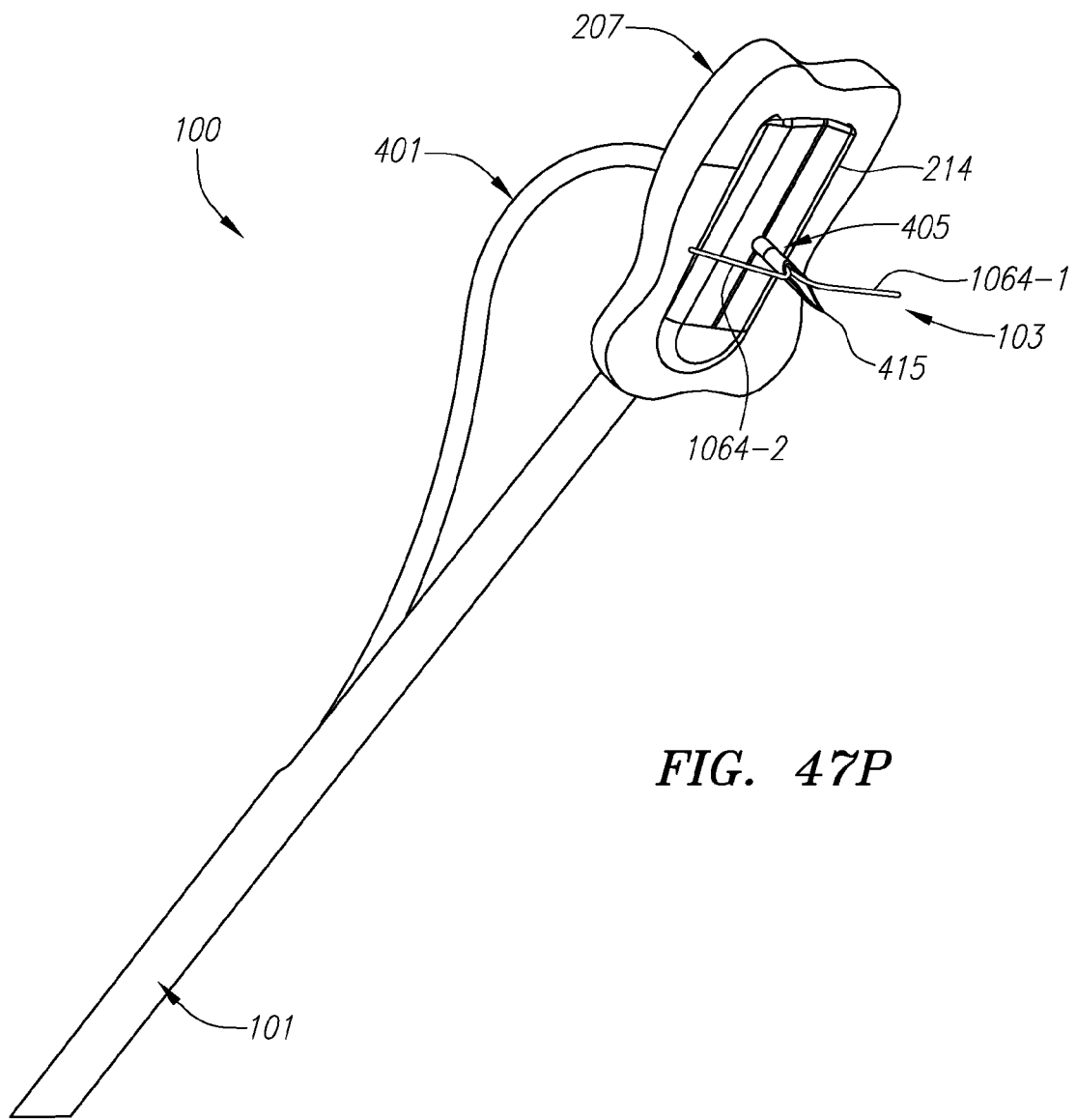
Figure 47Q:
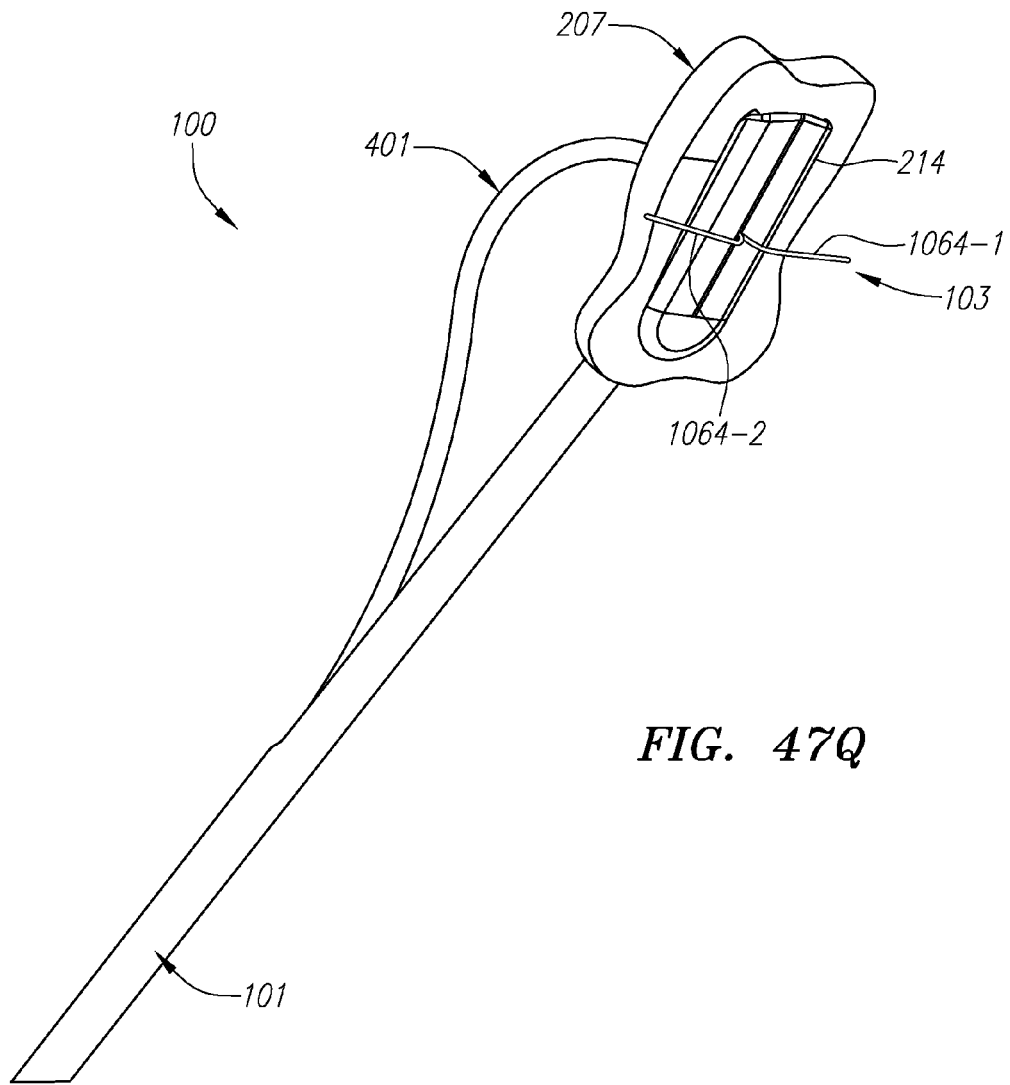

FIG. 47P depicts system 100 with clip 103 advanced into the left atrium and ready for deployment. FIG. 47Q depicts clip 103 after retraction of needle member 405 back through septal wall 207. Here, the only components still present in the left atrium is left atrial anchors 1064-1 and 1064-2 of clip 103. Left atrial anchors 1064-1 and 1064-2 are preferably pulled flush against the left atrial surface of septal wall 207.

Figure 47R:
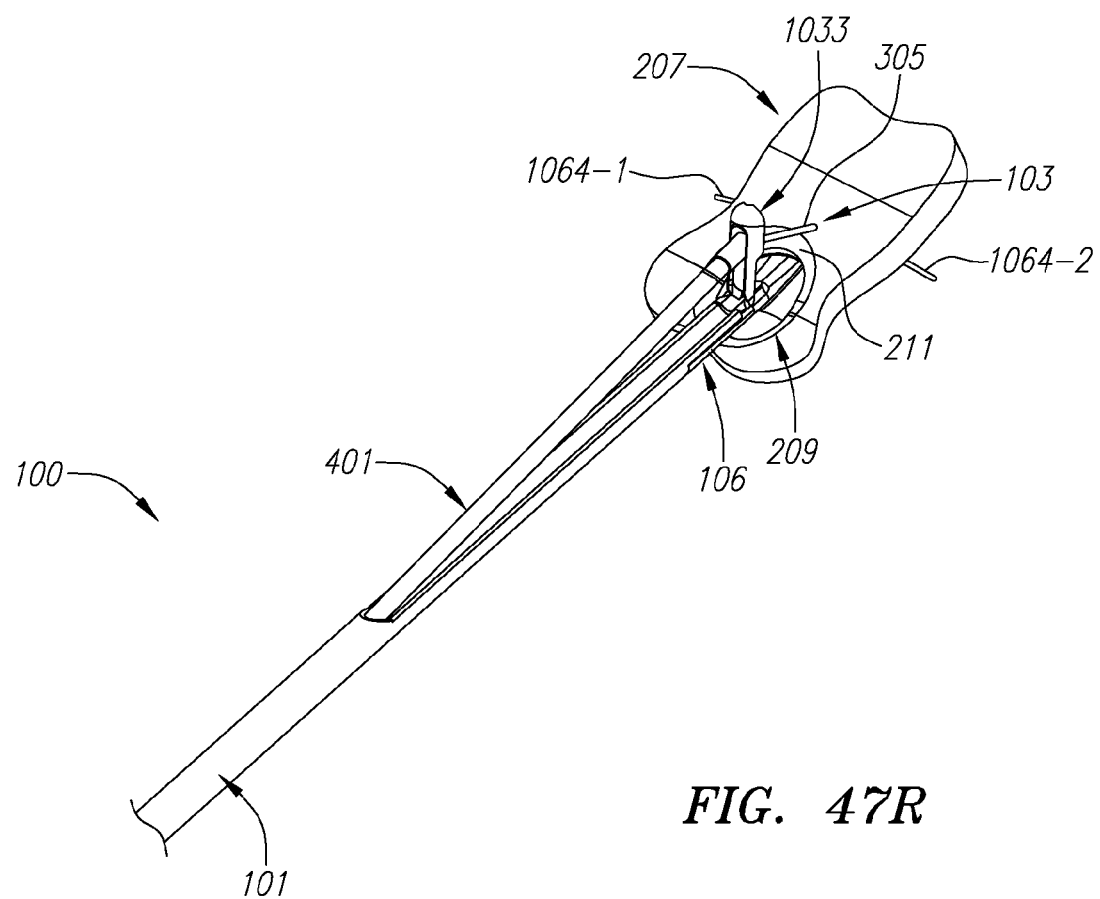

FIG. 47R depicts OA delivery member 401 after being proximally retracted out of the arc-up state and back to a position where upper jaw 1033 is retracted away from limbus 211. Here, clip 103 has not been fully deployed and the right atrial anchors are still contained within needle 405 which has been retracted inside OA delivery member 401. A central section 305 of clip 103 is shown extending from the puncture site back into OA delivery member 401. The ability to retain clip 103 during this retraction of needle 405 is preferably achieved by use of an interlocking pusher member, such as that described with respect to FIG. 46C.

Figure 47S:
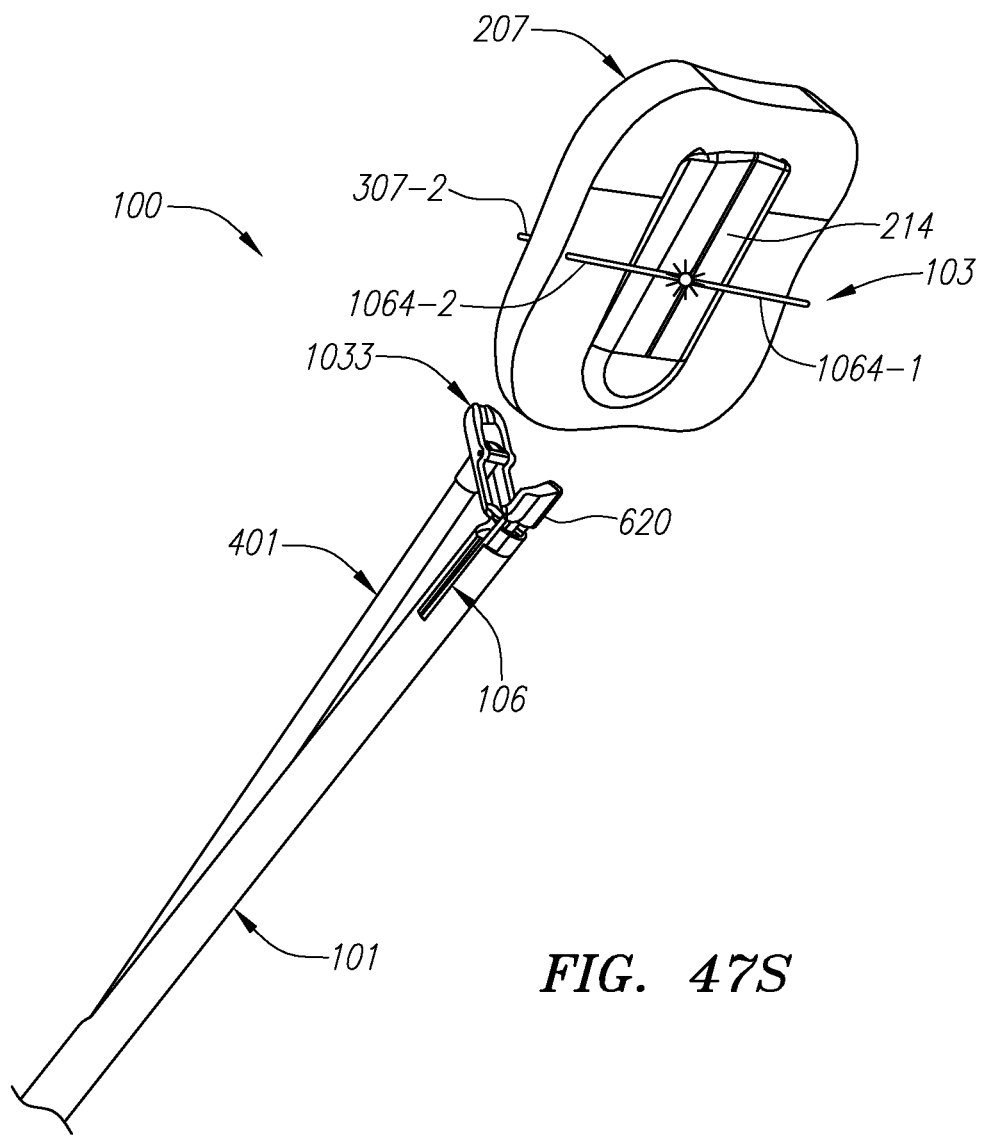
Figure 47T:
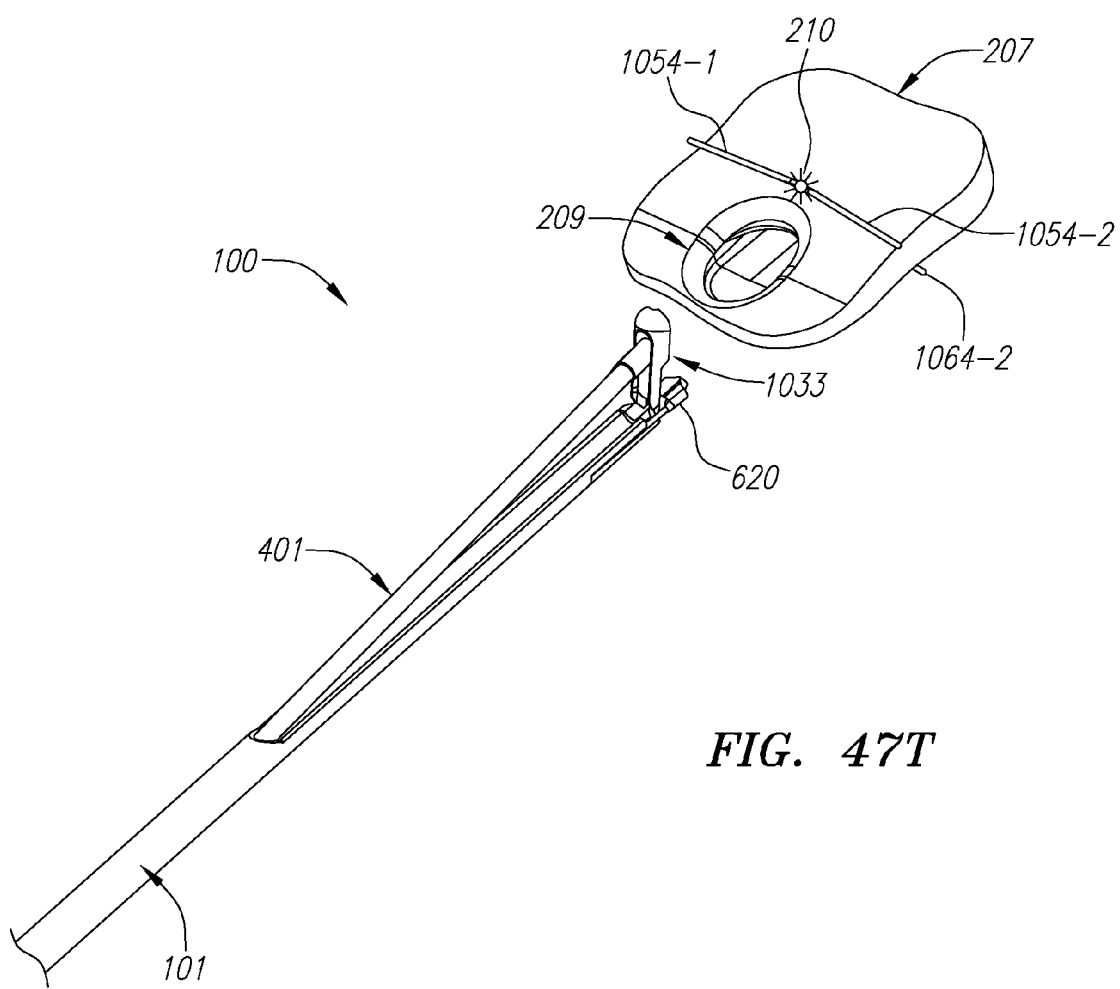

FIG. 47S depicts system 100 after being fully retracted from septal wall 207 with implantable device 103 fully deployed. Release of clip 103 is preferably achieved by withdrawal of system 100 proximally to a point where right atrial anchors 1054 are pulled from within needle member 405 and are free to deflect and deploy. Here, upper jaw 1033 is still in the up position. This view is taken from the left atrium, while the view in FIG. 47T is taken from the right atrium. Right atrial anchors 1054-1 and 1054-2 are shown fully deployed across the septum secundum 210. Because the width of the PFO tunnel can vary, it is desirable to have the puncture location placed in the center of the tunnel to ensure that the anchors 1064 and 1054 extend across the width of the entire tunnel to affect the most complete closure. From this position, OA delivery member 401 can be advanced to place upper jaw 1033 is free to move to the down position against tracking element 620, when body member 101 is withdrawn from the patient.

Figure 48A:
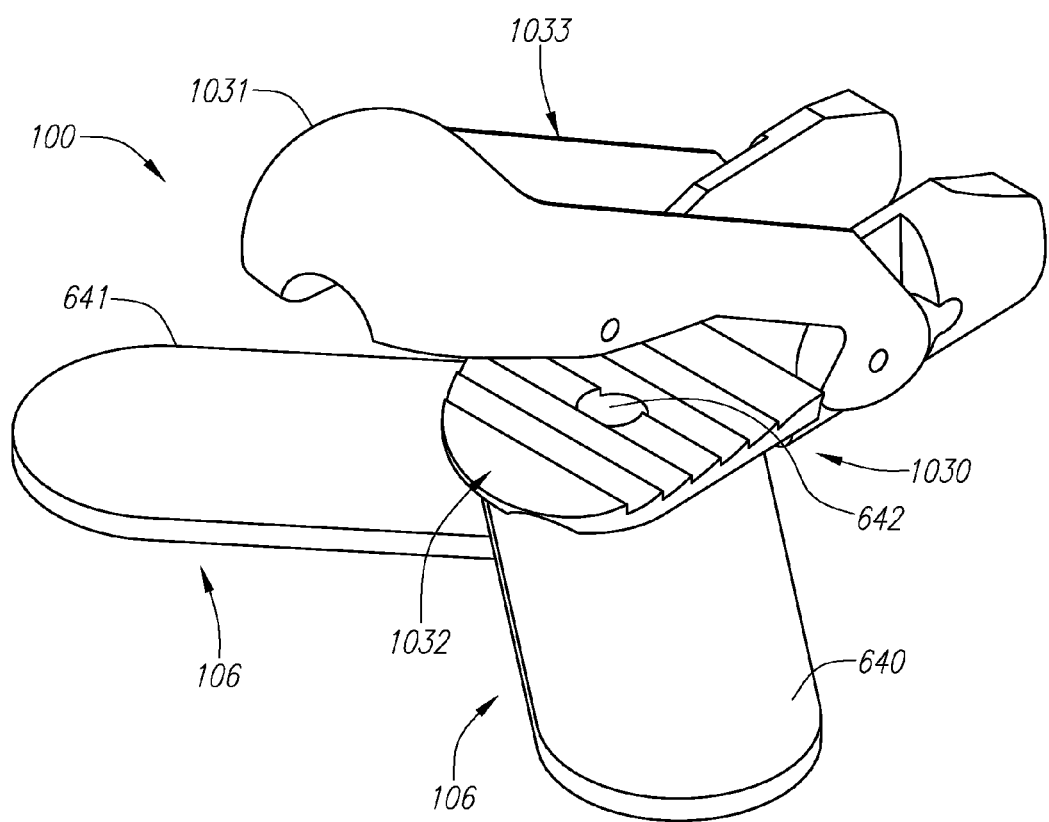
FIGS. 48A-D are perspective views depicting additional exemplary embodiments of centering devices that can be used as part of a PFO treatment system.

FIG. 48A is a perspective view showing the distal portion of system 100, specifically upper jaw 1033 and lower jaw 1032 of distal end section 1030. Here, centering device 106 includes two pivotable centering struts 640 and 641, which couple with lower jaw 1032 by way of a hinge 642. Centering struts 640 and 641 are overlaid, with strut 640 located between strut 641 and lower jaw 1032. Centering struts 640 and 641 can pivot with respect to each other in a scissor-like fashion with strut 640 pivotable to the right as shown here and strut 641 pivotable to the left. When lower jaw 1032 is advanced into the PFO tunnel, struts 640 and 641 can be separated apart to center the device with respect to the PFO tunnel. The gap between struts 640 and 641 is preferably wide enough to allow passage of the piercing member there through. It should be noted that other elements of system 100 are not shown (e.g., distal tip 430, needle member 405, OA delivery member 401 and body member 101) for ease of illustration. Actuation of centering struts 640 and 641 can be achieved via the use of a push-pull wire as known in the art.

Figure 48B:
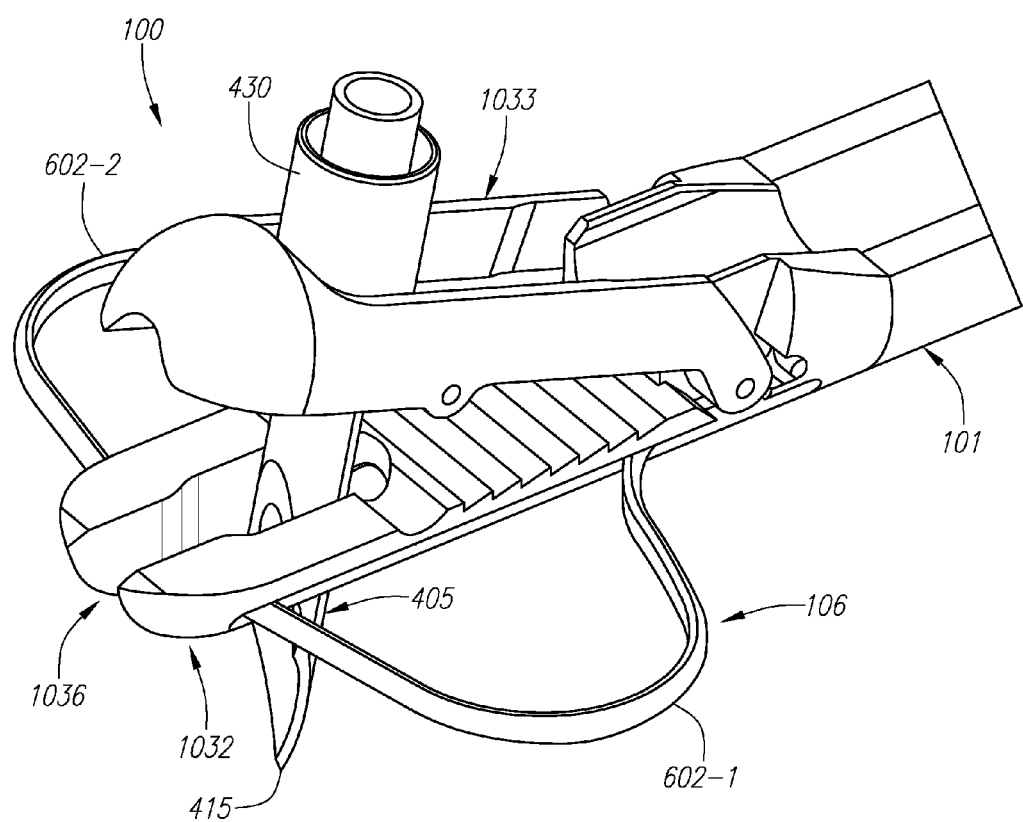

FIG. 48B is another perspective view depicting a distal region of system 100. Here, centering device 106 includes centering arms 602-1 and 602-2 which are shown in the deployed, outwardly extending position. In contrast to the embodiment discussed with respect to FIGS. 47A-T, in this embodiment the distal end of each centering arm 602 can be pivotally coupled with the distal end of lower jaw 1032, which is inserted into the PFO tunnel during the closure procedure. Although not shown, the coupling can be any type that allows pivoting, such as a swivel-type hinge (e.g., a pin received through an aperture(s), a ball and socket, and the like). In another example, the distal end of each centering arm 602 removably sits within a pocket that allows pivoting, with distally applied force on the centering arms 602 acting to keep the distal end within the pocket. The needle member 405 is then inserted through a gap 1036 in lower jaw 1032 as shown. Deployment of centering arms 602 is similar to that previously described, namely the centering arms are advanced with respect to body member 101 to cause them to deflect outwards into the configuration shown here. In this embodiment, centering arms 602 can remain in this outwardly extended position during advancement of needle member 405 and deployment of any closure device (e.g., clip, etc.), without risk of trapping the closure device inside a centering arm. This allows the primum to remain taught (i.e., without substantial folding) during the entire implantation procedure.

Figure 48C:
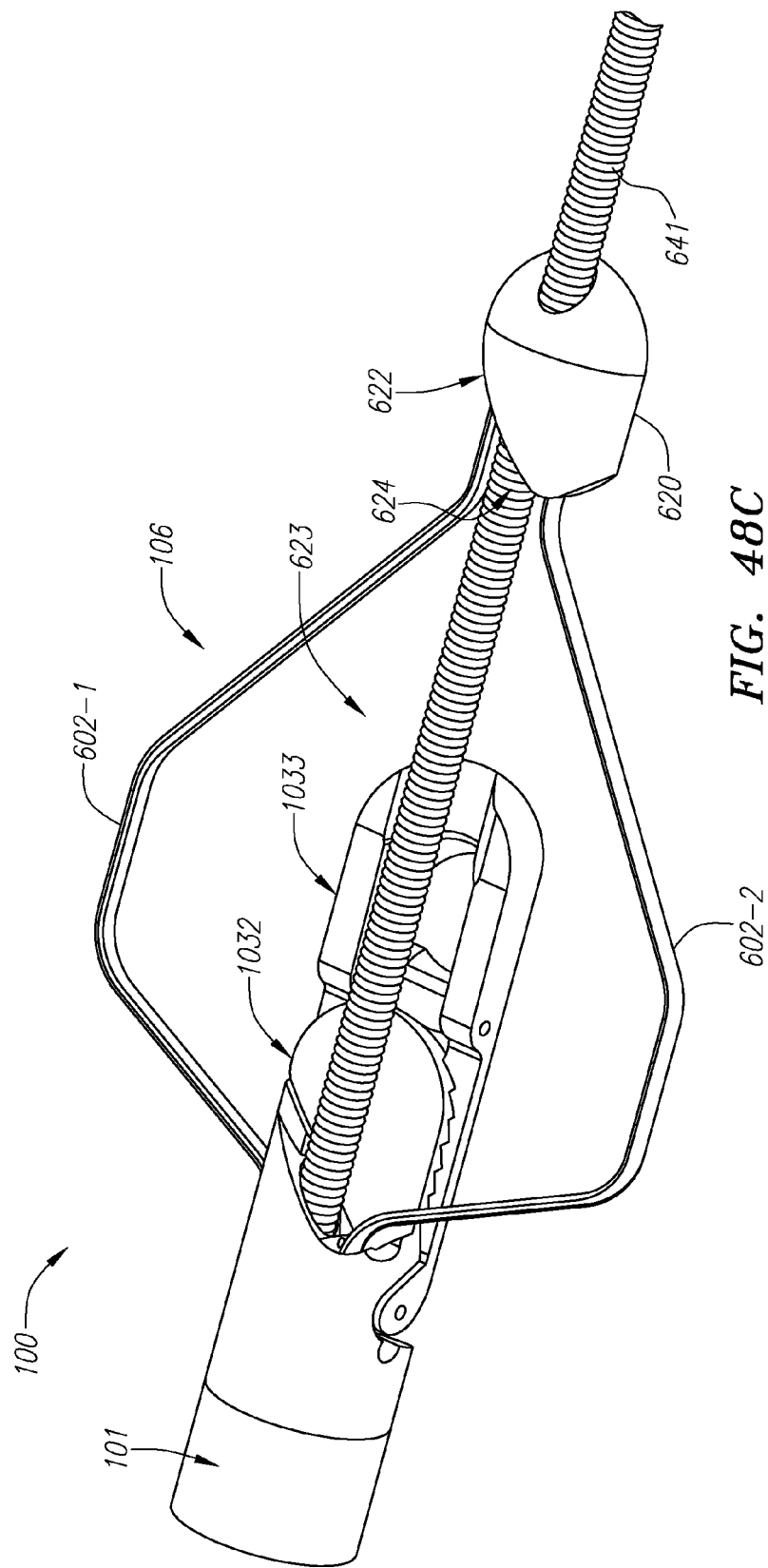

FIG. 48C is a perspective view depicting another exemplary embodiment of system 100 with centering device 106. Here, system 100 includes a lower jaw 1032 that is approximately half the length of upper jaw 1033. (This view is taken from the underside of the device). Each centering arm 602 is coupled with tracking element 620 which has a lumen for sliding over guidewire 641. However, in this embodiment, there is no centering core wire that couples with tracking element 620 (although the embodiment can be configured to have a centering core wire). Tracking element 620 is movable via translation in arms 602 alone.

This embodiment allows for deployment of the closure element within the space 623 between centering arm 602-1 and centering arm 602-2. Prior to implantation of the closure device, guidewire 641 can be retracted, leaving tracking element 620 and centering arms 602-1 and 602-2 behind. Next, needle member 405 can be advanced through septal wall 207 and left atrial anchors 360-1 and 360-2 are deployed and pulled up against the left atrial surface of septal wall 207. Once the left atrial anchors 360 are in contact with the tissue, centering arm 602-1 is retracted, which disengages its distal end from a socket (not shown) in tracking element 620. Retraction of tracking element 620 forces the closure device against the proximal face 622 of tracking element 620. Face 622 is sloped or angled to allow the closure device to slide past tracking element 620 as it is refracted further. Thus, the closure device can be implanted in space 623 with the centering device 106 having the capability to open up and allow removal of system 100 past the implanted closure device. In this embodiment, the proximal controller (not shown) can be configured to distally advance centering arms 602 together in one forward motion. The use interface to the proximal controller can allow retraction of centering arms 602 with two or more motions, i.e., independently, or can allow retraction of both arms 602 in one motion using a fast rate of retraction for arm 602-1 and a slower (or altogether delayed) retraction of centering arm 602-2.

Figure 48D:
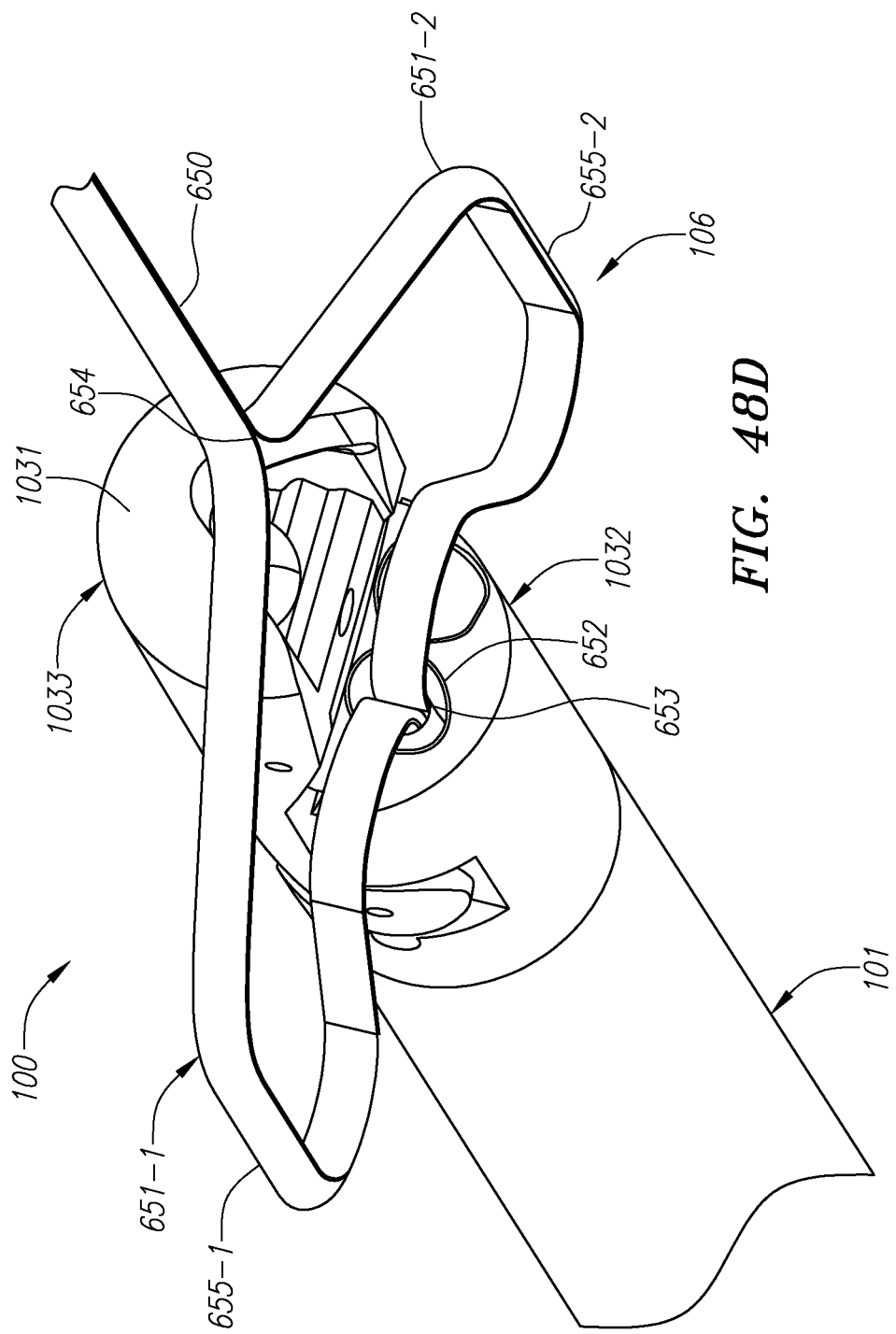

FIG. 48D is a perspective view depicting another exemplary embodiment of system 100 having centering device 106. Here, centering device 106 includes an elongate flexible wire-like member 650 that has a central slit that allows it to separate into opposing centering arms 651-1 and 651-2, as shown here. After wire-like member 650 exits a lumen 652 in body member 101 (specifically, lower jaw 1032), centering arms 651 are free to deflect outwardly away from body member 101 into the configuration shown here. Wire-like member 650 has a proximal joint 653 and a distal joint 654 where centering arms 651 separate from wire-like member 650. Here, centering arms 651 are configured to deflect such that they extend proximally to proximal joint 653, to allow the centering feature to extend laterally directly adjacent to lower jaw 1032. Each centering arm 651 also has a straight section 655 that extends generally parallel to the central axis of body member 101. Prior to piercing the septal tissue, centering device 106 can be undeployed by retracting wire-like member 650 proximally back into lumen 652. This embodiment allows deployment of two centering arms 602 through control of only a single shaft (portion of member 650 proximal to joint 653). Accordingly, proximal controller 900 need only provide control capability for one shaft as opposed to two (or more).

Figure 49A:
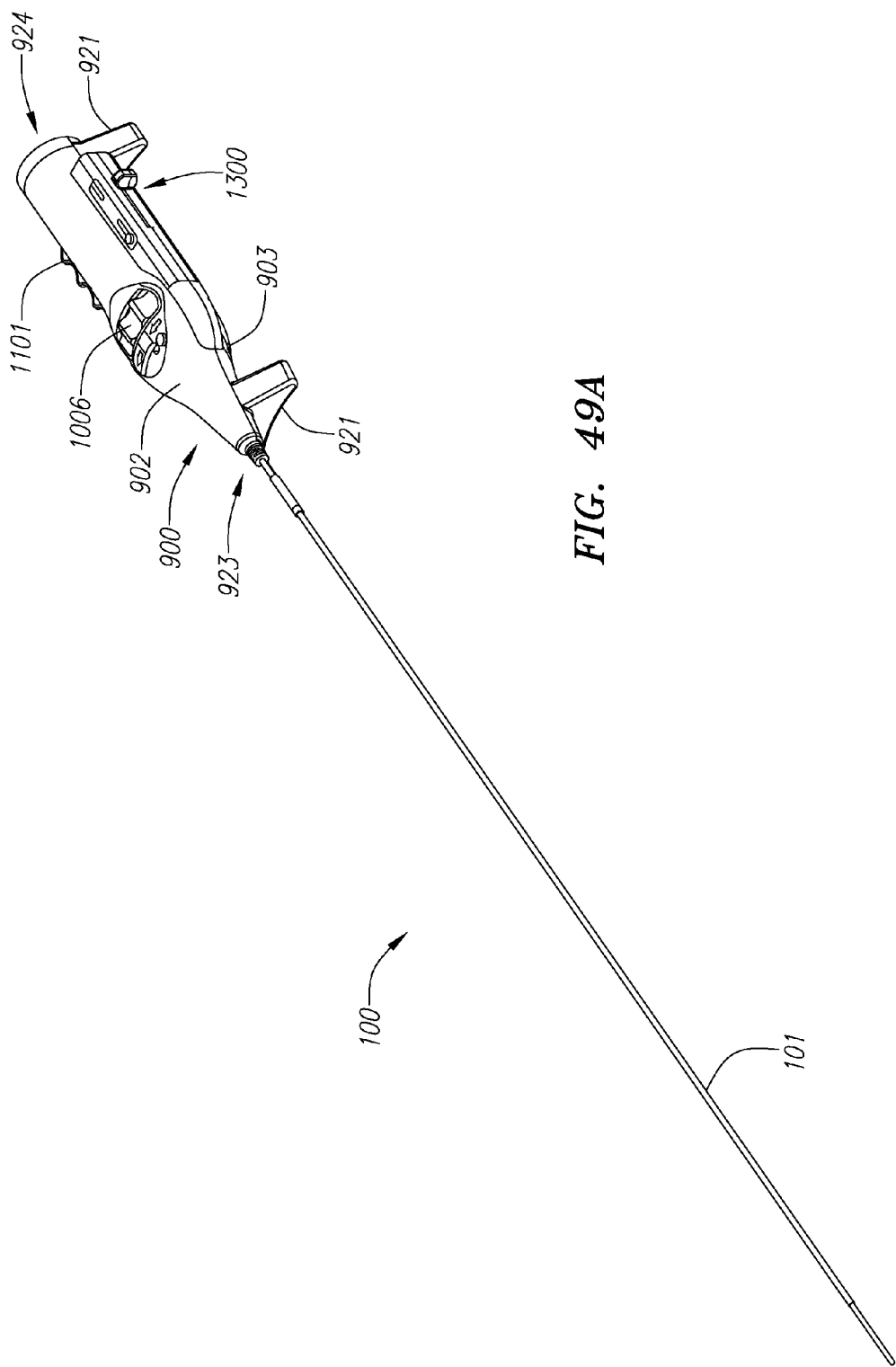
FIG. 49A is a perspective view depicting an additional exemplary embodiment of a treatment system.

FIG. 49A is a perspective view depicting another exemplary embodiment of system 100 having proximal controller 900 connected to a proximal end of body member 101. Like the embodiment described with respect to FIGS. 43E-43I, the embodiment depicted here has a rotatable knob 1006 that interfaces with a rotatable cam 1104 (not shown). This embodiment introduces a centering actuator assembly 1300 for controlling the deployment of a centering mechanism to be described below.

Figure 49B:
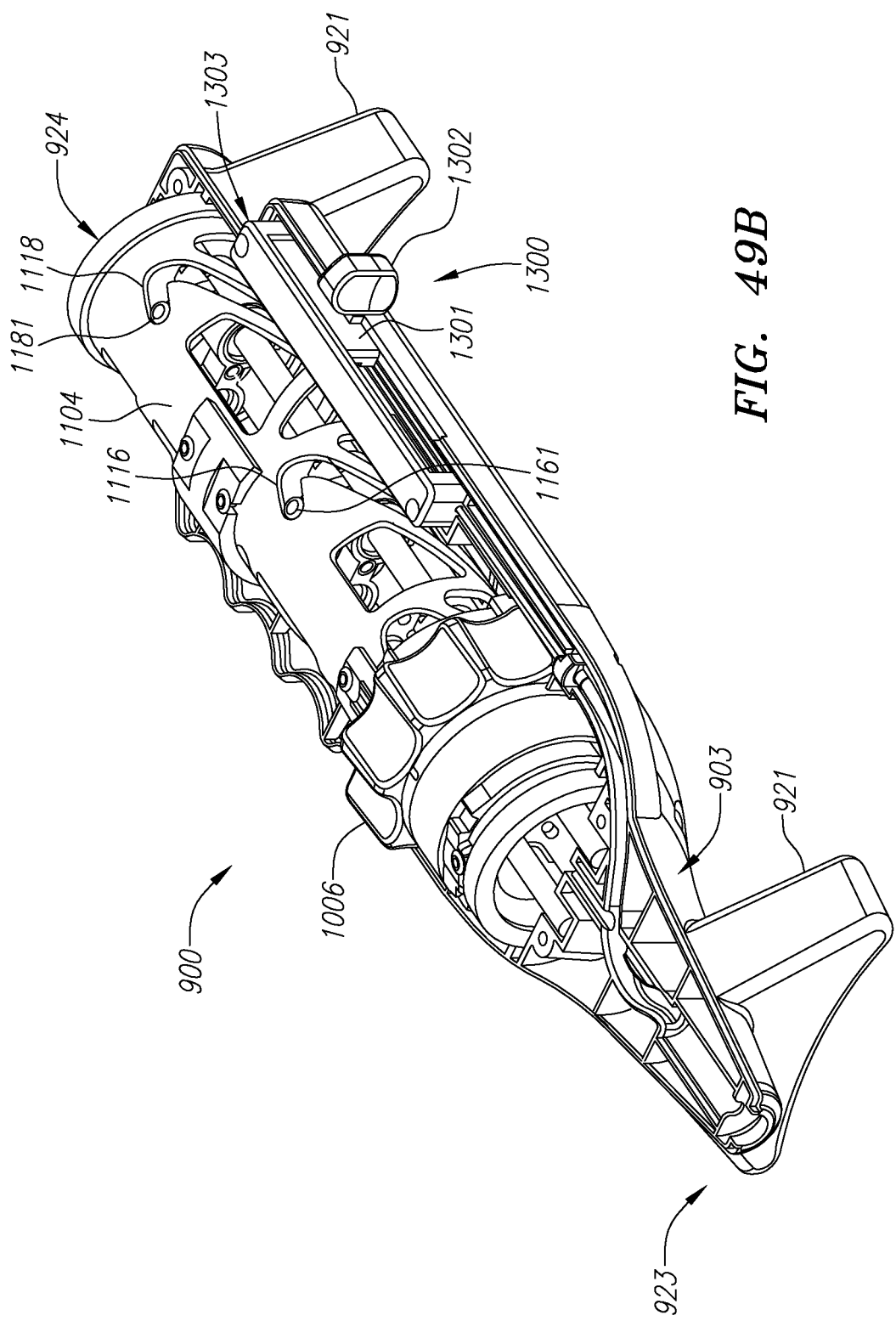
FIGS. 49B-F are perspective views of an exemplary embodiment of a proximal controller for use with a treatment system.

FIG. 49B is a perspective view of proximal controller 900 with upper housing 902 removed so that the inner components can be seen. Controller 900 includes distal end 923 and proximal end 924, lower housing 903, base stands 921, rotatable knob 1006, rotatable cam 1104, and centering actuator assembly 1300. Like the earlier embodiments, rotatable cam 1104 includes slots 1114 (not shown), 1116, and 1118 for receiving actuator interfaces 1141 (not shown), 1161, and 1181, respectively. Centering actuator assembly 1300 includes slidable actuator 1301, handle or knob 1302, and housing or cover 1303, in which actuator 1301 and knob 1302 are slidable proximally and distally.

Figure 49C:
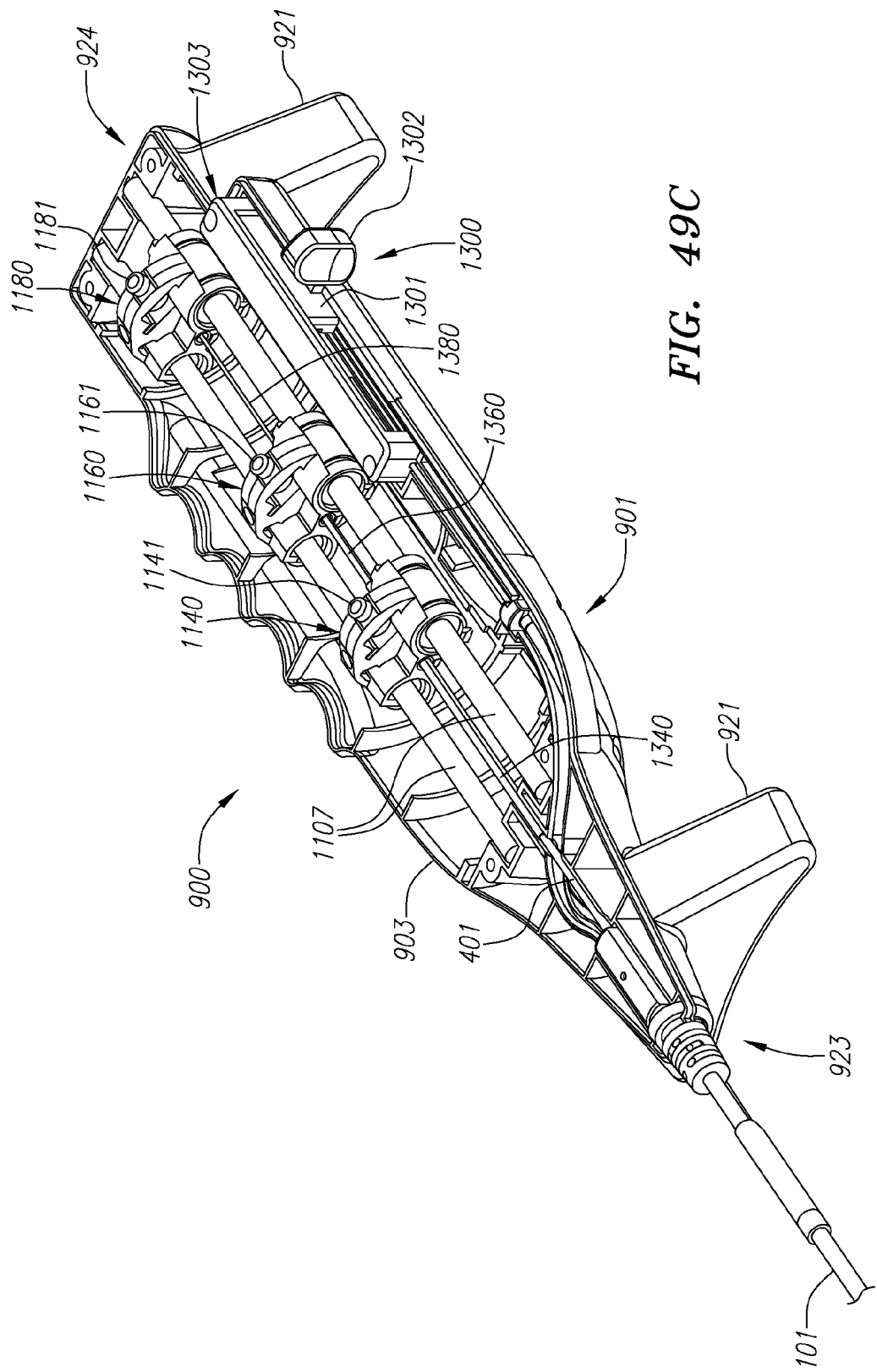

FIG. 49C is a perspective view similar to FIG. 49B but with rotatable knob 1006 and rotatable cam 1104 omitted to show the components located therein. Here, guiderails 1107, OA delivery member actuator 1140, needle member actuator 1160, and pusher member actuator 1180 can be seen. OA delivery member actuator 1140 is coupled to a sleeve 1340 for housing OA delivery member 401 (not shown) and providing increased pushability (e.g., resistance to buckling) for OA delivery member 401. Likewise, both needle member actuator 1160 and pusher member actuator 1180 are also coupled with sleeves 1360 and 1380, respectively, for adding pushability to needle member 405 and pusher member 406 (both not shown), respectively.

Figure 49D:
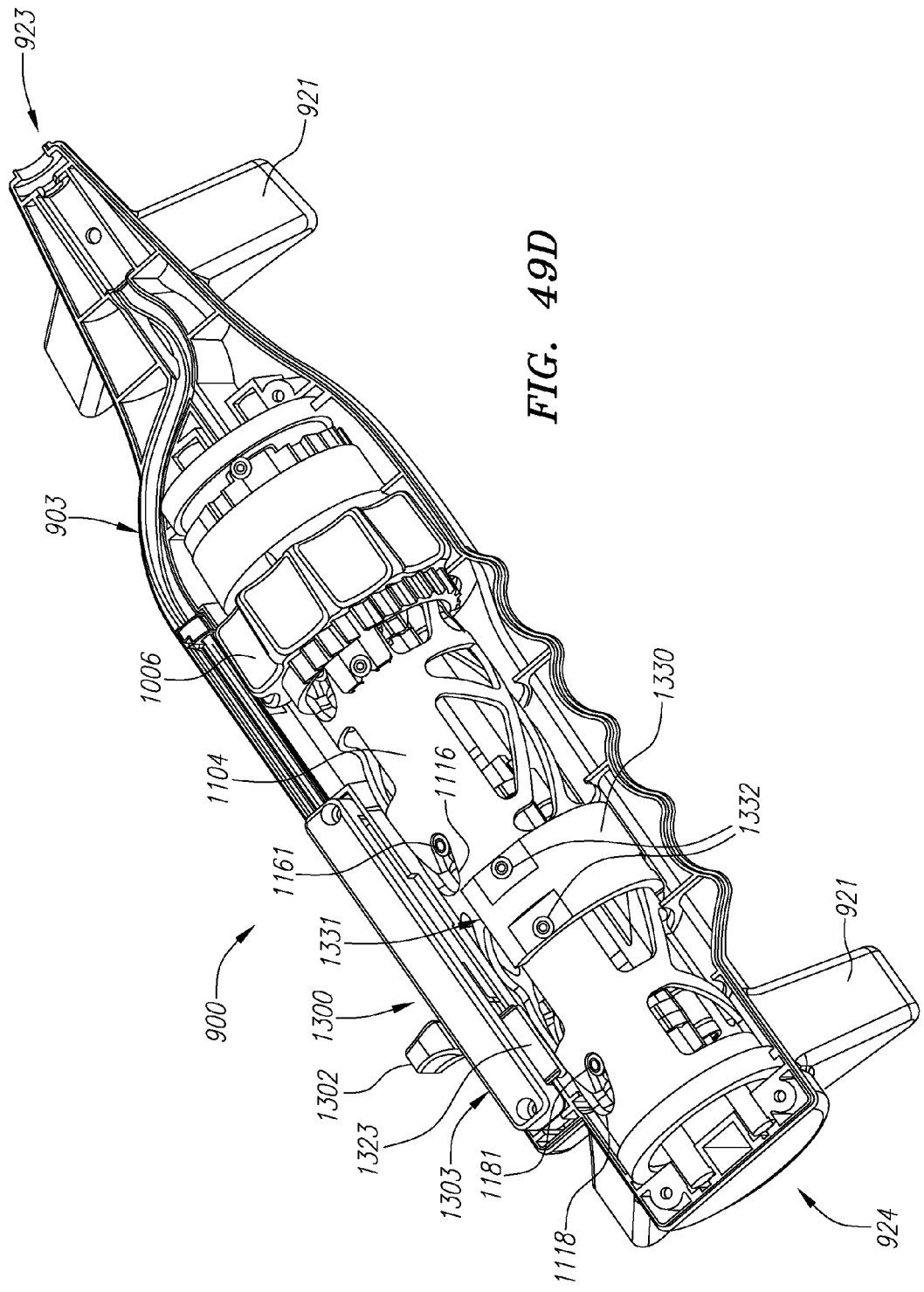

FIG. 49D is another perspective view similar to FIG. 49B but rotated 180 degrees to show locking tab 1323 of centering actuator assembly 1300. Locking tab 1323 is coupled with actuator 1301 (not shown) and therefore moves along with actuator 1301. Locking tab 1323 projects into the interior of controller 900 into a space where locking tab can contact cam locking element 1330. Cam locking element 1330 is configured here as a partial ring, specifically a C-shape, that is coupled to the exterior of cam 1104 by fasteners (e.g., rivets and the like) 1332 and therefore rotates along with cam 1104.

Cam locking element 1330 and locking tab 1323 together form a position dependent lock mechanism that prevents advancement of needle member 405 (not shown) until centering device 106 (not shown) is retracted from the deployed to the undeployed state, in order to prevent the deployment (and subsequent trapping) of the closure device within the deployed centering arms.

Figure 49E:
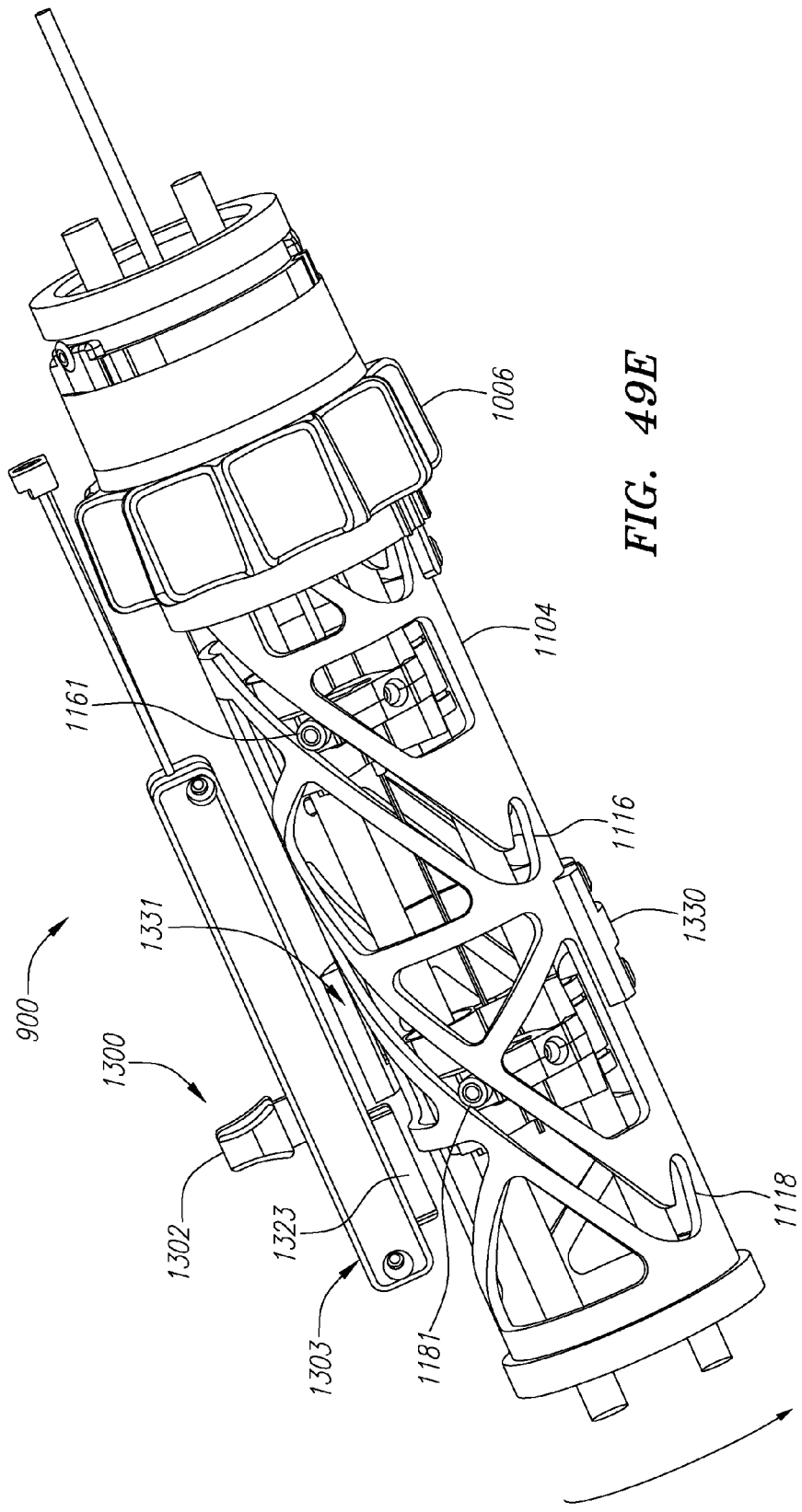
Figure 49F:
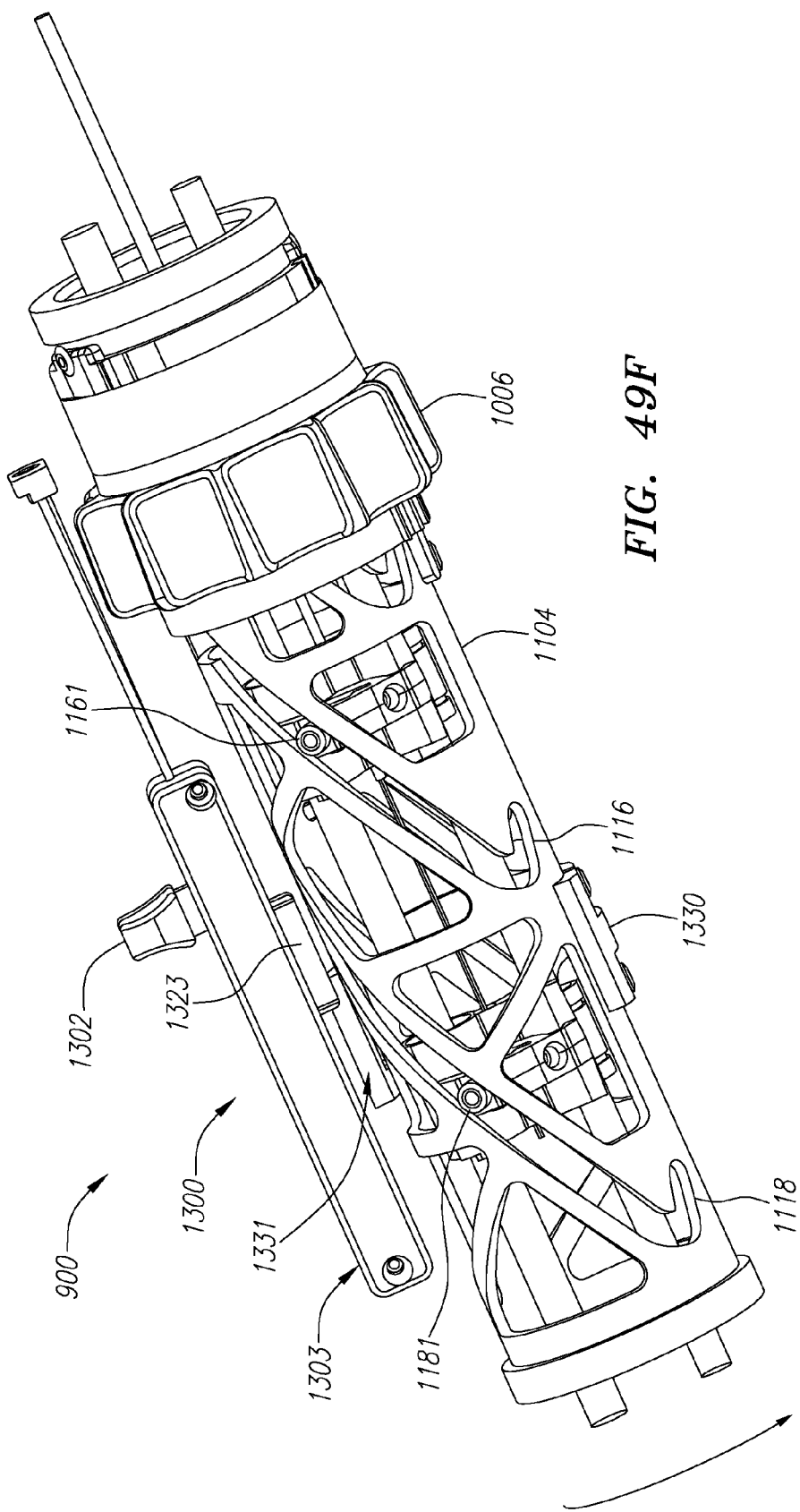

Here, centering actuator knob 1302 is in its proximal-most position and locking tab 1323 is out of alignment with cam locking element 1330, meaning cam 1104 can rotate without interference from locking tab 1323. This is also shown in FIG. 49E, which is a perspective view of controller 900 without housing 903. When centering actuator knob 1302 is advanced distally to deploy centering device 106, locking tab 1323 is placed in a position that is adjacent to cam locking element 1330. This is shown in FIG. 49F, which is another perspective view of controller 900 without housing 903. In this deployed state, rotation of cam 1104 will cause face 1331 of cam locking element to hit locking tab 1323, at which point further rotation of cam 1104 is prevented. This keeps the user from advancing the needle member into the tissue. In this embodiment, the user must retract centering knob 1302 back to its most proximal position (where the centering device is fully retracted to the undeployed state) to clear locking tab 1323 from face 1331 before cam 1104 can be rotated to advance the needle member and begin the deployment of the closure device. It should be noted that the cam locking element is positioned such that even partial advancement of centering knob 1302 will cause the cam to lock. Thus, if the user only partially deploys the centering device, e.g., in a case where the PFO tunnel is relatively narrow, then cam rotation (and needle deployment) will still be prevented.

Figure 50A:
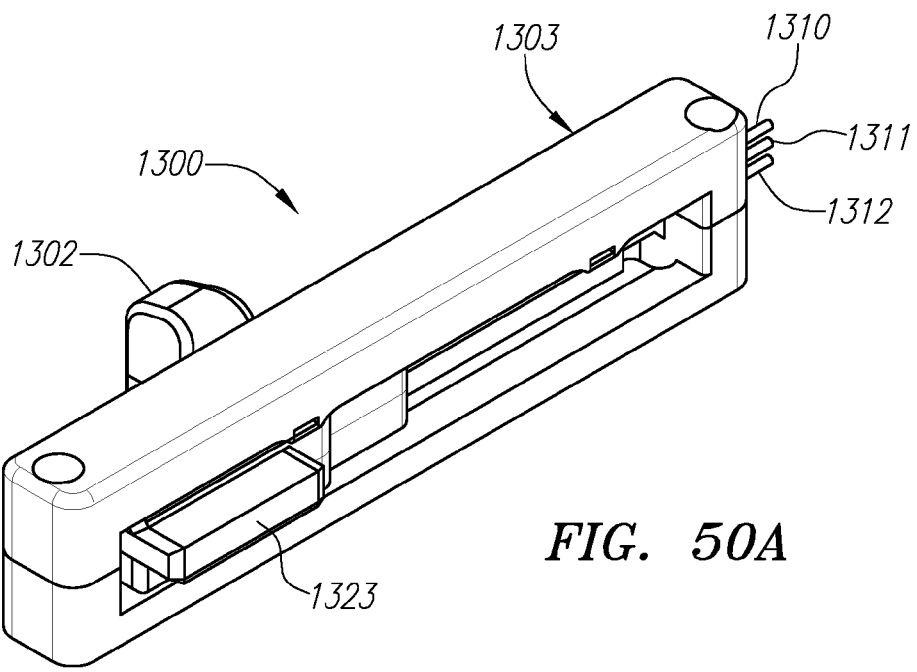
FIGS. 50A-B are perspective views of a exemplary embodiment of a centering actuator assembly.
Figure 50B:
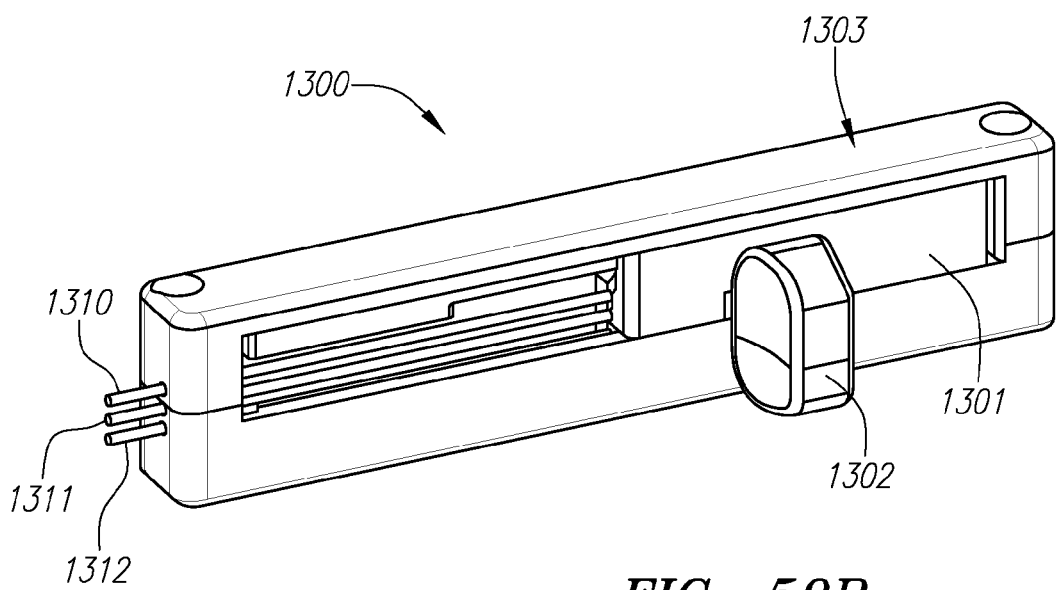

FIGS. 50A-B are perspective views depicting an exemplary embodiment of centering actuator assembly 1300 as viewed from the back and front, respectively. Shown here is actuator 1301, knob 1302, housing 1303, and sleeves 1310-1312. Each of sleeves 1310-1312 has an open distal end and is configured to slidably receive an elongate element of the centering device 106 (not shown). For example, sleeve 1310 can receive a first centering arm 602 (not shown), sleeve 1311 can receive a centering core wire 621 (not shown), and sleeve 1312 can receive a second centering arm 602 (not shown). Sleeves 1310-1312 provide increased pushability to the centering elements, e.g., they resist buckling during distal pushing. Housing 1303 can be a two-piece hollow assembly to allow and sliding of actuator 1301 back and forth therein so that the user can advance the centering distally and retract the centering wires proximally. Centering actuator assembly 1300 is coupled to proximal controller 900 as depicted in FIGS. 49A-D, and can be integrated into the method of use of controller 900 to operate centering device 106, as described with respect to FIGS. 47A-T.

Figure 50C:
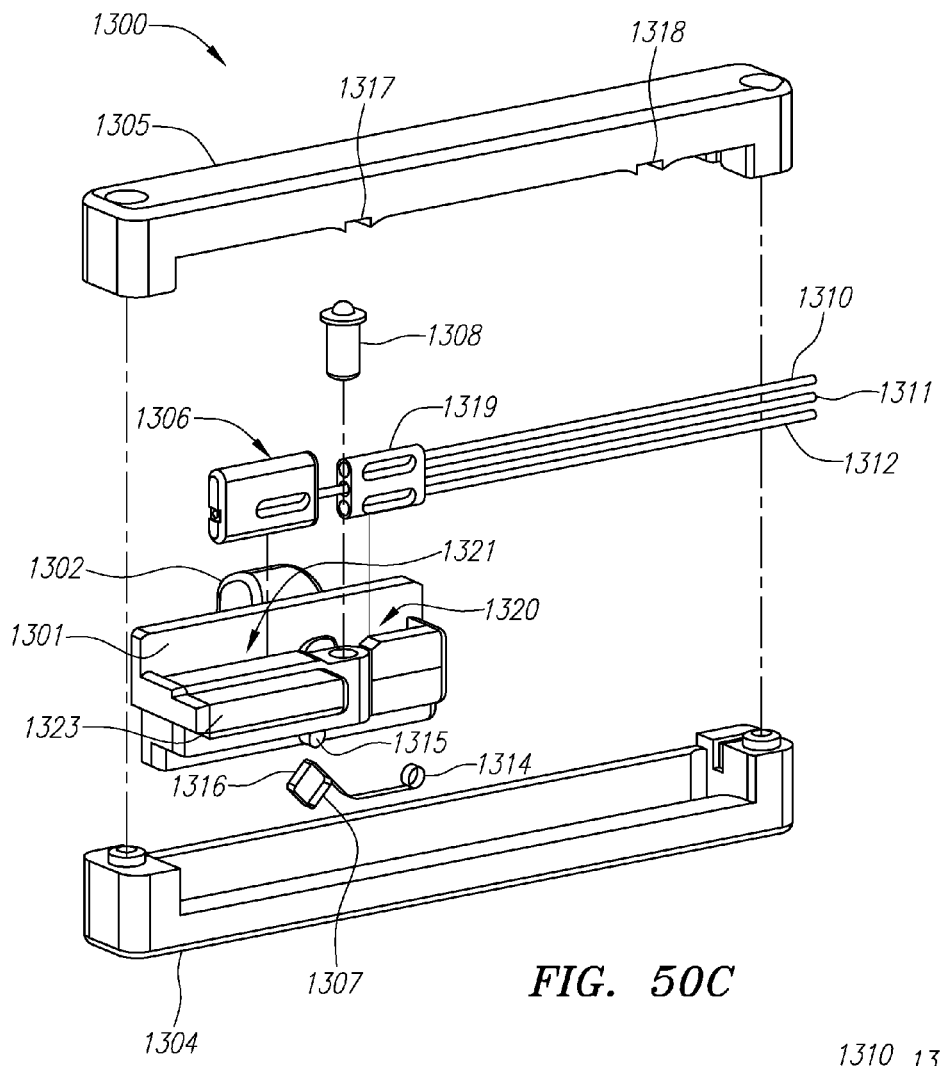
FIG. 50C is an exploded perspective view of an exemplary embodiment of a centering actuator assembly.

FIG. 50C is an exploded perspective view of centering assembly 1300. In addition to the components depicted in FIGS. 50A-B, this figure shows overall housing 1303 broken into a housing base section 1304 and a housing cover section 1305. Also shown is a slidable centering core hub 1306 and a slidable centering arm hub 1319. Core hub 1306 is coupled with sleeve 1311 which is, in turn, slidably received within a central lumen of arm hub 1319. Arm hub 1319 is further coupled with sleeves 1310 and 1312. Arm hub 1319 is fixed to actuator 1301 in a distal seat (or pocket) 1320. A proximal seat 1321 in actuator 1301 receives core hub 1306. Proximal seat 1321 is longer than the length of core hub 1306 and allows core hub 1306 to slide proximally and distally by a limited amount therein.

Also shown here are a tactile feedback element 1308 and an optional locking member 1307. Actuator 1301 is configured to slide between a proximal position, where centering device 106 is undeployed, and a distal position, where centering device 106 is fully deployed, i.e., centering arms 602 have been fully extended outwards from body member 101 and tracking element 620 has been fully advanced distally. Tactile feedback element 1308 is coupled with actuator 1301 and is configured to provide tactile feedback to the user when the actuator 1301 is in the proximal position and the distal position.

In this embodiment, this feature is implemented by use of a spring-ball plunger that interfaces with corresponding detents 1317 and 1318 in housing cover 1305. When actuator 1301 is in the proximal position, the spring-ball is located within detent 1317 and the user must provide the required amount of force to drive plunger 1308 from within detent 1317 and towards distal detent 1318, at which point the spring-ball plunger will click into detent 1318 and will click and will provide the user with noticeable tactile feedback that the device has been fully advanced.

Sleeves 1310 and 1312 receive centering arms 602 and arm hub 1319 is used to control the advancement of centering arms 602 (or retraction thereof). Sleeve 1311 receives core wire 621 and core hub 1306 is used to control the advancement or retraction of core wire 621. Sleeves 1310-1312 can be adhesively bonded to the respective hubs 1306 and 1319. Alternatively, sleeves 1310-1312 can be omitted and the core member 621 and centering arms 602 can be directly connected to the respective hubs 1306 and 1319.

Locking member 1307 is configured here as a leaf spring having a proximal wire loop abutment 1316 and a distal ring 1314 that is configured to mate with projection (or peg) 1315 in actuator 1301. Leaf spring 1307 is configured to deflect outwards away from actuator 1301. Leaf spring 1307 is aligned with pocket 1321 such that wire loop 1316 can extend into pocket 1321 and can contact the proximal end of core hub 1306. When wire loop 1316 is pressed behind the proximal end of core hub 1306, hubs 1306 and 1319 are effectively locked in position with respect to each other.

Figure 50D:
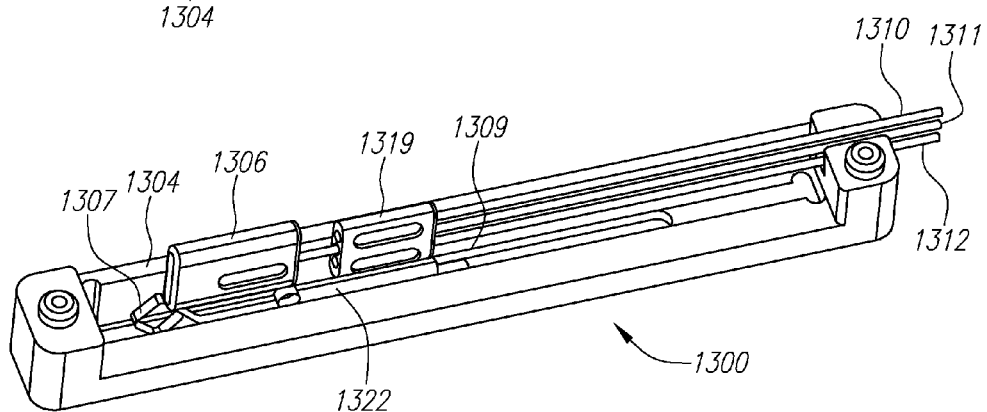
FIG. 50D is a partial assembled view of an exemplary embodiment of a centering actuator assembly.

This arrangement is shown in FIG. 50D, which is a partial assembled view of actuator assembly 1300. Actuator 1301, housing cover 1305, and plunger element 1308 are not shown for purposes of clarity. Here, it can be seen that a floor or raised surface 1322 in housing base 1304 pushes against leaf spring 1307 and causes it to move into a locking position behind the core hub 1306. As actuator 1301 is distally advanced, hubs 1306 and 1319 remain locked in position with respect to each other. This corresponds to advancement of tracking element 620 and centering arms 602 to a position just prior to expansion of arms 602 from within body member 101.

A channel or recess 1309 is present at a position distal to raised surface 1322 in housing base 1304. When wire loop 1316 reaches channel 1309, leaf spring 1307 becomes free to deflect outwards away from actuator 1301. The result is that further distal translation of actuator 1301 causes centering arms 602 to continue to deploy outwards away from body member 101. But, because leaf spring 1307 is no longer in contact with core hub 1306, hub 1306 is free floating with respect to actuator 1301 and remains in a static position. Actuator 1301 can then be advanced until plunger element 1308 mates with distal detent 1318 at which point centering arms 602 have been fully deployed.

Different amounts of travel are required to deploy centering arms 602 as opposed to core wire 621 and therefore it becomes desirable to allow core hub 1306 to become detached from the continued advancement of arm hub 1319 (and actuator 1301). Preferably, core hub 1306 experiences a significant amount of device surface friction that causes hub 1306 to remain in a static position after leaf spring 1307 is released. Alternatively, a mechanical stop can be used either in controller 900 or at the distal end of the catheter. This friction can be generated by the routing of core wire 621 through the various channels in proximal controller 900 and the vasculature of the patient itself, which can be fairly tortuous.

The entire procedure can then be performed in reverse to retract centering arms 602 into the undeployed position. The user retracts actuator 1301 such that plunger element 1308 becomes detached from detent 1318 at which point arm hub 1319 moves proximally with respect to core hub 1306 as the two are unattached due to the presence of channel 1309. Hub 1306 remains in a static position due to the friction applied by the catheter and the proximal controller 900. Once core hub 1306 has reached the distal end of seat 1321, it begins to move proximally with the rest of actuator 1301. Leaf spring 1307 contacts raised surface 1322 and moves back into the position that locks core hub 1306 with respect to arm hub 1319 and the entire assembly can be continually retracted until plunger element 1308 interfaces with proximal detent 1317, at which point retraction of centering device 106 is complete.

Figure 51A:
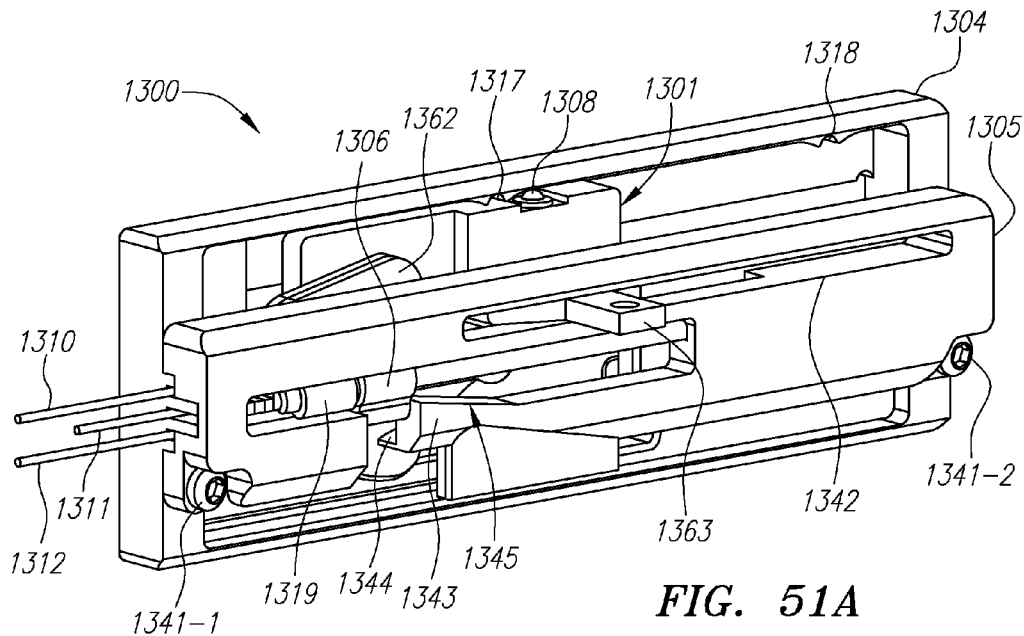
FIG. 51A is a perspective view of an exemplary embodiment of a centering actuator assembly.
Figure 51B:
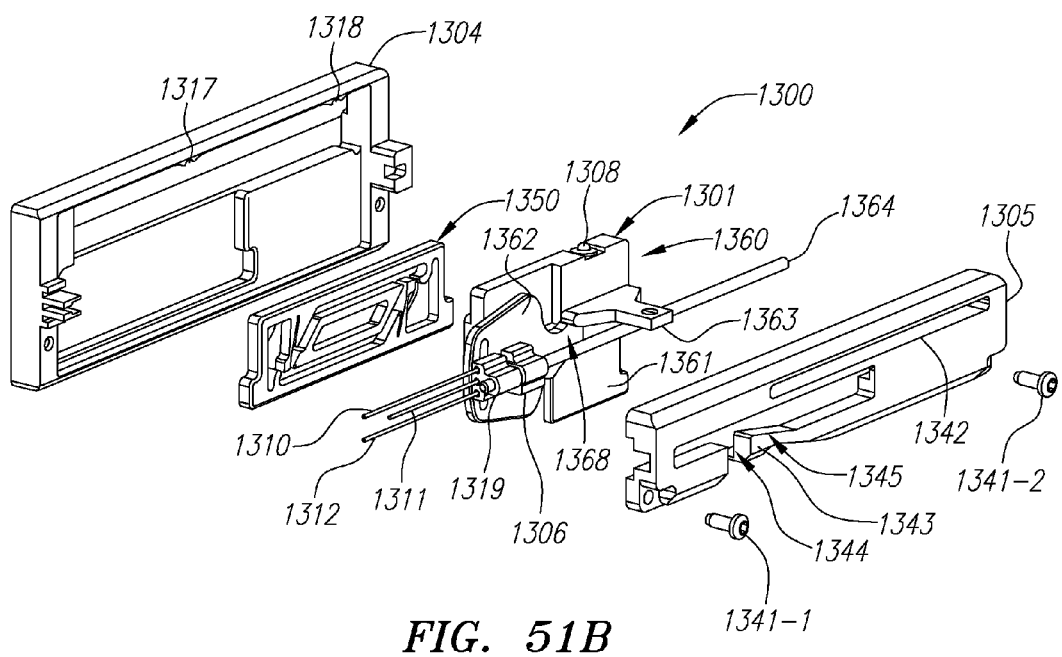
FIG. 51B is an exploded perspective view of an exemplary embodiment of a centering actuator assembly.

FIGS. 51A-B depict another example embodiment of centering actuator assembly 1300. FIG. 51A is a perspective view of centering actuator assembly 1300 while FIG. 51B is an exploded perspective view showing the various components of centering actuator assembly 1300 spaced apart. Here, centering actuator assembly 1300 includes a housing base 1304 and a housing cover 1305, which can be coupled together via fasteners 1341-1 and 1341-2. An actuator subassembly 1360, including actuator 1301, and a guide platform 1350 are coupled together within housing section 1304 and 1305.

Actuator subassembly 1360 includes a main body 1361 that is pivotably coupled with a selector body 1362 via hinge 1368. Actuator subassembly 1360 also includes a hub guide 1364 configured to slidably receive core hub 1306 and centering arm hub 1319. Each of hubs 1306 and 1319 can slide proximally and distally along guide 1364, which in this embodiment is configured as a rod. Main body portion 1361 also includes a strut 1363 upon which a knob or other type of handle can be mounted. A tactile feedback element 1308, configured in this example as a spring ball plunger, is located on the top side (as shown here) of subassembly 1360 and is configured to interface with corresponding detents 1317 and 1318 located on housing base 1304.

As in the previous embodiment, core hub 1306 is coupled with a sleeve 1311 which is configured to receive the core wire (not shown) and aid in resistance to buckling during advancement of the core wire. Centering arm hub 1319 is likewise coupled with sleeves 1310 and 1312 for receiving the centering arms (not shown). Sleeves 1310-1312 can be adhesively bonded within the oval-shaped pockets shown on the backside of core hub 1306 and centering arm hub 1319 in FIG. 51C.

Strut 1363, of main body portion 1361, is configured to extend through slot 1342 in housing cover 1305. Housing cover 1305 also includes a deflectable locking element 1343 which is configured to lock core hub 1306 in place and will be described in more detail below.

Figure 51C:
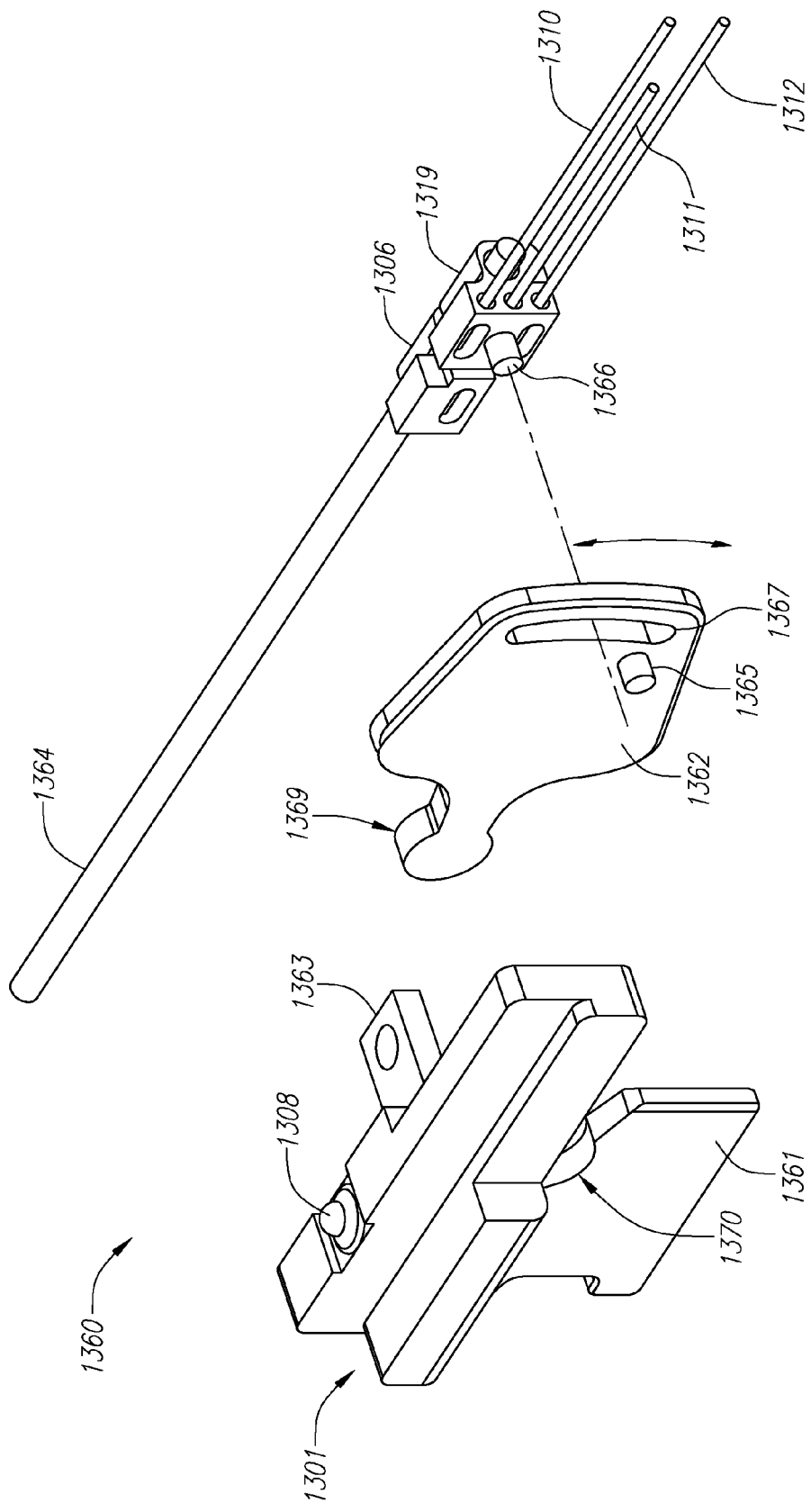
FIG. 51C is an exploded perspective view of an exemplary embodiment of a centering actuator subassembly.

FIG. 51C is an exploded perspective view of actuator subassembly 1360 taken from the opposite side as compared to FIG. 51B. Shown here is slidable actuator 1301, selector body 1362 and hub guide 1364, which is coupled with hubs 1306 and 1319. Selector body 1362 is pivotably coupled with actuator main body 1361 by hinge 1368 (seen in FIG. 51B), which is implemented here by interlocking elements 1369 and 1370. A projection extends from selector body 1362, the projection having a rounded or semi-circular end portion 1369 that forms an axle-type element that can be laterally inserted into a complementary recess 1370 in actuator main body 1361. When main body 1361 and selector 1362 are held in alignment, selector body 1362 can pivot or rotate with respect to main body portion 1361.

Centering arm hub 1319 includes a hub projection 1366 which is slidably received within a curved slot (or track) 1367 in selector body 1362. The interface mechanism formed by projection 1366 and slot 1367 allows hub 1319 to remain coupled to selector body 1362 while selector body 1362 remains free to pivot with respect to hub 1319. Selector body 1362 includes a guide projection 1365, which is configured to be received within a slot (or track) in guide platform 1350.

Figure 51D:
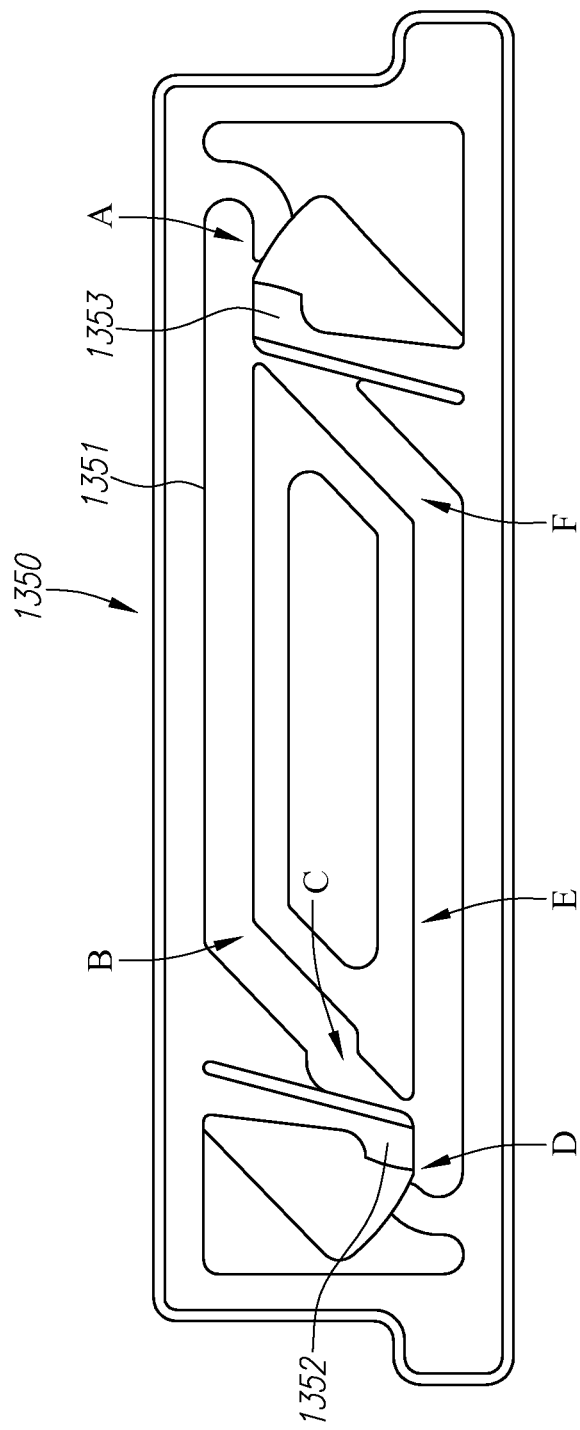
FIGS. 51D-G are top down views of various components of an exemplary embodiment of a centering actuator assembly.

FIG. 51D is a top-down view of guide platform 1350. Guide platform 1350 (which can also be referred to as a cam) has a slot (or track) 1351 that guides the movement of actuator subassembly 1360 by interfacing with the guide projection 1365 of selector body 1362. As the user applies proximal or distal force to the handle connected to strut 1363 of actuator main body 1361, subassembly 1360 will move as directed by slot 1351.

The letters (A, B, C, D, E, F) appearing on FIG. 51D correspond to various positions that subassembly 1360 traverses during an example deployment procedure. Deflectable locking elements 1352 and 1353 (which are configured here as arms or struts) are biased towards the position shown extending into the path defined by slot 1351 at an angle that allows elements 1352 and 1353 to deflect out of the way of guide projection 1365 as it slides past. Once past, the respective locking element 1352 or 1353 deflects (or snaps) back into the position shown to prevent reverse movement.

Figure 51E:
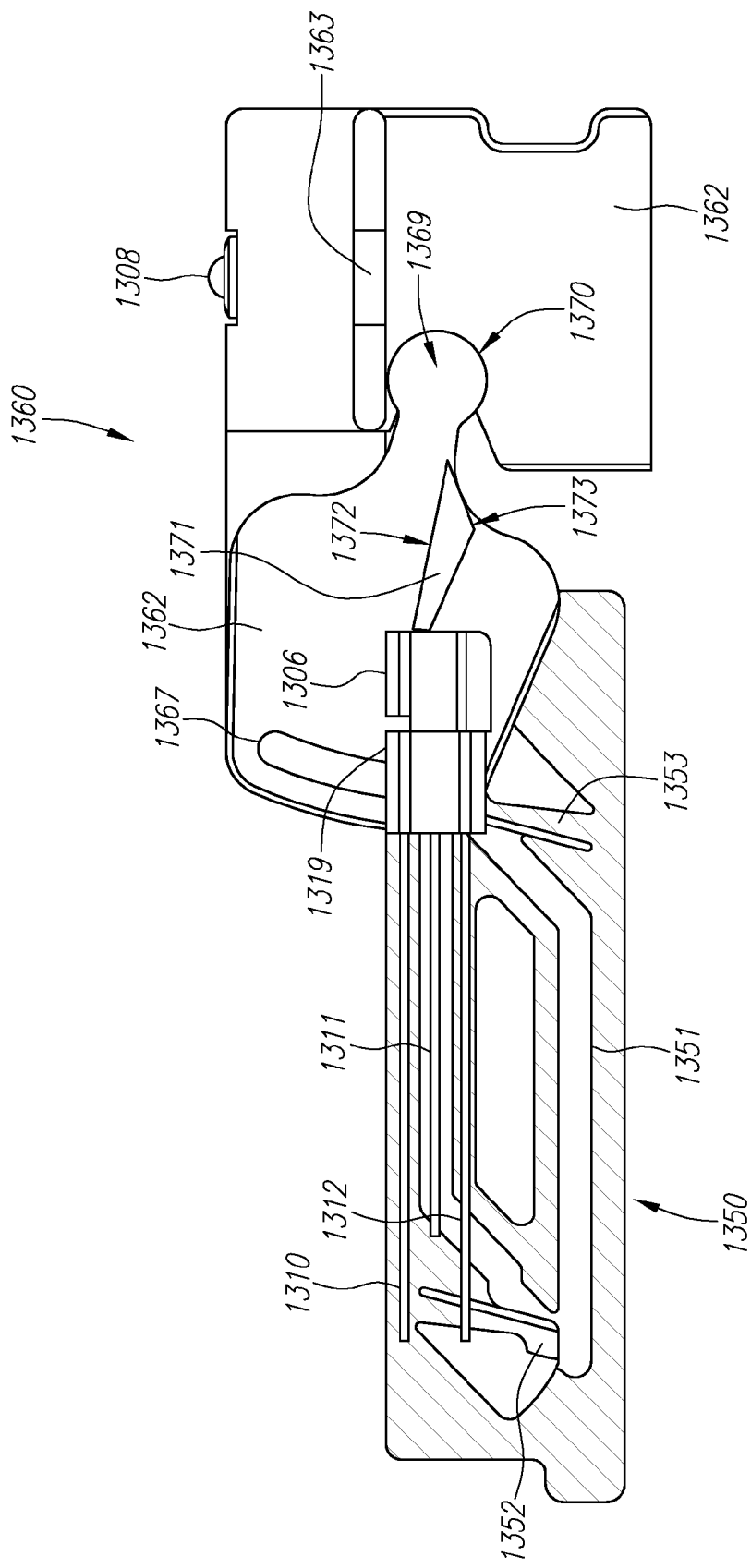

Position A corresponds to the initial position of deployment of the centering device in a medical procedure (PFO closure or other). In this starting position, selector body 1362 is in a fully raised position as shown in FIG. 51E. Selector body 1362 holds core hub 1306 in position against arm hub 1319 by a projection 1371. Projection 1371 is multi-faceted and, based on its position, can be used to selectively lock core hub 1306 and arm hub 1319 together or to allow them to move in relation to each other.

As actuator subassembly 1360 is advanced to position B, the core member and centering arm members (not shown) move together distally by an equivalent amount. At position B, the path of slot 1351 changes to guide subassembly 1360 both distally and laterally, causing selector body 1362 to rotate from the position shown in FIG. 51E downwards. This is in order to disengage projection 1371 and allow independent movement of arm hub 1319 in relation to core hub 1306, i.e., to unlock core hub 1306 from arm hub 1319.

Figure 51F:
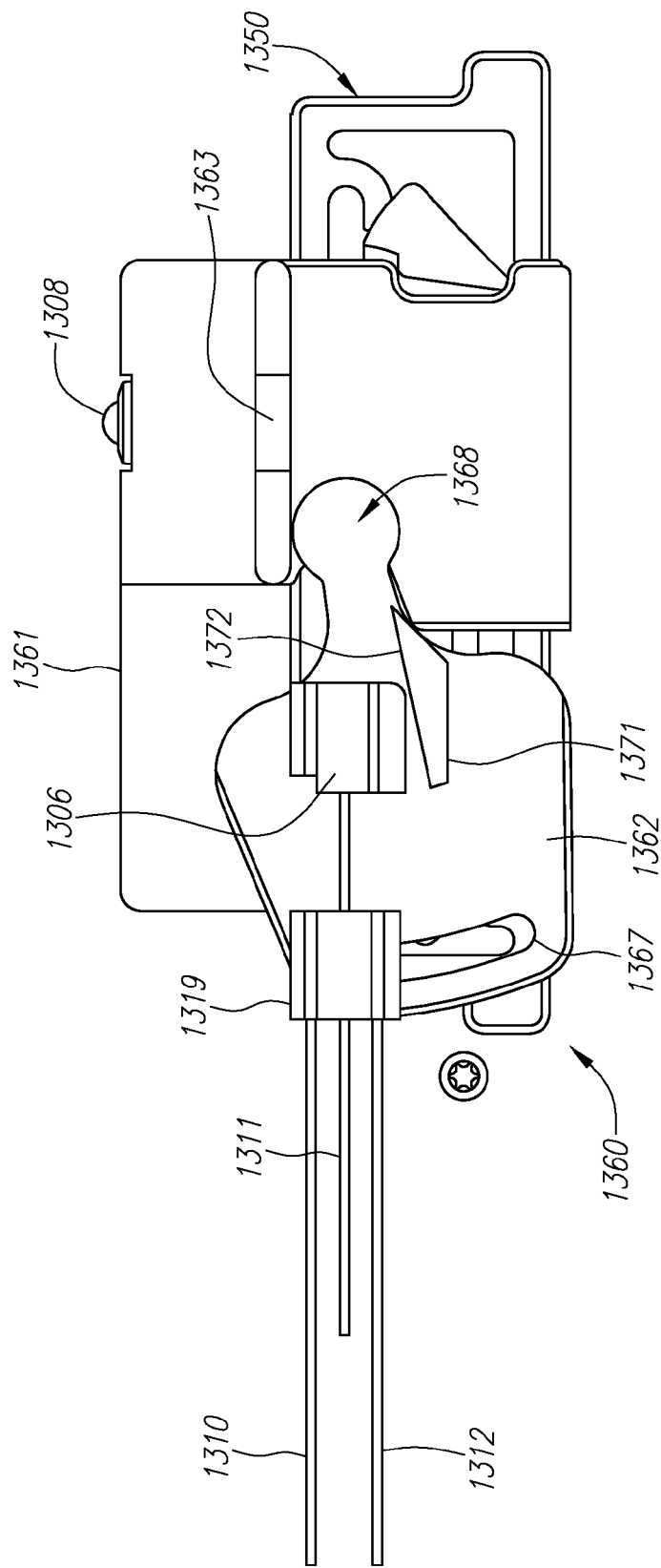

Once actuator subassembly 1360 has been advanced to position C shown in FIG. MD, selector body 1362 has pivoted downwards by an amount sufficient to release core hub 1306 and allow distal forward movement of arm hub 1319 alone. This is shown in the top-down view of FIG. 51F (housing 1303 and guide platform 1350 omitted for clarity). In FIG. 51F, selector body 1362 is shown extended downwards by the full amount of travel. Projection 1371 is no longer behind core hub 1306 and has a top surface 1372 that can ride alongside core hub 1306 and can help drive selector body 1362 to this full downward position during continued forward motion of subassembly 1360.

Figure 51G:
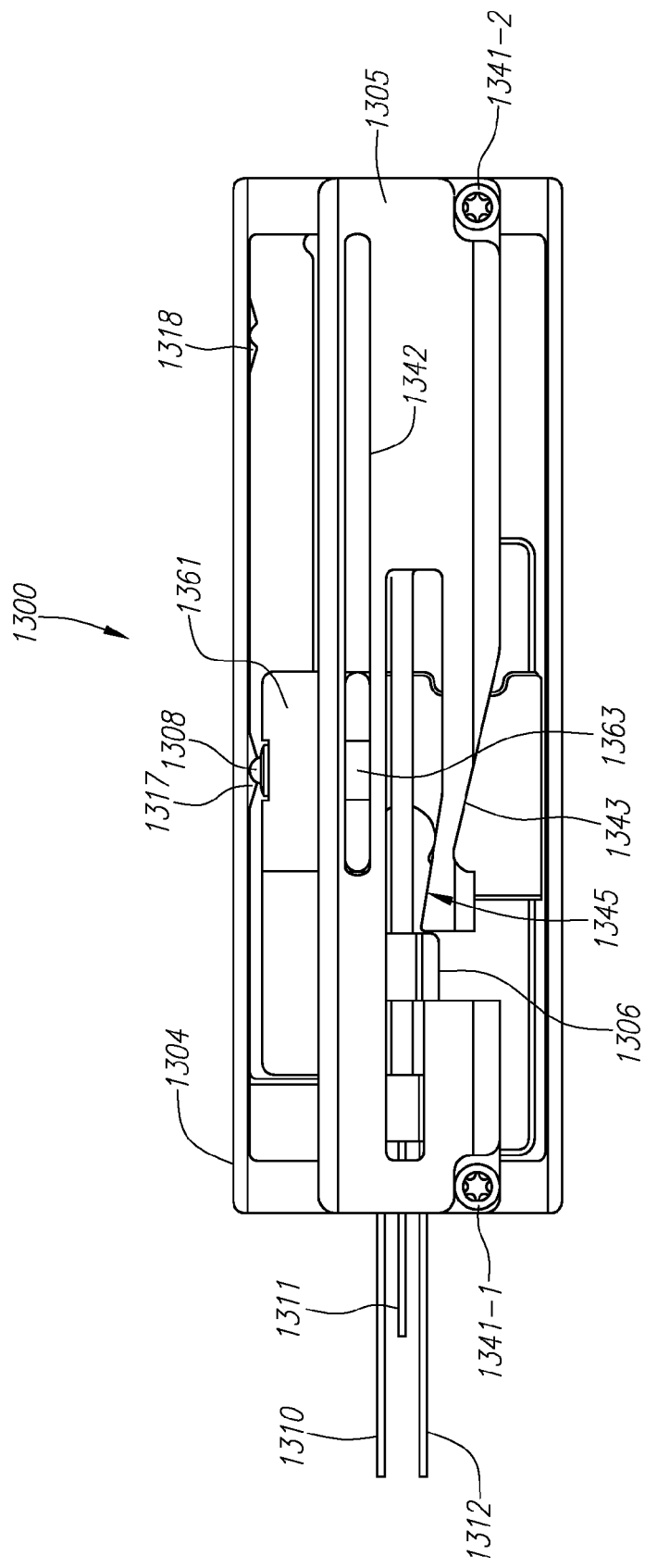

Core hub 1306 is restricted from proximal retraction by deflectable locking element 1343 on housing cover 1305 (see FIG. 5G). Prior to reaching this state, as core hub 1306 is moved distally forward, it slides against top surface 1345 of locking element 1343 maintaining locking element 1343 in a downwardly deflected position. As core hub 1306 reaches the position shown in. FIG. 51G it passes the distal end of locking element 1343 at which point locking element 1343 deflects to its at-rest state, towards which it is biased as shown here.

Upon reaching position D in guide platform 1350, locking element 1352 engages guide projection 1365 and prevents proximal travel of subassembly 1370 back towards position C. Locking element 1352 is deflectable but biased towards the position shown here, and ensures unidirectional motion through positions C and D. Position D marks the end of forward travel for the centering arms contained within sleeves 1310 and 1312. At this position, the centering arms are preferably fully deployed outwardly from the catheter (e.g., body member 101—not shown).

When ready to retract the centering arms back into the housed location, the user will retract actuator subassembly 1360 proximally from position D to position E, which retracts arm hub 1319 with respect to core hub 1306, which is held in place by locking element 1343. Rear surface 1373 on projection 1371 of selector body 1362. engages a corresponding opposing surface 1344 on the inner side of housing cover 1305 (see FIGS. 51A-B). This surface 1344 is positioned on locking element 1343 such that continued retraction of subassembly 1360 forces locking element 1343 downwards to disengage from the rear of core hub 1306, at which point both hub 1319 and 1306 are free to retract together.

Referring back to FIG. 51A, continued retraction from position E to F causes core hub 1306 and arm hub 1319 to be simultaneously retracted towards the initial starting position, which is reached when guide projection 1365 reaches position A. It should be noted that, at position A, a second locking arm 1353 engages behind guide projection 1365 and prevents travel back towards position F. One of skill in the art will readily recognize that, by varying the layout of slot 1351 and guide platform 1350, one can alter the deployment procedure. Likewise, by altering the shape and angled surfaces of projection 1371 one can adjust the point at which core hub 1306 becomes released in relation to arm hub 1319. Similarly, locking elements 1352 and 1353 can be moved or additional locking elements can be added to guide platform 1350 that provide further safeguards to prevent reverse movement if desired.

Figure 52A:
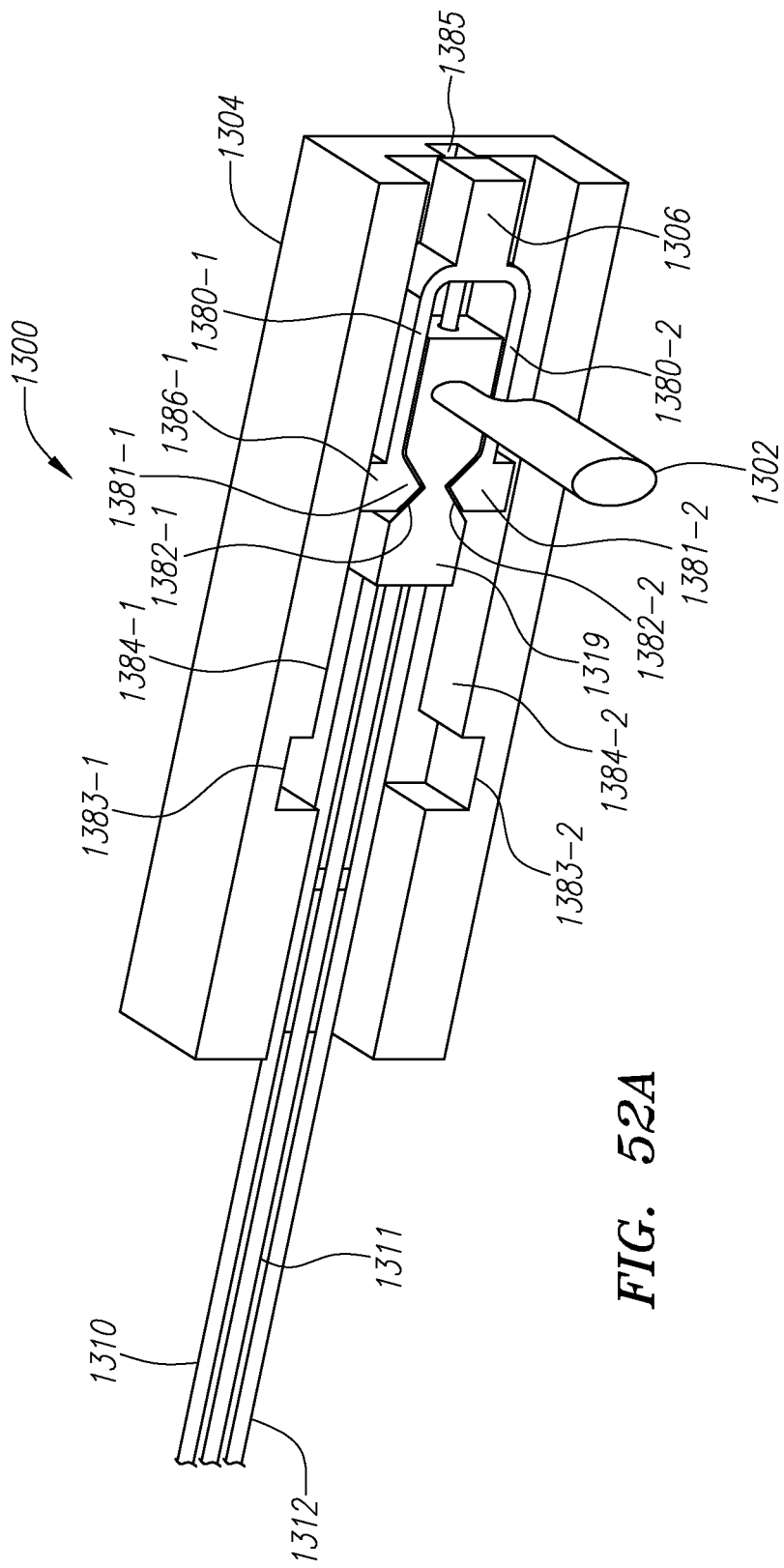
FIGS. 52A-B are perspective views of an exemplary embodiment of a centering actuator assembly.
Figure 52B:
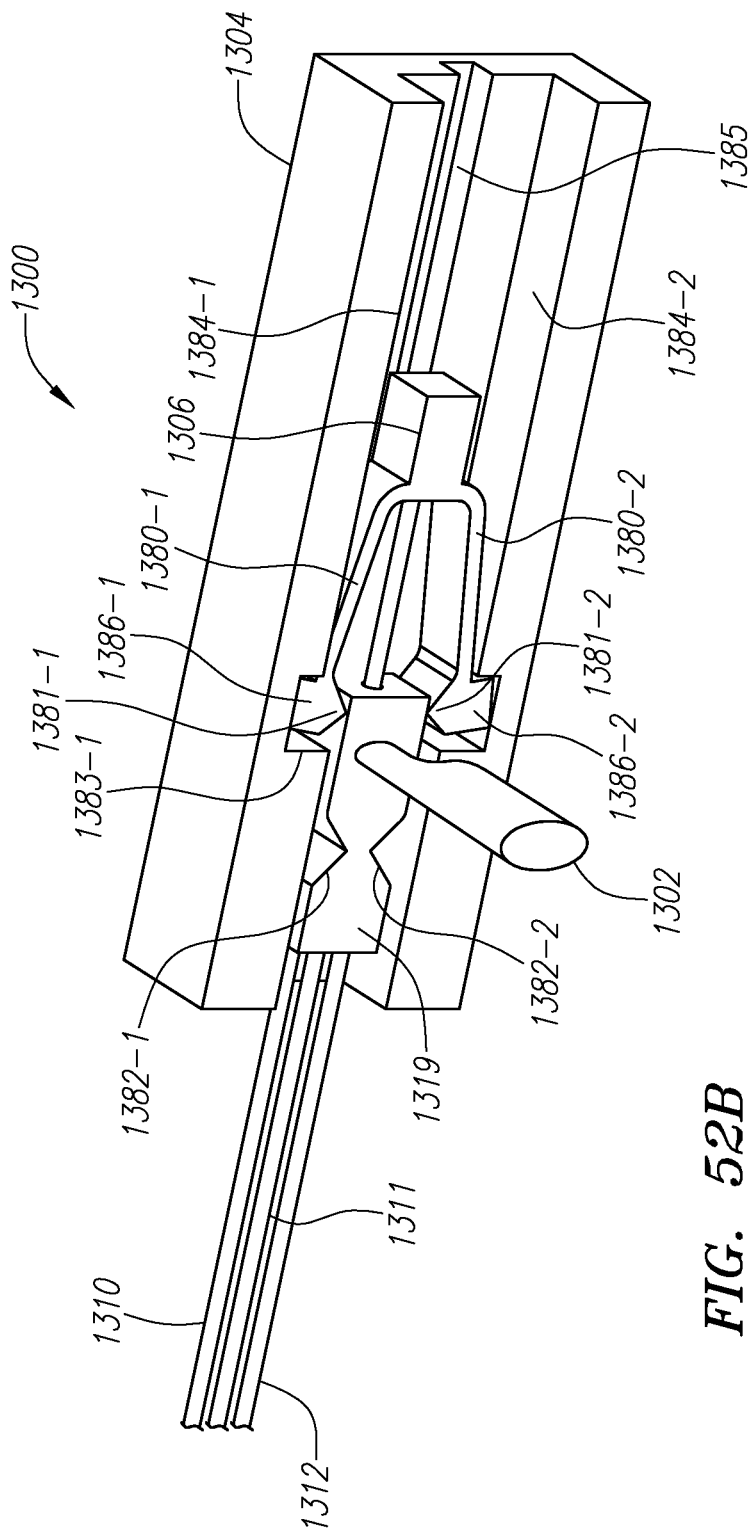

FIGS. 52A-B are perspective views of another example embodiment of centering actuator assembly 1300. FIG. 52A shows centering actuator assembly 1300 in an initial starting position corresponding to an undeployed centering device, while FIG. 52B shows the centering actuator assembly 1300 in a second position after the arm hub 1319 has been detached from core hub 1306. In this embodiment, core hub 1306 has a U-shaped distal portion including two deflectable locking elements 1380-1 and 1380-2, which extend distally alongside arm hub 1319 such that arm hub 1319 is located therebetween. Locking elements 1380 are biased to deflect outwards, away from each other. The distal end of locking elements 1380-1 and 1380-2 each have an inwardly projecting tab 1381-1 and 1381-2 that interfaces with corresponding detents 1382-1 and 1382-2, respectively, in arm hub 1319. The distal end of locking elements 1380-1 and 1380-2 also include outwardly projecting tabs 1386-1 and 1386-2 that interface with corresponding detents (or recesses) 1383-1 and 1383-2 in sidewalls 1384-1 and 1384-2 of housing base 1304. (Housing cover 1305 not shown for clarity).

In FIG. 52A, core hub 1306 is shown locked to arm hub 1319 because the spacing between side walls 1384-1 and 1384-2 is small enough to maintain arms 1380-1 and 1380-2 deflected towards each other such that tabs 1381-1 and 1381-2 are locked in place within detents 1382-1 and 1382-2 respectively. As knob 1302 is forced distally, hubs 1306 and 1319 will slide together along guide track 1385 until reaching recesses 1383-1 and 1383-2, at which point, the outwardly extending projections 1386-1 and 1386-2 are free to enter recesses 1383-1 and 1383-2, allowing arms 1380 to deflect outwards away from arm hub 1319. This releases core hub 1306 from arm hub 1319. Recesses 1383 have a distal side wall that acts as a physical stop to prevent further distal motion of core hub 1306. The user is free to continue distal advancement of arm hub 1319, alone, to deploy the centering arms outwards away from the catheter (e.g., body member 101). Because locking elements 1380 are biased outwards, core hub 1306 is retained in the position shown in FIG. 52B during manipulation of the centering arms via arm hub 1319.

To retract the centering arms, knob 1302 is retracted proximally back towards core hub 1306. The user brings arm hub 1319 into contact with core hub 1306 and drives core hub 1306 backwards to remove tabs 1386 from recesses 1381. Although shown here to be stepped, the proximal edge of recess 1383 can be sloped or rounded to allow easier retraction of core hub 1306. It should also be noted that a slot 1324 is present in housing base 1304 through which a locking tab 1323 can extend (see description with respect to FIGS. 49D-F.

It should be noted that while the term "centering" is used herein to describe centering of a device with respect to a PFO tunnel, one can place the device in any desired position with respect to the PFO tunnel, offset to either the left or right, depending on the design and outward travel of the centering components. The term "lateral positioning" can be used instead of "centering." The centering components can be used to spread or space the PFO tunnel sidewalls apart, and can also be referred to as "spreading" components.

The devices and methods herein may be used in any part of the body, in order to treat a variety of disease states. Of particular interest are applications within hollow organs including but not limited to the heart and blood vessels (arterial and venous), lungs and air passageways, digestive organs (esophagus, stomach, intestines, biliary tree, etc.). The devices and methods will also find use within the genitourinary tract in such areas as the bladder, urethra, ureters, and other areas.

Furthermore, the off-axis delivery systems may be used to pierce tissue and deliver medication, fillers, toxins, and the like in order to offer benefit to a patient. For instance, the device could be used to deliver bulking agent such as collagen, pyrolytic carbon beads, and/or various polymers to the urethra to treat urinary incontinence and other urologic conditions or to the lower esophagus/upper stomach to treat gastroesophageal reflux disease. Alternatively, the devices could be used to deliver drug or other agent to a preferred location or preferred depth within an organ. For example, various medications could be administered into the superficial or deeper areas of the esophagus to treat Barrett's esophagus, or into the heart to promote angiogenesis or myogenesis. Alternatively, the off-axis system can be useful in taking biopsies, both within the lumen and deep into the lumen. For example, the system could be used to take bronchoscopic biopsy specimens of lymph nodes that are located outside of the bronchial tree or flexible endoscopic biopsy specimens that are located outside the gastrointestinal tract. The above list is not meant to limit the scope of the inventive subject matter.

In some embodiments, the off-axis delivery system is used with an anchoring means in order to anchor the device to a location within the body prior to rotation of the off-axis system. This anchoring means may involve the use of a tissue grasper or forceps. It should be noted that any device or set of devices can be advanced within the lumen of the off-axis delivery system, including but not limited to needles, biopsy forceps, aspiration catheters, drug infusion devices, brushes, stents, balloon catheters, drainage catheters, and the like.

While the subject matter described herein is susceptible to various modifications and alternative forms, a specific example thereof has been shown in the drawings and is herein described in detail. It should be understood, however, that the subject matter described herein is not to be limited to the particular form disclosed, but to the contrary, is to cover all modifications, equivalents, and alternatives falling within the spirit of the disclosure.

What is claimed is:

1. An apparatus for treating a patent foramen ovale ("PFO"), comprising:
    an elongate body member;
    an elongate delivery device slidably housed within an inner lumen of the elongate body member;
    an elongate piercing element slidably housed within the elongate delivery device;
    a pusher member;
    an implantable closure device releasably coupled with the pusher member, the pusher member and implantable closure device being slidably housed within the elongate piercing element;
    a tissue engagement device pivotably coupled with the elongate body member with a first hinge and pivotably coupled with the elongate delivery device with a second hinge;
    a hub element slidable over a guidewire;
    at least two centering arms coupled with the hub element, the hub element and centering arms being slidable with respect to the elongate body member, wherein the centering arms are biased to deflect laterally outwards away from the elongate body member upon advancement of the hub element distally over the guidewire; and
    an elongate core element coupled with the hub element and slidable with respect to the elongate body member.

2. The apparatus of claim 1, wherein the centering arms form a tear-drop shape profile when deployed.

3. The apparatus of claim 1, wherein the elongate body member includes a recess and the centering arms are configured to deploy through the recess in the elongate body member.

4. The apparatus of claim 1, further comprising a proximal controller configured to control deployment of the centering arms, wherein the proximal controller comprises a centering actuator assembly comprising a slidable actuator.

5. The apparatus of claim 4, wherein the slidable actuator is coupled with the centering arms.

6. The apparatus of claim 1, further comprising a proximal controller configured to control deployment of the centering arms and core member, wherein the proximal controller comprises a centering actuator assembly comprising a slidable actuator and a core hub configured to slide with respect to the actuator.

7. The apparatus of claim 6, wherein the core hub is coupled with the core member and the actuator is coupled with the centering arms.

8. The apparatus of claim 7, wherein the core hub is releasably lockable to the actuator.

9. The apparatus of claim 8, wherein the core hub is slidable within a seat in the actuator.

10. The apparatus of claim 9, further comprising a spring for locking the actuator to the core hub.

11. The apparatus of claim 10, wherein the spring is configured to unlock the actuator from the core hub as the actuator is advanced distally.

12. The apparatus of claim 9, wherein the core hub is coupled with the core member by way of a sleeve.

13. An apparatus for treating a patent foramen ovale ("PFO"), comprising:
    an elongate body member;
    an elongate delivery device slidably housed within an inner lumen of the elongate body member;
    a tissue engagement device pivotally coupled with the elongate body member with a first hinge and pivotally coupled with the elongate delivery device with a second hinge; and
    at least two centering arms coupled with a hub element, the hub element and centering arms being slidable with respect to the elongate body member;
    an elongate core element coupled with the hub element and slidable with respect to the elongate body member; and
    a proximal controller configured to control deployment of the centering arms and core member, wherein the proximal controller comprises a centering actuator assembly comprising a slidable actuator and a core hub configured to slide with respect to the actuator.

14. The apparatus of claim 13, wherein the centering arms are biased to deflect laterally outwards away from the elongate body member.

15. The apparatus of claim 13, wherein the hub element is slidable over a guidewire.

16. The apparatus of claim 15, wherein the centering arms are configured to deflect outwards upon advancement of the hub element distally over the guidewire.

17. The apparatus of claim 16, wherein the centering arms form a tear-drop shape profile when deployed.

18. The apparatus of claim 16, wherein the elongate body member includes a recess and the centering arms are configured to deploy through the recess in the elongate body member.

19. The apparatus of claim 16, further comprising an elongate piercing element slidably housed within the elongate delivery device.

20. The apparatus of claim 19, further comprising an implantable closure device releasably coupled with a pusher member, the pusher member and closure device being slidably housed within the elongate piercing element.

21. The apparatus of claim 13, wherein the core hub is coupled with the core member and the actuator is coupled with the centering arms.

22. The apparatus of claim 21, wherein the core hub is releasably lockable to the actuator.

23. The apparatus of claim 22, wherein the core hub is slidable within a seat in the actuator.

24. The apparatus of claim 23, further comprising a spring for locking the actuator to the core hub.

25. The apparatus of claim 24, wherein the spring is configured to unlock the actuator from the core hub as the actuator is advanced distally.

26. The apparatus of claim 23, wherein the core hub is coupled with the core member by way of a sleeve.

* * * * *